(12) United States Patent
Xue et al.

(10) Patent No.: US 8,323,960 B2
(45) Date of Patent: Dec. 4, 2012

(54) AMMONIUM TRANSPORTER PROMOTERS FOR GENE EXPRESSION IN OLEAGINOUS YEAST

(75) Inventors: Zhixiong Xue, Chadds Ford, PA (US); Quinn Qun Zhu, West Chester, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 294 days.

(21) Appl. No.: 12/618,070

(22) Filed: Nov. 13, 2009

(65) Prior Publication Data

US 2010/0068789 A1    Mar. 18, 2010

Related U.S. Application Data

(63) Continuation-in-part of application No. 11/185,301, filed on Jul. 20, 2005, now abandoned.

(60) Provisional application No. 60/624,812, filed on Nov. 4, 2004.

(51) Int. Cl.
*C12N 15/00* (2006.01)
*C12N 1/20* (2006.01)
*C12N 15/74* (2006.01)
*A01N 63/00* (2006.01)

(52) U.S. Cl. .................. 435/320.1; 435/252.3; 435/471; 424/93.2; 514/44 R; 536/23.1; 536/23.2; 536/24.1

(58) Field of Classification Search ............... 435/320.1, 435/252.3, 254.11, 254.2, 471; 424/93.2; 514/44 R; 536/23.1, 23.2, 24.1

See application file for complete search history.

(56) References Cited

U.S. PATENT DOCUMENTS

| | | | |
|---|---|---|---|
| 4,937,189 A | 6/1990 | Davidow et al. | |
| 6,265,185 B1 | 7/2001 | Muller et al. | |
| 7,264,949 B2 | 9/2007 | Xue et al. | |
| 2006/0115881 A1 | 6/2006 | Zhu et al. | |

FOREIGN PATENT DOCUMENTS

| | | |
|---|---|---|
| EP | 0 005 277 B1 | 11/1979 |
| EP | 0005277 B1 | 11/1979 |
| EP | 0 220 864 B1 | 5/1987 |
| EP | 0220864 B1 | 5/1987 |
| WO | 2004101757 A2 | 11/2004 |
| WO | WO 2004/101757 A2 | 11/2004 |
| WO | 2005003310 A2 | 1/2005 |
| WO | WO 2005/003310 A2 | 1/2005 |
| WO | 2005049805 A2 | 6/2005 |
| WO | WO 2005/049805 A2 | 6/2005 |

OTHER PUBLICATIONS

U.S. Appl. No. 60/624,812, Nov. 4, 2004, Zhu et al.
U.S. Appl. No. 60/610,060, Sep. 15, 2005, Zhixiong Xue.
Bernard Dujon et. al., Genome Evolution in Yeasts, Nature, 2004, vol. 430:35-44.
Wolfgang Schmalix et. al., The Ethanol-Inducible YAT1 Gene From Yeast Encodes a Presumptive Mitochondrial Outer Carnitine Acetyltransferase, The Journal of Biological Chemistry, 1993, vol. 268:27428-27439.
Anne-Marie Marini et al., A Family of Ammonium Transporters in *Saccharomyces cerevisiae*, Molecular and Cellular Biology, vol. 17(8):4282-4293, 1997.
Colin Ratledge, Microbial Oils and Fats: An Assessment of Their Commercial Potential, Progress in Industrial Microbiology, vol. 16:119-206, 1982.
National Center for Biotechnology Information General Identifier No. 50554096, Accession No. XM_504457, Sep. 28, 2005, B. Dujon et al., Genome Evolution in Yeasts.
National Center for Biotechnology Information General Identifier No. 619513, Accession No. X83608, Jan. 5, 1995, A.M. Marini et al.
National Center for Biotechnology Information General Identifier No. 536818, Accession No. X77608, Sep. 7, 1994, A.M. Marini et al., Cloning and expression of the MEP1 gene encoding an ammonium transporter in *Saccharomyces cerevisiae*.
National Center for Biotechnology Information General Identifier No. 1708982, Accession No. P53390, Sep. 13, 2005, H. Bussey et al., The nucleotide sequence of *Saccharomyces cerevisiae* chromosome XVI.
Thomas Juretzek et al., Comparison of Promoters Suitable for Regulated Overexpression of beta-Galactosidase in the Alkane-Utilizing Yeast Yarrowia lipolytica, Biotechnol. Bioprocess Eng., vol. 5:320-326, 2000.
Anne-Marie Marini et al., Cloning and expression of the MEP1 gene encoding an ammonium transporter in *Saccharomyces cerevisiae*, The EMBO Journal, vol. 13(15):3456-3463, 1994.
National Center for Biotechnology Information General Identifier No. 619513, Accession No. XM83608, Jan. 5, 1995, A.M. Marini et al.
National Center for Biotechnology Information General Identifier No. 536818, Accession No. XM77608, Sep. 7, 1994, A.M. Marini et al., Cloning and expression of the MEP1 gene encoding an ammonium transporter in *Saccharomyces cerevisiae*.
National Center for Biotechnology Information General Identifier No. 1708982, Accession No. P53390, Sep. 13, 2005, H. Bussey et al., The nucleotide sequence of *Saccharomyces cervisiae* chromosome XVI.
Anne-Marie Marini et al., Cloning and expression of the MEP1 gene encoding an ammonium transporter in *Saccharomyces cervisiae*, The EMBO Journal, vol. 13(15):3456-3463, 1994.

*Primary Examiner* — Maria Leavitt

(57) ABSTRACT

The promoter region associated with the *Yarrowia lipolytica* ammonium transporter (yat1) gene has been found to be particularly effective for the expression of heterologous genes in oleaginous yeast. The promoter regions of the instant invention have been shown to be advantageously inducible under oleaginous conditions (i.e., nitrogen limitation) and are useful to drive expression of genes involved in the production of ω-3 and ω-6 fatty acids.

5 Claims, 14 Drawing Sheets

FIG. 6A

Figure 1:
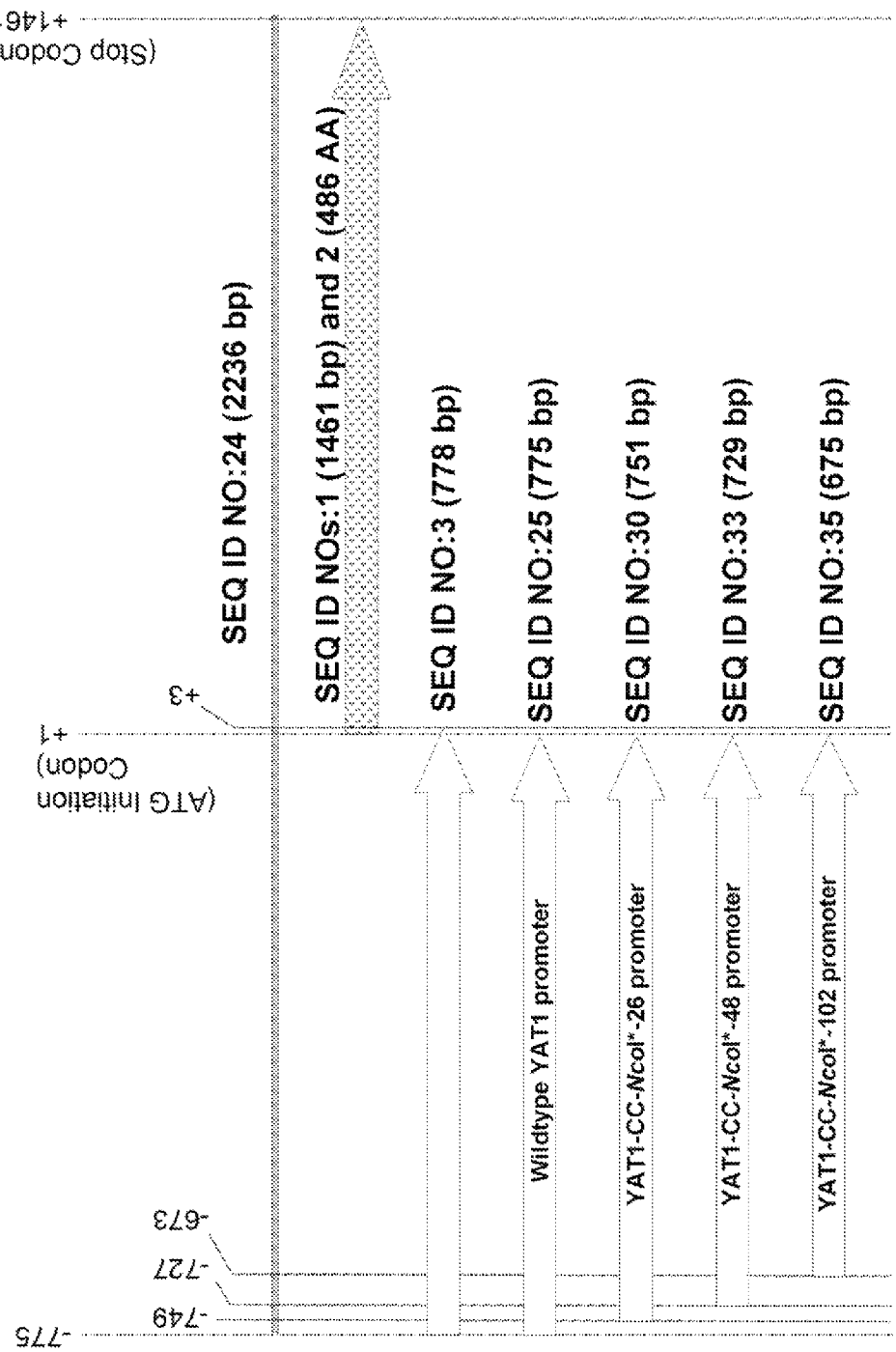

```
                                          1                                                    50
675 bp YAT1-CC-NcoI-102       (1)  --------------------------------------------------
681 bp YAT1-CC-NcoI-102-EcoR1 (1)  --------------------------------------------------
729 bp YAT1-CC-NcoI-48        (1)  --------------------------------------------------
737 bp YAT1-CC-NcoI-48-PmeI   (1)  ------------------------------------------GTTT
751 bp YAT1-CC-NcoI-26        (1)  ------------------------------AGTTGGAGCAAGGGAGAA
757 bp YAT1-CC-NcoI-26-ClaI   (1)  ----------------ATCGATATAGTTGGAGCAAGGGAGAA
759 bp YAT1-CC-NcoI-26-SwaI   (1)  ----------ATTTAAATAGTTGGAGCAAGCAAGGGAGAA
775 bp wt YAT1                (1)  ----ATAAGTTTGCAAAAAGATCGTATTATAGTTGGAGCAAGGGAGAA
777 bp YAT1-CC                (1)  ----ATAAGTTTGCAAAAAGATCGTATTATAGTTGGAGCAAGGGAGAA
777 bp YAT1-CC-NcoI           (1)  ----ATAAGTTTGCAAAAAGATCGTATTATAGTTGGAGCAAGGGAGAA
783 bp YAT1-CC-NcoI-SalI      (1)  GTCGACATAAGTTTGCAAAAAGATCGTATTATAGTTGGAGCAAGGGAGAA
783 bp YAT1-CC-NcoI-SalI      (1)  GTCGACATAAGTTTGCAAAAAGATCGTATTATAGTTGGAGCAAGGGAGAA 51                                                   100
675 bp YAT1-CC-NcoI-102       (1)  --------------------------------------------------
681 bp YAT1-CC-NcoI-102-EcoR1 (1)  --------------------------------------------------
729 bp YAT1-CC-NcoI-48        (1)  ----AAACAGAGTGTGAAAGACTCACTATGGTCCGGGCTTATCTCGACCAATAG
737 bp YAT1-CC-NcoI-48-PmeI   (5)  AAACAGAGTGTGAAAGACTCACTATGGTCCGGGCTTATCTCGACCAATAG
751 bp YAT1-CC-NcoI-26        (19) ATGTAGAGTGTGAAAGACTCACTATGGTCCGGGCTTATCTCGACCAATAG
757 bp YAT1-CC-NcoI-26-ClaI   (25) ATGTAGAGTGTGAAAGACTCACTATGGTCCGGGCTTATCTCGACCAATAG
759 bp YAT1-CC-NcoI-26-SwaI   (27) ATGTAGAGTGTGAAAGACTCACTATGGTCCGGGCTTATCTCGACCAATAG
775 bp wt YAT1                (45) ATGTAGAGTGTGAAAGACTCACTATGGTCCGGGCTTATCTCGACCAATAG
777 bp YAT1-CC                (45) ATGTAGAGTGTGAAAGACTCACTATGGTCCGGGCTTATCTCGACCAATAG
777 bp YAT1-CC-NcoI           (45) ATGTAGAGTGTGAAAGACTCACTATGGTCCGGGCTTATCTCGACCAATAG
783 bp YAT1-CC-NcoI-SalI      (51) ATGTAGAGTGTGAAAGACTCACTATGGTCCGGGCTTATCTCGACCAATAG
783 bp YAT1-CC-NcoI-SalI      (51) ATGTAGAGTGTGAAAGACTCACTATGGTCCGGGCTTATCTCGACCAATAG
```

FIG. 6B

```
                                                  101                                               150
   675 bp YAT1-CC-NcoI-102    (1)   ------TGGAGTTTCTGAGAGAAAAAGGCAAGATACGTATGTAACAAA
   681 bp YAT1-CC-NcoI-102-EcoRI (1)  --GAATTCTGGAGTTTCTGAGAGAAAAAGGCAAGATACGTATGTAACAAA
   729 bp YAT1-CC-NcoI-48    (47)  CCAAAGTCTGGAGTTTCTGAGAGAAAAAGGCAAGATACGTATGTAACAAA
   737 bp YAT1-CC-NcoI-48-PmeI (55)  CCAAAGTCTGGAGTTTCTGAGAGAAAAAGGCAAGATACGTATGTAACAAA
   751 bp YAT1-CC-NcoI-26    (69)  CCAAAGTCTGGAGTTTCTGAGAGAAAAAGGCAAGATACGTATGTAACAAA
   757 bp YAT1-CC-NcoI-26-ClaI (75)  CCAAAGTCTGGAGTTTCTGAGAGAAAAAGGCAAGATACGTATGTAACAAA
   759 bp YAT1-CC-NcoI-26-SwaI (77)  CCAAAGTCTGGAGTTTCTGAGAGAAAAAGGCAAGATACGTATGTAACAAA
   775 bp wt YAT1            (95)  CCAAAGTCTGGAGTTTCTGAGAGAAAAAGGCAAGATACGTATGTAACAAA
   777 bp YAT1-CC            (95)  CCAAAGTCTGGAGTTTCTGAGAGAAAAAGGCAAGATACGTATGTAACAAA
   777 bp YAT1-CC-NcoI       (95)  CCAAAGTCTGGAGTTTCTGAGAGAAAAAGGCAAGATACGTATGTAACAAA
   783 bp YAT1-CC-NcoI-SalI (101)  CCAAAGTCTGGAGTTTCTGAGAGAAAAAGGCAAGATACGTATGTAACAAA
   783 bp YAT1-CC-SalI      (101)  CCAAAGTCTGGAGTTTCTGAGAGAAAAAGGCAAGATACGTATGTAACAAA 151                                               200
   675 bp YAT1-CC-NcoI-102    (43)  GCGACGCATGGTACAATAATAATACCGGAGGCATGTATCATAGAGAGTTAGTG
   681 bp YAT1-CC-NcoI-102-EcoRI (49)  GCGACGCATGGTACAATAATAATACCGGAGGCATGTATCATAGAGAGTTAGTG
   729 bp YAT1-CC-NcoI-48    (97)  GCGACGCATGGTACAATAATAATACCGGAGGCATGTATCATAGAGAGTTAGTG
   737 bp YAT1-CC-NcoI-48-PmeI (105) GCGACGCATGGTACAATAATAATACCGGAGGCATGTATCATAGAGAGTTAGTG
   751 bp YAT1-CC-NcoI-26   (119)  GCGACGCATGGTACAATAATAATACCGGAGGCATGTATCATAGAGAGTTAGTG
   757 bp YAT1-CC-NcoI-26-ClaI (125) GCGACGCATGGTACAATAATAATACCGGAGGCATGTATCATAGAGAGTTAGTG
   759 bp YAT1-CC-NcoI-26-SwaI (127) GCGACGCATGGTACAATAATAATACCGGAGGCATGTATCATAGAGAGTTAGTG
   775 bp wt YAT1           (145)  GCGACGCATGGTACAATAATAATACCGGAGGCATGTATCATAGAGAGTTAGTG
   777 bp YAT1-CC           (145)  GCGACGCATGGTACAATAATAATACCGGAGGCATGTATCATAGAGAGTTAGTG
   777 bp YAT1-CC-NcoI      (145)  GCGACGCATGGTACAATAATAATACCGGAGGCATGTATCATAGAGAGTTAGTG
   783 bp YAT1-CC-NcoI-SalI (151)  GCGACGCATGGTACAATAATAATACCGGAGGCATGTATCATAGAGAGTTAGTG
   783 bp YAT1-CC-SalI      (151)  GCGACGCATGGTACAATAATAATACCGGAGGCATGTATCATAGAGAGTTAGTG
```

FIG. 6C

```
                                                                    250
                                                      201
675 bp YAT1-CC-NcoI-102      (93)  GTTCGATGATGGCACTGGTATGCCTGGTATGACTTTATACGGCTGACTACAT
681 bp YAT1-CC-NcoI-102-EcoR1 (99) GTTCGATGATGGCACTGGTATGCCTGGTATGACTTTATACGGCTGACTACAT
729 bp YAT1-CC-NcoI-48       (147) GTTCGATGATGGCACTGGTATGCCTGGTATGACTTTATACGGCTGACTACAT
737 bp YAT1-CC-NcoI-48-PmeI  (155) GTTCGATGATGGCACTGGTATGCCTGGTATGACTTTATACGGCTGACTACAT
751 bp YAT1-CC-NcoI-26       (169) GTTCGATGATGGCACTGGTATGCCTGGTATGACTTTATACGGCTGACTACAT
757 bp YAT1-CC-NcoI-26-ClaI  (175) GTTCGATGATGGCACTGGTATGCCTGGTATGACTTTATACGGCTGACTACAT
759 bp YAT1-CC-NcoI-26-SwaI  (177) GTTCGATGATGGCACTGGTATGCCTGGTATGACTTTATACGGCTGACTACAT
775 bp wt YAT1               (195) GTTCGATGATGGCACTGGTATGCCTGGTATGACTTTATACGGCTGACTACAT
777 bp YAT1-CC               (195) GTTCGATGATGGCACTGGTATGCCTGGTATGACTTTATACGGCTGACTACAT
783 bp YAT1-CC-NcoI          (195) GTTCGATGATGGCACTGGTATGCCTGGTATGACTTTATACGGCTGACTACAT
783 bp YAT1-CC-NcoI-SalI     (201) GTTCGATGATGGCACTGGTATGCCTGGTATGACTTTATACGGCTGACTACAT
783 bp YAT1-CC-SalI          (201) GTTCGATGATGGCACTGGTATGCCTGGTATGACTTTATACGGCTGACTACAT 300
                                                      251
675 bp YAT1-CC-NcoI-102      (143) ATTTGTCCTCAGACATACAATTACAGTCAAGCACTTACCCTTGGACATCT
681 bp YAT1-CC-NcoI-102-EcoR1 (149) ATTTGTCCTCAGACATACAATTACAGTCAAGCACTTACCCTTGGACATCT
729 bp YAT1-CC-NcoI-48       (197) ATTTGTCCTCAGACATACAATTACAGTCAAGCACTTACCCTTGGACATCT
737 bp YAT1-CC-NcoI-48-PmeI  (205) ATTTGTCCTCAGACATACAATTACAGTCAAGCACTTACCCTTGGACATCT
751 bp YAT1-CC-NcoI-26       (219) ATTTGTCCTCAGACATACAATTACAGTCAAGCACTTACCCTTGGACATCT
757 bp YAT1-CC-NcoI-26-ClaI  (225) ATTTGTCCTCAGACATACAATTACAGTCAAGCACTTACCCTTGGACATCT
759 bp YAT1-CC-NcoI-26-SwaI  (227) ATTTGTCCTCAGACATACAATTACAGTCAAGCACTTACCCTTGGACATCT
775 bp wt YAT1               (245) ATTTGTCCTCAGACATACAATTACAGTCAAGCACTTACCCTTGGACATCT
777 bp YAT1-CC               (245) ATTTGTCCTCAGACATACAATTACAGTCAAGCACTTACCCTTGGACATCT
783 bp YAT1-CC-NcoI          (245) ATTTGTCCTCAGACATACAATTACAGTCAAGCACTTACCCTTGGACATCT
783 bp YAT1-CC-NcoI-SalI     (251) ATTTGTCCTCAGACATACAATTACAGTCAAGCACTTACCCTTGGACATCT
783 bp YAT1-CC-SalI          (251) ATTTGTCCTCAGACATACAATTACAGTCAAGCACTTACCCTTGGACATCT
```

FIG. 6D

```
                                    301                                                350
675 bp YAT1-CC-NcoI-102         (193) GTAGGTACCCCCCGGCCAAGACGATCTCAGCGTGTCGTATGTCGGATTGG
681 bp YAT1-CC-NcoI-102-EcoRI   (199) GTAGGTACCCCCCGGCCAAGACGATCTCAGCGTGTCGTATGTCGGATTGG
729 bp YAT1-CC-NcoI-48          (247) GTAGGTACCCCCCGGCCAAGACGATCTCAGCGTGTCGTATGTCGGATTGG
737 bp YAT1-CC-NcoI-48-PmeI     (255) GTAGGTACCCCCCGGCCAAGACGATCTCAGCGTGTCGTATGTCGGATTGG
751 bp YAT1-CC-NcoI-26          (269) GTAGGTACCCCCCGGCCAAGACGATCTCAGCGTGTCGTATGTCGGATTGG
757 bp YAT1-CC-NcoI-26-ClaI     (275) GTAGGTACCCCCCGGCCAAGACGATCTCAGCGTGTCGTATGTCGGATTGG
759 bp YAT1-CC-NcoI-26-SwaI     (277) GTAGGTACCCCCCGGCCAAGACGATCTCAGCGTGTCGTATGTCGGATTGG
775 bp wt YAT1                  (295) GTAGGTACCCCCCGGCCAAGACGATCTCAGCGTGTCGTATGTCGGATTGG
777 bp YAT1-CC                  (295) GTAGGTACCCCCCGGCCAAGACGATCTCAGCGTGTCGTATGTCGGATTGG
777 bp YAT1-CC-NcoI             (295) GTAGGTACCCCCCGGCCAAGACGATCTCAGCGTGTCGTATGTCGGATTGG
783 bp YAT1-CC-NcoI-SalI        (301) GTAGGTACCCCCCGGCCAAGACGATCTCAGCGTGTCGTATGTCGGATTGG
783 bp YAT1-CC-SalI             (301) GTAGGTACCCCCCGGCCAAGACGATCTCAGCGTGTCGTATGTCGGATTGG 351                                                400
675 bp YAT1-CC-NcoI-102         (243) CGTAGCTCCCCTGCTCGCTCGTCGTCGTCAATTGGCTCCCATCTACTTTCTTCTGCTTGG
681 bp YAT1-CC-NcoI-102-EcoRI   (249) CGTAGCTCCCCTGCTCGCTCGTCGTCGTCAATTGGCTCCCATCTACTTTCTTCTGCTTGG
729 bp YAT1-CC-NcoI-48          (297) CGTAGCTCCCCTGCTCGCTCGTCGTCGTCAATTGGCTCCCATCTACTTTCTTCTGCTTGG
737 bp YAT1-CC-NcoI-48-PmeI     (305) CGTAGCTCCCCTGCTCGCTCGTCGTCGTCAATTGGCTCCCATCTACTTTCTTCTGCTTGG
751 bp YAT1-CC-NcoI-26          (319) CGTAGCTCCCCTGCTCGCTCGTCGTCGTCAATTGGCTCCCATCTACTTTCTTCTGCTTGG
757 bp YAT1-CC-NcoI-26-ClaI     (325) CGTAGCTCCCCTGCTCGCTCGTCGTCGTCAATTGGCTCCCATCTACTTTCTTCTGCTTGG
759 bp YAT1-CC-NcoI-26-SwaI     (327) CGTAGCTCCCCTGCTCGCTCGTCGTCGTCAATTGGCTCCCATCTACTTTCTTCTGCTTGG
775 bp wt YAT1                  (345) CGTAGCTCCCCTGCTCGCTCGTCGTCGTCAATTGGCTCCCATCTACTTTCTTCTGCTTGG
777 bp YAT1-CC                  (345) CGTAGCTCCCCTGCTCGCTCGTCGTCGTCAATTGGCTCCCATCTACTTTCTTCTGCTTGG
777 bp YAT1-CC-NcoI             (345) CGTAGCTCCCCTGCTCGCTCGTCGTCGTCAATTGGCTCCCATCTACTTTCTTCTGCTTGG
783 bp YAT1-CC-NcoI-SalI        (351) CGTAGCTCCCCTGCTCGCTCGTCGTCGTCAATTGGCTCCCATCTACTTTCTTCTGCTTGG
783 bp YAT1-CC-SalI             (351) CGTAGCTCCCCTGCTCGCTCGTCGTCGTCAATTGGCTCCCATCTACTTTCTTCTGCTTGG
```

FIG. 6E

```
                                        401                                                        450
675 bp YAT1-CC-NcoI-102         (293)   CTACACCCAGCATGTCTGCTCGTTTCGTGCCTTATCTATCCTC
681 bp YAT1-CC-NcoI-102-EcoRI   (299)   CTACACCCAGCATGTCTGCTCGTTTCGTGCCTTATCTATCCTC
729 bp YAT1-CC-NcoI-48          (347)   CTACACCCAGCATGTCTGCTCGTTTCGTGCCTTATCTATCCTC
737 bp YAT1-CC-NcoI-48-PmeI     (355)   CTACACCCAGCATGTCTGCTCGTTTTCGTGCCTTATCTATCCTC
751 bp YAT1-CC-NcoI-26          (369)   CTACACCCAGCATGTCTGCTCGTTTCGTGCCTTATCTATCCTC
757 bp YAT1-CC-NcoI-26-ClaI     (375)   CTACACCCAGCATGTCTGCTCGTTTTCGTGCCTTATCTATCCTC
759 bp YAT1-CC-NcoI-26-SwaI     (377)   CTACACCCAGCATGTCTGCTCGTTTTCGTGCCTTATCTATCCTC
775 bp wt YAT1                  (395)   CTACACCCAGCATGTCTGCCATGGCTCGTTTCGTGCCTTATCTATCCTC
777 bp YAT1-CC                  (395)   CTACACCCAGCATGTCTGCCATGGCTCGTTTCGTGCCTTATCTATCCTC
783 bp YAT1-CC-NcoI             (401)   CTACACCCAGCATGTCTGCCATGGCTCGTTTCGTGCCTTATCTATCCTC
783 bp YAT1-CC-SalI             (401)   CTACACCCAGCATGTCTGCCATGGCTCGTTTCGTGCCTTATCTATCCTC 451                                                        500
675 bp YAT1-CC-NcoI-102         (343)   CCAGTATTACCAACTCTAAATGACATGATGATTGGGTCTACACTTTCA
681 bp YAT1-CC-NcoI-102-EcoRI   (349)   CCAGTATTACCAACTCTAAATGACATGATGATTGGGTCTACACTTTCA
729 bp YAT1-CC-NcoI-48          (397)   CCAGTATTACCAACTCTAAATGACATGATGATTGGGTCTACACTTTCA
737 bp YAT1-CC-NcoI-48-PmeI     (405)   CCAGTATTACCAACTCTAAATGACATGATGATTGGGTCTACACTTTCA
751 bp YAT1-CC-NcoI-26          (419)   CCAGTATTACCAACTCTAAATGACATGATGATTGGGTCTACACTTTCA
757 bp YAT1-CC-NcoI-26-ClaI     (425)   CCAGTATTACCAACTCTAAATGACATGATGATTGGGTCTACACTTTCA
759 bp YAT1-CC-NcoI-26-SwaI     (427)   CCAGTATTACCAACTCTAAATGACATGATGATTGGGTCTACACTTTCA
775 bp wt YAT1                  (445)   CCAGTATTACCAACTCTAAATGACATGATGATTGGGTCTACACTTTCA
777 bp YAT1-CC                  (445)   CCAGTATTACCAACTCTAAATGACATGATGATTGGGTCTACACTTTCA
783 bp YAT1-CC-NcoI             (451)   CCAGTATTACCAACTCTAAATGACATGATGATTGGGTCTACACTTTCA
783 bp YAT1-CC-SalI             (451)   CCAGTATTACCAACTCTAAATGACATGATGATTGGGTCTACACTTTCA
```

FIG. 6F

```
                                        501                                                    550
675 bp YAT1-CC-NcoI-102        (393)    TATCAGAGATAAGGAGTAGCACAGTTGCATAAAAAGCCCAACTCTAATCA
681 bp YAT1-CC-NcoI-102-EcoR1  (399)    TATCAGAGATAAGGAGTAGCACAGTTGCATAAAAAGCCCAACTCTAATCA
729 bp YAT1-CC-NcoI-48         (447)    TATCAGAGATAAGGAGTAGCACAGTTGCATAAAAAGCCCAACTCTAATCA
737 bp YAT1-CC-NcoI-48-PmeI    (455)    TATCAGAGATAAGGAGTAGCACAGTTGCATAAAAAGCCCAACTCTAATCA
751 bp YAT1-CC-NcoI-26         (469)    TATCAGAGATAAGGAGTAGCACAGTTGCATAAAAAGCCCAACTCTAATCA
757 bp YAT1-CC-NcoI-26-ClaI    (475)    TATCAGAGATAAGGAGTAGCACAGTTGCATAAAAAGCCCAACTCTAATCA
759 bp YAT1-CC-NcoI-26-SwaI    (477)    TATCAGAGATAAGGAGTAGCACAGTTGCATAAAAAGCCCAACTCTAATCA
775 bp wt YAT1                 (495)    TATCAGAGATAAGGAGTAGCACAGTTGCATAAAAAGCCCAACTCTAATCA
777 bp YAT1-CC                 (495)    TATCAGAGATAAGGAGTAGCACAGTTGCATAAAAAGCCCAACTCTAATCA
777 bp YAT1-CC-NcoI            (501)    TATCAGAGATAAGGAGTAGCACAGTTGCATAAAAAGCCCAACTCTAATCA
783 bp YAT1-CC-NcoI-SalI       (501)    TATCAGAGATAAGGAGTAGCACAGTTGCATAAAAAGCCCAACTCTAATCA
783 bp YAT1-CC-SalI            (501)    TATCAGAGATAAGGAGTAGCACAGTTGCATAAAAAGCCCAACTCTAATCA 551                                                    600
675 bp YAT1-CC-NcoI-102        (443)    GCTTCTTCCTTTCTTCTTGTAATTAGTACAAAGGTGATTAGCGAAATCTGGAA
681 bp YAT1-CC-NcoI-102-EcoR1  (449)    GCTTCTTCCTTTCTTCTTGTAATTAGTACAAAGGTGATTAGCGAAATCTGGAA
729 bp YAT1-CC-NcoI-48         (497)    GCTTCTTCCTTTCTTCTTGTAATTAGTACAAAGGTGATTAGCGAAATCTGGAA
737 bp YAT1-CC-NcoI-48-PmeI    (505)    GCTTCTTCCTTTCTTCTTGTAATTAGTACAAAGGTGATTAGCGAAATCTGGAA
751 bp YAT1-CC-NcoI-26         (519)    GCTTCTTCCTTTCTTCTTGTAATTAGTACAAAGGTGATTAGCGAAATCTGGAA
757 bp YAT1-CC-NcoI-26-ClaI    (525)    GCTTCTTCCTTTCTTCTTGTAATTAGTACAAAGGTGATTAGCGAAATCTGGAA
759 bp YAT1-CC-NcoI-26-SwaI    (527)    GCTTCTTCCTTTCTTCTTGTAATTAGTACAAAGGTGATTAGCGAAATCTGGAA
775 bp wt YAT1                 (545)    GCTTCTTCCTTTCTTCTTGTAATTAGTACAAAGGTGATTAGCGAAATCTGGAA
777 bp YAT1-CC                 (545)    GCTTCTTCCTTTCTTCTTGTAATTAGTACAAAGGTGATTAGCGAAATCTGGAA
777 bp YAT1-CC-NcoI            (551)    GCTTCTTCCTTTCTTCTTGTAATTAGTACAAAGGTGATTAGCGAAATCTGGAA
783 bp YAT1-CC-NcoI-SalI       (551)    GCTTCTTCCTTTCTTCTTGTAATTAGTACAAAGGTGATTAGCGAAATCTGGAA
783 bp YAT1-CC-SalI            (551)    GCTTCTTCCTTTCTTCTTGTAATTAGTACAAAGGTGATTAGCGAAATCTGGAA
```

FIG. 6G

```
                                    601                                                  650
675 bp YAT1-CC-NcoI-102       (493) GCTTAGTTGGCCCCTAAAAAAATCAAAAAAAAGCAAAAAACGAAAAACGAAA
681 bp YAT1-CC-NcoI-102-EcoRI (499) GCTTAGTTGGCCCCTAAAAAAATCAAAAAAAAGCAAAAAACGAAAAACGAAA
729 bp YAT1-CC-NcoI-48        (547) GCTTAGTTGGCCCCTAAAAAAATCAAAAAAAAGCAAAAAACGAAAAACGAAA
737 bp YAT1-CC-NcoI-48-PmeI   (555) GCTTAGTTGGCCCCTAAAAAAATCAAAAAAAAGCAAAAAACGAAAAACGAAA
751 bp YAT1-CC-NcoI-26        (569) GCTTAGTTGGCCCCTAAAAAAATCAAAAAAAAGCAAAAAACGAAAAACGAAA
757 bp YAT1-CC-NcoI-26-ClaI   (575) GCTTAGTTGGCCCCTAAAAAAATCAAAAAAAAGCAAAAAACGAAAAACGAAA
759 bp YAT1-CC-NcoI-26-SwaI   (577) GCTTAGTTGGCCCCTAAAAAAATCAAAAAAAAGCAAAAAACGAAAAACGAAA
775 bp wt YAT1                (595) GCTTAGTTGGCCCCTAAAAAAATCAAAAAAAAGCAAAAAACGAAAAACGAAA
777 bp YAT1-CC                (595) GCTTAGTTGGCCCCTAAAAAAATCAAAAAAAAGCAAAAAACGAAAAACGAAA
777 bp YAT1-CC-NcoI           (595) GCTTAGTTGGCCCCTAAAAAAATCAAAAAAAAGCAAAAAACGAAAAACGAAA
783 bp YAT1-CC-NcoI-SalI      (601) GCTTAGTTGGCCCCTAAAAAAATCAAAAAAAAGCAAAAAACGAAAAACGAAA
783 bp YAT1-CC-SalI           (601) GCTTAGTTGGCCCCTAAAAAAATCAAAAAAAAGCAAAAAACGAAAAACGAAA 651                                                  700
675 bp YAT1-CC-NcoI-102       (543) AACCACAGTTTTGAGAACAGGGAGGTAACGAAGGATCGTATATATATATATA
681 bp YAT1-CC-NcoI-102-EcoRI (549) AACCACAGTTTTGAGAACAGGGAGGTAACGAAGGATCGTATATATATATATA
729 bp YAT1-CC-NcoI-48        (597) AACCACAGTTTTGAGAACAGGGAGGTAACGAAGGATCGTATATATATATATA
737 bp YAT1-CC-NcoI-48-PmeI   (605) AACCACAGTTTTGAGAACAGGGAGGTAACGAAGGATCGTATATATATATATA
751 bp YAT1-CC-NcoI-26        (619) AACCACAGTTTTGAGAACAGGGAGGTAACGAAGGATCGTATATATATATATA
757 bp YAT1-CC-NcoI-26-ClaI   (625) AACCACAGTTTTGAGAACAGGGAGGTAACGAAGGATCGTATATATATATATA
759 bp YAT1-CC-NcoI-26-SwaI   (627) AACCACAGTTTTGAGAACAGGGAGGTAACGAAGGATCGTATATATATATATA
775 bp wt YAT1                (645) AACCACAGTTTTGAGAACAGGGAGGTAACGAAGGATCGTATATATATATATA
777 bp YAT1-CC                (645) AACCACAGTTTTGAGAACAGGGAGGTAACGAAGGATCGTATATATATATATA
777 bp YAT1-CC-NcoI           (645) AACCACAGTTTTGAGAACAGGGAGGTAACGAAGGATCGTATATATATATATA
783 bp YAT1-CC-NcoI-SalI      (651) AACCACAGTTTTGAGAACAGGGAGGTAACGAAGGATCGTATATATATATATA
783 bp YAT1-CC-SalI           (651) AACCACAGTTTTGAGAACAGGGAGGTAACGAAGGATCGTATATATATATATA
```

FIG. 6H

```
                                    701                                                      750
675 bp YAT1-CC-NcoI-102      (593) TATATATATATATACCCACGGATCCCGAGACCGGCCTTTGATTCTTCCCTAC
681 bp YAT1-CC-NcoI-102-EcoR1 (599) TATATATATATATACCCACGGATCCCGAGACCGGCCTTTGATTCTTCCCTAC
729 bp YAT1-CC-NcoI-48       (647) TATATATATATATACCCACGGATCCCGAGACCGGCCTTTGATTCTTCCCTAC
737 bp YAT1-CC-NcoI-48-PmeI  (655) TATATATATATATACCCACGGATCCCGAGACCGGCCTTTGATTCTTCCCTAC
751 bp YAT1-CC-NcoI-26       (669) TATATATATATATACCCACGGATCCCGAGACCGGCCTTTGATTCTTCCCTAC
757 bp YAT1-CC-NcoI-26-ClaI  (675) TATATATATATATACCCACGGATCCCGAGACCGGCCTTTGATTCTTCCCTAC
759 bp YAT1-CC-NcoI-26-SwaI  (677) TATATATATATATACCCACGGATCCCGAGACCGGCCTTTGATTCTTCCCTAC
775 bp wt YAT1               (695) TATATATATATATACCCACGGATCCCGAGACCGGCCTTTGATTCTTCCCTAC
777 bp YAT1-CC               (695) TATATATATATATACCCACGGATCCCGAGACCGGCCTTTGATTCTTCCCTAC
777 bp YAT1-CC-NcoI          (695) TATATATATATATACCCACGGATCCCGAGACCGGCCTTTGATTCTTCCCTAC
783 bp YAT1-CC-NcoI-SalI     (701) TATATATATATATACCCACGGATCCCGAGACCGGCCTTTGATTCTTCCCTAC
783 bp YAT1-CC-SalI          (701) TATATATATATATACCCACGGATCCCGAGACCGGCCTTTGATTCTTCCCTAC 751                                              784
675 bp YAT1-CC-NcoI-102      (643) AACCAACCATTCTCACCACCCTAATTCACAACC-
681 bp YAT1-CC-NcoI-102-EcoR1 (649) AACCAACCATTCTCACCACCCTAATTCACAACC-
729 bp YAT1-CC-NcoI-48       (697) AACCAACCATTCTCACCACCCTAATTCACAACC-
737 bp YAT1-CC-NcoI-48-PmeI  (705) AACCAACCATTCTCACCACCCTAATTCACAACC-
751 bp YAT1-CC-NcoI-26       (719) AACCAACCATTCTCACCACCCTAATTCACAACC-
757 bp YAT1-CC-NcoI-26-ClaI  (725) AACCAACCATTCTCACCACCCTAATTCACAACC-
759 bp YAT1-CC-NcoI-26-SwaI  (727) AACCAACCATTCTCACCACCCTAATTCACAACC-
775 bp wt YAT1               (745) AACCAACCATTCTCACCACCCTAATTCACAA--
777 bp YAT1-CC               (745) AACCAACCATTCTCACCACCCTAATTCACAACC-
777 bp YAT1-CC-NcoI          (745) AACCAACCATTCTCACCACCCTAATTCACAACC-
783 bp YAT1-CC-NcoI-SalI     (751) AACCAACCATTCTCACCACCCTAATTCACAACC-
783 bp YAT1-CC-SalI          (751) AACCAACCATTCTCACCACCCTAATTCACAACC-
```

SEQUENCE LISTING

```
<160> NUMBER OF SEQ ID NOS: 45

<210> SEQ ID NO 1
<211> LENGTH: 1461
<212> TYPE: DNA
<213> ORGANISM: Yarrowia lipolytica
<220> FEATURE:
<221> NAME/KEY: CDS
```

<222> LOCATION: (1)..(1461)
<223> OTHER INFORMATION: GenBank Accession No. XM_504457

<400> SEQUENCE: 1

| | | | | | | | | | | | | | | | | |
|---|---|---|---|---|---|---|---|---|---|---|---|---|---|---|---|---|
| atg | gct | gac | gct | acc | tca | acg | caa | gct | ccc | ctt | ccg | acc | act | ggc | aat | 48 |
| Met | Ala | Asp | Ala | Thr | Ser | Thr | Gln | Ala | Pro | Leu | Pro | Thr | Thr | Gly | Asn | |
| 1 | | | | 5 | | | | | 10 | | | | | 15 | | |

| gga | gga | gac | tcc | ctc | aca | caa | aac | ctg | aac | gtc | ccc | ttc | ctg | ggt | gcc | 96 |
|---|---|---|---|---|---|---|---|---|---|---|---|---|---|---|---|---|
| Gly | Gly | Asp | Ser | Leu | Thr | Gln | Asn | Leu | Asn | Val | Pro | Phe | Leu | Gly | Ala | |
| | | | 20 | | | | | 25 | | | | | 30 | | | |

| gat | atg | gtc | tgg | atc | atg | acc | tct | tcg | gca | ctg | gtc | tgg | atc | atg | att | 144 |
|---|---|---|---|---|---|---|---|---|---|---|---|---|---|---|---|---|
| Asp | Met | Val | Trp | Ile | Met | Thr | Ser | Ser | Ala | Leu | Val | Trp | Ile | Met | Ile | |
| | | 35 | | | | | 40 | | | | | 45 | | | | |

| cca | gga | gtc | ggt | ctg | ctc | tac | tct | ggt | atg | tcg | cgt | aag | cac | cac | gcc | 192 |
|---|---|---|---|---|---|---|---|---|---|---|---|---|---|---|---|---|
| Pro | Gly | Val | Gly | Leu | Leu | Tyr | Ser | Gly | Met | Ser | Arg | Lys | His | His | Ala | |
| 50 | | | | | 55 | | | | | 60 | | | | | | |

| ctg | tct | ctc | ctg | tgg | gca | tcc | atc | atg | tgc | tgt | gcc | ctc | gtc | tct | ttc | 240 |
|---|---|---|---|---|---|---|---|---|---|---|---|---|---|---|---|---|
| Leu | Ser | Leu | Leu | Trp | Ala | Ser | Ile | Met | Cys | Cys | Ala | Leu | Val | Ser | Phe | |
| 65 | | | | 70 | | | | | 75 | | | | | 80 | | |

| gag | tgg | ttt | ttc | tgg | ggt | tac | act | ctg | gca | ttc | tct | cac | aag | gcc | gga | 288 |
|---|---|---|---|---|---|---|---|---|---|---|---|---|---|---|---|---|
| Glu | Trp | Phe | Phe | Trp | Gly | Tyr | Thr | Leu | Ala | Phe | Ser | His | Lys | Ala | Gly | |
| | | | | 85 | | | | | 90 | | | | | 95 | | |

| aag | ttc | att | gga | acc | atg | gat | aac | ttc | ggt | ctt | atg | aat | gtt | ctc | gct | 336 |
|---|---|---|---|---|---|---|---|---|---|---|---|---|---|---|---|---|
| Lys | Phe | Ile | Gly | Thr | Met | Asp | Asn | Phe | Gly | Leu | Met | Asn | Val | Leu | Ala | |
| | | | 100 | | | | | 105 | | | | | 110 | | | |

| gct | ccc | tct | gtt | ggc | tcc | tct | gct | gtc | ccc | gat | atc | ctg | tat | atg | ttc | 384 |
|---|---|---|---|---|---|---|---|---|---|---|---|---|---|---|---|---|
| Ala | Pro | Ser | Val | Gly | Ser | Ser | Ala | Val | Pro | Asp | Ile | Leu | Tyr | Met | Phe | |
| | | 115 | | | | | 120 | | | | | 125 | | | | |

| tac | cag | ggc | atg | ttc | gca | tgc | atc | acc | ggt | atg | ctc | atg | gtt | ggt | gga | 432 |
|---|---|---|---|---|---|---|---|---|---|---|---|---|---|---|---|---|
| Tyr | Gln | Gly | Met | Phe | Ala | Cys | Ile | Thr | Gly | Met | Leu | Met | Val | Gly | Gly | |
| | 130 | | | | | 135 | | | | | 140 | | | | | |

| gct | cac | gag | cga | gct | cga | ctc | ggc | ccc | atg | atg | gta | tat | ctc | ttc | att | 480 |
|---|---|---|---|---|---|---|---|---|---|---|---|---|---|---|---|---|
| Ala | His | Glu | Arg | Ala | Arg | Leu | Gly | Pro | Met | Met | Val | Tyr | Leu | Phe | Ile | |
| 145 | | | | | 150 | | | | | 155 | | | | | 160 | |

| tgg | atg | act | gtc | gtc | tac | tct | cct | att | gca | tgc | tgg | aca | tgg | aac | cct | 528 |
|---|---|---|---|---|---|---|---|---|---|---|---|---|---|---|---|---|
| Trp | Met | Thr | Val | Val | Tyr | Ser | Pro | Ile | Ala | Cys | Trp | Thr | Trp | Asn | Pro | |
| | | | | 165 | | | | | 170 | | | | | 175 | | |

| agt | gga | tgg | ctc | gcc | gtc | ctt | gga | gga | ctt | gat | ttc | gca | ggt | gga | gga | 576 |
|---|---|---|---|---|---|---|---|---|---|---|---|---|---|---|---|---|
| Ser | Gly | Trp | Leu | Ala | Val | Leu | Gly | Gly | Leu | Asp | Phe | Ala | Gly | Gly | Gly | |
| | | 180 | | | | | 185 | | | | | 190 | | | | |

| cct | gtt | cac | atg | tct | tcc | ggt | gcg | ggt | gcc | ctt | gcc | tat | gct | ctc | tgg | 624 |
|---|---|---|---|---|---|---|---|---|---|---|---|---|---|---|---|---|
| Pro | Val | His | Met | Ser | Ser | Gly | Ala | Gly | Ala | Leu | Ala | Tyr | Ala | Leu | Trp | |
| | | 195 | | | | | 200 | | | | | 205 | | | | |

| tgt | ggt | aag | aga | cgt | gac | cct | gct | gtt | gag | aag | ctg | cct | cac | tac | cgg | 672 |
|---|---|---|---|---|---|---|---|---|---|---|---|---|---|---|---|---|
| Cys | Gly | Lys | Arg | Arg | Asp | Pro | Ala | Val | Glu | Lys | Leu | Pro | His | Tyr | Arg | |
| | 210 | | | | | 215 | | | | | 220 | | | | | |

| ccc | tct | tcc | gtt | act | tcc | gtt | gtt | ctc | ggc | act | gtt | ttg | ctt | tgg | ttc | 720 |
|---|---|---|---|---|---|---|---|---|---|---|---|---|---|---|---|---|
| Pro | Ser | Ser | Val | Thr | Ser | Val | Val | Leu | Gly | Thr | Val | Leu | Leu | Trp | Phe | |
| 225 | | | | | 230 | | | | | 235 | | | | | 240 | |

| gga | tgg | ttc | gga | ttc | aac | ggt | ggt | tcc | tct | ggt | aac | gcc | tcc | atc | cga | 768 |
|---|---|---|---|---|---|---|---|---|---|---|---|---|---|---|---|---|
| Gly | Trp | Phe | Gly | Phe | Asn | Gly | Gly | Ser | Ser | Gly | Asn | Ala | Ser | Ile | Arg | |
| | | | | 245 | | | | | 250 | | | | | 255 | | |

| ggc | ttc | tac | gct | gcc | gct | aat | act | aac | ctt | gct | gct | gct | tgc | ggt | gct | 816 |
|---|---|---|---|---|---|---|---|---|---|---|---|---|---|---|---|---|
| Gly | Phe | Tyr | Ala | Ala | Ala | Asn | Thr | Asn | Leu | Ala | Ala | Ala | Cys | Gly | Ala | |
| | | | 260 | | | | | 265 | | | | | 270 | | | |

| ctc | gct | tgg | atg | tgt | gtc | gac | ttc | ttc | cga | aag | ggc | cga | aag | tgg | tcc | 864 |
|---|---|---|---|---|---|---|---|---|---|---|---|---|---|---|---|---|
| Leu | Ala | Trp | Met | Cys | Val | Asp | Phe | Phe | Arg | Lys | Gly | Arg | Lys | Trp | Ser | |
| | | 275 | | | | | 280 | | | | | 285 | | | | |

| act | gtt | ggt | ctc | tgt | tct | ggt | gcc | atc | gca | ggt | ctc | gtt | ggc | atc | acc | 912 |
|---|---|---|---|---|---|---|---|---|---|---|---|---|---|---|---|---|
| Thr | Val | Gly | Leu | Cys | Ser | Gly | Ala | Ile | Ala | Gly | Leu | Val | Gly | Ile | Thr | |
| | 290 | | | | | 295 | | | | | 300 | | | | | |

```
ccc gcc gcc ggc ttc gtc cct atc tgg tct gct gtc cct att ggt atc       960
Pro Ala Ala Gly Phe Val Pro Ile Trp Ser Ala Val Pro Ile Gly Ile
305                 310                 315                 320 atc acc gcc gtc ttc gct aac att tct ggt gac ctt aag aat ctg ctc      1008
Ile Thr Ala Val Phe Ala Asn Ile Ser Gly Asp Leu Lys Asn Leu Leu
                325                 330                 335 cga att gat gat ggt ctc gat gtc ttc tct ctc cat ggt gtg gga gga      1056
Arg Ile Asp Asp Gly Leu Asp Val Phe Ser Leu His Gly Val Gly Gly
            340                 345                 350 ttc tgc ggc tct gtt ctt act gcc ttc ttt gct gct gac tac att gcc      1104
Phe Cys Gly Ser Val Leu Thr Ala Phe Phe Ala Ala Asp Tyr Ile Ala
        355                 360                 365 cat ctg gat ggt gcc aca gag atc aag ggt gga tgg ctc aac cac cac      1152
His Leu Asp Gly Ala Thr Glu Ile Lys Gly Gly Trp Leu Asn His His
    370                 375                 380 tgg gct cag ctg ggt tac cag ctg gct ggt gcg ttt gct acc ctc ggc      1200
Trp Ala Gln Leu Gly Tyr Gln Leu Ala Gly Ala Phe Ala Thr Leu Gly
385                 390                 395                 400 tac tcc ttt gtg gtc tct tca gtt att ctt gtc atc atg aac aga atc      1248
Tyr Ser Phe Val Val Ser Ser Val Ile Leu Val Ile Met Asn Arg Ile
                405                 410                 415 ccc tac ctc aac gtc cga atg acc gag gag gag gag atg ctt gga acc      1296
Pro Tyr Leu Asn Val Arg Met Thr Glu Glu Glu Glu Met Leu Gly Thr
            420                 425                 430 gac atg gcc cag atc ggc gag ttt gcc ttc gac tgg gag gac tct gga      1344
Asp Met Ala Gln Ile Gly Glu Phe Ala Phe Asp Trp Glu Asp Ser Gly
        435                 440                 445 gtc ctg gac ctg cat ggc cag aac ccc aat ggt atg ggc gtc acc ccc      1392
Val Leu Asp Leu His Gly Gln Asn Pro Asn Gly Met Gly Val Thr Pro
    450                 455                 460 aac gtc cag act ccc aag ccc agc agc atc aac gaa aac aag gag gct      1440
Asn Val Gln Thr Pro Lys Pro Ser Ser Ile Asn Glu Asn Lys Glu Ala
465                 470                 475                 480 gct gag agt gat tcg gtt taa                                          1461
Ala Glu Ser Asp Ser Val
                485

<210> SEQ ID NO 2
<211> LENGTH: 486
<212> TYPE: PRT
<213> ORGANISM: Yarrowia lipolytica

<400> SEQUENCE: 2

Met Ala Asp Ala Thr Ser Thr Gln Ala Pro Leu Pro Thr Thr Gly Asn
1               5                   10                  15

Gly Gly Asp Ser Leu Thr Gln Asn Leu Asn Val Pro Phe Leu Gly Ala
            20                  25                  30

Asp Met Val Trp Ile Met Thr Ser Ser Ala Leu Val Trp Ile Met Ile
        35                  40                  45

Pro Gly Val Gly Leu Leu Tyr Ser Gly Met Ser Arg Lys His His Ala
    50                  55                  60

Leu Ser Leu Leu Trp Ala Ser Ile Met Cys Cys Ala Leu Val Ser Phe
65                  70                  75                  80

Glu Trp Phe Phe Trp Gly Tyr Thr Leu Ala Phe Ser His Lys Ala Gly
                85                  90                  95

Lys Phe Ile Gly Thr Met Asp Asn Phe Gly Leu Met Asn Val Leu Ala
            100                 105                 110

Ala Pro Ser Val Gly Ser Ser Ala Val Pro Asp Ile Leu Tyr Met Phe
        115                 120                 125
```

```
Tyr Gln Gly Met Phe Ala Cys Ile Thr Gly Met Leu Met Val Gly
        130                 135                 140
Ala His Glu Arg Ala Arg Leu Gly Pro Met Met Val Tyr Leu Phe Ile
145                 150                 155                 160
Trp Met Thr Val Val Tyr Ser Pro Ile Ala Cys Trp Thr Trp Asn Pro
                165                 170                 175
Ser Gly Trp Leu Ala Val Leu Gly Gly Leu Asp Phe Ala Gly Gly Gly
                180                 185                 190
Pro Val His Met Ser Ser Gly Ala Gly Ala Leu Ala Tyr Ala Leu Trp
            195                 200                 205
Cys Gly Lys Arg Arg Asp Pro Ala Val Glu Lys Leu Pro His Tyr Arg
210                 215                 220
Pro Ser Ser Val Thr Ser Val Val Leu Gly Thr Val Leu Leu Trp Phe
225                 230                 235                 240
Gly Trp Phe Gly Phe Asn Gly Gly Ser Ser Gly Asn Ala Ser Ile Arg
                245                 250                 255
Gly Phe Tyr Ala Ala Ala Asn Thr Asn Leu Ala Ala Ala Cys Gly Ala
                260                 265                 270
Leu Ala Trp Met Cys Val Asp Phe Phe Arg Lys Gly Arg Lys Trp Ser
            275                 280                 285
Thr Val Gly Leu Cys Ser Gly Ala Ile Ala Gly Leu Val Gly Ile Thr
290                 295                 300
Pro Ala Ala Gly Phe Val Pro Ile Trp Ser Ala Val Pro Ile Gly Ile
305                 310                 315                 320
Ile Thr Ala Val Phe Ala Asn Ile Ser Gly Asp Leu Lys Asn Leu Leu
                325                 330                 335
Arg Ile Asp Asp Gly Leu Asp Val Phe Ser Leu His Gly Val Gly Gly
                340                 345                 350
Phe Cys Gly Ser Val Leu Thr Ala Phe Phe Ala Ala Asp Tyr Ile Ala
            355                 360                 365
His Leu Asp Gly Ala Thr Glu Ile Lys Gly Gly Trp Leu Asn His His
370                 375                 380
Trp Ala Gln Leu Gly Tyr Gln Leu Ala Gly Ala Phe Ala Thr Leu Gly
385                 390                 395                 400
Tyr Ser Phe Val Val Ser Ser Val Ile Leu Val Ile Met Asn Arg Ile
                405                 410                 415
Pro Tyr Leu Asn Val Arg Met Thr Glu Glu Glu Met Leu Gly Thr
                420                 425                 430
Asp Met Ala Gln Ile Gly Glu Phe Ala Phe Asp Trp Glu Asp Ser Gly
            435                 440                 445
Val Leu Asp Leu His Gly Gln Asn Pro Asn Gly Met Gly Val Thr Pro
            450                 455                 460
Asn Val Gln Thr Pro Lys Pro Ser Ser Ile Asn Glu Asn Lys Glu Ala
465                 470                 475                 480
Ala Glu Ser Asp Ser Val
                485

<210> SEQ ID NO 3
<211> LENGTH: 778
<212> TYPE: DNA
<213> ORGANISM: Yarrowia lipolytica

<400> SEQUENCE: 3
ataagtttgc aaaaagatcg tattatagtt ggagcaaggg agaaatgtag agtgtgaaag   60
```

```
actcactatg gtccgggctt atctcgacca atagccaaag tctggagttt ctgagagaaa    120
aaggcaagat acgtatgtaa caaagcgacg catggtacaa taataccgga ggcatgtatc    180
atagagagtt agtggttcga tgatggcact ggtgcctggt atgactttat acggctgact    240
acatatttgt cctcagacat acaattacag tcaagcactt acccttggac atctgtaggt    300 acccccggc caagacgatc tcagcgtgtc gtatgtcgga ttggcgtagc tccctcgctc     360
gtcaattggc tcccatctac tttcttctgc ttggctacac ccagcatgtc tgccatggct    420
cgttttcgtg ccttatctat cctcccagta ttaccaactc taaatgacat gatgtgattg    480
ggtctacact ttcatatcag agataaggag tagcacagtt gcataaaaag cccaactcta    540
atcagcttct tcctttcttg taattagtac aaaggtgatt agcgaaatct ggaagcttag    600
ttggccctaa aaaatcaaa aaaagcaaaa acgaaaaac gaaaaccac agttttgaga       660 acagggaggt aacgaaggat cgtatatata tatatatata tataccca cggatcccga      720 gaccggcctt tgattcttcc ctacaaccaa ccattctcac caccctaatt cacaaatg     778
```

<210> SEQ ID NO 4
<211> LENGTH: 39
<212> TYPE: DNA
<213> ORGANISM: Artificial Sequence
<220> FEATURE:
<223> OTHER INFORMATION: SMART IV oligonucleotide

<400> SEQUENCE: 4

```
aagcagtggt atcaacgcag agtggccatt acggccggg                            39
```

<210> SEQ ID NO 5
<211> LENGTH: 59
<212> TYPE: DNA
<213> ORGANISM: Artificial Sequence
<220> FEATURE:
<223> OTHER INFORMATION: CDSIII/3'PCR primer
<220> FEATURE:
<221> NAME/KEY: misc_feature
<222> LOCATION: (28)..(57)
<223> OTHER INFORMATION: thymidine (dT); see BD Biosciences Clontech's
      SMART cDNA technology
<220> FEATURE:
<221> NAME/KEY: misc_feature
<222> LOCATION: (59)..(59)
<223> OTHER INFORMATION: n is a, c, g, or t

<400> SEQUENCE: 5

```
attctagagg ccgaggcggc cgacatgttt tttttttttt tttttttttt tttttttvn     59
```

<210> SEQ ID NO 6
<211> LENGTH: 23
<212> TYPE: DNA
<213> ORGANISM: Artificial Sequence
<220> FEATURE:
<223> OTHER INFORMATION: 5'-PCR primer

<400> SEQUENCE: 6

```
aagcagtggt atcaacgcag agt                                             23
```

<210> SEQ ID NO 7
<211> LENGTH: 18
<212> TYPE: DNA
<213> ORGANISM: Artificial Sequence
<220> FEATURE:
<223> OTHER INFORMATION: Primer M13

<400> SEQUENCE: 7

```
tgtaaaacga cggccagt                                                   18
```

-continued

<210> SEQ ID NO 8
<211> LENGTH: 32
<212> TYPE: DNA
<213> ORGANISM: Artificial Sequence
<220> FEATURE:
<223> OTHER INFORMATION: Primer 27203-F

<400> SEQUENCE: 8
gatcgtcgac ataagtttgc aaaaagatcg ta                                    32

<210> SEQ ID NO 9
<211> LENGTH: 34
<212> TYPE: DNA
<213> ORGANISM: Artificial Sequence
<220> FEATURE:
<223> OTHER INFORMATION: Primer 27203-R

<400> SEQUENCE: 9
gatcccatgg ttgtgaatta gggtggtgag aatg                                  34

<210> SEQ ID NO 10
<211> LENGTH: 8953
<212> TYPE: DNA
<213> ORGANISM: Artificial Sequence
<220> FEATURE:
<223> OTHER INFORMATION: Plasmid pY5-30

<400> SEQUENCE: 10
ggtggagctc cagcttttgt tccctttagt gagggttaat ttcgagcttg gcgtaatcat      60
ggtcatagct gtttcctgtg tgaaattgtt atccgctcac aattccacac aacatacgag    120
ccggaagcat aaagtgtaaa gcctggggtg cctaatgagt gagctaactc acattaattg    180
cgttgcgctc actgcccgct ttccagtcgg gaaacctgtc gtgccagctg cattaatgaa    240
tcggccaacg cgcggggaga ggcggtttgc gtattgggcg ctcttccgct tcctcgctca    300
ctgactcgct gcgctcggtc gttcggctgc ggcgagcggt atcagctcac tcaaaggcgg    360
taatacggtt atccacagaa tcaggggata acgcaggaaa gaacatgtga gcaaaaggcc    420
agcaaaaggc caggaaccgt aaaaaggccg cgttgctggc gtttttccat aggctccgcc    480
cccctgacga gcatcacaaa aatcgacgct caagtcagag gtggcgaaac ccgacaggac    540
tataaagata ccaggcgttt ccccctggaa gctccctcgt gcgctctcct gttccgaccc    600
tgccgcttac cggatacctg tccgcctttc tcccttcggg aagcgtggcg ctttctcata    660
gctcacgctg taggtatctc agttcggtgt aggtcgttcg ctccaagctg ggctgtgtgc    720
acgaaccccc cgttcagccc gaccgctgcg ccttatccgg taactatcgt cttgagtcca    780
acccggtaag acacgactta tcgccactgg cagcagccac tggtaacagg attagcagag    840
cgaggtatgt aggcggtgct acagagttct tgaagtggtg gcctaactac ggctacacta    900
gaaggacagt atttggtatc tgcgctctgc tgaagccagt taccttcgga aaaagagttg    960
gtagctcttg atccggcaaa caaaccaccg ctggtagcgg tggttttttt gtttgcaagc   1020
agcagattac gcgcagaaaa aaaggatctc aagaagatcc tttgatcttt tctacggggt   1080
ctgacgctca gtggaacgaa aactcacgtt aagggatttt ggtcatgaga ttatcaaaaa   1140
ggatcttcac ctagatcctt ttaaattaaa aatgaagttt aaatcaatc taaagtatat    1200
atgagtaaac ttggtctgac agttaccaat gcttaatcag tgaggcacct atctcagcga   1260
tctgtctatt tcgttcatcc atagttgcct gactccccgt cgtgtagata actacgatac   1320
gggagggctt accatctggc cccagtgctg caatgatacc gcgagaccca cgctcaccgg   1380

```
ctccagattt atcagcaata aaccagccag ccggaagggc cgagcgcaga agtggtcctg   1440
caactttatc cgcctccatc cagtctatta attgttgccg ggaagctaga gtaagtagtt   1500
cgccagttaa tagtttgcgc aacgttgttg ccattgctac aggcatcgtg gtgtcacgct   1560
cgtcgtttgg tatggcttca ttcagctccg gttcccaacg atcaaggcga gttacatgat   1620
cccccatgtt gtgcaaaaaa gcggttagct ccttcggtcc tccgatcgtt gtcagaagta   1680
agttggccgc agtgttatca ctcatggtta tggcagcact gcataattct cttactgtca   1740
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
cagcatcttt tactttcacc agcgtttctg ggtgagcaaa aacaggaagg caaaatgccg   2040
caaaaaaggg aataagggcg acacggaaat gttgaatact catactcttc cttttcaat   2100 attattgaag catttatcag ggttattgtc tcatgagcgg atacatattt gaatgtattt   2160
agaaaaataa acaaataggg gttccgcgca catttccccg aaaagtgcca cctgacgcgc   2220
cctgtagcgg cgcattaagc gcggcgggtg tggtggttac gcgcagcgtg accgctacac   2280
ttgccagcgc cctagcgccc gctcctttcg ctttcttccc ttcctttctc gccacgttcg   2340
ccggctttcc ccgtcaagct ctaaatcggg gctccctttt agggttccga tttagtgctt   2400
tacggcacct cgaccccaaa aaacttgatt agggtgatgg ttcacgtagt gggccatcgc   2460
cctgatagac ggttttttcg ccttttgacgt tggagtccac gttctttaat agtggactct   2520
tgttccaaac tggaacaaca ctcaacccta tctcggtcta ttcttttgat ttataaggga   2580
ttttgccgat ttcggcctat tggttaaaaa atgagctgat ttaacaaaaa tttaacgcga   2640
attttaacaa aatattaacg cttacaattt ccattcgcca ttcaggctgc gcaactgttg   2700
ggaagggcga tcggtgcggg cctcttcgct attacgccag ctggcgaaag ggggatgtgc   2760
tgcaaggcga ttaagttggg taacgccagg gttttcccag tcacgacgtt gtaaaacgac   2820
ggccagtgaa ttgtaatacg actcactata gggcgaattg ggtaccgggc ccccctcga   2880 ggtcgatggt gtcgataagc ttgatatcga attcatgtca cacaaaccga tcttcgcctc   2940
aaggaaacct aattctacat ccgagagact gccgagatcc agtctacact gattaatttt   3000
cgggccaata atttaaaaaa atcgtgttat ataatattat atgtattata tatatacatc   3060
atgatgatac tgacagtcat gtcccattgc taaatagaca gactccatct gccgcctcca   3120
actgatgttc tcaatattta aggggtcatc tcgcattgtt taataataaa cagactccat   3180
ctaccgcctc caaatgatgt tctcaaaata tattgtatga acttattttt attacttagt   3240
attattagac aacttacttg ctttatgaaa aacacttcct attaggaaa caatttataa   3300 tggcagttcg ttcatttaac aatttatgta gaataaatgt tataaatgcg tatgggaaat   3360
cttaaatatg gatagcataa atgatatctg cattgcctaa ttcgaaatca acagcaacga   3420
aaaaaatccc ttgtacaaca taaatagtca tcgagaaata tcaactatca aagaacagct   3480
attcacacgt tactattgag attattattg gacgagaatc acacactcaa ctgtctttct   3540
ctcttctaga aatacaggta caagtatgta ctattctcat tgttcatact tctagtcatt   3600
tcatcccaca tattccttgg atttctctcc aatgaatgac attctatctt gcaaattcaa   3660
caattataat aagatatacc aaagtagcgg tatagtggca atcaaaaagc ttctctggtg   3720
tgcttctcgt atttattttt attctaatga tccattaaag gtatatattt atttcttgtt   3780
```

| | |
|---|---|
| atataatcct tttgtttatt acatgggctg gatacataaa ggtattttga tttaattttt | 3840 |
| tgcttaaatt caatccccc tcgttcagtg tcaactgtaa tggtaggaaa ttaccatact | 3900 |
| tttgaagaag caaaaaaaat gaaagaaaaa aaaaatcgta tttccaggtt agacgttccg | 3960 |
| cagaatctag aatgcggtat gcggtacatt gttcttcgaa cgtaaaagtt gcgctccctg | 4020 |
| agatattgta catttttgct tttacaagta caagtacatc gtacaactat gtactactgt | 4080 |
| tgatgcatcc acaacagttt gttttgtttt tttttgtttt tttttttttct aatgattcat | 4140 |
| taccgctatg tatacctact tgtacttgta gtaagcccggg ttattggcgt tcaattaatc | 4200 |
| atagacttat gaatctgcac ggtgtgcgct gcgagttact tttagcttat gcatgctact | 4260 |
| tgggtgtaat attgggatct gttcggaaat caacggatgc tcaaccgatt tcgacagtaa | 4320 |
| taatttgaat cgaatcggag cctaaaatga acccgagtat atctcataaa attctcggtg | 4380 |
| agaggtctgt gactgtcagt acaaggtgcc ttcattatgc cctcaacctt accatacctc | 4440 |
| actgaatgta gtgtacctct aaaaatgaaa tacagtgcca aaagccaagg cactgagctc | 4500 |
| gtctaacgga cttgatatac aaccaattaa aacaaatgaa agaaataca gttctttgta | 4560 |
| tcatttgtaa caattaccct gtacaaacta aggtattgaa atcccacaat attcccaaag | 4620 |
| tccaccccctt tccaaattgt catgcctaca actcatatac caagcactaa cctaccaaac | 4680 |
| accactaaaa ccccacaaaa tatatcttac cgaatataca gtaacaagct accaccacac | 4740 |
| tcgttgggtg cagtcgccag cttaaagata tctatccaca tcagccacaa ctcccttcct | 4800 |
| ttaataaacc gactacaccc ttggctattg aggttatgag tgaatatact gtagacaaga | 4860 |
| cactttcaag aagactgttt ccaaaacgta ccactgtcct ccactacaaa cacacccaat | 4920 |
| ctgcttcttc tagtcaaggt tgctacaccg gtaaattata aatcatcatt tcattagcag | 4980 |
| ggcagggccc ttttttataga gtcttataca ctagcggacc ctgccggtag accaacccgc | 5040 |
| aggcgcgtca gtttgctcct tccatcaatg cgtcgtagaa acgacttact ccttcttgag | 5100 |
| cagctccttg accttgttgg caacaagtct ccgacctcgg aggtggagga agagcctccg | 5160 |
| atatcggcgg tagtgatacc agcctcgacg gactccttga cggcagcctc aacagcgtca | 5220 |
| ccggcgggct tcatgttaag agagaacttg agcatcatgg cggcagacag aatggtggca | 5280 |
| atggggttga ccttctgctt gccgagatcg ggggcagatc cgtgacaggg ctcgtacaga | 5340 |
| ccgaacgcct cgttggtgtc gggcagagaa gccagagagg cggagggcag cagacccaga | 5400 |
| gaaccgggga tgacggaggc ctcgtcgag atgatatcgc caaacatgtt ggtggtgatg | 5460 |
| atgataccat tcatcttgga gggctgcttg atgaggatca tggcggccga gtcgatcagc | 5520 |
| tggtggttga gctcgagctg ggggaattcg tccttgagga ctcgagtgac agtctttcgc | 5580 |
| caaagtcgag aggaggccag cacgttggcc ttgtcaagag accacacggg aagaggggggg | 5640 |
| ttgtgctgaa gggccaggaa ggcggccatt cgggcaattc gctcaacctc aggaacggag | 5700 |
| taggtctcgg tgtcggaagc gacgccagat ccgtcatcct cctttcgctc tccaaagtag | 5760 |
| atacctccga cgagctctcg gacaatgatg aagtcggtgc cctcaacgtt tcggatgggg | 5820 |
| gagagatcgg cgagcttggg cgacagcagc tggcagggtc gcaggttggc gtacaggttc | 5880 |
| aggtcctttc gcagcttgag gagaccctgc tcgggtcgca cgtcggttcg tccgtcggga | 5940 |
| gtggtccata cggtgttggc agcgcctccg acagcaccga gcataataga gtcagccttt | 6000 |
| cggcagatgt cgagagtagc gtcggtgatg ggctcgccct ccttctcaat ggcagctcct | 6060 |
| ccaatgagtc ggtcctcaaa cacaaactcg gtgccgagg cctcagcaac agacttgagc | 6120 |
| accttgacgg cctcggcaat cacctcgggg ccacagaagt cgccgccgag aagaacaatc | 6180 |

```
ttcttggagt cagtcttggt cttcttagtt tcgggttcca ttgtggatgt gtgtggttgt    6240
atgtgtgatg tggtgtgtgg agtgaaaatc tgtggctggc aaacgctctt gtatatatac    6300
gcacttttgc ccgtgctatg tggaagacta aacctccgaa gattgtgact caggtagtgc    6360
ggtatcggct agggacccaa accttgtcga tgccgatagc gctatcgaac gtaccccagc    6420
cggccgggag tatgtcggag gggacatacg agatcgtcaa gggtttgtgg ccaactggta    6480
aataaatgat gtcgactcag gcgacgacgg aattcctgca gcccatctgc agaattcagg    6540
agagaccggg ttggcggcgt atttgtgtcc caaaaaacag ccccaattgc cccaattgac    6600
cccaaattga cccagtagcg ggcccaaccc cggcgagagc ccccttcacc ccacatatca    6660
aacctccccc ggttcccaca cttgccgtta agggcgtagg gtactgcagt ctggaatcta    6720
cgcttgttca gactttgtac tagtttcttt gtctggccat ccgggtaacc catgccggac    6780
gcaaaataga ctactgaaaa ttttttttgct ttgtggttgg gactttagcc aagggtataa    6840
aagaccaccg tcccccgaatt acctttcctc ttcttttctc tctctccttg tcaactcaca    6900
cccgaaatcg ttaagcattt ccttctgagt ataagaatca ttcaccatgg atggtacgtc    6960
ctgtagaaac cccaacccgt gaaatcaaaa aactcgacgg cctgtgggca ttcagtctgg    7020
atcgcgaaaa ctgtggaatt gatcagcgtt ggtgggaaag cgcgttacaa gaaagccggg    7080
caattgctgt gccaggcagt tttaacgatc agttcgccga tgcagatatt cgtaattatg    7140
cgggcaacgt ctggtatcag cgcgaagtct ttataccgaa aggttgggca ggccagcgta    7200
tcgtgctgcg tttcgatgcg gtcactcatt acggcaaagt gtgggtcaat aatcaggaag    7260
tgatggagca tcagggcggc tatacgccat ttgaagccga tgtcacgccg tatgttattg    7320
ccgggaaaag tgtacgtatc accgtttgtg tgaacaacga actgaactgg cagactatcc    7380
cgccgggaat ggtgattacc gacgaaaacg gcaagaaaaa gcagtcttac ttccatgatt    7440
tctttaacta tgccgggatc catcgcagcg taatgctcta caccacgccg aacacctggg    7500
tggacgatat caccgtggtg acgcatgtcg cgcaagactg taaccacgcg tctgttgact    7560
ggcaggtggt ggccaatggt gatgtcagcg ttgaactgcg tgatgcggat caacaggtgg    7620
ttgcaactgg acaaggcact agcgggactt gcaagtggt gaatccgcac ctctggcaac    7680
cgggtgaagg ttatctctat gaactgtgcg tcacagccaa aagccagaca gagtgtgata    7740
tctacccgct tcgcgtcggc atccggtcag tggcagtgaa gggcgaacag ttcctgatta    7800
accacaaacc gttctacttt actggctttg gtcgtcatga agatgcggac ttacgtggca    7860
aaggattcga taacgtgctg atggtgcacg accacgcatt aatggactgg attggggcca    7920
actcctaccg tacctcgcat taccccttacg ctgaagagat gctcgactgg gcagatgaac    7980
atggcatcgt ggtgattgat gaaactgctg ctgtcggctt taacctctct ttaggcattg    8040
gtttcgaagc gggcaacaag ccgaaagaac tgtacagcga agaggcagtc aacgggaaa    8100
ctcagcaagc gcacttacag gcgattaaag agctgatagc gcgtgacaaa aaccacccaa    8160
gcgtggtgat gtggagtatt gccaacgaac cggatacccg tccgcaagtg cacgggaata    8220
tttcgccact ggcggaagca acgcgtaaac tcgacccgac gcgtccgatc acctgcgtca    8280
atgtaatgtt ctgcgacgct cacaccgata ccatcagcga tctctttgat gtgctgtgcc    8340
tgaaccgtta ttacggatgg tatgtccaaa gcggcgattt ggaaacggca gagaaggtac    8400
tggaaaaaga acttctggcc tggcaggaga aactgcatca gccgattatc atcaccgaat    8460
acggcgtgga tacgttagcc gggctgcact caatgtacac cgacatgtgg agtgaagagt    8520
atcagtgtgc atggctggat atgtatcacc gcgtctttga tcgcgtcagc gccgtcgtcg    8580
```

```
gtgaacaggt atggaatttc gccgattttg cgacctcgca aggcatattg cgcgttggcg    8640
gtaacaagaa agggatcttc actcgcgacc gcaaaccgaa gtcggcggct tttctgctgc    8700
aaaaacgctg gactggcatg aacttcggtg aaaaaccgca gcagggaggc aaacaatgat    8760
taattaacta gagcggccgc caccgcggcc cgagattccg gcctcttcgg ccgccaagcg    8820
acccgggtgg acgtctagag gtacctagca attaacagat agtttgccgg tgataattct    8880
cttaacctcc cacactcctt tgacataacg atttatgtaa cgaaactgaa atttgaccag    8940
atattgtgtc cgc                                                       8953
```

<210> SEQ ID NO 11
<211> LENGTH: 973
<212> TYPE: DNA
<213> ORGANISM: Yarrowia lipolytica
<220> FEATURE:
<221> NAME/KEY: misc_feature
<223> OTHER INFORMATION: Promoter FBAIN
<300> PUBLICATION INFORMATION:
<302> TITLE: FRUCTOSE-BISPHOSPHATE ALDOLASE REGULATORY SEQUENCES FOR
      GENE EXPRESSION IN OLEAGINOUS YEAST
<310> PATENT DOCUMENT NUMBER: U.S. Pat. 7,202,356
<311> PATENT FILING DATE: 2004-11-12
<312> PUBLICATION DATE: 2007-04-10
<313> RELEVANT RESIDUES: (1)..(973)

<400> SEQUENCE: 11

```
aaattgcccc ggagaagacg gccaggccgc ctagatgaca aattcaacaa ctcacagctg     60
actttctgcc attgccacta gggggggggcc ttttatatg gccaagccaa gctctccacg    120
tcggttgggc tgcacccaac aataaatggg tagggttgca ccaacaaagg gatgggatgg    180
ggggtagaag atacgaggat aacgggctc aatggcacaa ataagaacga atactgccat    240
taagactcgt gatccagcga ctgacaccat tgcatcatct aagggcctca aaactacctc    300
ggaactgctg cgctgatctg gacaccacag aggttccgag cactttaggt tgcaccaaat    360
gtcccaccag gtgcaggcag aaaacgctgg aacagcgtgt acagtttgtc ttaacaaaaa    420
gtgagggcgc tgaggtcgag cagggtggtg tgacttgtta tagcctttag agctgcgaaa    480
gcgcgtatgg atttggctca tcaggccaga ttgagggtct gtggacacat gtcatgttag    540
tgtacttcaa tcgcccctg gatatagccc cgacaatagg ccgtggcctc attttttgc     600 cttccgcaca tttccattgc tcggtaccca caccttgctt ctcctgcact tgccaacctt    660
aatactggtt tacattgacc aacatcttac aagcggggg cttgtctagg gtatatataa    720
acagtggctc tcccaatcgg ttgccagtct cttttttcct ttctttcccc acagattcga    780
aatctaaact acacatcaca caatgcctgt tactgacgtc cttaagcgaa agtccggtgt    840
catcgtcggc gacgatgtcc gagccgtgag tatccacgac aagatcagtg tcgagacgac    900
gcgttttgtg taatgacaca atccgaaagt cgctagcaac acacactctc tacacaaact    960
aacccagctc tcc                                                       973
```

<210> SEQ ID NO 12
<211> LENGTH: 1130
<212> TYPE: DNA
<213> ORGANISM: Yarrowia lipolytica
<220> FEATURE:
<221> NAME/KEY: misc_feature
<223> OTHER INFORMATION: GPAT promoter
<300> PUBLICATION INFORMATION:
<302> TITLE: GLYCEROL-3-PHOSPHATE O-ACYLTRANSFERASE PROMOTER FOR GENE
      EXPRESSION IN OLEAGINOUS YEAST
<310> PATENT DOCUMENT NUMBER: U.S. Pat. 7,264,949
<311> PATENT FILING DATE: 2005-09-13

<312> PUBLICATION DATE: 2007-09-04
<313> RELEVANT RESIDUES: (1)..(1130)

<400> SEQUENCE: 12

```
caacttttct tgtcgacctg agataccgag gttgcgcagg ggatcaactt ttgtgtctca      60
gagggaccca agtgcgtacg gagagtacag tacatactgt agctaacggt agcaggcgaa     120
ctactggtac atacctcccc cggaatatgt acaggcataa tgcgtatctg tgggacatgt     180
ggtcgttgcg ccattatgta agcagcgtgt actcctctga ctgtccatat ggtttgctcc     240
atctcaccct catcgttttc attgttcaca ggcggccaca aaaaaactgt cttctctcct     300
tctctcttcg ccttagtcta ctcggaccag ttttagttta gcttggcgcc actggataaa     360
tgagacctca ggccttgtga tgaggaggtc acttatgaag catgttagga ggtgcttgta     420
tggatagaga agcacccaaa ataataagaa taataataaa acaggggcg ttgtcatttc      480
atatcgtgtt ttcaccatca atacacctcc aaacaatgcc cttcatgtgg ccagccccaa     540
tattgtcctg tagttcaact ctatgcagct cgtatcttat tgagcaagta aaactctgtc     600
agccgatatt gcccgacccg cgacaagggt caacaaggtg gtgtaaggcc ttcgcagaag     660
tcaaaactgt gccaaacaaa catctagagt ctctttggtg tttctcgcat atatttaatc     720
ggctgtctta cgtatttggc ctcggtaccg gactaatttc ggatcatccc caatacgctt     780
tttcttcgca gctgtcaaca gtgtccatga tctatccacc taaatgggtc atatgaggcg     840
tataatttcg tggtgctgat aataattccc atatatttga cacaaaactt ccccccctag     900
acatacatct cacaatctca cttcttgtgc ttctgtcaca catctcctcc agctgacttc     960
aactcacacc tctgccccag ttggtctaca gcggtataag gtttctccgc atagaggtgc    1020
accactcctc ccgatacttg tttgtgtgac ttgtgggtca cgacatatat atctacacac    1080
attgcgccac cctttggttc ttccagcaca acaaaaacac gacacgctaa               1130
```

<210> SEQ ID NO 13
<211> LENGTH: 12649
<212> TYPE: DNA
<213> ORGANISM: Artificial Sequence
<220> FEATURE:
<223> OTHER INFORMATION: Plasmid pKUNF12T6E
<220> FEATURE:
<221> NAME/KEY: misc_feature
<222> LOCATION: (2507)..(2507)
<223> OTHER INFORMATION: n is a, c, g, or t
<220> FEATURE:
<221> NAME/KEY: misc_feature
<222> LOCATION: (2512)..(2515)
<223> OTHER INFORMATION: n is a, c, g, or t

<400> SEQUENCE: 13

```
taaccctcac taaagggaac aaaagctgga gctccaccgc ggacacaata tctggtcaaa      60
tttcagtttc gttacataaa tcgttatgtc aaaggagtgt gggaggttaa gagaattatc     120
accggcaaac tatctgttaa ttgctaggta cctctagacg tccacccggg tcgcttggcg     180
gccgaagagg ccggaatctc gggccgcggt ggcggccgct tagttggtct tggacttctt     240
gggcttcttc aggtaggact ggacaaagaa gttgccgaac agagcgagca gggtgatcat     300
gtacacgccg agcagctgga ccagagcctg agggtagtcg caggggaaga ggtagtcgta     360
cagggactgc accagcatag ccatgaactg gtcatctgc agagtggtga tgtagggctt      420
gatgggcttg acgaagccga agccctgaga ggaaaagaag tagtaggcgt acatgacggt     480
gtggacgaag gagttgagga tgacggagaa gtaggcgtcg ccaccaggag cgtacttggc     540
aatagcccac cagatggcga agatggtggc atggtggtac acgtgcagga aggagacctg     600
```

```
gttgaacttc ttgcacagga tcatgatagc ggtgtccagg aactcgtagg ccttggagac    660
gtagaacacg tagacgattc gggacatgcc ctgagcgtgg gactcgttgc ccttctccat    720
gtcgttgccg aagaccttgt agccacccag gatagcctgt cggatggtct cgacgcacat    780
gtagagggac agtccgaaga ggaacaggtt gtggagcagc ttgatggtct tcagctcgaa    840
gggcttctcc atctgcttca tgatgggaat gccgaagagc agcatggcca tgtagccgac    900
ctcgaaggcg agcatggtgg agacgtccat catgggcaga ccgtcggtca gagcgtaggg    960
cttagctccg tccatccact ggtcgacacc ggtctcgact cgtccgacca cgtcgtccca   1020
gacagaggag ttggccatgg tgaatgattc ttatactcag aaggaaatgc ttaacgattt   1080
cgggtgtgag ttgacaagga gagagagaaa agaagaggaa aggtaattcg ggacggtgg    1140
tcttttatac ccttggctaa agtcccaacc acaaagcaaa aaaattttca gtagtctatt   1200
ttgcgtccgg catgggttac ccggatggcc agacaaagaa actagtacaa agtctgaaca   1260
agcgtagatt ccagactgca gtaccctacg cccttaacgg caagtgtggg aaccggggga   1320
ggtttgatat gtggggtgaa gggggctctc gccggggttg ggcccgctac tgggtcaatt   1380
tggggtcaat tggggcaatt ggggctgttt tttgggacac aaatacgccg ccaacccggt   1440
ctctcctgaa ttctgcatcg atcgaggaag aggacaagcg gctgcttctt aagtttgtga   1500
catcagtatc caaggcacca ttgcaaggat tcaaggcttt gaacccgtca tttgccattc   1560
gtaacgctgg tagacaggtt gatcggttcc ctacggcctc cacctgtgtc aatcttctca   1620
agctgcctga ctatcaggac attgatcaac ttcggaagaa acttttgtat gccattcgat   1680
cacatgctgg tttcgatttg tcttagagga acgcatatac agtaatcata gagaataaac   1740
gatattcatt tattaaagta gatagttgag gtagaagttg taaagagtga taaatagcgg   1800
ccgcgcctac ttaagcaacg ggcttgataa cagcggggg ggtgcccacg ttgttgcggt    1860
tgcggaagaa cagaacaccc ttaccagcac cctcggcacc agcgctgggc tcaacccact   1920
ggcacatacg cgcactgcgg tacatggcgc ggatgaagcc acgaggacca tcctggacat   1980
cagcccggta gtgcttgccc atgatgggct taatggcctc ggtggcctcg tccgcgttgt   2040
agaaggggat gctgctgacg tagtggtgga ggacatgagt ctcgatgatg ccgtggagaa   2100
ggtggcggcc gatgaagccc atctcacggt caatggtagc agcggcacca cggacgaagt   2160
tccactcgtc gttggtgtag tggggaaggg tagggtcggt gtgctggagg aaggtgatgg   2220
caacgagcca gtggttaacc cagaggtagg gaacaaagta ccagatggcc atgttgtaga   2280
aaccgaactt ctgaacgagg aagtacagag cagtggccat cagaccgata ccaatatcgc   2340
tgaggacgat gagcttagcg tcactgttct cgtacagagg gctgcgggga tcgaagtggt   2400
taacaccacc gccgaggccg ttatgcttgc ccttgccgcg accctcacgc tggcgctcgt   2460
ggtagttgtg gccggtaaca ttggtgatga ggtagttggg ccagccacg annnnctcag    2520
taagatgagc gagctcgtgg gtcatctttc cgagacgagt agcctgctgc tcgcgggttc   2580
ggggaacgaa gaccatgtca cgctccatgt tgccagtggc cttgtggtgc tttcggtggg   2640
agatttgcca gctgaagtag gggacaagga gggaagagtg aagaacccag ccagtaatgt   2700
cgttgatgat gcgagaatcg gagaaagcac cgtgaccgca ctcatgggca ataacccaga   2760
gaccagtacc gaaaagaccc tgaagaacgg tgtacacggc ccacagacca gcgcgggcg    2820
gggtggaggg gatatattcg ggggtcacaa agttgtacca gatgctgaaa gtggtagtca   2880
ggaggacaat gtcgcggagg atataaccgt atcccttgag agcggagcgc ttgaagcagt   2940
gcttagggat ggcattgtag atgtccttga tggtaaagtc gggaacctcg aactggttgc   3000
```

```
cgtaggtgtc gagcatgaca ccatactcgg acttgggctt ggcgatatca acctcggaca   3060
tggacgagag cgatgtggaa gaggccgagt ggcggggaga gtctgaagga gagacggcgg   3120
cagactcaga atccgtcaca gtagttgagg tgacggtgcg tctaagcgca gggttctgct   3180
tgggcagagc cgaagtggac gccatggaga gctgggttag tttgtgtaga gagtgtgtgt   3240
tgctagcgac tttcggattg tgtcattaca caaaacgcgt cgtctcgaca ctgatcttgt   3300
cgtggatact cacggctcgg acatcgtcgc cgacgatgac accggacttt cgcttaagga   3360
cgtcagtaac aggcattgtg tgatgtgtag tttagatttc gaatctgtgg ggaaagaaag   3420 gaaaaagag actggcaacc gattgggaga gccactgttt atatataccc tagacaagcc   3480
ccccgcttgt aagatgttgg tcaatgtaaa ccagtattaa ggttggcaag tgcaggagaa   3540
gcaaggtgtg ggtaccgagc aatggaaatg tgcggaaggc aaaaaaatga ggccacggcc   3600
tattgtcggg gctatatcca gggggcgatt gaagtacact aacatgacat gtgtccacag   3660
accctcaatc tggcctgatg agccaaatcc atacgcgctt tcgcagctct aaaggctata   3720
acaagtcaca ccaccctgct cgacctcagc gccctcactt tttgttaaga caaactgtac   3780
acgctgttcc agcgttttct gcctgcacct ggtgggacat ttggtgcaac ctaaagtgct   3840
cggaacctct gtggtgtcca gatcagcgca gcagttccga ggtagttttg aggcccttag   3900
atgatgcaat ggtgtcagtc gctggatcac gagtcttaat ggcagtattc gttcttattt   3960
gtgccattga gccccgttat cctcgtatct tctacccccc atcccatccc tttgttggtg   4020
caaccctacc catttattgt ggggtgcagc ccaaccgacg tggagagctt ggcttggcca   4080
tataaaaagg ccccccccta gtggcaatgg cagaaagtca gctgtgagtt gttgaatttg   4140
tcatctaggc ggcctggccg tcttctccgg ggcaattgtt cctctatagt actgcgtaca   4200
ctgtttaaac agtgtacgca gatctgcgac gacggaattc ctgcagccca tctgcagaat   4260
tcaggagaga ccgggttggc ggcgtatttg tgtcccaaaa aacagcccca attgccccaa   4320
ttgaccccaa attgacccag tagcgggccc aaccccggcg agagccccct tcaccccaca   4380
tatcaaacct cccccggttc ccacacttgc cgttaagggc gtagggtact gcagtctgga   4440
atctacgctt gttcagactt tgtactagtt tctttgtctg gccatccggg taacccatgc   4500
cggacgcaaa atagactact gaaaattttt ttgctttgtg gttgggactt tagccaaggg   4560
tataaaagac caccgtcccc gaattacctt tcctcttctt ttctctctct ccttgtcaac   4620
tcacacccga aatcgttaag catttccttc tgagtataag aatcattcac catggctgcc   4680
gctccctctg tgcgaaccct tacccgagcc gaggttctga acgctgaggc tctgaacgag   4740
ggcaagaagg acgctgaggc tcccttcctg atgatcatcg acaacaaggt gtacgacgtc   4800
cgagagttcg tccctgacca tcctggaggc tccgtgattc tcacccacgt tggcaaggac   4860
ggcaccgacg tctttgacac ctttcatccc gaggctgctt gggagactct cgccaacttc   4920
tacgttggag acattgacga gtccgaccga gacatcaaga acgatgactt tgccgctgag   4980
gtccgaaagc tgcgaaccct gttccagtct ctcggctact acgactcctc taaggcctac   5040
tacgccttca aggtctcctt caacctctgc atctgggac tgtccaccgt cattgtggcc   5100 aagtgggtc agacctccac cctgccaac gtgctctctg ctgccctgct cggcctgttc   5160
tggcagcagt gcggatggct ggctcacgac tttctgcacc accaggtctt ccaggaccga   5220
ttctggggtg atctcttcgg agccttcctg ggaggtgtct gccagggctt ctcctcttcc   5280
tggtggaagg acaagcacaa cactcaccat gccgctccca acgtgcatgg cgaggatcct   5340
gacattgaca cccacccctct cctgacctgg tccgagcacg ctctggagat gttctccgac   5400
```

-continued

| | |
|---|---|
| gtccccgatg aggagctgac ccgaatgtgg tctcgattca tggtcctgaa ccagacctgg | 5460 |
| ttctacttcc ccattctctc cttcgctcga ctgtcttggt gcctccagtc cattctcttt | 5520 |
| gtgctgccca acggtcaggc tcacaagccc tccggagctc gagtgcccat ctccctggtc | 5580 |
| gagcagctgt ccctcgccat gcactggacc tggtacctcg ctaccatgtt cctgttcatc | 5640 |
| aaggatcctg tcaacatgct cgtgtacttc ctggtgtctc aggctgtgtg cggaaacctg | 5700 |
| ctcgccatcg tgttctccct caaccacaac ggtatgcctg tgatctccaa ggaggaggct | 5760 |
| gtcgacatgg atttctttac caagcagatc atcactggtc gagatgtcca tcctggactg | 5820 |
| ttcgccaact ggttcaccgg tggcctgaac taccagatcg agcatcacct gttcccttcc | 5880 |
| atgcctcgac acaacttctc caagatccag cctgccgtcg agaccctgtg caagaagtac | 5940 |
| aacgtccgat accacaccac tggtatgatc gagggaactg ccgaggtctt ctcccgactg | 6000 |
| aacgaggtct ccaaggccac ctccaagatg ggcaaggctc agtaagcggc cgcatgagaa | 6060 |
| gataaatata taaatacatt gagatattaa atgcgctaga ttagagagcc tcatactgct | 6120 |
| cggagagaag ccaagacgag tactcaaagg ggattacacc atccatatcc acagacacaa | 6180 |
| gctggggaaa ggttctatat acactttccg gaataccgta gtttccgatg ttatcaatgg | 6240 |
| gggcagccag gatttcaggc acttcggtgt ctcggggtga atggcgttc ttggcctcca | 6300 |
| tcaagtcgta ccatgtcttc atttgcctgt caaagtaaaa cagaagcaga tgaagaatga | 6360 |
| acttgaagtg aaggaattta aattgccccg gagaagacgg ccaggccgcc tagatgacaa | 6420 |
| attcaacaac tcacagctga ctttctgcca ttgccactag gggggggcct ttttatatgg | 6480 |
| ccaagccaag ctctccacgt cggttgggct gcacccaaca ataaatgggt agggttgcac | 6540 |
| caacaaaggg atgggatggg gggtagaaga tacgaggata acggggctca atggcacaaa | 6600 |
| taagaacgaa tactgccatt aagactcgtg atccagcgac tgacaccatt gcatcatcta | 6660 |
| agggcctcaa aactacctcg gaactgctgc gctgatctgg acaccacaga ggttccgagc | 6720 |
| actttaggtt gcaccaaatg tcccaccagg tgcaggcaga aaacgctgga acagcgtgta | 6780 |
| cagtttgtct taacaaaaag tgagggcgct gaggtcgagc agggtggtgt gacttgttat | 6840 |
| agcctttaga gctgcgaaag cgcgtatgga tttggctcat caggccagat tgagggtctg | 6900 |
| tggacacatg tcatgttagt gtacttcaat cgcccctgg atatagcccc gacaataggc | 6960 |
| cgtggcctca ttttttttgcc ttccgcacat ttccattgct cggtacccac accttgcttc | 7020 |
| tcctgcactt gccaacctta atactggttt acattgacca acatcttaca agcgggggc | 7080 |
| ttgtctaggg tatatataaa cagtggctct cccaatcggt tgccagtctc tttttttcctt | 7140 |
| tctttcccca cagattcgaa atctaaacta cacatcacac aatgcctgtt actgacgtcc | 7200 |
| ttaagcgaaa gtccggtgtc atcgtcggcg acgatgtccg agccgtgagt atccacgaca | 7260 |
| agatcagtgt cgagacgacg cgttttgtgt aatgacacaa tccgaaagtc gctagcaaca | 7320 |
| cacactctct acacaaacta acccagctct ccatggagtc cattgctccc ttcctgccct | 7380 |
| ccaagatgcc tcaggacctg ttcatggacc tcgccagcgc tatcggtgtc cgagctgctc | 7440 |
| cctacgtcga tcccctggag gctgcccctgg ttgcccaggc cgagaagtac attcccacca | 7500 |
| ttgtccatca cactcgaggc ttcctggttg ccgtggagtc tcccctggct cgagagctgc | 7560 |
| ctctgatgaa ccccttccac gtgctcctga tcgtgctcgc ctacctggtc accgtgtttg | 7620 |
| tgggtatgca gatcatgaag aactttgaac gattcgaggt caagaccttc tccctcctgc | 7680 |
| acaacttctg tctggtctcc atctccgcct acatgtgcgg tggcatcctg tacgaggctt | 7740 |
| atcaggccaa ctatggactg tttgagaacg ctgccgatca caccttcaag ggtctcccta | 7800 |

```
tggctaagat gatctggctc ttctacttct ccaagatcat ggagtttgtc gacaccatga    7860
tcatggtcct caagaagaac aaccgacaga tttcctttct gcacgtgtac caccactctt    7920
ccatcttcac catctggtgg ctggtcacct tcgttgctcc caacggtgaa gcctacttct    7980
ctgctgccct gaactccttc atccacgtca tcatgtacgg ctactacttt ctgtctgccc    8040
tgggcttcaa gcaggtgtcg ttcatcaagt tctacatcac tcgatcccag atgacccagt    8100
tctgcatgat gtctgtccag tcttcctggg acatgtacgc catgaaggtc cttggccgac    8160
ctggataccc cttcttcatc accgctctgc tctggttcta catgtggacc atgctcggtc    8220
tcttctacaa cttttaccga aagaacgcca agctcgccaa gcaggccaag gctgacgctg    8280
ccaaggagaa ggccagaaag ctccagtaag cggccgcaag tgtggatggg gaagtgagtg    8340
cccggttctg tgtgcacaat ggcaatcca agatggatgg attcaacaca gggatatagc    8400
gagctacgtg gtggtgcgag atatagcaa cggatattta tgtttgacac ttgagaatgt    8460
acgatacaag cactgtccaa gtacaatact aaacatactg tacatactca tactcgtacc    8520
cgggcaacgg tttcacttga gtgcagtggc tagtgctctt actcgtacag tgtgcaatac    8580
tgcgtatcat agtctttgat gtatatcgta ttcattcatg ttagttgcgt acgaagtcgt    8640
caatgatgtc gatatgggtt ttgatcatgc acacataagg tccgaccta tcggcaagct    8700 caatgagctc cttggtggtg gtaacatcca gagaagcaca caggttggtt ttcttggctg    8760
ccacgagctt gagcactcga gcggcaaagg cggacttgtg gacgttagct cgagcttcgt    8820
aggagggcat tttggtggtg aagaggagac tgaaataaat ttagtctgca gaacttttta    8880
tcggaacctt atctggggca gtgaagtata tgttatggta atagttacga gttagttgaa    8940
cttatagata gactggacta tacgctatc ggtccaaatt agaaagaacg tcaatggctc    9000
tctgggcgtc gcctttgccg acaaaaatgt gatcatgatg aaagccagca atgacgttgc    9060
agctgatatt gttgtcggcc aaccgcgccg aaaacgcagc tgtcagaccc acagcctcca    9120
acgaagaatg tatcgtcaaa gtgatccaag cacactcata gttggagtcg tactccaaag    9180
gcggcaatga cgagtcagac agatactcgt cgaccttttc cttgggaacc accaccgtca    9240
gcccttctga ctcacgtatt gtagccaccg acacaggcaa cagtccgtgg atagcagaat    9300
atgtcttgtc ggtccatttc tcaccaactt taggcgtcaa gtgaatgttg cagaagaagt    9360
atgtgccttc attgagaatc ggtgttgctg atttcaataa agtcttgaga tcagtttggc    9420
gcgccagctg cattaatgaa tcggccaacg cgcggggaga ggcggtttgc gtattgggcg    9480
ctcttccgct tcctcgctca ctgactcgct gcgctcggtc gttcggctgc ggcgagcggt    9540
atcagctcac tcaaaggcgg taatacggtt atccacagaa tcaggggata acgcaggaaa    9600
gaacatgtga gcaaaaggcc agcaaaaggc caggaaccgt aaaaaggccg cgttgctggc    9660 gttttccat aggctccgcc cccctgacga gcatcacaaa aatcgacgct caagtcagag    9720
gtggcgaaac ccgacaggac tataaagata ccaggcgttt ccccctggaa gctccctcgt    9780
gcgctctcct gttccgaccc tgccgcttac cggatacctg tccgcctttc tcccttcggg    9840
aagcgtggcg ctttctcata gctcacgctg taggtatctc agttcggtgt aggtcgttcg    9900
ctccaagctg ggctgtgtgc acgaaccccc cgttcagccc gaccgctgcg ccttatccgg    9960
taactatcgt cttgagtcca acccggtaag acacgactta tcgccactgg cagcagccac    10020
tggtaacagg attagcagag cgaggtatgt aggcggtgct acagagttct tgaagtggtg    10080
gcctaactac ggctacacta agaacagt atttggtatc tgcgctctgc tgaagccagt    10140
taccttcgga aaaagagttg gtagctcttg atccggcaaa caaaccaccg ctggtagcgg    10200
```

```
tggttttttt gtttgcaagc agcagattac gcgcagaaaa aaaggatctc aagaagatcc   10260
tttgatcttt tctacggggt ctgacgctca gtggaacgaa aactcacgtt aagggatttt   10320
ggtcatgaga ttatcaaaaa ggatcttcac ctagatcctt ttaaattaaa aatgaagttt   10380
taaatcaatc taaagtatat atgagtaaac ttggtctgac agttaccaat gcttaatcag   10440
tgaggcacct atctcagcga tctgtctatt tcgttcatcc atagttgcct gactccccgt   10500
cgtgtagata actacgatac gggagggctt accatctggc cccagtgctg caatgatacc   10560
gcgagaccca cgctcaccgg ctccagattt atcagcaata aaccagccag ccggaagggc   10620
cgagcgcaga agtggtcctg caactttatc cgcctccatc cagtctatta attgttgccg   10680
ggaagctaga gtaagtagtt cgccagttaa tagtttgcgc aacgttgttg ccattgctac   10740
aggcatcgtg gtgtcacgct cgtcgtttgg tatggcttca ttcagctccg gttcccaacg   10800
atcaaggcga gttacatgat cccccatgtt gtgcaaaaaa gcggttagct ccttcggtcc   10860
tccgatcgtt gtcagaagta agttggccgc agtgttatca ctcatggtta tggcagcact   10920
gcataattct cttactgtca tgccatccgt aagatgcttt tctgtgactg gtgagtactc   10980
aaccaagtca ttctgagaat agtgtatgcg gcgaccgagt tgctcttgcc cggcgtcaat   11040
acgggataat accgcgccac atagcagaac tttaaaagtg ctcatcattg gaaaacgttc   11100
ttcggggcga aaactctcaa ggatcttacc gctgttgaga tccagttcga tgtaacccac   11160
tcgtgcaccc aactgatctt cagcatcttt tactttcacc agcgtttctg ggtgagcaaa   11220
aacaggaagg caaaatgccg caaaaaaggg aataagggcg acacggaaat gttgaatact   11280
catactcttc ctttttcaat attattgaag catttatcag ggttattgtc tcatgagcgg   11340
atacatattt gaatgtattt agaaaaataa acaaataggg gttccgcgca catttccccg   11400
aaaagtgcca cctgatgcgg tgtgaaatac cgcacagatg cgtaaggaga aaataccgca   11460
tcaggaaatt gtaagcgtta atattttgtt aaaattcgcg ttaaattttt gttaaatcag   11520 ctcattttt aaccaatagg ccgaaatcgg caaaatccct tataaatcaa agaatagac    11580 cgagatagggg ttgagtgttg ttccagtttg gaacaagagt ccactattaa agaacgtgga   11640
ctccaacgtc aaagggcgaa aaaccgtcta tcagggcgat ggcccactac gtgaaccatc   11700
accctaatca agttttttgg ggtcgaggtg ccgtaaagca ctaaatcgga acctaaagg    11760 gagcccccga tttagagctt gacggggaaa gccggcgaac gtggcgagaa aggaagggaa   11820
gaaagcgaaa ggagcgggcg ctagggcgct ggcaagtgta gcggtcacgc tgcgcgtaac   11880
caccacaccc gccgcgctta atgcgccgct acagggcgcg tccattcgcc attcaggctg   11940
cgcaactgtt gggaagggcg atcggtgcgg gcctcttcgc tattacgcca gctggcgaaa   12000
gggggatgtg ctgcaaggcg attaagttgg gtaacgccag ggttttccca gtcacgacgt   12060
tgtaaaacga cggccagtga attgtaatac gactcactat agggcgaatt gggcccgacg   12120
tcgcatgcag tggtggtatt gtgactgggg atgtagttga gaataagtca tacacaagtc   12180
agctttcttc gagcctcata taagtataag tagttcaacg tattagcact gtacccagca   12240
tctccgtatc gagaaacaca acaacatgcc ccattggaca gatcatgcgg atacacaggt   12300
tgtgcagtat catacatact cgatcagaca ggtcgtctga ccatcataca agctgaacaa   12360
gcgctccata cttgcacgct ctctatatac acagttaaat tacatatcca tagtctaacc   12420
tctaacagtt aatcttctgg taagcctccc agccagcctt ctggtatcgc ttggcctcct   12480
caataggatc tcggttctgg ccgtacagac ctcggccgac aattatgata tccgttccgg   12540
tagacatgac atcctcaaca gttcggtact gctgtccgag agcgtctccc ttgtcgtcaa   12600
```

```
gacccacccc gggggtcaga ataagccagt cctcagagtc gcccttaat           12649
```

<210> SEQ ID NO 14
<211> LENGTH: 957
<212> TYPE: DNA
<213> ORGANISM: Mortierella alpina
<220> FEATURE:
<221> NAME/KEY: CDS
<222> LOCATION: (1)..(957)
<223> OTHER INFORMATION: synthetic elongase 1 (codon-optimized),
      derived from GenBank Accession No. AX464731

<400> SEQUENCE: 14

```
atg gag tcc att gct ccc ttc ctg ccc tcc aag atg cct cag gac ctg         48
Met Glu Ser Ile Ala Pro Phe Leu Pro Ser Lys Met Pro Gln Asp Leu
1               5                   10                  15 ttc atg gac ctc gcc agc gct atc ggt gtc cga gct gct ccc tac gtc         96
Phe Met Asp Leu Ala Ser Ala Ile Gly Val Arg Ala Ala Pro Tyr Val
            20                  25                  30 gat ccc ctg gag gct gcc ctg gtt gcc cag gcc gag aag tac att ccc        144
Asp Pro Leu Glu Ala Ala Leu Val Ala Gln Ala Glu Lys Tyr Ile Pro
        35                  40                  45 acc att gtc cat cac act cga ggc ttc ctg gtt gcc gtg gag tct ccc        192
Thr Ile Val His His Thr Arg Gly Phe Leu Val Ala Val Glu Ser Pro
    50                  55                  60 ctg gct cga gag ctg cct ctg atg aac ccc ttc cac gtg ctc ctg atc        240
Leu Ala Arg Glu Leu Pro Leu Met Asn Pro Phe His Val Leu Leu Ile
65                  70                  75                  80 gtg ctc gcc tac ctg gtc acc gtg ttt gtg ggt atg cag atc atg aag        288
Val Leu Ala Tyr Leu Val Thr Val Phe Val Gly Met Gln Ile Met Lys
                85                  90                  95 aac ttt gaa cga ttc gag gtc aag acc ttc tcc ctc ctg cac aac ttc        336
Asn Phe Glu Arg Phe Glu Val Lys Thr Phe Ser Leu Leu His Asn Phe
            100                 105                 110 tgt ctg gtc tcc atc tcc gcc tac atg tgc ggt ggc atc ctg tac gag        384
Cys Leu Val Ser Ile Ser Ala Tyr Met Cys Gly Gly Ile Leu Tyr Glu
        115                 120                 125 gct tat cag gcc aac tat gga ctg ttt gag aac gct gcc gat cac acc        432
Ala Tyr Gln Ala Asn Tyr Gly Leu Phe Glu Asn Ala Ala Asp His Thr
    130                 135                 140 ttc aag ggt ctc cct atg gct aag atg atc tgg ctc ttc tac ttc tcc        480
Phe Lys Gly Leu Pro Met Ala Lys Met Ile Trp Leu Phe Tyr Phe Ser
145                 150                 155                 160 aag atc atg gag ttt gtc gac acc atg atc atg gtc ctc aag aag aac        528
Lys Ile Met Glu Phe Val Asp Thr Met Ile Met Val Leu Lys Lys Asn
                165                 170                 175 aac cga cag att tcc ttt ctg cac gtg tac cac cac tct tcc atc ttc        576
Asn Arg Gln Ile Ser Phe Leu His Val Tyr His His Ser Ser Ile Phe
            180                 185                 190 acc atc tgg tgg ctg gtc acc ttc gtt gct ccc aac ggt gaa gcc tac        624
Thr Ile Trp Trp Leu Val Thr Phe Val Ala Pro Asn Gly Glu Ala Tyr
        195                 200                 205 ttc tct gct gcc ctg aac tcc ttc atc cac gtc atc atg tac ggc tac        672
Phe Ser Ala Ala Leu Asn Ser Phe Ile His Val Ile Met Tyr Gly Tyr
    210                 215                 220 tac ttt ctg tct gcc ctg ggc ttc aag cag gtg tcg ttc atc aag ttc        720
Tyr Phe Leu Ser Ala Leu Gly Phe Lys Gln Val Ser Phe Ile Lys Phe
225                 230                 235                 240 tac atc act cga tcc cag atg acc cag ttc tgc atg atg tct gtc cag        768
Tyr Ile Thr Arg Ser Gln Met Thr Gln Phe Cys Met Met Ser Val Gln
                245                 250                 255
```

```
tct tcc tgg gac atg tac gcc atg aag gtc ctt ggc cga cct gga tac    816
Ser Ser Trp Asp Met Tyr Ala Met Lys Val Leu Gly Arg Pro Gly Tyr
        260                 265                 270 ccc ttc ttc atc acc gct ctg ctc tgg ttc tac atg tgg acc atg ctc    864
Pro Phe Phe Ile Thr Ala Leu Leu Trp Phe Tyr Met Trp Thr Met Leu
        275                 280                 285 ggt ctc ttc tac aac ttt tac cga aag aac gcc aag ctc gcc aag cag    912
Gly Leu Phe Tyr Asn Phe Tyr Arg Lys Asn Ala Lys Leu Ala Lys Gln
        290                 295                 300 gcc aag gct gac gct gcc aag gag aag gcc aga aag ctc cag taa        957
Ala Lys Ala Asp Ala Ala Lys Glu Lys Ala Arg Lys Leu Gln
305                 310                 315

<210> SEQ ID NO 15
<211> LENGTH: 318
<212> TYPE: PRT
<213> ORGANISM: Mortierella alpina

<400> SEQUENCE: 15

Met Glu Ser Ile Ala Pro Phe Leu Pro Ser Lys Met Pro Gln Asp Leu
1               5                   10                  15

Phe Met Asp Leu Ala Ser Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Glu Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
    290                 295                 300
```

```
                                Ala Lys Ala Asp Ala Ala Lys Glu Lys Ala Arg Lys Leu Gln
                                305                 310                 315

<210> SEQ ID NO 16
<211> LENGTH: 1374
<212> TYPE: DNA
<213> ORGANISM: Mortierella alpina
<220> FEATURE:
<221> NAME/KEY: CDS
<222> LOCATION: (1)..(1374)
<223> OTHER INFORMATION: synthetic delta-6 desaturase (codon-optimized),
      derived from GenBank Accession No. AF465281

<400> SEQUENCE: 16 atg gct gcc gct ccc tct gtg cga acc ttt acc cga gcc gag gtt ctg        48
Met Ala Ala Ala Pro Ser Val Arg Thr Phe Thr Arg Ala Glu Val Leu
1               5                   10                  15 aac gct gag gct ctg aac gag ggc aag aag gac gct gag gct ccc ttc        96
Asn Ala Glu Ala Leu Asn Glu Gly Lys Lys Asp Ala Glu Ala Pro Phe
            20                  25                  30 ctg atg atc atc gac aac aag gtg tac gac gtc cga gag ttc gtc cct       144
Leu Met Ile Ile Asp Asn Lys Val Tyr Asp Val Arg Glu Phe Val Pro
        35                  40                  45 gac cat cct gga ggc tcc gtg att ctc acc cac gtt ggc aag gac ggc       192
Asp His Pro Gly Gly Ser Val Ile Leu Thr His Val Gly Lys Asp Gly
    50                  55                  60 acc gac gtc ttt gac acc ttt cat ccc gag gct gct tgg gag act ctc       240
Thr Asp Val Phe Asp Thr Phe His Pro Glu Ala Ala Trp Glu Thr Leu
65                  70                  75                  80 gcc aac ttc tac gtt gga gac att gac gag tcc gac cga gac atc aag       288
Ala Asn Phe Tyr Val Gly Asp Ile Asp Glu Ser Asp Arg Asp Ile Lys
                85                  90                  95 aac gat gac ttt gcc gct gag gtc cga aag ctg cga acc ctg ttc cag       336
Asn Asp Asp Phe Ala Ala Glu Val Arg Lys Leu Arg Thr Leu Phe Gln
            100                 105                 110 tct ctc ggc tac tac gac tcc tct aag gcc tac tac gcc ttc aag gtc       384
Ser Leu Gly Tyr Tyr Asp Ser Ser Lys Ala Tyr Tyr Ala Phe Lys Val
        115                 120                 125 tcc ttc aac ctc tgc atc tgg gga ctg tcc acc gtc att gtg gcc aag       432
Ser Phe Asn Leu Cys Ile Trp Gly Leu Ser Thr Val Ile Val Ala Lys
    130                 135                 140 tgg ggt cag acc tcc acc ctc gcc aac gtg ctc tct gct gcc ctg ctc       480
Trp Gly Gln Thr Ser Thr Leu Ala Asn Val Leu Ser Ala Ala Leu Leu
145                 150                 155                 160 ggc ctg ttc tgg cag cag tgc gga tgg ctg gct cac gac ttt ctg cac       528
Gly Leu Phe Trp Gln Gln Cys Gly Trp Leu Ala His Asp Phe Leu His
                165                 170                 175 cac cag gtc ttc cag gac cga ttc tgg ggt gat ctc ttc gga gcc ttc       576
His Gln Val Phe Gln Asp Arg Phe Trp Gly Asp Leu Phe Gly Ala Phe
            180                 185                 190 ctg gga ggt gtc tgc cag ggc ttc tcc tct tcc tgg tgg aag gac aag       624
Leu Gly Gly Val Cys Gln Gly Phe Ser Ser Ser Trp Trp Lys Asp Lys
        195                 200                 205 cac aac act cac cat gcc gct ccc aac gtg cat ggc gag gat cct gac       672
His Asn Thr His His Ala Ala Pro Asn Val His Gly Glu Asp Pro Asp
    210                 215                 220 att gac acc cac cct ctc ctg acc tgg tcc gag cac gct ctg gag atg       720
Ile Asp Thr His Pro Leu Leu Thr Trp Ser Glu His Ala Leu Glu Met
225                 230                 235                 240 ttc tcc gac gtc ccc gat gag gag ctg acc cga atg tgg tct cga ttc       768
Phe Ser Asp Val Pro Asp Glu Glu Leu Thr Arg Met Trp Ser Arg Phe
                245                 250                 255
```

```
atg gtc ctg aac cag acc tgg ttc tac ttc ccc att ctc tcc ttc gct        816
Met Val Leu Asn Gln Thr Trp Phe Tyr Phe Pro Ile Leu Ser Phe Ala
        260                 265                 270 cga ctg tct tgg tgc ctc cag tcc att ctc ttt gtg ctg ccc aac ggt        864
Arg Leu Ser Trp Cys Leu Gln Ser Ile Leu Phe Val Leu Pro Asn Gly
        275                 280                 285 cag gct cac aag ccc tcc gga gct cga gtg ccc atc tcc ctg gtc gag        912
Gln Ala His Lys Pro Ser Gly Ala Arg Val Pro Ile Ser Leu Val Glu
    290                 295                 300 cag ctg tcc ctc gcc atg cac tgg acc tgg tac ctc gct acc atg ttc        960
Gln Leu Ser Leu Ala Met His Trp Thr Trp Tyr Leu Ala Thr Met Phe
305                 310                 315                 320 ctg ttc atc aag gat cct gtc aac atg ctc gtg tac ttc ctg gtg tct       1008
Leu Phe Ile Lys Asp Pro Val Asn Met Leu Val Tyr Phe Leu Val Ser
                325                 330                 335 cag gct gtg tgc gga aac ctg ctc gcc atc gtg ttc tcc ctc aac cac       1056
Gln Ala Val Cys Gly Asn Leu Leu Ala Ile Val Phe Ser Leu Asn His
            340                 345                 350 aac ggt atg cct gtg atc tcc aag gag gag gct gtc gac atg gat ttc       1104
Asn Gly Met Pro Val Ile Ser Lys Glu Glu Ala Val Asp Met Asp Phe
        355                 360                 365 ttt acc aag cag atc atc act ggt cga gat gtc cat cct gga ctg ttc       1152
Phe Thr Lys Gln Ile Ile Thr Gly Arg Asp Val His Pro Gly Leu Phe
370                 375                 380 gcc aac tgg ttc acc ggt ggc ctg aac tac cag atc gag cat cac ctg       1200
Ala Asn Trp Phe Thr Gly Gly Leu Asn Tyr Gln Ile Glu His His Leu
385                 390                 395                 400 ttc cct tcc atg cct cga cac aac ttc tcc aag atc cag cct gcc gtc       1248
Phe Pro Ser Met Pro Arg His Asn Phe Ser Lys Ile Gln Pro Ala Val
                405                 410                 415 gag acc ctg tgc aag aag tac aac gtc cga tac cac acc act ggt atg       1296
Glu Thr Leu Cys Lys Lys Tyr Asn Val Arg Tyr His Thr Thr Gly Met
            420                 425                 430 atc gag gga act gcc gag gtc ttc tcc cga ctg aac gag gtc tcc aag       1344
Ile Glu Gly Thr Ala Glu Val Phe Ser Arg Leu Asn Glu Val Ser Lys
        435                 440                 445 gcc acc tcc aag atg ggc aag gct cag taa                               1374
Ala Thr Ser Lys Met Gly Lys Ala Gln
450                 455

<210> SEQ ID NO 17
<211> LENGTH: 457
<212> TYPE: PRT
<213> ORGANISM: Mortierella alpina

<400> SEQUENCE: 17

Met Ala Ala Ala Pro Ser Val Arg Thr Phe Thr Arg Ala Glu Val Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Asp Ile Lys
                85                  90                  95

Asn Asp Asp Phe Ala Ala Glu Val Arg Lys Leu Arg Thr Leu Phe Gln
```

```
                     100                 105                 110
Ser Leu Gly Tyr Tyr Asp Ser Ser Lys Ala Tyr Ala Phe Lys Val
            115                 120                 125

Ser Phe Asn Leu Cys Ile Trp Gly Leu Ser Thr Val Ile Val Ala Lys
130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
                180                 185                 190

Leu Gly Gly Val Cys Gln Gly Phe Ser Ser Trp Trp Lys Asp Lys
                195                 200                 205

His Asn Thr His His Ala Ala Pro Asn Val His Gly Glu Asp Pro Asp
                210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
                260                 265                 270

Arg Leu Ser Trp Cys Leu Gln Ser Ile Leu Phe Val Leu Pro Asn Gly
                275                 280                 285

Gln Ala His Lys Pro Ser Gly Ala Arg Val Pro Ile Ser Leu Val Glu
                290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
                340                 345                 350

Asn Gly Met Pro Val Ile Ser Lys Glu Glu Ala Val Asp Met Asp Phe
                355                 360                 365

Phe Thr Lys Gln Ile Ile Thr Gly Arg Asp Val His Pro Gly Leu Phe
370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
                420                 425                 430

Ile Glu Gly Thr Ala Glu Val Phe Ser Arg Leu Asn Glu Val Ser Lys
                435                 440                 445

Ala Thr Ser Lys Met Gly Lys Ala Gln
                450                 455

<210> SEQ ID NO 18

<400> SEQUENCE: 18

000

<210> SEQ ID NO 19
<211> LENGTH: 1434
<212> TYPE: DNA
<213> ORGANISM: Fusarium monoliforme
```

```
<220> FEATURE:
<221> NAME/KEY: CDS
<222> LOCATION: (1)..(1434)
<223> OTHER INFORMATION: delta-12 desaturase
<300> PUBLICATION INFORMATION:
<302> TITLE: DELTA-12 DESATURASES SUITABLE FOR ALTERING LEVELS OF
      POLYUNSATURATED FATTY ACIDS IN OLEAGINOUS YEAST
<310> PATENT DOCUMENT NUMBER: U.S. Pat. 7,504,259
<311> PATENT FILING DATE: 2004-11-10
<312> PUBLICATION DATE: 2009-03-17
<313> RELEVANT RESIDUES: (1)..(1434)

<400> SEQUENCE: 19 atg gcg tcc act tcg gct ctg ccc aag cag aac cct gcg ctt aga cgc      48
Met Ala Ser Thr Ser Ala Leu Pro Lys Gln Asn Pro Ala Leu Arg Arg
1               5                  10                  15 acc gtc acc tca act act gtg acg gat tct gag tct gcc gcc gtc tct      96
Thr Val Thr Ser Thr Thr Val Thr Asp Ser Glu Ser Ala Ala Val Ser
            20                  25                  30 cct tca gac tct ccc cgc cac tcg gcc tct tcc aca tcg ctc tcg tcc     144
Pro Ser Asp Ser Pro Arg His Ser Ala Ser Ser Thr Ser Leu Ser Ser
        35                  40                  45 atg tcc gag gtt gat atc gcc aag ccc aag tcc gag tat ggt gtc atg     192
Met Ser Glu Val Asp Ile Ala Lys Pro Lys Ser Glu Tyr Gly Val Met
50                  55                  60 ctc gac acc tac ggc aac cag ttc gag gtt ccc gac ttt acc atc aag     240
Leu Asp Thr Tyr Gly Asn Gln Phe Glu Val Pro Asp Phe Thr Ile Lys
65                  70                  75                  80 gac atc tac aat gcc atc cct aag cac tgc ttc aag cgc tcc gct ctc     288
Asp Ile Tyr Asn Ala Ile Pro Lys His Cys Phe Lys Arg Ser Ala Leu
                85                  90                  95 aag gga tac ggt tat atc ctc cgc gac att gtc ctc ctg act acc act     336
Lys Gly Tyr Gly Tyr Ile Leu Arg Asp Ile Val Leu Leu Thr Thr Thr
            100                 105                 110 ttc agc atc tgg tac aac ttt gtg acc ccc gaa tat atc ccc tcc acc     384
Phe Ser Ile Trp Tyr Asn Phe Val Thr Pro Glu Tyr Ile Pro Ser Thr
        115                 120                 125 ccc gcc cgc gct ggt ctg tgg gcc gtg tac acc gtt ctt cag ggt ctt     432
Pro Ala Arg Ala Gly Leu Trp Ala Val Tyr Thr Val Leu Gln Gly Leu
    130                 135                 140 ttc ggt act ggt ctc tgg gtt att gcc cat gag tgc ggt cac ggt gct     480
Phe Gly Thr Gly Leu Trp Val Ile Ala His Glu Cys Gly His Gly Ala
145                 150                 155                 160 ttc tcc gat tct cgc atc atc aac gac att act ggc tgg gtt ctt cac     528
Phe Ser Asp Ser Arg Ile Ile Asn Asp Ile Thr Gly Trp Val Leu His
                165                 170                 175 tct tcc ctc ctt gtc ccc tac ttc agc tgg caa atc tcc cac cga aag     576
Ser Ser Leu Leu Val Pro Tyr Phe Ser Trp Gln Ile Ser His Arg Lys
            180                 185                 190 cac cac aag gcc act ggc aac atg gag cgt gac atg gtc ttc gtt ccc     624
His His Lys Ala Thr Gly Asn Met Glu Arg Asp Met Val Phe Val Pro
        195                 200                 205 cga acc cgc gag cag cag gct act cgt ctc gga aag atg acc cac gag     672
Arg Thr Arg Glu Gln Gln Ala Thr Arg Leu Gly Lys Met Thr His Glu
    210                 215                 220 ctc gct cat ctt act gag gag acc ccc gct ttc act ctt ctc atg ctc     720
Leu Ala His Leu Thr Glu Glu Thr Pro Ala Phe Thr Leu Leu Met Leu
225                 230                 235                 240 gtc ctt cag cag ctc gtt ggc tgg ccc aac tac ctc atc acc aat gtt     768
Val Leu Gln Gln Leu Val Gly Trp Pro Asn Tyr Leu Ile Thr Asn Val
                245                 250                 255 acc ggc cac aac tac cac gag cgc cag cgt gag ggt cgc ggc aag ggc     816
Thr Gly His Asn Tyr His Glu Arg Gln Arg Glu Gly Arg Gly Lys Gly
```

```
                        260                 265                 270
aag cat aac ggc ctc ggc ggt ggt gtt aac cac ttc gat ccc cgc agc        864
Lys His Asn Gly Leu Gly Gly Gly Val Asn His Phe Asp Pro Arg Ser
            275                 280                 285 cct ctg tac gag aac agt gac gct aag ctc atc gtc ctc agc gat att        912
Pro Leu Tyr Glu Asn Ser Asp Ala Lys Leu Ile Val Leu Ser Asp Ile
290                 295                 300 ggt atc ggt ctg atg gcc act gct ctg tac ttc ctc gtt cag aag ttc        960
Gly Ile Gly Leu Met Ala Thr Ala Leu Tyr Phe Leu Val Gln Lys Phe
305                 310                 315                 320 ggt ttc tac aac atg gcc atc tgg tac ttt gtt ccc tac ctc tgg gtt       1008
Gly Phe Tyr Asn Met Ala Ile Trp Tyr Phe Val Pro Tyr Leu Trp Val
            325                 330                 335 aac cac tgg ctc gtt gcc atc acc ttc ctc cag cac acc gac cct acc       1056
Asn His Trp Leu Val Ala Ile Thr Phe Leu Gln His Thr Asp Pro Thr
            340                 345                 350 ctt ccc cac tac acc aac gac gag tgg aac ttc gtc cgt ggt gcc gct       1104
Leu Pro His Tyr Thr Asn Asp Glu Trp Asn Phe Val Arg Gly Ala Ala
            355                 360                 365 gct acc att gac cgt gag atg ggc ttc atc ggc cgc cac ctt ctc cac       1152
Ala Thr Ile Asp Arg Glu Met Gly Phe Ile Gly Arg His Leu Leu His
370                 375                 380 ggc atc atc gag act cat gtc ctc cac cac tac gtc agc agc atc ccc       1200
Gly Ile Ile Glu Thr His Val Leu His His Tyr Val Ser Ser Ile Pro
385                 390                 395                 400 ttc tac aac gcg gac gag gcc acc gag gcc att aag ccc atc atg ggc       1248
Phe Tyr Asn Ala Asp Glu Ala Thr Glu Ala Ile Lys Pro Ile Met Gly
                405                 410                 415 aag cac tac cgg gct gat gtc cag gat ggt cct cgt ggc ttc atc cgc       1296
Lys His Tyr Arg Ala Asp Val Gln Asp Gly Pro Arg Gly Phe Ile Arg
            420                 425                 430 gcc atg tac cgc agt gcg cgt atg tgc cag tgg gtt gag ccc agc gct       1344
Ala Met Tyr Arg Ser Ala Arg Met Cys Gln Trp Val Glu Pro Ser Ala
            435                 440                 445 ggt gcc gag ggt gct ggt aag ggt gtt ctg ttc ttc cgc aac cgc aac       1392
Gly Ala Glu Gly Ala Gly Lys Gly Val Leu Phe Phe Arg Asn Arg Asn
450                 455                 460 aac gtg ggc acc ccc ccc gct gtt atc aag ccc gtt gct taa              1434
Asn Val Gly Thr Pro Pro Ala Val Ile Lys Pro Val Ala
465                 470                 475

<210> SEQ ID NO 20
<211> LENGTH: 477
<212> TYPE: PRT
<213> ORGANISM: Fusarium moniliforme

<400> SEQUENCE: 20

Met Ala Ser Thr Ser Ala Leu Pro Lys Gln Asn Pro Ala Leu Arg Arg
1               5                   10                  15

Thr Val Thr Ser Thr Val Thr Asp Ser Glu Ser Ala Ala Val Ser
            20                  25                  30

Pro Ser Asp Ser Pro Arg His Ser Ala Ser Thr Ser Leu Ser Ser
        35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95
```

Lys Gly Tyr Gly Tyr Ile Leu Arg Asp Ile Val Leu Leu Thr Thr Thr
            100                 105                 110

Phe Ser Ile Trp Tyr Asn Phe Val Thr Pro Glu Tyr Ile Pro Ser Thr
        115                 120                 125

Pro Ala Arg Ala Gly Leu Trp Ala Val Tyr Thr Val Leu Gln Gly Leu
    130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
        195                 200                 205

Arg Thr Arg Glu Gln Gln Ala Thr Arg Leu Gly Lys Met Thr His Glu
    210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Val Asn His Phe Asp Pro Arg Ser
        275                 280                 285

Pro Leu Tyr Glu Asn Ser Asp Ala Lys Leu Ile Val Leu Ser Asp Ile
    290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
            340                 345                 350

Leu Pro His Tyr Thr Asn Asp Glu Trp Asn Phe Val Arg Gly Ala Ala
        355                 360                 365

Ala Thr Ile Asp Arg Glu Met Gly Phe Ile Gly Arg His Leu Leu His
    370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
                405                 410                 415

Lys His Tyr Arg Ala Asp Val Gln Asp Gly Pro Arg Gly Phe Ile Arg
            420                 425                 430

Ala Met Tyr Arg Ser Ala Arg Met Cys Gln Trp Val Glu Pro Ser Ala
        435                 440                 445

Gly Ala Glu Gly Ala Gly Lys Gly Val Leu Phe Phe Arg Asn Arg Asn
    450                 455                 460

Asn Val Gly Thr Pro Pro Ala Val Ile Lys Pro Val Ala
465                 470                 475

<210> SEQ ID NO 21
<211> LENGTH: 819
<212> TYPE: DNA
<213> ORGANISM: Thraustochytrium aureum
<220> FEATURE:
<221> NAME/KEY: CDS
<222> LOCATION: (1)..(819)

<223> OTHER INFORMATION: synthetic elongase (codon-optimized)

<400> SEQUENCE: 21

```
atg gcc aac tcc tct gtc tgg gac gac gtg gtc gga cga gtc gag acc        48
Met Ala Asn Ser Ser Val Trp Asp Asp Val Val Gly Arg Val Glu Thr
1               5                   10                  15 ggt gtc gac cag tgg atg gac gga gct aag ccc tac gct ctg acc gac        96
Gly Val Asp Gln Trp Met Asp Gly Ala Lys Pro Tyr Ala Leu Thr Asp
            20                  25                  30 ggt ctg ccc atg atg gac gtc tcc acc atg ctc gcc ttc gag gtc ggc       144
Gly Leu Pro Met Met Asp Val Ser Thr Met Leu Ala Phe Glu Val Gly
        35                  40                  45 tac atg gcc atg ctg ctc ttc ggc att ccc atc atg aag cag atg gag       192
Tyr Met Ala Met Leu Leu Phe Gly Ile Pro Ile Met Lys Gln Met Glu
    50                  55                  60 aag ccc ttc gag ctg aag acc atc aag ctg ctc cac aac ctg ttc ctc       240
Lys Pro Phe Glu Leu Lys Thr Ile Lys Leu Leu His Asn Leu Phe Leu
65                  70                  75                  80 ttc gga ctg tcc ctc tac atg tgc gtc gag acc atc cga cag gct atc       288
Phe Gly Leu Ser Leu Tyr Met Cys Val Glu Thr Ile Arg Gln Ala Ile
                85                  90                  95 ctg ggt ggc tac aag gtc ttc ggc aac gac atg gag aag ggc aac gag       336
Leu Gly Gly Tyr Lys Val Phe Gly Asn Asp Met Glu Lys Gly Asn Glu
            100                 105                 110 tcc cac gct cag ggc atg tcc cga atc gtc tac gtg ttc tac gtc tcc       384
Ser His Ala Gln Gly Met Ser Arg Ile Val Tyr Val Phe Tyr Val Ser
        115                 120                 125 aag gcc tac gag ttc ctg gac acc gct atc atg atc ctg tgc aag aag       432
Lys Ala Tyr Glu Phe Leu Asp Thr Ala Ile Met Ile Leu Cys Lys Lys
    130                 135                 140 ttc aac cag gtc tcc ttc ctg cac gtg tac cac cat gcc acc atc ttc       480
Phe Asn Gln Val Ser Phe Leu His Val Tyr His His Ala Thr Ile Phe
145                 150                 155                 160 gcc atc tgg tgg gct att gcc aag tac gct cct ggt ggc gac gcc tac       528
Ala Ile Trp Trp Ala Ile Ala Lys Tyr Ala Pro Gly Gly Asp Ala Tyr
                165                 170                 175 ttc tcc gtc atc ctc aac tcc ttc gtc cac acc gtc atg tac gcc tac       576
Phe Ser Val Ile Leu Asn Ser Phe Val His Thr Val Met Tyr Ala Tyr
            180                 185                 190 tac ttc ttt tcc tct cag ggc ttc ggc ttc gtc aag ccc atc aag ccc       624
Tyr Phe Phe Ser Ser Gln Gly Phe Gly Phe Val Lys Pro Ile Lys Pro
        195                 200                 205 tac atc acc act ctg cag atg acc cag ttc atg gct atg ctg gtg cag       672
Tyr Ile Thr Thr Leu Gln Met Thr Gln Phe Met Ala Met Leu Val Gln
    210                 215                 220 tcc ctg tac gac tac ctc ttc ccc tgc gac tac cct cag gct ctg gtc       720
Ser Leu Tyr Asp Tyr Leu Phe Pro Cys Asp Tyr Pro Gln Ala Leu Val
225                 230                 235                 240 cag ctg ctc ggc gtg tac atg atc acc ctg ctc gct ctg ttc ggc aac       768
Gln Leu Leu Gly Val Tyr Met Ile Thr Leu Leu Ala Leu Phe Gly Asn
                245                 250                 255 ttc ttt gtc cag tcc tac ctg aag aag ccc aag aag tcc aag acc aac       816
Phe Phe Val Gln Ser Tyr Leu Lys Lys Pro Lys Lys Ser Lys Thr Asn
            260                 265                 270 taa                                                                    819
```

<210> SEQ ID NO 22
<211> LENGTH: 272
<212> TYPE: PRT
<213> ORGANISM: Thraustochytrium aureum

<400> SEQUENCE: 22

```
Met Ala Asn Ser Ser Val Trp Asp Asp Val Gly Arg Val Glu Thr
1               5                   10                  15

Gly Val Asp Gln Trp Met Asp Gly Ala Lys Pro Tyr Ala Leu Thr Asp
            20                  25                  30

Gly Leu Pro Met Met Asp Val Ser Thr Met Leu Ala Phe Glu Val Gly
                35                  40                  45

Tyr Met Ala Met Leu Leu Phe Gly Ile Pro Ile Met Lys Gln Met Glu
    50                  55                  60

Lys Pro Phe Glu Leu Lys Thr Ile Lys Leu Leu His Asn Leu Phe Leu
65                  70                  75                  80

Phe Gly Leu Ser Leu Tyr Met Cys Val Glu Thr Ile Arg Gln Ala Ile
                85                  90                  95

Leu Gly Gly Tyr Lys Val Phe Gly Asn Asp Met Glu Lys Gly Asn Glu
            100                 105                 110

Ser His Ala Gln Gly Met Ser Arg Ile Val Tyr Val Phe Tyr Val Ser
        115                 120                 125

Lys Ala Tyr Glu Phe Leu Asp Thr Ala Ile Met Ile Leu Cys Lys Lys
130                 135                 140

Phe Asn Gln Val Ser Phe Leu His Val Tyr His His Ala Thr Ile Phe
145                 150                 155                 160

Ala Ile Trp Trp Ala Ile Ala Lys Tyr Ala Pro Gly Gly Asp Ala Tyr
                165                 170                 175

Phe Ser Val Ile Leu Asn Ser Phe Val His Thr Val Met Tyr Ala Tyr
            180                 185                 190

Tyr Phe Phe Ser Ser Gln Gly Phe Gly Phe Val Lys Pro Ile Lys Pro
        195                 200                 205

Tyr Ile Thr Thr Leu Gln Met Thr Gln Phe Met Ala Met Leu Val Gln
    210                 215                 220

Ser Leu Tyr Asp Tyr Leu Phe Pro Cys Asp Tyr Pro Gln Ala Leu Val
225                 230                 235                 240

Gln Leu Leu Gly Val Tyr Met Ile Thr Leu Leu Ala Leu Phe Gly Asn
                245                 250                 255

Phe Phe Val Gln Ser Tyr Leu Lys Lys Pro Lys Lys Ser Lys Thr Asn
            260                 265                 270
```

<210> SEQ ID NO 23
<211> LENGTH: 10945
<212> TYPE: DNA
<213> ORGANISM: Artificial Sequence
<220> FEATURE:
<223> OTHER INFORMATION: Plasmid pDMW232

<400> SEQUENCE: 23

```
aattcctgca gcccatcgat caggagagac cgggttggcg gcgtatttgt gtcccaaaaa      60
acagccccaa ttgccccaat tgaccccaaa ttgacccagt agcgggccca accccggcga     120
gagccccctt cacccacat atcaaacctc cccggttcc cacacttgcc gttaagggcg       180
tagggtactg cagtctggaa tctacgcttg ttcagacttt gtactagttt ctttgtctgg     240
ccatccgggt aacccatgcc ggacgcaaaa tagactactg aaatttttt tgctttgtgg     300 ttgggacttt agccaagggt ataaagacc accgtccccg aattaccttt cctcttcttt     360
tctctctctc cttgtcaact cacacccgaa atcgttaagc atttccttct gagtataaga    420
atcattcacc atgggaacgg accaaggaaa aaccttcacc tgggaagagc tggcggccca    480
taacaccaag gacgacctac tcttggccat ccgcggcagg gtgtacgatg tcacaaagtt     540
```

```
cttgagccgc catcctggtg gagtggacac tctcctgctc ggagctggcc gagatgttac    600 tccggtctt  gagatgtatc acgcgtttgg ggctgcagat gccattatga agaagtacta    660
tgtcggtaca ctggtctcga atgagctgcc catcttcccg gagccaacgg tgttccacaa    720
aaccatcaag acgagagtcg agggctactt tacggatcgg aacattgatc ccaagaatag    780
accagagatc tggggacgat acgctcttat ctttggatcc ttgatcgctt cctactacgc    840
gcagctcttt gtgcctttcg ttgtcgaacg cacatggctt caggtggtgt ttgcaatcat    900
catgggattt gcgtgcgcac aagtcggact caaccctctt catgatgcgt ctcacttttc    960
agtgacccac aaccccactg tctggaagat tctgggagcc acgcacgact tttcaacgg    1020 agcatcgtac ctggtgtgga tgtaccaaca tatgctcggc catcacccct acaccaacat   1080
tgctggagca gatcccgacg tgtcgacgtc tgagcccgat gttcgtcgta tcaagcccaa   1140
ccaaaagtgg tttgtcaacc acatcaacca gcacatgttt gttcctttcc tgtacggact   1200
gctggcgttc aaggtgcgca ttcaggacat caacattttg tactttgtca agaccaatga   1260
cgctattcgt gtcaatccca tctcgacatg gcacactgtg atgttctggg gcggcaaggc   1320
tttctttgtc tggtatcgcc tgattgttcc cctgcagtat ctgcccctgg gcaaggtgct   1380
gctcttgttc acggtcgcgg acatggtgtc gtcttactgg ctggcgctga ccttccaggc   1440
gaaccacgtt gttgaggaag ttcagtggcc gttgcctgac gagaacggga tcatccaaaa   1500
ggactgggca gctatgcagg tcgagactac gcaggattac gcacacgatt cgcacctctg   1560
gaccagcatc actggcagct tgaactacca ggctgtgcac catctgttcc caacgtgtc   1620 gcagcaccat tatcccgata ttctggccat catcaagaac acctgcagcg agtacaaggt   1680
tccatacctt gtcaaggata cgttttggca agcatttgct tcacatttgg agcacttgcg   1740
tgttcttgga ctccgtccca aggaagagta ggcagctaag cggccgcatg agaagataaa   1800
tatataaata cattgagata ttaaatgcgc tagattagag agcctcatac tgctcggaga   1860
gaagccaaga cgagtactca aggggatta caccatccat atccacagac acaagctggg   1920
gaaaggttct atatacactt tccggaatac cgtagtttcc gatgttatca atggggcag    1980 ccaggatttc aggcacttcg gtgtctcggg gtgaaatggc gttcttggcc tccatcaagt   2040
cgtaccatgt cttcatttgc ctgtcaaagt aaaacagaag cagatgaaga atgaacttga   2100
agtgaaggaa tttaaattgc cccggagaag acggccaggc cgcctagatg acaaattcaa   2160
caactcacag ctgactttct gccattgcca ctagggggg gcctttttat atggccaagc   2220
caagctctcc acgtcggttg ggctgcaccc aacaataaat gggtagggtt gcaccaacaa   2280
agggatggga tgggggtag aagatacgag gataacgggg ctcaatggca caaataagaa   2340
cgaatactgc cattaagact cgtgatccag cgactgacac cattgcatca tctaagggcc   2400
tcaaaactac ctcggaactg ctgcgctgat ctggacacca cagaggttcc gagcacttta   2460
ggttgcacca aatgtcccac caggtgcagg cagaaaacgc tggaacagcg tgtacagttt   2520
gtcttaacaa aaagtgaggg cgctgaggtc gagcagggtg gtgtgacttg ttatagcctt   2580
tagagctgcg aaagcgcgta tggatttggc tcatcaggcc agattgaggg tctgtggaca   2640
catgtcatgt tagtgtactt caatcgcccc ctggatatag cccgacaat aggccgtggc    2700 ctcatttttt tgccttccgc acatttccat tgctcggtac ccacacctg cttctcctgc    2760 acttgccaac cttaatactg gtttacattg accaacatct tacaagcggg gggcttgtct   2820
agggtatata taaacagtgg ctctcccaat cggttgccag tctctttttt cctttctttc   2880
cccacagatt cgaaatctaa actacacatc acacaatgcc tgttactgac gtccttaagc   2940
```

```
gaaagtccgg tgtcatcgtc ggcgacgatg tccgagccgt gagtatccac gacaagatca    3000
gtgtcgagac gacgcgtttt gtgtaatgac acaatccgaa agtcgctagc aacacacact    3060
ctctacacaa actaacccag ctctccatgg gaacggacca aggaaaaacc ttcacctggg    3120
aagagctggc ggcccataac accaaggacg acctactctt ggccatccgc ggcagggtgt    3180
acgatgtcac aaagttcttg agccgccatc ctggtggagt ggacactctc ctgctcggag    3240
ctggccgaga tgttactccg gtctttgaga tgtatcacgc gtttgggct gcagatgcca     3300
ttatgaagaa gtactatgtc ggtacactgg tctcgaatga gctgcccatc ttcccggagc    3360
caacggtgtt ccacaaaacc atcaagacga gagtcgaggg ctactttacg gatcggaaca    3420
ttgatcccaa gaatagacca gagatctggg gacgatacgc tcttatcttt ggatccttga    3480
tcgcttccta ctacgcgcag ctctttgtgc ctttcgttgt cgaacgcaca tggcttcagg    3540
tggtgtttgc aatcatcatg ggatttgcgt gcgcacaagt cggactcaac cctcttcatg    3600
atgcgtctca cttttcagtg acccacaacc ccactgtctg gaagattctg ggagccacgc    3660
acgactttt caacggagca tcgtacctgg tgtggatgta ccaacatatg ctcggccatc     3720
acccctacac caacattgct ggagcagatc ccgacgtgtc gacgtctgag cccgatgttc    3780
gtcgtatcaa gcccaaccaa aagtggtttg tcaaccacat caaccagcac atgtttgttc    3840
ctttcctgta cggactgctg gcgttcaagg tgcgcattca ggacatcaac attttgtact    3900
ttgtcaagac caatgacgct attcgtgtca atcccatctc gacatggcac actgtgatgt    3960
tctgggggcgg caaggcttc tttgtctggt atcgcctgat tgttccctg cagtatctgc      4020
ccctgggcaa ggtgctgctc ttgttcacgg tcgcggacat ggtgtcgtct tactggctgg    4080
cgctgaccct tccaggcgaac cacgttgttg aggaagttca gtggccgttg cctgacgaga    4140
acgggatcat ccaaaaggac tgggcagcta tgcaggtcga gactacgcag gattacgcac    4200
acgattcgca cctctggacc agcatcactg gcagcttgaa ctaccaggct gtgcaccatc    4260
tgttcccaa cgtgtcgcag caccattatc ccgatattct ggccatcatc aagaacacct     4320
gcagcgagta caaggttcca taccttgtca aggatacgtt ttggcaagca tttgcttcac    4380
atttggagca cttgcgtgtt cttggactcc gtcccaagga agagtaggca gctaagcggc    4440
cgcaagtgtg gatgggggaag tgagtgcccg gttctgtgtg cacaattggc aatccaagat    4500
ggatggattc aacacaggga tatagcgagc tacgtggtgg tgcgaggata tagcaacgga    4560
tatttatgtt tgacacttga gaatgtacga tacaagcact gtccaagtac aatactaaac    4620
atactgtaca tactcatact cgtacccggg caacggtttc acttgagtgc agtggctagt    4680
gctcttactc gtacagtgtg caatactgcg tatcatagtc tttgatgtat atcgtattca    4740
ttcatgttag ttgcgtacgc caccattctg tctgccgcca tgatgctcaa gttctctctt    4800
aacatgaagc ccgccggtga cgctgttgag gctgccgtca aggagtccgt cgaggctggt    4860
atcactaccg ccgatatcgg aggctcttcc tccacctccg aggtcggaga cttgttgcca    4920
acaaggtcaa ggagctgctc aagaaggagt aagtcgtttc tacgacgcat tgatggaagg    4980
agcaaactga cgcgcctgcg ggttggtcta ccggcagggt ccgctagtgt ataagactct    5040
ataaaaaggg ccctgccctg ctaatgaaat gatgatttat aatttaccgg tgtagcaacc    5100
ttgactagaa gaagcagatt gggtgtgttt gtagtggagg acagtggtac gttttggaaa    5160
cagtcttctt gaaagtgtct tgtctacagt atattcactc ataacctcaa tagccaaggg    5220
tgtagtcggt ttattaaagg aagggagttg tggctgatgt ggatagatat ctttaagctg    5280
gcgactgcac ccaacgagtg tggtggtagc ttgttactgt atattcggta agatatattt    5340
```

```
tgtggggttt tagtggtgtt tggtaggtta gtgcttggta tatgagttgt aggcatgaca    5400
atttggaaag gggtggactt tgggaatatt gtgggatttc ataccttag tttgtacagg     5460 gtaattgtta caaatgatac aaagaactgt atttcttttc atttgtttta attggttgta    5520
tatcaagtcc gttagacgag ctcagtgggc gcgccagctg cattaatgaa tcggccaacg    5580
cgcggggaga ggcggtttgc gtattgggcg ctcttccgct tcctcgctca ctgactcgct    5640
gcgctcggtc gttcggctgc ggcgagcggt atcagctcac tcaaaggcgg taatacggtt    5700
atccacagaa tcaggggata acgcaggaaa gaacatgtga gcaaaaggcc agcaaaaggc    5760
caggaaccgt aaaaaggccg cgttgctggc gtttttccat aggctccgcc cccctgacga    5820
gcatcacaaa aatcgacgct caagtcagag gtggcgaaac ccgacaggac tataaagata    5880
ccaggcgttt cccccctggaa gctccctcgt gcgctctcct gttccgaccc tgccgcttac    5940
cggatacctg tccgcctttc tcccttcggg aagcgtggcg ctttctcata gctcacgctg    6000
taggtatctc agttcggtgt aggtcgttcg ctccaagctg ggctgtgtgc acgaacccc    6060 cgttcagccc gaccgctgcg ccttatccgg taactatcgt cttgagtcca acccggtaag    6120
acacgactta tcgccactgg cagcagccac tggtaacagg attagcagag cgaggtatgt    6180
aggcggtgct acagagttct tgaagtggtg gcctaactac ggctacacta agaacagt     6240 atttggtatc tgcgctctgc tgaagccagt taccttcgga aaaagagttg gtagctcttg    6300
atccggcaaa caaaccaccg ctggtagcgg tggtttttt gtttgcaagc agcagattac     6360
gcgcagaaaa aaggatctc aagaagatcc tttgatcttt tctacggggt ctgacgctca     6420
gtggaacgaa aactcacgtt aagggatttt ggtcatgaga ttatcaaaaa ggatcttcac    6480
ctagatcctt ttaaattaaa aatgaagttt taaatcaatc taaagtatat atgagtaaac    6540
ttggtctgac agttaccaat gcttaatcag tgaggcacct atctcagcga tctgtctatt    6600
tcgttcatcc atagttgcct gactccccgt cgtgtagata actacgatac gggagggctt    6660
accatctggc cccagtgctg caatgatacc gcgagaccca cgctcaccgg ctccagattt    6720
atcagcaata aaccagccag ccggaagggc cgagcgcaga agtggtcctg caactttatc    6780
cgcctccatc cagtctatta attgttgccg ggaagctaga gtaagtagtt cgccagttaa    6840
tagtttgcgc aacgttgttg ccattgctac aggcatcgtg gtgtcacgct cgtcgtttgg    6900
tatggcttca ttcagctccg gttcccaacg atcaaggcga gttacatgat cccccatgtt    6960
gtgcaaaaaa gcggttagct ccttcggtcc tccgatcgtt gtcagaagta agttggccgc    7020
agtgttatca ctcatggtta tggcagcact gcataattct cttactgtca tgccatccgt    7080
aagatgcttt tctgtgactg gtgagtactc aaccaagtca ttctgagaat agtgtatgcg    7140
gcgaccgagt tgctcttgcc cggcgtcaat acgggataat accgcgccac atagcagaac    7200
tttaaaagtg ctcatcattg gaaaacgttc ttcggggcga aaactctcaa ggatcttacc    7260
gctgttgaga tccagttcga tgtaacccac tcgtgcaccc aactgatctt cagcatcttt    7320
tactttcacc agcgtttctg ggtgagcaaa aacaggaagg caaaatgccg caaaaaggg    7380 aataagggcg acacggaaat gttgaatact catactcttc cttttcaat attattgaag    7440 catttatcag ggttattgtc tcatgagcgg atacatattt gaatgtattt agaaaaataa    7500
acaaataggg gttccgcgca catttccccg aaaagtgcca cctgatgcgg tgtgaaatac    7560
cgcacagatg cgtaaggaga aaataccgca tcaggaaatt gtaagcgtta atattttgtt    7620
aaaattcgcg ttaaattttt gttaaatcag ctcattttt aaccaatagg ccgaaatcgg     7680
caaaatccct tataaatcaa agaatagac cgagataggg ttgagtgttg ttccagtttg     7740
```

```
gaacaagagt ccactattaa agaacgtgga ctccaacgtc aaagggcgaa aaaccgtcta   7800
tcagggcgat ggcccactac gtgaaccatc accctaatca agttttttgg ggtcgaggtg   7860
ccgtaaagca ctaaatcgga accctaaagg gagcccccga tttagagctt gacggggaaa   7920
gccggcgaac gtggcgagaa aggaagggaa gaaagcgaaa ggagcgggcg ctagggcgct   7980
ggcaagtgta gcggtcacgc tgcgcgtaac caccacaccc gccgcgctta atgcgccgct   8040
acagggcgcg tccattcgcc attcaggctg cgcaactgtt gggaagggcg atcggtgcgg   8100
gcctcttcgc tattacgcca gctggcgaaa ggggatgtg ctgcaaggcg attaagttgg   8160
gtaacgccag ggttttccca gtcacgacgt tgtaaaacga cggccagtga attgtaatac   8220
gactcactat agggcgaatt gggcccgacg tcgcatgcta tcggcatcga caaggtttgg   8280
gtccctagcc gataccgcac tacctgagtc acaatcttcg gaggtttagt cttccacata   8340
gcacgggcaa aagtgcgtat atatacaaga gcgtttgcca gccacagatt ttcactccac   8400
acaccacatc acacatacaa ccacacacat ccacaatgga acccgaaact aagaagacca   8460
agactgactc caagaagatt gttcttctcg gcggcgactt ctgtggcccc gaggtgattg   8520
ccgaggccgt caaggtgctc aagtctgttg ctgaggcctc cggcaccgag tttgtgtttg   8580
aggaccgact cattggagga gctgccattg agaaggaggg cgagcccatc accgacgcta   8640
ctctcgacat ctgccgaaag gctgactcta ttatgctcgg tgctgtcgga ggcgctgcca   8700
acaccgtatg gaccactccc gacggacgaa ccgacgtgcg acccgagcag ggtctcctca   8760
agctgcgaaa ggacctgaac ctgtacgcca acctgcgacc ctgccagctg ctgtcgccca   8820
agctcgccga tctctccccc atccgaaacg ttgagggcac cgacttcatc attgtccgag   8880
agctcgtcgg aggtatctac tttgagagc gaaaggagga tgacggatct ggcgtcgctt   8940
ccgacaccga gacctactcc gttaattaat ttgaatcgaa tcgatgagcc taaaatgaac   9000
ccgagtatat ctcataaaat tctcggtgag aggtctgtga ctgtcagtac aaggtgcctt   9060
cattatgccc tcaaccttac catacctcac tgaatgtagt gtacctctaa aaatgaaata   9120
cagtgccaaa agccaaggca ctgagctcgt ctaacggact tgatatacaa ccaattaaaa   9180
caaatgaaaa gaaatacagt tctttgtatc atttgtaaca attaccctgt acaaactaag   9240
gtattgaaat cccacaatat tcccaaagtc caccccttc caaattgtca tgcctacaac   9300
tcatatacca agcactaacc taccgtttaa acagtgtacg cagatctggt gtagtggtag   9360
tgcagtggtg gtattgtgac tggggatgta gttgagaata agtcatacac aagtcagctt   9420
tcttcgagcc tcatataagt ataagtagtt caacgtatta gcactgtacc cagcatctcc   9480
gtatcgagaa acacaacaac atgccccatt ggacagatca tgcggataca caggttgtgc   9540
agtatcatac atactcgatc agacaggtcg tctgaccatc atacaagctg aacaagcgct   9600
ccatacttgc acgctctcta tatacacagt taaattacat atccatagtc taacctctaa   9660
cagttaatct tctggtaagc ctcccagcca gccttctggt atcgcttggc ctcctcaata   9720
ggatctcggt tctggccgta cagacctcgg ccgacaatta tgatatccgt tccggtagac   9780
atgacatcct caacagttcg gtactgctgt ccgagagcgt ctcccttgtc gtcaagaccc   9840
accccggggg tcagaataag ccagtcctca gagtcgccct taggtcggtt ctgggcaatg   9900
aagccaacca caaactcggg gtcggatcgg gcaagctcaa tggtctgctt ggagtactcg   9960
ccagtggcca gagagccctt gcaagacagc tcgccagca tgagcagacc tctggccagc  10020
ttctcgttgg gagaggggac taggaactcc ttgtactggg agttctcgta gtcagagacg  10080
tcctccttct tctgttcaga gacagtttcc tcggcaccag ctcgcaggcc agcaatgatt  10140
```

```
ccggttccgg gtacaccgtg ggcgttggtg atatcggacc actcggcgat tcggtgacac   10200
cggtactggt gcttgacagt gttgccaata tctgcgaact ttctgtcctc gaacaggaag   10260
aaaccgtgct taagagcaag ttccttgagg gggagcacag tgccggcgta ggtgaagtcg   10320
tcaatgatgt cgatatgggt tttgatcatg cacacataag gtccgacctt atcggcaagc   10380
tcaatgagcc ccttggtggt ggtaacatcc agagaagcac acaggttggt tttcttggct   10440
gccacgagct tgagcactcg agcggcaaag gcggacttgt ggacgttagc tcgagcttcg   10500
taggagggca ttttggtggt gaagaggaga ctgaaataaa tttagtctgc agaactttt    10560 atcggaacct tatctggggc agtgaagtat atgttatggt aatagttacg agttagttga   10620
acttatagat agactggact atacggctat cggtccaaat tagaaagaac gtcaatggct   10680
ctctgggcgt cgcctttgcc gacaaaaatg tgatcatgat gaaagccagc aatgacgttg   10740
cagctgatat tgttgtcggc caaccgcgcc gaaaacgcag ctgtcagacc cacagcctcc   10800
aacgaagaat gtatcgtcaa agtgatccaa gcacactcat agttggagtc gtactccaaa   10860
ggcggcaatg acgagtcaga cagatactcg tcgacctttt ccttgggaac caccaccgtc   10920
agcccttctg actcacgtat tgtag                                         10945

<210> SEQ ID NO 24
<211> LENGTH: 2236
<212> TYPE: DNA
<213> ORGANISM: Yarrowia lipolytica

<400> SEQUENCE: 24
ataagtttgc aaaaagatcg tattatagtt ggagcaaggg agaaatgtag agtgtgaaag     60
actcactatg gtccgggctt atctcgacca atagccaaag tctggagttt ctgagagaaa    120
aaggcaagat acgtatgtaa caaagcgacg catggtacaa taataccgga ggcatgtatc    180
atagagagtt agtggttcga tgatggcact ggtgcctggt atgactttat acggctgact    240
acatatttgt cctcagacat acaattacag tcaagcactt acccttggac atctgtaggt    300 acccccccggc caagacgatc tcagcgtgtc gtatgtcgga ttggcgtagc tccctcgctc    360
gtcaattggc tcccatctac tttcttctgc ttggctacac ccagcatgtc tgccatggct    420
cgttttcgtg cctatctat cctcccagta ttaccaactc taaatgacat gatgtgattg     480
ggtctacact ttcatatcag agataaggag tagcacagtt gcataaaaag cccaactcta    540
atcagcttct tcctttcttg taattagtac aaaggtgatt agcgaaatct ggaagcttag    600
ttggccctaa aaaatcaaa aaaagcaaaa aacgaaaaac gaaaaaccac agttttgaga    660
acagggaggt aacgaaggat cgtatatata tatatatata tatatatccca cggatcccga    720 gaccggcctt tgattcttcc ctacaaccaa ccattctcac caccctaatt cacaaatggc    780
tgacgctacc tcaacgcaag ctccccttcc gaccactggc aatggaggag actccctcac    840
acaaaacctg aacgtcccct tcctgggtgc cgatatggtc tggatcatga cctcttcggc    900
actggtctgg atcatgattc caggagtcgg tctgctctac tctggtatgt cgcgtaagca    960
ccacgccctg tctctcctgt gggcatccat catgtgctgt gccctcgtct ctttcgagtg   1020 gttttctgg ggttacactc tggcattctc tcacaaggcc ggaaagttca ttggaaccat   1080
ggataacttc ggtcttatga atgttctcgc tgctccctct gttggctcct ctgctgtccc   1140
cgatatcctg tatatgttct accagggcat gttcgcatgc atcaccggta tgctcatggt   1200
tggtggagct cacgagcgag ctcgactcgg ccccatgatg gtatatctct tcatttggat   1260
gactgtcgtc tactctccta ttgcatgctg gacatggaac cctagtggat ggctcgccgt   1320
```

```
ccttggagga cttgatttcg caggtggagg acctgttcac atgtcttccg gtgcgggtgc    1380
ccttgcctat gctctctggt gtggtaagag acgtgaccct gctgttgaga agctgcctca    1440
ctaccggccc tcttccgtta cttccgttgt tctcggcact gttttgcttt ggttcggatg    1500
gttcggattc aacggtggtt cctctggtaa cgcctccatc cgaggcttct acgctgccgc    1560
taatactaac cttgctgctg cttgcggtgc tctcgcttgg atgtgtgtcg acttcttccg    1620
aaagggccga agtggtcca ctgttggtct ctgttctggt gccatcgcag gtctcgttgg    1680
catcaccccc gccgcggct tcgtccctat ctggtctgct gtccctattg gtatcatcac    1740
cgccgtcttc gctaacattt ctggtgacct taagaatctg ctccgaattg atgatggtct    1800
cgatgtcttc tctctccatg gtgtgggagg attctgcggc tctgttctta ctgccttctt    1860
tgctgctgac tacattgccc atctggatgg tgccacagag atcaagggtg gatggctcaa    1920
ccaccactgg gctcagctgg gttaccagct ggctggtgcg tttgctaccc tcggctactc    1980
ctttgtggtc tcttcagtta ttcttgtcat catgaacaga atcccctacc tcaacgtccg    2040
aatgaccgag gaggaggaga tgcttggaac cgacatggcc cagatcggcg agtttgcctt    2100
cgactgggag gactctggag tcctggacct gcatggccag aaccccaatg gtatgggcgt    2160 caccccccaac gtccagactc ccaagcccag cagcatcaac gaaaacaagg aggctgctga    2220
gagtgattcg gtttaa                                                    2236

<210> SEQ ID NO 25
<211> LENGTH: 775
<212> TYPE: DNA
<213> ORGANISM: Yarrowia lipolytica

<400> SEQUENCE: 25
ataagtttgc aaaaagatcg tattatagtt ggagcaaggg agaaatgtag agtgtgaaag      60
actcactatg gtccgggctt atctcgacca atagccaaag tctggagttt ctgagagaaa     120
aaggcaagat acgtatgtaa caaagcgacg catggtacaa taataccgga ggcatgtatc     180
atagagagtt agtggttcga tgatggcact ggtgcctggt atgactttat acggctgact     240
acatatttgt cctcagacat acaattacag tcaagcactt acccttggac atctgtaggt     300
accccccggc caagacgatc tcagcgtgtc gtatgtcgga ttggcgtagc tccctcgctc     360
gtcaattggc tcccatctac tttcttctgc ttggctacac ccagcatgtc tgccatggct     420
cgttttcgtg cctatctat cctcccagta ttaccaactc taaatgacat gatgtgattg     480
ggtctacact ttcatatcag agataaggag tagcacagtt gcataaaaag cccaactcta     540
atcagcttct tcctttcttg taattagtac aaaggtgatt agcgaaatct ggaagcttag     600
ttggccctaa aaaatcaaa aaaagcaaaa acgaaaaac gaaaaccac agttttgaga      660 acagggaggt aacgaaggat cgtatatata tatatatata tatataccca cggatcccga     720
gaccggcctt tgattcttcc ctacaaccaa ccattctcac caccctaatt cacaa          775

<210> SEQ ID NO 26
<211> LENGTH: 777
<212> TYPE: DNA
<213> ORGANISM: Yarrowia lipolytica

<400> SEQUENCE: 26
ataagtttgc aaaaagatcg tattatagtt ggagcaaggg agaaatgtag agtgtgaaag      60
actcactatg gtccgggctt atctcgacca atagccaaag tctggagttt ctgagagaaa     120
aaggcaagat acgtatgtaa caaagcgacg catggtacaa taataccgga ggcatgtatc     180
```

```
atagagagtt agtggttcga tgatggcact ggtgcctggt atgactttat acggctgact     240
acatatttgt cctcagacat acaattacag tcaagcactt acccttggac atctgtaggt     300
accccccggc caagacgatc tcagcgtgtc gtatgtcgga ttggcgtagc tccctcgctc     360
gtcaattggc tcccatctac tttcttctgc ttggctacac ccagcatgtc tgccatggct     420
cgttttcgtg ccttatctat cctcccagta ttaccaactc taaatgacat gatgtgattg     480
ggtctacact ttcatatcag agataaggag tagcacagtt gcataaaaag cccaactcta     540
atcagcttct cctttcttg taattagtac aaaggtgatt agcgaaatct ggaagcttag      600
ttggccctaa aaaatcaaa aaaagcaaaa acgaaaaac gaaaaccac agttttgaga        660 acagggaggt aacgaaggat cgtatatata tatatatata tataccca cggatcccga       720 gaccggcctt tgattcttcc ctacaaccaa ccattctcac caccctaatt cacaacc        777
```

<210> SEQ ID NO 27
<211> LENGTH: 783
<212> TYPE: DNA
<213> ORGANISM: Yarrowia lipolytica

<400> SEQUENCE: 27

```
gtcgacataa gtttgcaaaa agatcgtatt atagttggag caagggagaa atgtagagtg     60
tgaaagactc actatggtcc gggcttatct cgaccaatag ccaaagtctg gagtttctga    120
gagaaaaagg caagatacgt atgtaacaaa gcgacgcatg gtacaataat accggaggca    180
tgtatcatag agagttagtg gttcgatgat ggcactggtg cctggtatga ctttatacgg    240
ctgactacat atttgtcctc agacatacaa ttacagtcaa gcacttaccc ttggacatct    300
gtaggtaccc cccggccaag acgatctcag cgtgtcgtat gtcggattgg cgtagctccc    360
tcgctcgtca attggctccc atctactttc ttctgcttgg ctacacccag catgtctgcc    420
atggctcgtt tcgtgccctt atctatcctc cagtattac aactctaaa tgacatgatg      480 tgattgggtc tacactttca tatcagagat aaggagtagc acagttgcat aaaaagccca    540
actctaatca gcttcttcct ttcttgtaat tagtacaaag gtgattagcg aaatctggaa    600
gcttagttgg ccctaaaaaa atcaaaaaaa gcaaaaaacg aaaaacgaaa accacagtt     660 ttgagaacag ggaggtaacg aaggatcgta tatatata tatatatata tacccacgga      720
tcccgagacc ggcctttgat tcttccctac aaccaaccat tctcaccacc ctaattcaca    780
acc                                                                  783
```

<210> SEQ ID NO 28
<211> LENGTH: 777
<212> TYPE: DNA
<213> ORGANISM: Yarrowia lipolytica

<400> SEQUENCE: 28

```
ataagtttgc aaaagatcg tattatagtt ggagcaaggg agaaatgtag agtgtgaaag     60
actcactatg gtccgggctt atctcgacca atagccaaag tctggagttt ctgagagaaa    120
aaggcaagat acgtatgtaa caaagcgacg catggtacaa taataccgga ggcatgtatc    180
atagagagtt agtggttcga tgatggcact ggtgcctggt atgactttat acggctgact    240
acatatttgt cctcagacat acaattacag tcaagcactt acccttggac atctgtaggt    300
accccccggc caagacgatc tcagcgtgtc gtatgtcgga ttggcgtagc tccctcgctc    360
gtcaattggc tcccatctac tttcttctgc ttggctacac ccagcatgtc tgctatggct    420
cgttttcgtg ccttatctat cctcccagta ttaccaactc taaatgacat gatgtgattg    480
```

| | |
|---|---|
| ggtctacact tcatatcag agataaggag tagcacagtt gcataaaaag cccaactcta | 540 |
| atcagcttct tcctttcttg taattagtac aaaggtgatt agcgaaatct ggaagcttag | 600 |
| ttggccctaa aaaaatcaaa aaaagcaaaa acgaaaaac gaaaaccac agttttgaga | 660 |
| acagggaggt aacgaaggat cgtatatata tatatatata tatatacccca cggatcccga | 720 |
| gaccggcctt tgattcttcc ctacaaccaa ccattctcac caccctaatt cacaacc | 777 |

<210> SEQ ID NO 29
<211> LENGTH: 783
<212> TYPE: DNA
<213> ORGANISM: Yarrowia lipolytica

<400> SEQUENCE: 29

| | |
|---|---|
| gtcgacataa gtttgcaaaa agatcgtatt atagttggag caagggagaa atgtagagtg | 60 |
| tgaaagactc actatggtcc gggcttatct cgaccaatag ccaaagtctg gagtttctga | 120 |
| gagaaaaagg caagatacgt atgtaacaaa gcgacgcatg gtacaataat accggaggca | 180 |
| tgtatcatag agagttagtg gttcgatgat ggcactggtg cctggtatga ctttatacgg | 240 |
| ctgactacat atttgtcctc agacatacaa ttacagtcaa gcacttaccc ttggacatct | 300 |
| gtaggtaccc cccggccaag acgatctcag cgtgtcgtat gtcggattgg cgtagctccc | 360 |
| tcgctcgtca attggctccc atctactttc ttctgcttgg ctacacccag catgtctgct | 420 |
| atggctcgtt tcgtgccctt atctatcctc ccagtattac caactctaaa tgacatgatg | 480 |
| tgattgggtc tacactttca tatcagagat aaggagtagc acagttgcat aaaaagccca | 540 |
| actctaatca gcttcttcct ttcttgtaat tagtacaaag gtgattagcg aaatctggaa | 600 |
| gcttagttgg ccctaaaaaa atcaaaaaaa gcaaaaaacg aaaacgaaa accacagtt | 660 |
| ttgagaacag ggaggtaacg aaggatcgta tatatatata tatatatata tacccacgga | 720 |
| tcccgagacc ggcctttgat tcttccctac aaccaaccat tctcaccacc ctaattcaca | 780 |
| acc | 783 |

<210> SEQ ID NO 30
<211> LENGTH: 751
<212> TYPE: DNA
<213> ORGANISM: Yarrowia lipolytica

<400> SEQUENCE: 30

| | |
|---|---|
| agttggagca agggagaaat gtagagtgtg aaagactcac tatggtccgg gcttatctcg | 60 |
| accaatagcc aaagtctgga gtttctgaga gaaaaaggca agatacgtat gtaacaaagc | 120 |
| gacgcatggt acaataatac cggaggcatg tatcatagag agttagtggt tcgatgatgg | 180 |
| cactggtgcc tggtatgact ttatacggct gactacatat ttgtcctcag acatacaatt | 240 |
| acagtcaagc acttaccctt ggacatctgt aggtaccccc cggccaagac gatctcagcg | 300 |
| tgtcgtatgt cggattggcg tagctccctc gctcgtcaat tggctcccat ctactttctt | 360 |
| ctgcttggct acaccagca tgtctgctat ggctcgtttt cgtgccttat ctatcctccc | 420 |
| agtattacca actctaaatg acatgatgtg attgggtcta cactttcata tcagagataa | 480 |
| ggagtagcac agttgcataa aaagcccaac tctaatcagc ttcttccttt cttgtaatta | 540 |
| gtacaaaggt gattagcgaa atctggaagc ttagttggcc ctaaaaaaat caaaaaaagc | 600 |
| aaaaaacgaa aacgaaaaa ccacagtttt gagaacaggg aggtaacgaa ggatcgtata | 660 |
| tatatatata tatatata cccacggatc ccgagaccgg cctttgattc ttccctacaa | 720 |
| ccaaccattc tcaccaccct aattcacaac c | 751 |

<210> SEQ ID NO 31
<211> LENGTH: 757
<212> TYPE: DNA
<213> ORGANISM: Yarrowia lipolytica

<400> SEQUENCE: 31

| | | | | | |
|---|---|---|---|---|---|
| atcgatagtt | ggagcaaggg | agaaatgtag | agtgtgaaag | actcactatg | gtccgggctt | 60 |
| atctcgacca | atagccaaag | tctggagttt | ctgagagaaa | aaggcaagat | acgtatgtaa | 120 |
| caaagcgacg | catggtacaa | taataccgga | ggcatgtatc | atagagagtt | agtggttcga | 180 |
| tgatggcact | ggtgcctggt | atgactttat | acggctgact | acatatttgt | cctcagacat | 240 |
| acaattacag | tcaagcactt | acccttggac | atctgtaggt | accccccggc | caagacgatc | 300 |
| tcagcgtgtc | gtatgtcgga | ttggcgtagc | tccctcgctc | gtcaattggc | tcccatctac | 360 |
| tttcttctgc | ttggctacac | ccagcatgtc | tgctatggct | cgttttcgtg | ccttatctat | 420 |
| cctcccagta | ttaccaactc | taaatgacat | gatgtgattg | ggtctacact | ttcatatcag | 480 |
| agataaggag | tagcacagtt | gcataaaaag | cccaactcta | atcagcttct | tcctttcttg | 540 |
| taattagtac | aaaggtgatt | agcgaaatct | ggaagcttag | ttggccctaa | aaaaatcaaa | 600 |
| aaaagcaaaa | aacgaaaaac | gaaaaaccac | agttttgaga | acagggaggt | aacgaaggat | 660 |
| cgtatatata | tatatatata | tatataccca | cggatcccga | gaccggcctt | tgattcttcc | 720 |
| ctacaaccaa | ccattctcac | caccctaatt | cacaacc | | | 757 |

<210> SEQ ID NO 32
<211> LENGTH: 759
<212> TYPE: DNA
<213> ORGANISM: Yarrowia lipolytica

<400> SEQUENCE: 32

| | | | | | |
|---|---|---|---|---|---|
| atttaaatag | ttggagcaag | ggagaaatgt | agagtgtgaa | agactcacta | tggtccgggc | 60 |
| ttatctcgac | caatagccaa | agtctggagt | ttctgagaga | aaaaggcaag | atacgtatgt | 120 |
| aacaaagcga | cgcatggtac | aataataccg | gaggcatgta | tcatagagag | ttagtggttc | 180 |
| gatgatggca | ctggtgcctg | gtatgacttt | atacggctga | ctacatattt | gtcctcagac | 240 |
| atacaattac | agtcaagcac | ttacccttgg | acatctgtag | gtaccccccg | gccaagacga | 300 |
| tctcagcgtg | tcgtatgtcg | gattggcgta | gctccctcgc | tcgtcaattg | gctcccatct | 360 |
| actttcttct | gcttggctac | acccagcatg | tctgctatgg | ctcgttttcg | tgccttatct | 420 |
| atcctcccag | tattaccaac | tctaaatgac | atgatgtgat | gggtctaca | ctttcatatc | 480 |
| agagataagg | agtagcacag | ttgcataaaa | agcccaactc | taatcagctt | cttcctttct | 540 |
| tgtaattagt | acaaaggtga | ttagcgaaat | ctggaagctt | agttggccct | aaaaaaatca | 600 |
| aaaaagcaa | aaacgaaaa | acgaaaaacc | acagttttga | gaacagggag | gtaacgaagg | 660 |
| atcgtatata | tatatatata | tatatatacc | cacggatccc | gagaccggcc | tttgattctt | 720 |
| ccctacaacc | aaccattctc | accacccta | ttcacaacc | | | 759 |

<210> SEQ ID NO 33
<211> LENGTH: 729
<212> TYPE: DNA
<213> ORGANISM: Yarrowia lipolytica

<400> SEQUENCE: 33

| | | | | | |
|---|---|---|---|---|---|
| agagtgtgaa | agactcacta | tggtccgggc | ttatctcgac | caatagccaa | agtctggagt | 60 |
| ttctgagaga | aaaaggcaag | atacgtatgt | aacaaagcga | cgcatggtac | aataataccg | 120 |

```
gaggcatgta tcatagagag ttagtggttc gatgatggca ctggtgcctg gtatgacttt      180
atacggctga ctacatattt gtcctcagac atacaattac agtcaagcac ttacccttgg      240
acatctgtag gtaccccccg gccaagacga tctcagcgtg tcgtatgtcg gattggcgta      300
gctccctcgc tcgtcaattg gctcccatct actttcttct gcttggctac acccagcatg      360
tctgctatgg ctcgttttcg tgccttatct atcctcccag tattaccaac tctaaatgac      420
atgatgtgat tgggtctaca ctttcatatc agagataagg agtagcacag ttgcataaaa      480
agcccaactc taatcagctt cttcctttct gtaattagt  acaaaggtga ttagcgaaat      540
ctggaagctt agttggccct aaaaaaatca aaaaagcaa  aaacgaaaa  acgaaaaacc      600 acagttttga aacagggag  gtaacgaagg atcgtatata tatatatata tatatatacc      660
cacggatccc gagaccggcc tttgattctt ccctacaacc aaccattctc accaccctaa      720
ttcacaacc                                                             729

<210> SEQ ID NO 34
<211> LENGTH: 737
<212> TYPE: DNA
<213> ORGANISM: Yarrowia lipolytica

<400> SEQUENCE: 34
gtttaaacag agtgtgaaag actcactatg gtccgggctt atctcgacca atagccaaag       60
tctggagttt ctgagagaaa aaggcaagat acgtatgtaa caaagcgacg catggtacaa      120
taataccgga ggcatgtatc atagagagtt agtggttcga tgatggcact ggtgcctggt      180
atgactttat acggctgact acatatttgt cctcagacat acaattacag tcaagcactt      240
acccttggac atctgtaggt accccccggc caagacgatc tcagcgtgtc gtatgtcgga      300
ttggcgtagc tccctcgctc gtcaattggc tcccatctac tttcttctgc ttggctacac      360
ccagcatgtc tgctatggct cgttttcgtg ccttatctat cctcccagta ttaccaactc      420
taaatgacat gatgtgattg ggtctacact ttcatatcag agataaggag tagcacagtt      480
gcataaaaag cccaactcta atcagcttct tcctttcttg taattagtac aaaggtgatt      540
agcgaaatct ggaagcttag ttggccctaa aaaatcaaa  aaagcaaaa  acgaaaaac      600 gaaaaaccac agttttgaga acagggaggt aacgaaggat cgtatatata tatatatata      660
tataccccca cggatcccga gaccggcctt tgattcttcc ctacaaccaa ccattctcac      720
caccctaatt cacaacc                                                    737

<210> SEQ ID NO 35
<211> LENGTH: 675
<212> TYPE: DNA
<213> ORGANISM: Yarrowia lipolytica

<400> SEQUENCE: 35
tggagtttct gagagaaaaa ggcaagatac gtatgtaaca aagcgacgca tggtacaata       60
ataccggagg catgtatcat agagagttag tggttcgatg atggcactgg tgcctggtat      120
gactttatac ggctgactac atatttgtcc tcagacatac aattacagtc aagcacttac      180
ccttggacat ctgtaggtac cccccggcca agacgatctc agcgtgtcgt atgtcggatt      240
ggcgtagctc cctcgctcgt caattggctc ccatctactt tcttctgctt ggctacaccc      300
agcatgtctg ctatggctcg ttttcgtgcc ttatctatcc ccagtatt    accaactcta      360 aatgacatga tgtgattggg tctacacttt catatcagag ataaggagta gcacagttgc      420
ataaaaagcc caactctaat cagcttcttc ctttcttgta attagtacaa aggtgattag      480
```

```
cgaaatctgg aagcttagtt ggccctaaaa aaatcaaaaa aagcaaaaaa cgaaaaacga    540
aaaaccacag ttttgagaac agggaggtaa cgaaggatcg tatatatata tatatatata    600
tatacccacg gatcccgaga ccggcctttg attcttccct acaaccaacc attctcacca    660
ccctaattca caacc                                                     675

<210> SEQ ID NO 36
<211> LENGTH: 681
<212> TYPE: DNA
<213> ORGANISM: Yarrowia lipolytica

<400> SEQUENCE: 36
gaattctgga gtttctgaga gaaaaaggca agatacgtat gtaacaaagc gacgcatggt     60
acaataatac cggaggcatg tatcatagag agttagtggt tcgatgatgg cactggtgcc    120
tggtatgact ttatacggct gactacatat ttgtcctcag acatacaatt acagtcaagc    180
acttacccct tggacatctgt aggtacccccc cggccaagac gatctcagcg tgtcgtatgt    240
cggattggcg tagctccctc gctcgtcaat tggctcccat ctactttctt ctgcttggct    300
acacccagca tgtctgctat ggctcgtttt cgtgccttat ctatcctccc agtattacca    360
actctaaatg acatgatgtg attgggtcta cactttcata tcagagataa ggagtagcac    420
agttgcataa aaagcccaac tctaatcagc ttcttccttt cttgtaatta gtacaaaggt    480
gattagcgaa atctggaagc ttagttggcc ctaaaaaaat caaaaaaagc aaaaaacgaa    540
aaacgaaaaa ccacagtttt gagaacaggg aggtaacgaa ggatcgtata tatatatata    600
tatatatata cccacggatc ccgagaccgg cctttgattc ttccctacaa ccaaccattc    660
tcaccaccct aattcacaac c                                              681

<210> SEQ ID NO 37
<211> LENGTH: 10
<212> TYPE: DNA
<213> ORGANISM: Yarrowia lipolytica
<220> FEATURE:
<221> NAME/KEY: misc_feature
<222> LOCATION: (8)..(8)
<223> OTHER INFORMATION: n is a, c, g, or t
<300> PUBLICATION INFORMATION:
<302> TITLE: CODON-OPTIMIZED GENES FOR THE PRODUCTION OF POLYUNSATURATED
      FATTY ACIDS IN OLEAGINOUS YEASTS
<310> PATENT DOCUMENT NUMBER: U.S. Pat. 7,125,672
<311> PATENT FILING DATE: 2004-05-06
<312> PUBLICATION DATE: 2006-10-24
<313> RELEVANT RESIDUES: (1)..(10)

<400> SEQUENCE: 37 mammatgnhs                                                            10

<210> SEQ ID NO 38
<211> LENGTH: 14688
<212> TYPE: DNA
<213> ORGANISM: Artificial Sequence
<220> FEATURE:
<223> OTHER INFORMATION: Plasmid pZKLeuN-29E3

<400> SEQUENCE: 38
cgattgttgt ctactaacta tcgtacgata acttcgtata gcatacatta tacgaagtta     60
tcgcgtcgac gagtatctgt ctgactcgtc attgccgcct ttggagtacg actccaacta    120
tgagtgtgct tggatcactt tgacgataca ttcttcgttg gaggctgtgg gtctgacagc    180
tgcgttttcg gcgcggttgg ccgacaacaa tatcagctgc aacgtcattg ctggctttca    240
```

```
tcatgatcac attttttgtcg gcaaaggcga cgcccagaga gccattgacg ttctttctaa    300
tttggaccga tagccgtata gtccagtcta tctataagtt caactaactc gtaactatta    360
ccataacata tacttcactg ccccagataa ggttccgata aaaagttctg cagactaaat    420
ttatttcagt ctcctcttca ccaccaaaat gccctcctac gaagctcgag ctaacgtcca    480
caagtccgcc tttgccgctc gagtgctcaa gctcgtggca gccaagaaaa ccaacctgtg    540
tgcttctctg gatgttacca ccaccaagga gctcattgag cttgccgata aggtcggacc    600
ttatgtgtgc atgatcaaaa cccatatcga catcattgac gacttcacct acgccggcac    660
tgtgctcccc ctcaaggaac ttgctcttaa gcacggtttc ttcctgttcg aggacagaaa    720
gttcgcagat attggcaaca ctgtcaagca ccagtaccgg tgtcaccgaa tcgccgagtg    780
gtccgatatc accaacgccc acggtgtacc cggaaccgga atcattgctg gcctgcgagc    840
tggtgccgag gaaactgtct ctgaacagaa gaaggaggac gtctctgact acgagaactc    900
ccagtacaag gagttcctag tccccctctcc caacgagaag ctggccagag gtctgctcat    960
gctggccgag ctgtcttgca agggctctct ggccactggc gagtactcca agcagaccat   1020
tgagcttgcc cgatccgacc ccgagtttgt ggttggcttc attgcccaga accgacctaa   1080
gggcgactct gaggactggc ttattctgac ccccggggtg ggtcttgacg acaagggaga   1140
cgctctcgga cagcagtacc gaactgttga ggatgtcatg tctaccggaa cggatatcat   1200
aattgtcggc cgaggtctgt acggccagaa ccgagatcct attgaggagg ccaagcgata   1260
ccagaaggct ggctgggagg cttaccagaa gattaactgt tagaggttag actatggata   1320
tgtaatttaa ctgtgtatat agagagcgtg caagtatgga gcgcttgttc agcttgtatg   1380
atggtcagac gacctgtctg atcgagtatg tatgatactg cacaacctgt gtatccgcat   1440
gatctgtcca atggggcatg ttgttgtgtt tctcgatacg gagatgctgg gtacagtgct   1500
aatacgttga actacttata cttatatgag gctcgaagaa agctgacttg tgtatgactt   1560
attctcaact acatccccag tcacaatacc accactgcac taccactaca ccaaaaccat   1620
gatcaaacca cccatggact tcctggaggc agaagaactt gttatggaaa agctcaagag   1680
agagatcata acttcgtata gcatacatta tacgaagtta tcctgcaggt aaaggaattc   1740 tggagttttct gagagaaaaa ggcaagatac gtatgtaaca aagcgacgca tggtacaata   1800
ataccggagg catgtatcat agagagttag tggttcgatg atggcactgg tgcctggtat   1860
gactttatac ggctgactac atatttgtcc tcagacatac aattacagtc aagcacttac   1920
ccttggacat ctgtaggtac ccccggcca agacgatctc agcgtgtcgt atgtcggatt   1980
ggcgtagctc cctcgctcgt caattggctc ccatctactt tcttctgctt ggctacaccc   2040
agcatgtctg ctatggctcg ttttcgtgcc ttatctatcc tcccagtatt accaactcta   2100
aatgacatga tgtgattggg tctacacttt catatcagag ataaggagta gcacagttgc   2160
ataaaaagcc caactctaat cagcttcttc ctttcttgta attagtacaa aggtgattag   2220
cgaaatctgg aagcttagtt ggccctaaaa aaatcaaaaa aagcaaaaaa cgaaaaacga   2280
aaaaccacag ttttgagaac agggaggtaa cgaaggatcg tatatatata tatatatata   2340
tatacccacg gatcccgaga ccggcctttg attcttccct acaaccaacc attctcacca   2400
ccctaattca caaccatgga gtctggaccc atgcctgctg gcattccctt ccctgagtac   2460
tatgacttct ttatggactg gaagactccc ctggccatcg ctgccaccta cactgctgcc   2520
gtcggtctct tcaaccccaa ggttggcaag gtctcccgag tggttgccaa gtcggctaac   2580
gcaaagcctg ccgagcgaac ccagtccgga gctgccatga ctgccttcgt ctttgtgcac   2640
```

-continued

```
aacctcattc tgtgtgtcta ctctggcatc accttctact acatgtttcc tgctatggtc   2700
aagaacttcc gaacccacac actgcacgaa gcctactgcg acacggatca gtccctctgg   2760
aacaacgcac ttggctactg gggttacctc ttctacctgt ccaagttcta cgaggtcatt   2820
gacaccatca tcatcatcct gaagggacga cggtcctcgc tgcttcagac ctaccaccat   2880
gctggagcca tgattaccat gtggtctggc atcaactacc aagccactcc catttggatc   2940
tttgtggtct tcaactcctt cattcacacc atcatgtact gttactatgc cttcacctct   3000
atcggattcc atcctcctgg caaaaagtac ctgacttcga tgcagattac tcagtttctg   3060
gtcggtatca ccattgccgt gtcctacctc ttcgttcctg gctgcatccg aacacccggt   3120
gctcagatgg ctgtctggat caacgtcggc tacctgtttc ccttgaccta tctgttcgtg   3180
gactttgcca agcgaaccta ctccaagcga tctgccattg ccgctcagaa aaaggctcag   3240
taagcggccg cattgatgat tggaaacaca cacatgggtt atatctaggt gagagttagt   3300
tggacagtta tatattaaat cagctatgcc aacggtaact tcattcatgt caacgaggaa   3360
ccagtgactg caagtaatat agaatttgac caccttgcca ttctcttgca ctcctttact   3420
atatctcatt tatttcttat atacaaatca cttcttcttc ccagcatcga gctcggaaac   3480
ctcatgagca ataacatcgt ggatctcgtc aatagagggc tttttggact ccttgctgtt   3540
ggccaccttg tccttgctgt ctggctcatt ctgtttcaac gccttttaat taacggagta   3600
ggtctcggtg tcggaagcga cgccagatcc gtcatcctcc tttcgctctc caaagtagat   3660
acctccgacg agctctcgga caatgatgaa gtcggtgccc tcaacgtttc ggatggggga   3720
gagatcggcg agcttgggcg acagcagctg gcagggtcgc aggttggcgt acaggttcag   3780
gtcctttcgc agcttgagga gaccctgctc gggtcgcacg tcggttcgtc cgtcgggagt   3840
ggtccatacg gtgttggcag cgcctccgac agcaccgagc ataatagagt cagcctttcg   3900
gcagatgtcg agagtagcgt cggtgatggg ctcgccctcc ttctcaatgg cagctcctcc   3960
aatgagtcgg tcctcaaaca caaactcggt gccggaggcc tcagcaacag acttgagcac   4020
cttgacggcc tcggcaatca cctcggggcc acagaagtcg ccgccgagaa gaacaatctt   4080
cttggagtca gtcttggtct tcttagtttc gggttccatt gtggatgtgt gtggttgtat   4140
gtgtgatgtg gtgtgtggag tgaaaatctg tggctggcaa acgctcttgt atatatacgc   4200
acttttgccc gtgctatgtg gaagactaaa cctccgaaga ttgtgactca ggtagtgcgg   4260
tatcggctag ggacccaaac cttgtcgatg ccgatagcat gcgacgtcgg gcccaattcg   4320
ccctatagtg agtcgtatta caattcactg gccgtcgttt tacaacgtcg tgactgggaa   4380
aaccctggcg ttacccaact taatcgcctt gcagcacatc cccctttcgc cagctggcgt   4440
aatagcgaag aggcccgcac cgatcgccct tcccaacagt tgcgcagcct gaatggcgaa   4500
tggacgcgcc ctgtagcggc gcattaagcg cggcgggtgt ggtggttacg cgcagcgtga   4560
ccgctacact tgccagcgcc ctagcgcccg ctcctttcgc tttcttccct tcctttctcg   4620
ccacgttcgc cggctttccc cgtcaagctc taaatcgggg gctcccttta gggttccgat   4680
ttagtgcttt acggcacctc gaccccaaaa aacttgatta gggtgatggt tcacgtagtg   4740
ggccatcgcc ctgatagacg gtttttcgcc ctttgacgtt ggagtccacg ttctttaata   4800
gtggactctt gttccaaact ggaacaacac tcaaccctat ctcggtctat tcttttgatt   4860
tataagggat tttgccgatt tcggcctatt ggttaaaaaa tgagctgatt taacaaaaat   4920
ttaacgcgaa ttttaacaaa atattaacgc ttacaatttc ctgatgcggt attttctcct   4980
tacgcatctg tgcggtattt cacaccgcat caggtggcac ttttcgggga aatgtgcgcg   5040
```

```
gaaccccagat ttgtttattt tctaaaatac attcaaatat gtatccgctc atgagacaat    5100
aaccctgata aatgcttcaa taatattgaa aaaggaagag tatgagtatt caacatttcc    5160
gtgtcgccct tattccctt tttgcggcat tttgccttcc tgttttgct cacccagaaa    5220 cgctggtgaa agtaaaagat gctgaagatc agttgggtgc acgagtgggt tacatcgaac    5280
tggatctcaa cagcggtaag atccttgaga gttttcgccc cgaagaacgt tttccaatga    5340
tgagcacttt taaagttctg ctatgtggcg cggtattatc ccgtattgac gccgggcaag    5400
agcaactcgg tcgccgcata cactattctc agaatgactt ggttgagtac tcaccagtca    5460
cagaaaagca tcttacggat ggcatgacag taagagaatt atgcagtgct gccataacca    5520
tgagtgataa cactgcggcc aacttacttc tgacaacgat cggaggaccg aaggagctaa    5580 ccgcttttt gcacaacatg ggggatcatg taactcgcct tgatcgttgg aaccggagc    5640 tgaatgaagc cataccaaac gacgagcgtg acaccacgat gcctgtagca atggcaacaa    5700
cgttgcgcaa actattaact ggcgaactac ttactctagc ttcccggcaa caattaatag    5760
actggatgga ggcggataaa gttgcaggac cacttctgcg ctcggccctt ccggctggct    5820
ggtttattgc tgataaatct ggagccggtg agcgtgggtc tcgcggtatc attgcagcac    5880
tggggccaga tggtaagccc tcccgtatcg tagttatcta cacgacgggg agtcaggcaa    5940
ctatggatga acgaaataga cagatcgctg agataggtgc ctcactgatt aagcattggt    6000
aactgtcaga ccaagtttac tcatatatac tttagattga tttaaaactt catttttaat    6060 ttaaaggat ctaggtgaag atcctttttg ataatctcat gaccaaaatc ccttaacgtg    6120
agttttcgtt ccactgagcg tcagaccccg tagaaaagat caaaggatct tcttgagatc    6180 cttttttct gcgcgtaatc tgctgcttgc aaacaaaaaa accaccgcta ccagcggtgg    6240
tttgtttgcc ggatcaagag ctaccaactc tttttccgaa ggtaactggc ttcagcagag    6300
cgcagatacc aaatactgtt cttctagtgt agccgtagtt aggccaccac ttcaagaact    6360
ctgtagcacc gcctacatac ctcgctctgc taatcctgtt accagtggct gctgccagtg    6420
gcgataagtc gtgtcttacc gggttggact caagacgata gttaccggat aaggcgcagc    6480
ggtcgggctg aacggggggt tcgtgcacac agcccagctt ggagcgaacg acctacaccg    6540
aactgagata cctacagcgt gagctatgag aaagcgccac gcttcccgaa gggagaaagg    6600
cggacaggta tccggtaagc ggcagggtcg aacaggaga cgcacgagg gagcttccag    6660 ggggaaacgc ctggtatctt tatagtcctg tcgggtttcg ccacctctga cttgagcgtc    6720
gatttttgtg atgctcgtca ggggggcgga gcctatggaa aaacgccagc aacgcggcct    6780
ttttacggtt cctggccttt tgctggcctt ttgctcacat gttctttcct gcgttatccc    6840
ctgattctgt ggataaccgt attaccgcct ttgagtgagc tgataccgct cgccgcagcc    6900
gaacgaccga gcgcagcgag tcagtgagcg aggaagcgga agagcgccca atacgcaaac    6960
cgcctctccc cgcgcgttgg ccgattcatt aatgcagctg gcgcgccac tgagctcgtc    7020 taacggactt gatatacaac caattaaaac aaatgaaaag aaatacagtt ctttgtatca    7080
tttgtaacaa ttaccctgta caaactaagg tattgaaatc ccacaatatt cccaaagtcc    7140
acccctttcc aaattgtcat gcctacaact catataccaa gcactaacct accaaacacc    7200
actaaaaccc cacaaaatat atcttaccga atatacagta acaagctacc accacactcg    7260
ttgggtgcag tcgccagctt aaagatatct atccacatca gccacaactc ccttcctta    7320 ataaaccgac tacaccttg gctattgagg ttatgagtga atatactgta gacaagacac    7380
tttcaagaag actgtttcca aaacgtacca ctgtcctcca ctacaaacac acccaatctg    7440
```

```
cttcttctag tcaaggttgc tacaccggta aattataaat catcatttca ttagcagggc    7500
agggcccttt ttatagagtc ttatacacta gcggaccctg ccggtagacc aacccgcagg    7560
cgcgtcagtt tgctccttcc atcaatgcgt cgtagaaacg acttactcct tcttgagcag    7620
ctccttgacc ttgttggcaa caagtctccg acctcgagg tggaggaaga gcctccgata    7680
tcggcggtag tgataccagc ctcgacggac tccttgacgg cagcctcaac agcgtcaccg    7740
gcgggcttca tgttaagaga gaacttgagc atcatggcgg cagacagaat ggtgcgtac    7800 gcaactaaca tgaatgaata cgatatacat caaagactat gatacgcagt attgcacact    7860
gtacgagtaa gagcactagc cactgcactc aagtgaaacc gttgcccggg tacgagtatg    7920
agtatgtaca gtatgtttag tattgtactt ggacagtgct tgtatcgtac attctcaagt    7980
gtcaaacata aatatccgtt gctatatcct cgcaccacca cgtagctcgc tatatccctg    8040
tgttgaatcc atccatcttg gattgccaat tgtgcacaca gaaccgggca ctcacttccc    8100
catccacact tgcggccgct taagcaacgg gcttgataac agcgggggg gtgcccacgt    8160 tgttgcggtt gcggaagaac agaacaccct taccagcacc ctcggcacca gcgctgggct    8220
caacccactg gcacatacgc gcactgcggt acatggcgcg gatgaagcca cgaggaccat    8280
cctggacatc agcccggtag tgcttgccca tgatgggctt aatggcctcg gtggcctcgt    8340
ccgcgttgta gaagggaatg ctgctgacgt agtggtggag gacatgagtc tcgatgatgc    8400
cgtggagaag gtggcggccg atgaagccca tctcacggtc aatggtagca gcggcaccac    8460
ggacgaagtt ccactcgtcg ttggtgtagt ggggaagggt agggtcggtg tgctggagga    8520
aggtgatggc aacgagccag tggttaaccc agaggtaggg aacaaagtac cagatggcca    8580
tgttgtagaa accgaacttc tgaacgagga agtacagagc agtggccatc agaccgatac    8640
caatatcgct gaggacgatg agcttagcgt cactgttctc gtacagaggg ctgcggggat    8700
cgaagtggtt aacaccaccg ccgaggccgt tatgcttgcc cttgccgcga ccctcacgct    8760
ggcgctcgtg gtagttgtgg ccggtaacat tggtgatgag gtagttgggc cagccaacga    8820
gctgctgaag gacgagcatg agaagagtga agcgggggt ctcctcagta agatgagcga    8880
gctcgtgggt catcttccg agacgagtag cctgctgctc gcgggttcgg ggaacgaaga    8940
ccatgtcacg ctccatgttg ccagtggcct tgtggtgctt tcggtgggag atttgccagc    9000
tgaagtaggg gacaaggagg gaagagtgaa gaacccagcc agtaatgtcg ttgatgatgc    9060
gagaatcgga gaaagcaccg tgaccgcact catgggcaat aacccagaga ccagtaccga    9120
aaagaccctg aagaacggtg tacacggccc acagaccagc gcgggcgggg gtggagggga    9180
tatattcggg ggtcacaaag ttgtaccaga tgctgaaagt ggtagtcagg aggacaatgt    9240
cgcggaggat ataaccgtat cccttgagag cggagcgctt gaagcagtgc ttagggatgg    9300
cattgtagat gtccttgatg gtaaagtcgg gaacctcgaa ctggttgccg taggtgtcga    9360
gcatgacacc atactcggac ttgggcttgg cgatatcaac ctcggacatg gacgagagcg    9420
atgtggaaga ggccgagtgg cggggagagt ctgaaggaga gacggcggca gactcagaat    9480
ccgtcacagt agttgaggtg acggtgcgtc taagcgcagg gttctgcttg gcagagccg    9540 aagtggacgc catggttgat gtgtgtttaa ttcaagaatg aatatagaga agagaagaag    9600 aaaaagagatt caattgagcc ggcgatgcag acccttatat aaatgttgcc ttggacagac    9660
ggagcaagcc cgcccaaacc tacgttcggt ataatatgtt aagctttta acacaaaggt    9720 ttggcttggg gtaacctgat gtggtgcaaa agaccgggcg ttggcgagcc attgcgcggg    9780
cgaatggggc cgtgactcgt ctcaaattcg agggcgtgcc tcaattcgtg cccccgtggc    9840
```

```
tttttcccgc cgtttccgcc ccgtttgcac cactgcagcc gcttctttgg ttcggacacc    9900
ttgctgcgag ctaggtgcct tgtgctactt aaaaagtggc ctcccaacac caacatgaca    9960
tgagtgcgtg ggccaagaca cgttggcggg gtcgcagtcg gctcaatggc ccggaaaaaa   10020
cgctgctgga gctggttcgg acgcagtccg ccgcggcgta tggatatccg caaggttcca   10080
tagcgccatt gccctccgtc ggcgtctatc ccgcaacctc taaatagagc gggaatataa   10140
cccaagcttc ttttttttcc tttaacacgc acacccccaa ctatcatgtt gctgctgctg   10200
tttgactcta ctctgtggag gggtgctccc acccaaccca acctacaggt ggatccggcg   10260
ctgtgattgg ctgataagtc tcctatccgg actaattctg accaatggga catgcgcgca   10320
ggacccaaat gccgcaatta cgtaaccccca acgaaatgcc tacccctctt tggagcccag   10380
```

```
cgtgccaaag ggtcctaggt gcgtttcgcg agctgggcgc caggccaagc cgctccaaaa    12300
cgcctctccg actccctcca gcggcctcca tatccccatc cctctccaca gcaatgttgt    12360
taagccttgc aaacgaaaaa atagaaaggc taataagctt ccaatattgt ggtgtacgct    12420
gcataacgca acaatgagcg ccaaacaaca cacacacaca gcacacagca gcattaacca    12480
cgatgaacag catgacatta caggtgggtg tgtaatcagg gccctgattg ctggtggtgg    12540
gagcccccat catgggcaga tctgcgtaca ctgtttaaac agtgtacgca gatctactat    12600
agaggaacat ttaaattgcc ccggagaaga cggccaggcc gcctagatga caaattcaac    12660
aactcacagc tgactttctg ccattgccac tagggggggg cctttttata tggccaagcc    12720
aagctctcca cgtcggttgg gctgcaccca acaataaatg ggtagggttg caccaacaaa    12780
gggatgggat gggggtaga agatacgagg ataacgggc tcaatggcac aaataagaac       12840
gaatactgcc attaagactc gtgatccagc gactgacacc attgcatcat ctaagggcct    12900
caaaactacc tcggaactgc tgcgctgatc tggacaccac agaggttccg agcactttag    12960
gttgcaccaa atgtcccacc aggtgcaggc agaaaacgct ggaacagcgt gtacagtttg    13020
tcttaacaaa aagtgagggc gctgaggtcg agcagggtgg tgtgacttgt tatagccttt    13080
agagctgcga aagcgcgtat ggatttggct catcaggcca gattgagggt ctgtggacac    13140
atgtcatgtt agtgtacttc aatcgccccc tggatatagc cccgacaata ggccgtggcc    13200
tcattttttt gccttccgca catttccatt gctcgatacc cacaccttgc ttctcctgca    13260
cttgccaacc ttaatactgg tttacattga ccaacatctt acaagcgggg ggcttgtcta    13320
gggtatatat aaacagtggc tctcccaatc ggttgccagt ctcttttttc ctttctttcc    13380
ccacagattc gaaatctaaa ctacacatca cagaattccg agccgtgagt atccacgaca    13440
agatcagtgt cgagacgacg cgttttgtgt aatgacacaa tccgaaagtc gctagcaaca    13500
cacactctct acacaaacta acccagctct ggtaccatgg aggtcgtgaa cgaaatcgtc    13560
tccattggcc aggaggttct tcccaaggtc gactatgctc agctctggtc tgatgcctcg    13620
cactgcgagg tgctgtacct ctccatcgcc ttcgtcatcc tgaagttcac ccttggtcct    13680
ctcggaccca agggtcagtc tcgaatgaag tttgtgttca ccaactacaa cctgctcatg    13740
tccatctact cgctgggctc cttcctctct atggcctacg ccatgtacac cattggtgtc    13800
atgtccgaca actgcgagaa ggcttttcgac aacaatgtct tccgaatcac cactcagctg    13860
ttctacctca gcaagttcct cgagtacatt gactccttct atctgcccct catgggcaag    13920
cctctgacct ggttgcagtt cttttcaccat ctcggagctc ctatggacat gtggctgttc    13980
tacaactacc gaaacgaagc cgtttggatc tttgtgctgc tcaacggctt cattcactgg    14040
atcatgtacg gctactattg gacccgactg atcaagctca gttccctat gcccaagtcc     14100 ctgattactt ctatgcagat cattcagttc aacgttggct tctacatcgt ctggaagtac    14160
cggaacattc cctgctaccg acaagatgga atgagaatgt ttggctggtt tttcaactac    14220
ttctacgttg gtactgtcct gtgtctgttc ctcaacttct acgtgcagac ctacatcgtc    14280
cgaaagcaca agggagccaa aaagattcag tgagcggccg catgtacata caagattatt    14340
tatagaaatg aatcgcgatc gaacaaagag tacgagtgta cgagtagggg atgatgataa    14400
aagtggaaga agttccgcat cttttggattt atcaacgtgt aggacgatac ttcctgtaaa    14460
aatgcaatgt ctttaccata ggttctgctg tagatgttat taactaccat taacatgtct    14520
acttgtacag ttgcagacca gttggagtat agaatggtac acttaccaaa aagtgttgat    14580
ggttgtaact acgatatata aaactgttga cgggatcccc gctgatatgc ctaaggaaca    14640
```

-continued

| | |
|---|---:|
| atcaaagagg aagatattaa ttcagaatgc tagtatacag ttagggat | 14688 |

<210> SEQ ID NO 39
<211> LENGTH: 15337
<212> TYPE: DNA
<213> ORGANISM: Artificial Sequence
<220> FEATURE:
<223> OTHER INFORMATION: Plasmid pKO2UF8289

<400> SEQUENCE: 39

| | |
|---|---:|
| cgatcgagga agaggacaag cggctgcttc ttaagtttgt gacatcagta tccaaggcac | 60 |
| cattgcaagg attcaaggct tgaacccgt catttgccat tcgtaacgct ggtagacagg | 120 |
| ttgatcggtt ccctacggcc tccacctgtg tcaatcttct caagctgcct gactatcagg | 180 |
| acattgatca acttcggaag aaacttttgt atgccattcg atcacatgct ggtttcgatt | 240 |
| tgtcttagag gaacgcatat acagtaatca tagagaataa acgatattca tttattaaag | 300 |
| tagatagttg aggtagaagt tgtaaagagt gataaatagc ggccgctcac tgaatctttt | 360 |
| tggctccctt gtgcttcctg acgatatacg tttgcacata gaaattcaag aacaaacaca | 420 |
| agactgtgcc aacataaaag taattgaaga accagccaaa catcctcatc ccatcttggc | 480 |
| gataacaggg aatgttcctg tacttccaga caatgtagaa accaacattg aattgaatga | 540 |
| tctgcattga tgtaatcagg gattttggca tggggaactt cagcttgatc aatctggtcc | 600 |
| aataataacc gtacatgatc cagtggatga aaccattcaa cagcacaaaa atccaaacag | 660 |
| cttcatttcg gtaattatag aacagccaca tatccatcgg tgcccccaaa tgatggaaga | 720 |
| attgcaacca ggtcagaggc ttgcccatca gtggcaaata gaaggagtca atatactcca | 780 |
| ggaacttgct caaatagaac aactgcgtgg tgatcctgaa gacgttgttg tcaaaagcct | 840 |
| tctcgcagtt gtcagacata acaccgatgg tgtacatggc atatgccatt gagaggaatg | 900 |
| atcccaacga ataaatggac atgagaaggt tgtaattggt gaaaacaaac ttcatcgag | 960 |
| actgaccttt tggaccaagg gggccaagag tgaacttcaa gatgacaaat gcgatggaca | 1020 |
| agtaaagcac ctcacagtga ctggcatcac tccagagttg gcataatca actggttggg | 1080 |
| taaaacttcc tgcccaattg agactatttc attcaccacc tccatggtta gcgtgtcgtg | 1140 |
| tttttgttgt gctggaagaa ccaaaggggtg gcgcaatgtg tgtagatata tatgtcgtga | 1200 |
| cccacaagtc acacaaacaa gtatcgggag gagtggtgca cctctatgcg gagaaacctt | 1260 |
| ataccgctgt agaccaactg gggcagaggt gtgagttgaa gtcagctgga ggagatgtgt | 1320 |
| gacagaagca caagaagtga gattgtgaga tgtatgtcta gggggggaag ttttgtgtca | 1380 |
| aatatatggg aattattatc agcaccacga aattatacgc ctcatatgac ccatttaggt | 1440 |
| ggatagatca tggacactgt tgacagctgc gaagaaaaag cgtattgggg atgatccgaa | 1500 |
| attagtccgg taccgaggcg caaatacgta agacagccga twaaatatat gcgagaaaca | 1560 |
| ccaaagagac tctagatgtt tgtttggcac agttttgact tctgcgaagg ccttacacca | 1620 |
| ccttgttgac ccttgtcgcg ggtcgggcaa tatcggctga cagagtttta cttgctcaat | 1680 |
| aagatacgag ctgcatagag ttgaactaca ggacaatatt gggctggcc acatgaaggg | 1740 |
| cattgtttgg aggtgtattg atggtgaaaa cacgatatga aatgacaacg cccctgttt | 1800 |
| tattattatt cttattattt tgggtgcttc tctatcccata caagcacctc ctaacatgct | 1860 |
| tcataagtga cctcctcatc acaaggcctg aggtctcatt tatccagtgg cgccaagcta | 1920 |
| aactaaaact ggtccgagta gactaaggcg aagagagaag gagagaagac agttttttg | 1980 |
| tggccgcctg tgaacaatga aaacgatgag ggtgagatgg agcaaaccat atggtttaaa | 2040 |

-continued

```
cagtcagagg agtacacgct gcttacataa tggcgcaacg accacatgtc ccacagatac    2100
gcatcgattc gattcaaatt aattaaaagg cgttgaaaca gaatgagcca gacagcaagg    2160
acaaggtggc caacagcaag gagtccaaaa agccctctat tgacgagatc cacgatgtta    2220
ttgctcatga ggtttccgag ctcgatgctg gaagaagaa gtgatttgta tataagaaat     2280
aaatgagata tagtaaagga gtgcaagaga atggcaaggt ggtcaaattc tatattactt    2340
gcagtcactg gttcctcgtt gacatgaatg aagttaccgt tggcatagct gatttaatat    2400
ataactgtcc aactaactct cacctagata taacccatgt gtgtgtttcc aatcatcaat    2460
gcggccgctt actgagcctt ggcaccgggc tgcttctcgg ccattcgagc gaactgggac    2520
aggtatcgga gcaggatgac gagaccttca tggggcagag ggtttcggta ggggaggttg    2580
tgcttctggc acagctgttc cacctggtag gaaacggcag tgaggttgtg tcgaggcagg    2640
gtgggccaga gatggtgctc gatctggtag ttcaggcctc caaagaacca gtcagtaatg    2700
atgcctcgtc gaatgttcat ggtctcatgg atctgaccca cagagaagcc atgtccgtcc    2760
cagacggaat caccgatctt ctccagaggg tagtggttca tgaagaccac gatggcaatt    2820
ccgaagccac cgacgagctc ggaaacaaag aacaccagca tcgaggtcag gatggagggc    2880
ataaagaaga ggtggaacag ggtcttgaga gtccagtgca gagcgagtcc aatggcctct    2940
ttcttgtact gagatcggta gaactggttg tctcggtcct tgagggatcg aacggtcagc    3000
acagactgga aacaccagat gaatcgcagg agaatacaga tgaccaggaa atagtactgt    3060
tggaactgaa tgagctttcg ggagatggga gaagctcgag tgacatcgtc ctcggaccag    3120
gcgagcagag gcaggttatc aatgtcggga tcgtgaccct gaacgttggt agcagaatga    3180
tgggcgttgt gtctgtcctt ccaccaggtc acggagaagc cctggagtcc gttgccaaag    3240
accagaccca ggacgttatt ccagtttcgg ttcttgaagg tctggtggtg gcagatgtca    3300
tgagacagcc atcccatttg ctggtagtgc ataccgagca cgagagcacc aatgaagtac    3360
aggtggtact ggaccagcat gaagaaggca agcacgccaa gacccagggt ggtcaagatc    3420
ttgtacgagt accagagggg agaggcgtca acatgccag tggcgatcag ctcttctcgg    3480
agctttcgga aatcctcctg agcttcgttg acggcagcct ggggaggcag ctcggaagcc    3540
tggttgatct tgggcattcg cttgagcttg tcgaaggctt cctgagagtg cataaccatg    3600
aaggcgtcag tagcatctcg tccctggtag ttctcaatga tttcagctcc accagggtgg    3660
aagttcaccc aagcggagac gtcgtacacc tttccgtcga tgacgagggg cagagcctgt    3720
cgagaagcct tcaccatggc cattgctgta gatatgtctt gtgtgtaagg gggttggggt    3780
ggttgtttgt gttcttgact tttgtgttag caagggaaga cgggcaaaaa agtgagtgtg    3840
gttgggaggg agagacgagc cttatatata atgcttgttt gtgtttgtgc aagtggacgc    3900
cgaaacgggc aggagccaaa ctaaacaagg cagacaatgc gagcttaatt ggattgcctg    3960
atgggcaggt gttagggctc gatcaatggg ggtgcgaagt gacaaaattg ggaattaggt    4020
tcgcaagcaa ggctgacaag actttggccc aaacatttgt acgcggtgga caacaggagc    4080
cacccatcgt ctgtcacggg ctagccggtc gtgcgtcctg tcaggctcca cctaggctcc    4140
atgccactcc atacaatccc actagtgtac cgctaggccg cttttagctc ccatctaaga    4200
cccccccaaa acctccactg tacagtgcac tgtactgtgt ggcgatcaag gcaagggaa     4260 aaaaggcgca acatgcacg catggaatga cgtaggtaag gcgttactag actgaaaagt     4320
ggcacatttc ggcgtgccaa agggtcctag gtgcgtttcg cgagctgggc gccaggccaa    4380
gccgctccaa aacgcctctc cgactccctc cagcggcctc catatcccca tccctctcca    4440
```

```
cagcaatgtt gttaagcctt gcaaacgaaa aaatagaaag gctaataagc ttccaatatt   4500
gtggtgtacg ctgcataacg caacaatgag cgccaaacaa cacacacaca cagcacacag   4560
cagcattaac cacgatgttt aaacagtgta cgcagatccc gtcaacagtt ttatatatcg   4620
tagttacaac catcaacact ttttggtaag tgtaccattc tatactccaa ctggtctgca   4680
actgtacaag tagacatgtt aatggtagtt aataacatct acagcagaac ctatggtaaa   4740
gacattgcat ttttacagga agtatcgtcc tacacgttga taaatccaaa gatgcggaac   4800
ttcttccact tttatcatca tcccctactc gtacactcgt actctttgtt cgatcgcgat   4860
tcatttctat aaataatctt gtatgtacat gcggccgctt aagcaacggg cttgataaca   4920
gcgggggggg tgcccacgtt gttgcggttg cggaagaaca gaacacccrtt accagcaccc   4980 tcggcaccag cgctgggctc aacccactgg cacatacgcg cactgcggta catgcgcgg    5040 atgaagccac gaggaccatc ctggacatca gcccggtagt gcttgcccat gatgggctta   5100
atggcctcgg tggcctcgtc cgcgttgtag aaggggatgc tgctgacgta gtggtggagg   5160
acatgagtct cgatgatgcc gtggagaagg tggcggccga tgaagcccat ctcacggtca   5220
atggtagcag cggcaccacg gacgaagttc cactcgtcgt tggtgtagtg gggaagggta   5280
gggtcggtgt gctggaggaa ggtgatggca acgagccagt ggttaaccca gaggtaggga   5340
acaaagtacc agatggccat gttgtagaaa ccgaacttct gaacgaggaa gtacagagca   5400
gtggccatca gaccgatacc aatatcgctg aggacgatga gcttagcgtc actgttctcg   5460
tacagagggc tgcggggatc gaagtggtta acaccaccgc cgaggccgtt atgcttgccc   5520
ttgccgcgac cctcacgctg gcgctcgtgg tagttgtggc cggtaacatt ggtgatgagg   5580
tagttgggcc agccaacgag ctgctgaagg acgagcatga aagagtgaa agcggggtc    5640 tcctcagtaa gatgagcgag ctcgtgggtc atctttccga gacgagtagc ctgctgctcg   5700
cgggttcggg gaacgaagac catgtcacgc tccatgttgc cagtggcctt gtggtgcttt   5760
cggtgggaga tttgccagct gaagtagggg acaaggaggg aagagtgaag aacccagcca   5820
gtaatgtcgt tgatgatgcg agaatcggag aaagcaccgt gaccgcactc atgggcaata   5880
acccagagac cagtaccgaa aagaccctga agaacggtgt acacggccca cagaccagcg   5940
cgggcggggg tggagggggat atattcgggg gtcacaaagt tgtaccagat gctgaaagtg   6000
gtagtcagga ggacaatgtc gcggaggata taaccgtatc ccttgagagc ggagcgcttg   6060
aagcagtgct tagggatggc attgtagatg tccttgatgg taaagtcggg aacctcgaac   6120
tggttgccgt aggtgtcgag catgacacca tactcggact tgggcttggc gatatcaacc   6180
tcggacatgg acgagagcga tgtggaagag gccgagtggc ggggagagtc tgaaggagag   6240
acggcggcag actcagaatc cgtcacagta gttgaggtga cggtgcgtct aagcgcaggg   6300
ttctgcttgg gcagagccga agtggacgcc atggttgtga attagggtgg tgagaatggt   6360
tggttgtagg gaagaatcaa aggccggtct cgggatccgt gggtatatat atatatatat   6420
atatatacga tccttcgtta cctccctgtt ctcaaaactg tggttttcg ttttcgttt    6480 tttgcttttt ttgattttttt tagggccaac taagcttcca gatttcgcta atcacctttg   6540
tactaattac aagaaaggaa gaagctgatt agagttgggc ttttatgca actgtgctac    6600 tccttatctc tgtatatgaaa gtgtagaccc aatcacatca tgtcatttag agttggtaat   6660
actgggagga tagataaggc acgaaaacga gccatagcag acatgctggg tgtagccaag   6720
cagaagaaag tagatgggag ccaattgacg agcgagggag ctacgccaat ccgacatacg   6780
acacgctgag atcgtcttgg ccgggggggta cctacagatg tccaagggta agtgcttgac   6840
```

```
tgtaattgta tgtctgagga caaatatgta gtcagccgta taaagtcata ccaggcacca    6900
gtgccatcat cgaaccacta actctctatg atacatgcct ccggtattat tgtaccatgc    6960
gtcgctttgt tacatacgta tcttgccttt ttctctcaga aactccagac tttggctatt    7020
ggtcgagata agcccggacc atagtgagtc tttcacactc tcatttctc ccttgctcca    7080 actatttaaa ttgccccgga gaagacggcc aggccgccta gatgacaaat tcaacaactc    7140
acagctgact ttctgccatt gccactaggg ggggcctttt ttatatggcc aagccaagct    7200
ctccacgtcg gttgggctgc acccaacaat aaatgggtag ggttgcacca acaaagggat    7260
gggatggggg gtagaagata cgaggataac gggctcaat ggcacaaata agaacgaata    7320
ctgccattaa gactcgtgat ccagcgactg acaccattgc atcatctaag ggcctcaaaa    7380
ctacctcgga actgctgcgc tgatctggac accacagagg ttccgagcac tttaggttgc    7440
accaaatgtc ccaccaggtg caggcagaaa acgctggaac agcgtgtaca gtttgtctta    7500
acaaaaagtg agggcgctga ggtcgagcag ggtggtgtga cttgttatag cctttagagc    7560
tgcgaaagcg cgtatggatt tggctcatca ggccagattg agggtctgtg gacacatgtc    7620
atgttagtgt acttcaatcg cccctggat atagccccga caataggccg tggcctcatt    7680
tttttgcctt ccgcacattt ccattgctcg gtacccacac cttgcttctc ctgcacttgc    7740
caaccttaat actggtttac attgaccaac atcttacaag cgggggggctt gtctagggta    7800 tatataaaca gtggctctcc caatcggttg ccagtctctt ttttcctttc tttccccaca    7860
gattcgaaat ctaaactaca catcacgaaa ttccgagccg tgagtatcca cgacaagatc    7920
agtgtcgaga cgacgcgttt tgtgtaatga cacaatccga aagtcgctag caacacacac    7980
tctctacaca aactaaccca gctctggtac catggtgaag gcttctcgac aggctctgcc    8040
cctcgtcatc gacggaaagg tgtacgacgt ctccgcttgg gtgaacttcc accctggtgg    8100
agctgaaatc attgagaact accagggacg agatgctact gacgccttca tggttatgca    8160
ctctcaggaa gccttcgaca agctcaagcg aatgcccaag atcaaccagg cttccgagct    8220
gcctccccag gctgccgtca acgaagctca ggaggatttc cgaaagctcc gagaagagct    8280
gatcgccact ggcatgtttg acgcctctcc cctctggtac tcgtacaaga tcttgaccac    8340
cctgggtctt ggcgtgcttg ccttcttcat gctggtccag taccacctgt acttcattgg    8400
tgctctcgtg ctcggtatgc actaccagca aatgggatgg ctgtctcatg acatctgcca    8460
ccaccagacc ttcaagaacc gaaactggaa taacgtcctg ggtctggtct ttggcaacgg    8520
actccagggc ttctccgtga cctggtggaa ggacagacac aacgcccatc attctgctac    8580
caacgttcag ggtcacgatc ccgacattga taacctgcct ctgctcgcct ggtccgagga    8640
cgatgtcact cgagcttctc ccatctcccg aaagctcatt cagttccaac agtactattt    8700
cctggtcatc tgtattctcc tgcgattcat ctggtgtttc cagtctgtgc tgaccgttcg    8760
atccctcaag gaccgagaca accagttcta ccgatctcag tacaagaaag aggccattgg    8820
actcgctctg cactggactc tcaagaccct gttccacctc ttctttatgc cctccatcct    8880
gacctcgatg ctggtgttct tgtttccga gctcgtcggt ggcttcggaa ttgccatcgt    8940
ggtcttcatg aaccactacc ctctggagaa gatcggtgat tccgtctggg acggacatgg    9000
cttctctgtg ggtcagatcc atgagaccat gaacattcga cgaggcatca ttactgactg    9060 gttcttttgga ggcctgaact accagatcga gcaccatctc tggcccaccc tgcctcgaca    9120
caacctcact gccgttttcct accaggtgga acagctgtgc cagaagcaca acctccccta    9180
ccgaaaccct ctgccccatg aaggtctcgt catcctgctc cgatacctgt cccagttcgc    9240
```

```
tcgaatggcc gagaagcagc ccggtgccaa ggctcagtaa gcggccgcaa gtgtggatgg   9300
ggaagtgagt gcccggttct gtgtgcacaa ttggcaatcc aagatggatg gattcaacac   9360
agggatatag cgagctacgt ggtggtgcga ggatatagca acggatattt atgtttgaca   9420
cttgagaatg tacgatacaa gcactgtcca agtacaatac taaacatact gtacatactc   9480
atactcgtac ccgggcaacg gtttcacttg agtgcagtgg ctagtgctct tactcgtaca   9540
gtgtgcaata ctgcgtatca tagtctttga tgtatatcgt attcattcat gttagttgcg   9600
tacgggtgaa gcttccactg gtcggcgtgg tagtggggca gagtgggggtc ggtgtgctgc   9660 aggtaggtga tggccacgag ccagtggttg acccacaggt aggggatcag gtagtagagg   9720
gtgacggaag ccaggcccca tcggttgatg gagtatgcga tgacggacat ggtgatacca   9780
ataccgacgt tagagatcca gatgttgaac cagtccttct tctcaaacag cggggcgttg   9840
gggttgaagt ggttgacagc ccatttgttg agcttgggga acttctgtcc ggtaacgtaa   9900
gacagcagat acagaggcca tccaaacacc tgctgggtga tgaggccgta gagggtcatg   9960
aggggagcgt cctcagcaag ctcagaccag tcatgggcgc ctcggttctc cataaactcc  10020
tttcggtcct tgggcacaaa caccatatca cgggtgaggt gaccagtgga cttgtggtgc  10080
atggagtggg tcagcttcca ggcgtagtaa gggaccagca tggaggagtg cagaacccat  10140
ccggtgacgt tgttgacggt gttagagtcg gagaaagcag agtggccaca ctcgtgggca  10200
agaacccaca gaccggtgcc aaacagaccc tggacaatgg agtacatggc ccaggccaca  10260
gctcggccgg aagccgaggg aataagaggc aggtacgcgt aggccatgta ggcaaaaacg  10320
gcgataaaga agcaggcgcg ccagctgcat taatgaatcg ccaacgcgc ggggagaggc  10380 ggtttgcgta ttgggcgctc ttccgcttcc tcgctcactg actcgctgcg ctcggtcgtt  10440
cggctgcggc gagcggtatc agctcactca aaggcggtaa tacggttatc cacagaatca  10500
ggggataacg caggaaagaa catgtgagca aaaggccagc aaaaggccag gaaccgtaaa  10560
aaggccgcgt tgctggcgtt tttccatagg ctccgccccc ctgacgagca tcacaaaaat  10620
cgacgctcaa gtcagaggtg gcgaaacccg acaggactat aaagatacca ggcgtttccc  10680
cctggaagct ccctcgtgcg ctctcctgtt ccgaccctgc cgcttaccgg atacctgtcc  10740
gcctttctcc cttcgggaag cgtggcgctt tctcatagct cacgctgtag gtatctcagt  10800
tcggtgtagg tcgttcgctc caagctgggc tgtgtgcacg aaccccccgt tcagcccgac  10860
cgctgcgcct tatccggtaa ctatcgtctt gagtccaacc cggtaagaca cgacttatcg  10920
ccactggcag cagccactgg taacaggatt agcagagcga ggtatgtagg cggtgctaca  10980
gagttcttga agtggtggcc taactacggc tacactagaa gaacagtatt tggtatctgc  11040
gctctgctga agccagttac cttcggaaaa agagttggta gctcttgatc cggcaaacaa  11100
accaccgctg gtagcggtgg tttttttgtt tgcaagcagc agattacgcg cagaaaaaaa  11160
ggatctcaag aagatccttt gatcttttct acggggtctg acgctcagtg gaacgaaaac  11220
tcacgttaag ggattttggt catgagatta tcaaaaagga tcttcaccta gatcctttta  11280
aattaaaaat gaagttttaa atcaatctaa agtatatatg agtaaacttg gtctgacagt  11340
taccaatgct taatcagtga ggcacctatc tcagcgatct gtctatttcg ttcatccata  11400
gttgcctgac tccccgtcgt gtagataact acgatacggg agggcttacc atctggcccc  11460
agtgctgcaa tgataccgcg agacccacgc tcaccggctc cagatttatc agcaataaac  11520
cagccagccg gaagggccga gcgcagaagt ggtcctgcaa ctttatccgc ctccatccag  11580
tctattaatt gttgccggga agctagagta agtagttcgc cagttaatag tttgcgcaac  11640
```

```
gttgttgcca ttgctacagg catcgtggtg tcacgctcgt cgtttggtat ggcttcattc   11700
agctccggtt cccaacgatc aaggcgagtt acatgatccc ccatgttgtg caaaaaagcg   11760
gttagctcct tcggtcctcc gatcgttgtc agaagtaagt tggccgcagt gttatcactc   11820
atggttatgg cagcactgca taattctctt actgtcatgc catccgtaag atgctttttct  11880 gtgactggtg agtactcaac caagtcattc tgagaatagt gtatgcggcg accgagttgc   11940
tcttgcccgg cgtcaatacg ggataatacc gcgccacata gcagaacttt aaaagtgctc   12000
atcattggaa aacgttcttc ggggcgaaaa ctctcaagga tcttaccgct gttgagatcc   12060
agttcgatgt aacccactcg tgcacccaac tgatcttcag catcttttac tttcaccagc   12120
gtttctgggt gagcaaaaac aggaaggcaa aatgccgcaa aaaagggaat aagggcgaca   12180
cggaaatgtt gaatactcat actcttcctt tttcaatatt attgaagcat ttatcagggt   12240
tattgtctca tgagcggata catatttgaa tgtatttaga aaaataaaca atagggggtt   12300
ccgcgcacat ttccccgaaa agtgccacct gatgcggtgt gaaataccgc acagatgcgt   12360
aaggagaaaa taccgcatca ggaaattgta agcgttaata ttttgttaaa attcgcgtta   12420 aattttgtt aaatcagctc attttttaac cataggccg aaatcggcaa atcccttat    12480 aaatcaaaag aatagaccga gatagggttg agtgttgttc cagtttggaa caagagtcca   12540
ctattaaaga acgtggactc caacgtcaaa gggcgaaaaa ccgtctatca gggcgatggc   12600
ccactacgtg aaccatcacc ctaatcaagt ttttgggt cgaggtgccg taaagcacta     12660
aatcggaacc ctaaagggag cccccgattt agagcttgac ggggaaagcc ggcgaacgtg   12720
gcgagaaagg aagggaagaa agcgaaagga gcgggcgcta gggcgctggc aagtgtagcg   12780
gtcacgctgc gcgtaaccac cacacccgcc gcgcttaatg cgccgctaca gggcgcgtcc   12840
attcgccatt caggctgcgc aactgttggg aagggcgatc ggtgcgggcc tcttcgctat   12900
tacgccagct ggcgaaaggg ggatgtgctg caaggcgatt aagttgggta acgccagggt   12960
tttcccagtc acgacgttgt aaaacgacgg ccagtgaatt gtaatacgac tcactatagg   13020
gcgaattggg cccgacgtcg catgcttgaa tctacaagta ggagggttgg agtgattaag   13080
tgaaacttct ttaacggctc tatgccagtt ctattgatat ccgaaacatc agtatgaagg   13140
tctgataagg gtgacttctt cccacagatt cgtatcagta cgagtacgag accggtactt   13200
gtaacagtat tgatactaaa gggaaactac aacggttgtc agcgtaatgt gacttcgccc   13260
atgaacgcag acacgcagtg ccgagtgcgg tgatatcgcc tactcgttac gtccatggac   13320
tacacaaccc ctcggcttcg cttggcttag cctcgggctc ggtgctgttc agttaaaaca   13380
caatcaaata acatttctac tttttagaag gcaggccgtc aggagcaact ccgactccat   13440
tgacgtttct aaacatctga atgccttcct taccttcaac aaactggcag gttcgggcga   13500
cagtgtaaag agacttgatg aagttggtgt cgtcgtgtcg gtagtgcttg cccatgacct   13560
tcttgatctt ctcagtggcg attcgggcgt tgtagaaggg aattccttta cctgcaggat   13620
aacttcgtat aatgtatgct atacgaagtt atgatctctc tcttgagctt ttccataaca   13680
agttcttctg cctccaggaa gtccatgggg ggtttgatca tggttttggt gtagtggtag   13740
tgcagtggtg gtattgtgac tggggatgta gttgagaata agtcatacac aagtcagctt   13800
tcttcgagcc tcatataagt ataagtagtt caacgtatta gcactgtacc cagcatctcc   13860
gtatcgagaa acacaacaac atgccccatt ggacagatca tgcggataca caggttgtgc   13920
agtatcatac atactcgatc agacaggtcg tctgaccatc atacaagctg aacaagcgct   13980
ccatacttgc acgctctcta tatacacagt taaattacat atccatagtc taacctctaa   14040
```

```
cagttaatct tctggtaagc ctcccagcca gccttctggt atcgcttggc ctcctcaata    14100
ggatctcggt tctggccgta cagacctcgg ccgacaatta tgatatccgt tccggtagac    14160
atgacatcct caacagttcg gtactgctgt ccgagagcgt ctcccttgtc gtcaagaccc    14220
accccggggg tcagaataag ccagtcctca gagtcgccct taggtcggtt ctgggcaatg    14280
aagccaacca caaactcggg gtcggatcgg gcaagctcaa tggtctgctt ggagtactcg    14340
ccagtggcca gagagccctt gcaagacagc tcggccagca tgagcagacc tctgccagc    14400 ttctcgttgg gagaggggac taggaactcc ttgtactggg agttctcgta gtcagagacg    14460
tcctccttct tctgttcaga gacagtttcc tcggcaccag ctcgcaggcc agcaatgatt    14520
ccggttccgg gtacaccgtg ggcgttggtg atatcggacc actcggcgat tcggtgacac    14580
cggtactggt gcttgacagt gttgccaata tctgcgaact ttctgtcctc gaacaggaag    14640
aaaccgtgct taagagcaag ttccttgagg gggagcacag tgccggcgta ggtgaagtcg    14700
tcaatgatgt cgatatgggt tttgatcatg cacacataag gtccgacctt atcggcaagc    14760
tcaatgagct ccttggtggt ggtaacatcc agagaagcac acaggttggt tttcttggct    14820
gccacgagct tgagcactcg agcggcaaag gcggacttgt ggacgttagc tcgagcttcg    14880
taggagggca ttttggtggt gaagaggaga ctgaaataaa tttagtctgc agaacttttt    14940
atcggaacct tatctggggc agtgaagtat atgttatggt aatagttacg agttagttga    15000
acttatagat agactggact atacggctat cggtccaaat tagaaagaac gtcaatggct    15060
ctctgggcgt cgccttttgcc gacaaaaatg tgatcatgat gaaagccagc aatgacgttg    15120
cagctgatat tgttgtcggc caaccgcgcc gaaaacgcag ctgtcagacc cacagcctcc    15180
aacgaagaat gtatcgtcaa agtgatccaa gcacactcat agttggagtc gtactccaaa    15240
ggcggcaatg acgagtcaga cagatactcg tcgacgcgat aacttcgtat aatgtatgct    15300
atacgaagtt atcgtacgat agttagtaga caacaat                              15337

<210> SEQ ID NO 40
<211> LENGTH: 13707
<212> TYPE: DNA
<213> ORGANISM: Artificial Sequence
<220> FEATURE:
<223> OTHER INFORMATION: Plasmid pZKSL-555R

<400> SEQUENCE: 40
aaacagtgta cgcagatctg cccatgatgg gggctcccac caccagcaat cagggccctg      60
attacacacc cacctgtaat gtcatgctgt tcatcgtggt taatgctgct gtgtgctgtg     120
tgtgtgtgtt gtttggcgct cattgttgcg ttatgcagcg tacaccacaa tattggaagc     180
ttattagcct ttctattttt tcgtttgcaa ggcttaacaa cattgctgtg gagagggatg     240
gggatatgga ggccgctgga gggagtcgga gaggcgtttt ggagcggctt ggcctggcgc     300
ccagctcgcg aaacgcacct aggaccctt ggcacgccga aatgtgccac ttttcagtct     360
agtaacgcct tacctacgtc attccatgcg tgcatgtttg cgccttttt cccttgccct     420 tgatcgccac acagtacagt gcactgtaca gtggaggttt tggggggggtc ttagatggga     480 gctaaaagcg gcctagcggt acactagtgg gattgtatgg agtggcatgg agcctaggtg     540
gagcctgaca ggacgcacga ccggctagcc cgtgacagac gatgggtggc tcctgttgtc     600
caccgcgtac aaatgtttgg gccaaagtct tgtcagcctt gcttgcgaac ctaattccca     660
attttgtcac ttcgcacccc cattgatcga gccctaaccc ctgcccatca ggcaatccaa     720
ttaagctcgc attgtctgcc ttgtttagtt tggctcctgc ccgttcggc gtccacttgc     780
```

```
acaaacacaa acaagcatta tatataaggc tcgtctctcc ctcccaacca cactcacttt    840
tttgcccgtc ttcccttgct aacacaaaag tcaagaacac aaacaaccac cccaaccccc    900
ttacacacaa gacatatcta cagcaatggc catggctctc tcccttacta ccgagcagct    960
gctcgagcga cccgacctgg ttgccatcga cggcattctc tacgatctgg aaggtcttgc   1020
caaggtccat cccggaggcg acttgatcct cgcttctggt gcctccgatg cttctcctct   1080
gttctactcc atgcacccct tacgtcaagc cgagaactcg aagctgcttc aacagttcgt   1140
gcgaggcaag cacgaccgaa cctccaagga cattgtctac acctacgact ctcccttgc    1200 acaggacgtc aagcgaacta tgcgagaggt catgaaaggt cggaactggt atgccacacc   1260
tggattctgg ctgcgaaccg ttggcatcat tgctgtcacc gccttttgcg agtggcactg   1320
ggctactacc ggaatggtgc tgtgggtct cttgactgga ttcatgcaca tgcagatcgg    1380
cctgtccatt cagcacgatg cctctcatgg tgccatcagc aaaaagccct gggtcaacgc   1440
tctctttgcc tacggcatcg acgtcattgg atcgtccaga tggatctggc tgcagtctca   1500
catcatgcga catcacacct acaccaatca gcatggtctc gacctggatg ccgagtccgc   1560
agaaccattc cttgtgttcc acaactaccc tgctgccaac actgctcgaa agtggtttca   1620
ccgattccag gcctggtaca tgtacctcgt gcttggagcc tacggcgttt cgctggtgta   1680
caaccctctc tacatcttcc gaatgcagca caacgcacc attcccgagt ctgtcacagc    1740
catgcgagag aacggctttc tgcgacggta ccgaaccctt gcattcgtta tgcgagcttt   1800
cttcatcttt cgaaccgcct tcttgccctg gtatctcact ggaacctccc tgctcatcac   1860
cattcctctg gtgcccactg ctaccggtgc cttcctcacc ttcttttca tcttgtctca    1920 caacttcgat ggctcggagc gaatccccga caagaactgc aaggtcaaga gctccgagaa   1980
ggacgttgaa gccgatcaga tcgactggta cagagctcag gtggagacct cttccaccta   2040
cggtggaccc attgccatgt tctttactgg cggtctcaac ttccagatcg agcatcacct   2100 cttcctcga atgtcgtctt ggcactatcc cttcgtgcag caagctgtcc gagagtgttg    2160
cgaacgacac ggagttcggt acgtcttcta ccctaccatt gtgggcaaca tcatttccac   2220
cctcaagtac atgcacaaag tcggtgtggt tcactgtgtc aaggacgctc aggattccta   2280
agcggccgca agtgtggatg gggaagtgag tgcccggttc tgtgtgcaca attggcaatc   2340
caagatggat ggattcaaca cagggatata gcgagctacg tggtggtgcg aggatatagc   2400
aacggatatt tatgtttgac acttgagaat gtacgataca agcactgtcc aagtacaata   2460
ctaaacatac tgtacatact catactcgta cccgggcaac ggtttcactt gagtgcagtg   2520
gctagtgctc ttactcgtac agtgtgcaat actgcgtatc atagtctttg atgtatatcg   2580
tattcattca tgttagttgc gtacgctgtg ttgttatg tggtgaagct tgacaatgga     2640
tggtgtgtcg tatcaggctg gggaacaatt gtgcttaagt atgctgcagt tgagtaagag   2700
tcatcgctcc accaaaataa agtttgccat tagggttgga gagagagatg gtggctggaa   2760
gaattaaatg acatcaagct gaggattgtg ggtgtgcaat aacacatgtt aggggtgacc   2820
tgtggctcga aatctgataa ttatttgta actttatgat tattcttaga tttttaata     2880 ttcctctata taacacataa gtagctgtcg tctagttgtt catagcctga ctcctgcaat   2940
agattagtgc agagtgattt tgtgcaattg agagccacgg ttgagtcaag tgactttgtg   3000
tgtgaagtca tcttacgttt caagtctcac aggttactca attggttggt tgtctgccct   3060
ttacagatat ttacagtacc tgagcgtaaa gtcgttcatc cacggaatga ctgttcctgt   3120
cacgcagtca tgatcatgga tgtggctggt caggaaccat tttggatagg agacttaggg   3180
```

-continued

```
attggactat tattgaaaaa actgagccga atatgatata gttctatttg aatgcagaac    3240
ttctgatggt caattcactt atttcaggca tatcggtcat ggtggcagct gccacgatgt    3300
tatctcgttg gaaacctcgg cgcgccagct gcattaatga atcggccaac gcgcggggag    3360
aggcggtttg cgtattgggc gctcttccgc ttcctcgctc actgactcgc tgcgctcggt    3420
cgttcggctg cggcgagcgg tatcagctca ctcaaaggcg gtaatacggt tatccacaga    3480
atcagggga t aacgcaggaa agaacatgtg agcaaaaggc cagcaaaagg ccaggaaccg    3540
taaaaaggcc gcgttgctgg cgttttttcca taggctccgc cccctgacg agcatcacaa    3600
aaatcgacgc tcaagtcaga ggtggcgaaa cccgacagga ctataaagat accaggcgtt    3660
tccccctgga agctccctcg tgcgctctcc tgttccgacc ctgccgctta ccggatacct    3720
gtccgccttt ctcccttcgg gaagcgtggc gctttctcat agctcacgct gtaggtatct    3780
cagttcggtg taggtcgttc gctccaagct gggctgtgtg cacgaacccc ccgttcagcc    3840
cgaccgctgc gccttatccg gtaactatcg tcttgagtcc aacccggtaa gacacgactt    3900
atcgccactg gcagcagcca ctggtaacag gattagcaga gcgaggtatg taggcggtgc    3960
tacagagttc ttgaagtggt ggcctaacta cggctacact agaagaacag tatttggtat    4020
ctgcgctctg ctgaagccag ttaccttcgg aaaaagagtt ggtagctctt gatccggcaa    4080
acaaaccacc gctggtagcg gtggtttttt tgtttgcaag cagcagatta cgcgcagaaa    4140
aaaaggatct caagaagatc ctttgatctt ttctacgggg tctgacgctc agtggaacga    4200
aaactcacgt taagggattt tggtcatgag attatcaaaa aggatcttca cctagatcct    4260
tttaaattaa aaatgaagtt ttaaatcaat ctaaagtata tatgagtaaa cttggtctga    4320
cagttaccaa tgcttaatca gtgaggcacc tatctcagcg atctgtctat ttcgttcatc    4380
catagttgcc tgactccccg tcgtgtagat aactacgata cgggagggct taccatctgg    4440
ccccagtgct gcaatgatac cgcgagaccc acgctcaccg gctccagatt tatcagcaat    4500
aaaccagcca gccggaaggg ccgagcgcag aagtggtcct gcaactttat ccgcctccat    4560
ccagtctatt aattgttgcc gggaagctag agtaagtagt tcgccagtta atagtttgcg    4620
caacgttgtt gccattgcta caggcatcgt ggtgtcacgc tcgtcgtttg gtatggcttc    4680
attcagctcc ggttcccaac gatcaaggcg agttacatga tcccccatgt tgtgcaaaaa    4740
agcggttagc tccttcggtc ctccgatcgt tgtcagaagt aagttggccg cagtgttatc    4800
actcatggtt atggcagcac tgcataattc tcttactgtc atgccatccg taagatgctt    4860
ttctgtgact ggtgagtact caaccaagtc attctgagaa tagtgtatgc ggcgaccgag    4920
ttgctcttgc ccggcgtcaa tacgggataa taccgcgcca catagcagaa ctttaaaagt    4980
gctcatcatt ggaaaacgtt cttcggggcg aaaactctca aggatcttac cgctgttgag    5040
atccagttcg atgtaaccca ctcgtgcacc caactgatct tcagcatctt ttactttcac    5100
cagcgtttct gggtgagcaa aaacaggaag gcaaaatgcc gcaaaaaagg gaataagggc    5160
gacacggaaa tgttgaatac tcatactctt cctttttcaa tattattgaa gcatttatca    5220
gggttattgt ctcatgagcg gatacatatt tgaatgtatt tagaaaaata aacaaatagg    5280
ggttccgcgc acatttcccc gaaaagtgcc acctgatgcg gtgtgaaata ccgcacagat    5340
gcgtaaggag aaaataccgc atcaggaaat tgtaagcgtt aatattttgt taaaattcgc    5400
gttaaatttt tgttaaatca gctcatttttt taaccaatag gccgaaatcg gcaaaatccc    5460
ttataaatca aaagaataga ccgagatagg gttgagtgtt gttccagttt ggaacaagag    5520
tccactatta agaacgtgg actccaacgt caaagggcga aaaccgtct atcagggcga    5580
```

```
tggcccacta cgtgaaccat caccctaatc aagttttttg gggtcgaggt gccgtaaagc   5640
actaaatcgg aaccctaaag ggagcccccg atttagagct tgacggggaa agccggcgaa   5700
cgtggcgaga aaggaaggga agaaagcgaa aggagcgggc gctagggcgc tggcaagtgt   5760
agcggtcacg ctgcgcgtaa ccaccacacc cgccgcgctt aatgcgccgc tacagggcgc   5820
gtccattcgc cattcaggct gcgcaactgt tgggaagggc gatcggtgcg gcctcttcg    5880 ctattacgcc agctggcgaa aggggatgt  gctgcaaggc gattaagttg ggtaacgcca   5940
gggttttccc agtcacgacg ttgtaaaacg acggccagtg aattgtaata cgactcacta   6000
tagggcgaat tgggcccgac gtcgcatgca ttccatagcc acacctttgc ctatggcttc   6060
acaaccgaag gcaattcgag aggtcgcgct tatggaatcg actcgtataa agctgaaggg   6120
aaagggagac gttccgagcg ctcagatgca atagtcgtcc agctaatgtg gattcaaaaa   6180 caacccaac  agtaatcttg aaaatttgaa cggatcaatc tgaacactct tgctccaggt   6240
cattcttcta acgcacatcc ccagagtcta gagggagttg tgttgtgaac atcctaataa   6300
acaatgcaat ggattcggga tatcttctgt ctcgccccct actcgatgtc gagtaaaccg   6360
atcaccaact aacaatactc ctccgcgttc tgccattgac tctcaaacag acatcgctat   6420
caacggaaca gcatatttta gcttcttagg acaataaata ttgataatgc cggctctccc   6480
tcggtatatt aagcaatcca ttcatacact cattcatcag gttaattta  tatatataat   6540 ttgtctattc aaacaccgta aattactggt accatcatct cctccttttc aaatacacgt   6600
ctatttgcat taatgaaatt actcgccaat tcgcagaacg tgtttgtcga acagagcctt   6660
agctcgggtc cagacaggag cagtgtctcg ctgaggaagc tgcaggagag ttaattaact   6720
cacctgcagg attgagacta tgaatggatt cccgtgcccg tattactcta ctaatttgat   6780
cttggaacgc gaaaatacgt ttctaggact ccaaagaatc tcaactcttg tccttactaa   6840
atatactacc catagttgat ggtttacttg aacagagagg acatgttcac ttgacccaaa   6900
gtttctcgca tctcttggat atttgaacaa cggcgtccac tgaccgtcag ttatccagtc   6960
acaaaacccc cacattcata cattcccatg tacgtttaca aagttctcaa ttccatcgtg   7020
caaatcaaaa tcacatctat tcattcatca tatataaacc catcatgtct actaacactc   7080
acaactccat agaaaacatc gactcagaac acacgctcca tgcggccgct taggaatcct   7140
gtgcgtcctt cacgcagtgg acgacaccca ccttatgcat gtacttcagg gtggagatga   7200
tgttgccgac gatggtaggg tagaaaacat atcgcactcc atgtcgttcg caacactccc   7260
ggaccgcctg ctgacgaag  gggtagtgcc aagacgacat ccggggaaag aggtggtgct   7320
cgatctggaa attgagaccg ccagtgaaga acatggcgat ggggccaccg tatgtggagg   7380
acgtctccac ctgcgcccga taccagtcaa tttggtcagc ctcaacgtcc ttctcagatc   7440
gcttaacctt gcagttcttg tcggggatcc gttcggagcc atcaaaattg tgggacaaaa   7500
tgaagaagaa cgtcaagaag gcaccagttg cggtgggcac cagaggaatg gtgatcagca   7560
atgaggtccc agtgaggtac cagggcaaga atgcggtccg gaagatgaag aaagctcgca   7620
tcacgaatgc aagtgtgcgg tagcgccgca gaaagccatt ttcccgcatg gccgtgacag   7680
actctgggat ggtgtcattg tgctgcatcc ggaaaatgta gagcgggttg tacaccagcg   7740
ataccccgta tgccccagc  acaaggtaca tgtaccaagc ctggaagcgg tggaaccact   7800
ttcgggcggt gtttgcggcg gggtagttgt ggaacaccag gaacggctct gccgactccg   7860
catccaggtc gaggccgtgc tggttggtgt aggtgtggtg ccgcatgatg tgcgactgca   7920
gccaaatcca ccgggacgat ccgatgacgt caatgccgta ggcgaagagg gcgttgaccc   7980
```

```
aaggcttctt gctgatggcc ccgtgggacg catcatgctg gatggataag ccgatctgca    8040
tgtgcatgaa tccagtcaac aggccccaca gcaccatccc cgtggtagcc cagtgccact    8100
cgcaaaaggc cgtcacggcg atgatcccaa cggtgcgcag ccagaagcca ggggttgcgt    8160
accagttcct ccctttcatc acctcgcgca ttgtccgctt aacgtcttgt gcgaagggag    8220
aatcatacgt gtagacaatg tccttcgagg tgcggtcatg cttccctcgg acgaactgtt    8280
gaagcaattt ggagttctcc ggtttgacgt atggatgcat tgaataaaag agaggggagg    8340
catcagaggc accagaagcg agaatcaaat ctcctcctgg atgaactttg caagcccctt    8400
caaggtcgta gaggatgcca tcaatcgcaa ccaaatcagg gcgttctaac agctgttctg    8460
tggtaagact gagagccatg gagagctggg ttagtttgtg tagagagtgt gtgttgctag    8520
cgactttcgg attgtgtcat tacacaaaac gcgtcgtctc gacactgatc ttgtcgtgga    8580
tactcacggc tcggacatcg tcgccgacga tgacaccgga cttttcgctta aggacgtcag    8640 taacaggcat tgtgtgatgt gtagtttaga tttcgaatct gtggggaaag aaaggaaaaa    8700
agagactggc aaccgattgg gagagccact gtttatatat accctagaca agccccccgc    8760
ttgtaagatg ttggtcaatg taaaccagta ttaaggttgg caagtgcagg agaagcaagg    8820
tgtgggtacc gagcaatgga aatgtgcgga aggcaaaaaa atgaggccac ggcctattgt    8880
cggggctata tccaggggggc gattgaagta cactaacatg acatgtgtcc acagaccctc    8940
aatctggcct gatgagccaa atccatacgc gctttcgcag ctctaaaggc tataacaagt    9000
cacaccaccc tgctcgacct cagcgccctc acttttttgtt aagacaaact gtacacgctg    9060
ttccagcgtt ttctgcctgc acctggtggg acatttggtg caacctaaag tgctcggaac    9120
ctctgtggtg tccagatcag cgcagcagtt ccgaggtagt tttgaggccc ttagatgatg    9180
caatggtgtc agtcgctgga tcacgagtct taatggcagt attcgttctt atttgtgcca    9240
ttgagccccg ttatcctcgt atcttctacc ccccatccca tccctttgtt ggtgcaaccc    9300 tacccatttta ttgttgggtg cagcccaacc gacgtggaga gcttggcttg gccatataaa    9360
aaggcccccc cctagtggca atggcagaaa gtcagctgtg agttgttgaa tttgtcatct    9420
aggcggcctg gccgtcttct ccggggcaat tgggctgtt ttttgggaca caaatacgcc    9480
gccaacccgg tctctcctga attccgtcgt cgcctgagtc gacatcattt atttaccagt    9540 tggcacaaa cccttgacga tctcgtatgt cccctccgac atactcccgg ccggctgggg     9600
tacgttcgat agcgctatcg gcatcgacaa ggtttgggtc cctagccgat accgcactac    9660
ctgagtcaca atcttcggag gtttagtctt ccacatagca cgggcaaaag tgcgtatata    9720
tacaagagcg tttgccagcc acagattttc actccacaca ccacatcaca catacaacca    9780
cacacatcca caatggaacc cgaaactaag aagaccaaga ctgactccaa gaagattgtt    9840
cttctcggcg gcgacttctg tggccccgag gtgattgccg aggccgtcaa ggtgctcaag    9900
tctgttgctg aggcctccgg caccgagttt gtgtttgagg accgactcat tggaggagct    9960
gccattgaga aggagggcga gcccatcacc gacgctactc tcgacatctg ccgaaaggct   10020
gactctatta tgctcggtgc tgtcggaggc gctgccaaca ccgtatggac cactcccgac   10080
ggacgaaccg acgtgcgacc cgagcagggt ctcctcaagc tgcgaaagga cctgaacctg   10140
tacgccaacc tgcgaccctg ccagctgctg tcgcccaagc tcgccgatct ctcccccatc   10200
cgaaacgttg agggcaccga cttcatcatt gtccgagagc tcgtcggagg tatctacttt   10260
ggagagcgaa aggaggatga cggatctggc gtcgcttccg acaccgagac ctactccgtt   10320
cctgaggttg agcgaattgc ccgaatggcc gccttcctgg cccttcagca caaccccccct   10380
```

```
cttcccgtgt ggtctcttga caaggccaac gtgctggcct cctctcgact ttggcgaaag   10440
actgtcactc gagtcctcaa ggacgaactc ccccagctcg agctcaacca ccagctgatc   10500
gactcggccg ccatgatcct catcaagcag ccctccaaga tgaatggtat catcatcacc   10560
accaacatgt tggcgatat catctccgac gaggcctccg tcatcccgg ttctctgggt     10620 ctgctgccct ccgcctctct ggcttctctg cccgacacca acgaggcgtt cggtctgtac   10680
gagccctgtc acggatctgc ccccgatctc ggcaagcaga aggtcaaccc cattgccacc   10740
attctgtctg ccgccatgat gctcaagttc tctcttaaca tgaagcccgc cggtgacgct   10800
gttgaggctg ccgtcaagga gtccgtcgag gctggtatca ctaccgccga tatcggaggc   10860
tcttcctcca cctccgaggt cggagacttg ttgccaacaa ggtcaaggag ctgctcaaga   10920
aggagtaagt cgtttctacg acgcattgat ggaaggagca aactgacgcg cctgcgggtt   10980
ggtctaccgg cagggtccgc tagtgtataa gactctataa aaagggccct gccctgctaa   11040
tgaaatgatg atttataatt taccggtgta gcaaccttga ctagaagaag cagattgggt   11100
gtgtttgtag tggaggacag tggtacgttt tggaaacagt cttcttgaaa gtgtcttgtc   11160
tacagtatat tcactcataa cctcaatagc caagggtgta gtcggtttat taaaggaagg   11220
gagttgtggc tgatgtggat atcgatagtt ggagcaaggg agaaatgtag agtgtgaaag   11280
actcactatg gtccgggctt atctcgacca atagccaaag tctggagttt ctgagagaaa   11340
aaggcaagat acgtatgtaa caaagcgacg catggtacaa taataccgga ggcatgtatc   11400
atagagagtt agtggttcga tgatggcact ggtgcctggt atgactttat acggctgact   11460
acatatttgt cctcagacat acaattacag tcaagcactt acccttggac atctgtaggt   11520
accccccggc caagacgatc tcagcgtgtc gtatgtcgga ttggcgtagc tccctcgctc   11580
gtcaattggc tcccatctac tttcttctgc ttggctacac ccagcatgtc tgctatggct   11640
cgttttcgtg ccttatctat cctcccagta ttaccaactc taaatgacat gatgtgattg   11700
ggtctacact ttcatatcag agataaggag tagcacagtt gcataaaaag cccaactcta   11760
atcagcttct tcctttcttg taattagtac aaaggtgatt agcgaaatct ggaagcttag   11820
ttggccctaa aaaaatcaaa aaaagcaaaa acgaaaaac gaaaaccac agttttgaga     11880 acagggaggt aacgaaggat cgtatatata tatatatata tataccca cggatcccga     11940 gaccggcctt tgattcttcc ctacaaccaa ccattctcac caccctaatt cacaaccatg   12000
gctcccgacg ccgacaagct gcgacagcga aaggctcagt ccatccagga cactgccgat   12060
tctcaggcta ccgagctcaa gattggcacc ctgaagggtc tccaaggcac cgagatcgtc   12120
attgatggcg acatctacga catcaaagac ttcgatcacc ctggaggcga atccatcatg   12180
acctttggtg gcaacgacgt tactgccacc tacaagatga ttcatcccta ccactcgaag   12240
catcacctgg agaagatgaa aaaggtcggt cgagtgcccg actacacctc cgagtacaag   12300
ttcgatactc ccttcgaacg agagatcaaa caggaggtct tcaagattgt gcgaagaggt   12360
cgagagtttg gaacacctgg ctacttcttt cgagccttct gctacatcgg tctcttcttt   12420
tacctgcagt atctctgggt taccactcct accactttcg cccttgctat cttctacggt   12480
gtgtctcagg ccttcattgg cctgaacgtc cagcacgacg ccaaccacgg agctgcctcc   12540
aaaaagccct ggatcaacaa tttgctcggc ctgggtgccg actttatcgg aggctccaag   12600
tggctctgga tgaaccagca ctggaccat cacacttaca ccaaccatca cgagaaggat    12660
cccgacgccc tgggtgcaga gcctatgctg ctcttcaacg actatccctt gggtcacccc   12720
aagcgaaccc tcattcatca cttccaagcc ttctactatc tgtttgtcct tgctggctac   12780
```

```
tgggtgtctt cggtgttcaa ccctcagatc ctggacctcc agcaccgagg tgcccaggct    12840
gtcggcatga agatggagaa cgactacatt gccaagtctc gaaagtacgc tatcttcctg    12900
cgactcctgt acatctacac caacattgtg gctcccatcc agaaccaagg cttttcgctc    12960
accgtcgttg ctcacattct tactatgggt gtcgcctcca gcctgaccct cgctactctg    13020
ttcgccctct cccacaactt cgagaacgca gatcgggatc ccacctacga ggctcgaaag    13080
ggaggcgagc ctgtctgttg gttcaagtcg caggtggaaa cctcctctac ttacggtggc    13140
ttcatttccg gttgccttac aggcggactc aactttcagg tcgagcatca cctgtttcct    13200
cgaatgtcct ctgcctggta ccctacatc gctcctaccg ttcgagaggt ctgcaaaaag     13260
cacggcgtca agtacgccta ctatccctgg gtgtggcaga acctcatctc gaccgtcaag    13320
tacctgcatc agtccggaac tggctcgaac tggaagaacg gtgccaatcc ctactctggc    13380
aagctgtaag cggccgcatg tacatacaag attatttata gaaatgaatc gcgatcgaac    13440
aaagagtacg agtgtacgag taggggatga tgataaaagt ggaagaagtt ccgcatcttt    13500
ggatttatca acgtgtagga cgatacttcc tgtaaaaatg caatgtcttt accataggtt    13560
ctgctgtaga tgttattaac taccattaac atgtctactt gtacagttgc agaccagttg    13620
gagtatagaa tggtacactt accaaaaagt gttgatggtt gtaactacga tatataaaac    13680
tgttgacggg atctgcgtac actgttt                                        13707

<210> SEQ ID NO 41
<211> LENGTH: 13066
<212> TYPE: DNA
<213> ORGANISM: Artificial Sequence
<220> FEATURE:
<223> OTHER INFORMATION: Plasmid pZP3-Pa777U

<400> SEQUENCE: 41
tctcggtcta ttcttttgat ttataaggga ttttgccgat ttcggcctat tggttaaaaa      60
atgagctgat ttaacaaaaa tttaacgcga attttaacaa atattaacg cttacaattt      120 cctgatgcgg tattttctcc ttacgcatct gtgcggtatt tcacaccgca tcaggtggca    180
cttttcgggg aaatgtgcgc ggaaccccta tttgtttatt tttctaaata cattcaaata    240
tgtatccgct catgagacaa taaccctgat aaatgcttca ataatattga aaaaggaaga    300
gtatgagtat tcaacatttc cgtgtcgccc ttattccctt ttttgcggca ttttgccttc    360
ctgtttttgc tcacccagaa acgctggtga agtaaaaga tgctgaagat cagttgggtg    420
cacgagtggg ttacatcgaa ctggatctca acagcggtaa gatccttgag agttttcgcc    480
ccgaagaacg ttttccaatg atgagcactt ttaaagttct gctatgtggc gcggtattat    540
cccgtattga cgccgggcaa gagcaactcg gtcgccgcat acactattct cagaatgact    600
tggttgagta ctcaccagtc acagaaaagc atcttacgga tggcatgaca gtaagagaat    660
tatgcagtgc tgccataacc atgagtgata acactgcggc caacttactt ctgacaacga    720
tcggaggacc gaaggagcta accgcttttt tgcacaacat ggggggatcat gtaactcgcc    780 ttgatcgttg ggaaccggag ctgaatgaag ccataccaaa cgacgagcgt gacaccacga    840
tgcctgtagc aatggcaaca acgttgcgca aactattaac tggcgaacta cttactctag    900
cttcccggca caattaata gactggatgg aggcggataa agttgcagga ccacttctgc    960
gctcggccct tccggctggc tggtttattg ctgataaatc tggagccggt gagcgtgggt    1020
ctcgcggtat cattgcagca ctggggccag atggtaagcc ctcccgtatc gtagttatct    1080
acacgacggg gagtcaggca actatggatg aacgaaatag acagatcgct gagataggtg    1140
```

```
cctcactgat taagcattgg taactgtcag accaagttta ctcatatata ctttagattg    1200
atttaaaact tcatttttaa tttaaaagga tctaggtgaa gatccttttt gataatctca    1260
tgaccaaaat cccttaacgt gagttttcgt tccactgagc gtcagacccc gtagaaaaga    1320
tcaaaggatc ttcttgagat cctttttttc tgcgcgtaat ctgctgcttg caaacaaaaa    1380
aaccaccgct accagcggtg gtttgtttgc cggatcaaga gctaccaact cttttttccga   1440 aggtaactgg cttcagcaga gcgcagatac caaatactgt tcttctagtg tagccgtagt    1500
taggccacca cttcaagaac tctgtagcac cgcctacata cctcgctctg ctaatcctgt    1560
taccagtggc tgctgccagt ggcgataagt cgtgtcttac cgggttggac tcaagacgat    1620
agttaccgga taaggcgcag cggtcgggct gaacggggggt tcgtgcaca cagcccagct    1680 tggagcgaac gacctacacc gaactgagat acctacagcg tgagctatga aaagcgcca    1740 cgcttcccga agggagaaag gcggacaggt atccggtaag cggcagggtc ggaacaggag    1800
agcgcacgag ggagcttcca ggggaaacg cctggtatct ttatagtcct gtcgggtttc    1860
gccacctctg acttgagcgt cgatttttgt gatgctcgtc aggggggcgg agcctatgga    1920
aaaacgccag caacgcggcc ttttacggt tcctggcctt ttgctggcct tttgctcaca    1980
tgttctttcc tgcgttatcc cctgattctg tggataaccg tattaccgcc tttgagtgag    2040
ctgataccgc tcgccgcagc cgaacgaccg agcgcagcga gtcagtgagc gaggaagcgg    2100
aagagcgccc aatacgcaaa ccgcctctcc ccgcgcgttg gccgattcat taatgcagct    2160
ggcgcgccac caatcacaat tctgaaaagc acatcttgat ctcctcattg cggggagtcc    2220
aacggtggtc ttattccccc gaatttcccg ctcaatctcg ttccagaccg acccggacac    2280
agtgcttaac gccgttccga aactctaccg cagatatgct ccaacggact gggctgcata    2340
gatgtgatcc tcggcttgga gaaatggata aaagccggcc aaaaaaaaag cggaaaaaag    2400
cggaaaaaaa gagaaaaaaa atcgcaaaat ttgaaaaata gggggaaaag acgcaaaaac    2460
gcaaggaggg gggagtatat gacactgata agcaagctca caacggttcc tcttattttt    2520
ttcctcatct tctgcctagg ttcccaaaat cccagatgct tctctccagt gccaaaagta    2580
agtaccccac aggttttcgg ccgaaaattc cacgtgcagc aacgtcgtgt ggggtgttaa    2640
aatgtggggg gggggaacca ggacaagagg ctcttgtggg agccgaatga gagcacaaag    2700
cgggcgggtg tgataagggc atttttgccc attttcccctt ctcctgtctc tccgacggtg    2760
atggcgttgt gcgtcctcta tttctttta tttctttttg ttttatttct ctgactaccg    2820
atttggtttg atttcctcaa ccccacacaa ataagctcgg gccgaggaat atatatatac    2880
acggacacag tcgccctgtg gacaacacgt cactacctct acgatacaca ccgtacgttg    2940
tgtggaagct tgtgagcgga taacaatttc acacaggaaa cagctatgac catgattacg    3000
ccaagctcga aattaaccct cactaaaggg aacaaaagct ggagctccac cgcggacaca    3060
atatctggtc aaatttcagt ttcgttacat ttaaattcct tcacttcaag ttcattcttc    3120
atctgcttct gttttacttt gacaggcaaa tgaagacatg gtacgacttg atggaggcca    3180
agaacgccat ttcaccccga gacaccgaag tgcctgaaat cctggctgcc cccattgata    3240
acatcggaaa ctacggtatt ccggaaagtg tatatagaac ctttccccag cttgtgtctg    3300
tggatatgga tggtgtaatc ccctttgagt actcgtcttg gcttctctcc gagcagtatg    3360
aggctctcta atctagcgca tttaatatct caatgtattt atatatttat cttctcatgc    3420
ggccgcttag ttggctttgg tcttggcagc cttggcctcc ttgagggtaa acatcttggc    3480
atccttgtcg accacgccgt acttggcgta cataagacca attcggatga aggtgggaat    3540
```

```
gatgggagaa gccgactttc gcaccagttc gggaaaggcc tgagcgaagg cagcagtggc    3600
ctcgttgagc ttgtagtgag gaatgatggg aaacagatgg tggatctgat gtgtaccaat    3660
gttgtgggac aggttgtcga tgagggctcc gtagcttcgg tccacagagg acaagttgcc    3720
cttgacatag gtccactccg aatcggcgta ccagggagtt tcctcgtcgt tgtgatggag    3780
gaaggtagtg acaaccagca tggtggcgaa tccaaagaga ggtgcgaagt aatacagagc    3840
catggtcttg aggccgtaga cgtaggtaag gtaggcgtac agaccagcaa aggccacgag    3900
agagccgagg gaaatgatga cggcagacat tcttcgcagg tagagaggct cccagggatt    3960
gaagtggttg acctttcggg gaggaaatcc agcaacgagg taggcaaacc aagccgaacc    4020
aagggagatg accatgtgtc gggacagggg atgagagtcg gcttctcgct gagggtagaa    4080
gatctcatcc ttgtcgatgt tgccggtgtt cttgtgatgg tgtcgatggc tgatcttcca    4140
cgactcgtag ggagtcagaa tgatggagtg aatgagtgtg ccaacagaga agttgagcag    4200
gtgggatcgc gagaaggcac catgtccaca gtcgtgaccg atggtaaaga atccccagaa    4260
cacgataccc tggagcagaa tgtagccagt gcaaggacg gcatcgagca gtgcaaactc    4320
ctgcacgata gcaagggctc gagcatagta cagtccgaga gcaagggaac cggcaatgcc    4380
cagagctcgc acggtatagt agagggacca gggaacagag gcttcgaagc agtgggcagg    4440
cagggatcgc ttgatctcgg tgagagtagg gaactcgtag ggagcggcaa cggtagagga    4500
agccatggtt gtgaattagg gtggtgagaa tggttggttg tagggaagaa tcaaaggccg    4560
gtctcgggat ccgtgggtat atatatatat atatatatat acgatccttc gttacctccc    4620
tgttctcaaa actgtggttt tcgtttttc gtttttgct tttttgatt tttttagggc    4680 caactaagct tccagatttc gctaatcacc tttgtactaa ttacaagaaa ggaagaagct    4740
gattagagtt gggcttttta tgcaactgtg ctactcctta tctctgatat gaaagtgtag    4800
acccaatcac atcatgtcat ttagagttgg taatactggg aggatagata aggcacgaaa    4860
acgagccata gcagacatgc tgggtgtagc caagcagaag aaagtagatg ggagccaatt    4920
gacgagcgag ggagctacgc caatccgaca tacgacacgc tgagtcgtc ttggccgggg    4980 ggtacctaca gatgtccaag ggtaagtgct tgactgtaat tgtatgtctg aggacaaata    5040
tgtagtcagc cgtataaagt cataccaggc accagtgcca tcatcgaacc actaactctc    5100
tatgatacat gcctccggta ttattgtacc atgcgtcgct tgttacata cgtatccttgc    5160 cttttctct cagaaactcc agactttggc tattggtcga gataagcccg gaccatagtg    5220
agtctttcac actctacatt tctcccttgc tccaactatc gattgttgtc tactaactat    5280
cgtacgataa cttcgtatag catacattat acgaagttat cgcgtcgacg agtatctgtc    5340
tgactcgtca ttgccgcctt tggagtacga ctccaactat gagtgtgctt ggatcacttt    5400
gacgatacat tcttcgttgg aggctgtggg tctgacagct gcgttttcgg cgcggttggc    5460
cgacaacaat atcagctgca acgtcattgc tggctttcat catgatcaca tttttgtcgg    5520
caaaggcgac gcccagagag ccattgacgt tctttctaat ttggaccgat agccgtatag    5580
tccagtctat ctataagttc aactaactcg taactattac cataacatat acttcactgc    5640
cccagataag gttccgataa aaagttctgc agactaaatt tatttcagtc tcctcttcac    5700
caccaaaatg ccctcctacg aagctcgagc taacgtccac aagtccgcct ttgccgctcg    5760
agtgctcaag ctcgtggcag ccaagaaaac caacctgtgt gcttctctgg atgttaccac    5820
caccaaggag ctcattgagc ttgccgataa ggtcggacct tatgtgtgca tgatcaaaac    5880
ccatatcgac atcattgacg acttcaccta cgccggcact gtgctccccc tcaaggaact    5940
```

```
tgctcttaag cacggtttct tcctgttcga ggacagaaag ttcgcagata ttggcaacac   6000
tgtcaagcac cagtaccggt gtcaccgaat cgccgagtgg tccgatatca ccaacgccca   6060
cggtgtaccc ggaaccggaa tcattgctgg cctgcgagct ggtgccgagg aaactgtctc   6120
tgaacagaag aaggaggacg tctctgacta cgagaactcc cagtacaagg agttcctagt   6180
cccctctccc aacgagaagc tggccagagg tctgctcatg ctggccgagc tgtcttgcaa   6240
gggctctctg gccactggcg agtactccaa gcagaccatt gagcttgccc gatccgaccc   6300
cgagtttgtg gttggcttca ttgcccagaa ccgacctaag ggcgactctg aggactggct   6360
tattctgacc cccggggtgg gtcttgacga caagggagac gctctcggac agcagtaccg   6420
aactgttgag gatgtcatgt ctaccggaac ggatatcata attgtcggcc gaggtctgta   6480
cggccagaac cgagatccta ttgaggaggc caagcgatac cagaaggctg gctgggaggc   6540
ttaccagaag attaactgtt agaggttaga ctatggatat gtaatttaac tgtgtatata   6600
gagagcgtgc aagtatggag cgcttgttca gcttgtatga tggtcagacg acctgtctga   6660
tcgagtatgt atgatactgc acaacctgtg tatccgcatg atctgtccaa tggggcatgt   6720
tgttgtgttt ctcgatacgg agatgctggg tacagtgcta atacgttgaa ctacttatac   6780
ttatatgagg ctcgaagaaa gctgacttgt gtatgactta ttctcaacta catccccagt   6840
cacaatacca ccactgcact accactacac caaaaccatg atcaaaccac ccatggactt   6900
cctggaggca gaagaacttg ttatggaaaa gctcaagaga gagatcataa cttcgtatag   6960
catacattat acgaagttat cctgcaggta aaggaattca tgctgttcat cgtggttaat   7020
gctgctgtgt gctgtgtgtg tgtgttgttt ggcgctcatt gttgcgttat gcagcgtaca   7080
ccacaatatt ggaagcttat tagcctttct attttttcgt ttgcaaggct taacaacatt   7140
gctgtggaga gggatgggga tatggaggcc gctgagggga gtcggagagg cgttttggag   7200
cggcttggcc tggcgcccag ctcgcgaaac gcacctagga ccctttggca cgccgaaatg   7260
tgccactttt cagtctagta acgccttacc tacgtcattc catgcgtgca tgtttgcgcc   7320
ttttttccct tgcccttgat cgccacacag tacagtgcac tgtacagtgg aggttttggg   7380
ggggtcttag atgggagcta aaagcggcct agcggtacac tagtgggatt gtatggagtg   7440
gcatggagcc taggtggagc ctgacaggac gcacgaccgg ctagcccgtg acagacgatg   7500
ggtggctcct gttgtccacc gcgtacaaat gtttgggcca aagtcttgtc agccttgctt   7560
gcgaacctaa ttcccaattt tgtcacttcg caccccatt gatcgagccc taaccctgc    7620 ccatcaggca atccaattaa gctcgcattg tctgccttgt ttagtttggc tcctgcccgt   7680
ttcggcgtcc acttgcacaa acacaaacaa gcattatata taaggctcgt ctctcccctcc  7740 caaccacact cactttttg cccgtcttcc cttgctaaca caaagtcaa gaacacaaac     7800 aaccacccca accccttac acacaagaca tatctacagc aatggccatg cttcttcca     7860 ctgttgctgc gccgtacgag ttcccgacgc tgacggagat caagcgctcg ctgccagcgc   7920
actgctttga ggcctcggtc ccgtggtcgc tctactacac cgtgcgcgcg ctgggcatcg   7980
ccggctcgct cgcgctcggc ctctactacg cgcgcgcgct cgcgatcgtg caggagtttg   8040
ccctgctgga tgcggtgctc tgcacggggt acattctgct gcagggcatc gtattctggg   8100
ggttcttcac catcggccat gactgcggcc acggcgcgtt ctcgcgttcg cacctgctca   8160
acttcagcgt cggcacgctc attcactcga tcatcctcac gccgtacgag tcatggaaga   8220
tctcgcaccg ccaccaccac aagaacacgg gcaacatcga caaggacgag attttctacc   8280
cgcagcgcga ggccgactcg cacccactgt cccgacacat ggtgatctcg ctcggctcgg   8340
```

```
cctggttcgc gtacctcgtt gcgggcttcc ctcctcgcaa ggtgaaccac ttcaacccct    8400
gggaaccgtt gtacctgcgc cgcatgtctg ccgtcatcat ctcactcggc tcgctcgtgg    8460
cgttcgcggg cttgtatgcg tatctcacct acgtctatgg ccttaagacc atggcgctgt    8520
actacttcgc ccctctcttt gggttcgcca cgatgctcgt ggtcactacc tttttgcacc    8580
acaatgacga ggaaacgcca tggtacgccg actcggagtg gacgtacgtc aagggcaacc    8640
tctcgtccgt ggaccgctcg tacgcgcgc tcatcgacaa cctgagccac aacatcggca    8700
cgcaccagat ccaccacctg tttccgatca tcccgcacta caagctgaac gaggcgacgg    8760
cagcgttcgc gcaggcgttc ccggagctcg tgcgcaagag cgcgtcgccg atcatcccga    8820
cgttcatccg catcgggctc atgtacgcca agtacggcgt cgtggacaag gacgccaaga    8880
tgtttacgct caaggaggcc aaggccgcca agaccaaggc caactaggcg gccgcattga    8940
tgattggaaa cacacacatg ggttatatct aggtgagagt tagttggaca gttatatatt    9000
aaatcagcta tgccaacggt aacttcattc atgtcaacga ggaaccagtg actgcaagta    9060
atatagaatt tgaccacctt gccattctct tgcactcctt tactatatct catttatttc    9120
ttatatacaa atcacttctt cttcccagca tcgagctcgg aaacctcatg agcaataaca    9180
tcgtggatct cgtcaataga gggcttttg gactccttgc tgttggccac cttgtccttg    9240
ctgtttaaac agtgtacgca gatctactat agaggaacat ttaaattgcc ccggagaaga    9300
cggccaggcc gcctagatga caaattcaac aactcacagc tgactttctg ccattgccac    9360
tagggggggg ccttttata tggccaagcc aagctctcca cgtcggttgg gctgcaccca    9420
acaataaatg ggtagggttg caccaacaaa gggatgggat gggggtaga agatacgagg    9480 ataacggggc tcaatggcac aaataagaac gaatactgcc attaagactc gtgatccagc    9540
gactgacacc attgcatcat ctaagggcct caaaactacc tcggaactgc tgcgctgatc    9600
tggacaccac agaggttccg agcactttag gttgcaccaa atgtcccacc aggtgcaggc    9660
agaaaacgct ggaacagcgt gtacagtttg tcttaacaaa aagtgagggc gctgaggtcg    9720
agcagggtgg tgtgacttgt tatagccttt agagctgcga aagcgcgtat ggatttggct    9780
catcaggcca gattgagggt ctgtggacac atgtcatgtt agtgtacttc aatcgccccc    9840
tggatatagc cccgacaata ggccgtggcc tcattttttt gccttccgca catttccatt    9900
gctcggtacc cacaccttgc ttctcctgca cttgccaacc ttaatactgg tttacattga    9960
ccaacatctt acaagcgggg ggcttgtcta gggtatatat aaacagtggc tctcccaatc    10020
ggttgccagt ctcttttttc ctttctttcc ccacagattc gaaatctaaa ctacacatca    10080
cagaattccg agccgtgagt atccacgaca agatcagtgt cgagacgacg cgttttgtgt    10140
aatgacacaa tccgaaagtc gctagcaaca cacactctct acacaaacta acccagctct    10200
ggtaccatgg cttcttccac tgttgctgcg ccgtacgagt tcccgacgct gacggagatc    10260
aagcgctcgc tgccagcgca ctgctttgag gcctcggtcc cgtggtcgct ctactacacc    10320
gtgcgcgcgc tgggcatcgc cggctcgctc gcgctcggcc tctactacgc gcgcgcgctc    10380
gcgatcgtgc aggagtttgc cctgctggat gcggtgctct gcacggggta cattctgctg    10440
cagggcatcg tattctgggg gttcttcacc atcggccatg actgcggcca cggcgcgttc    10500
tcgcgttcgc acctgctcaa cttcagcgtc ggcacgctca ttcactcgat catcctcacg    10560
ccgtacgagt catggaagat ctcgcaccgc caccaccaca agaacacggg caacatcgac    10620
aaggacgaga ttttctaccc gcagcgcgag gccgactcgc acccactgtc ccgacacatg    10680
gtgatctcgc tcggctcggc ctggttcgcg tacctcgttg cgggcttccc tcctcgcaag    10740
```

```
gtgaaccact tcaacccttg ggaaccgttg tacctgcgcc gcatgtctgc cgtcatcatc    10800
tcactcggct cgctcgtggc gttcgcgggc ttgtatgcgt atctcaccta cgtctatggc    10860
cttaagacca tggcgctgta ctacttcgcc cctctctttg ggttcgccac gatgctcgtg    10920
gtcactacct ttttgcacca caatgacgag gaaacgccat ggtacgccga ctcggagtgg    10980
acgtacgtca agggcaacct ctcgtccgtg gaccgctcgt acggcgcgct catcgacaac    11040
ctgagccaca acatcggcac gcaccagatc caccacctgt ttccgatcat cccgcactac    11100
aagctgaacg aggcgacggc agcgttcgcg caggcgttcc cggagctcgt gcgcaagagc    11160
gcgtcgccga tcatcccgac gttcatccgc atcgggctca tgtacgccaa gtacggcgtc    11220
gtggacaagg acgccaagat gtttacgctc aaggaggcca aggccgccaa gaccaaggcc    11280
aactaggcgg ccgcatggag cgtgtgttct gagtcgatgt tttctatgga gttgtgagtg    11340
ttagtagaca tgatgggttt atatatgatg aatgaataga tgtgattttg atttgcacga    11400
tggaattgag aactttgtaa acgtacatgg gaatgtatga atgtggggt tttgtgactg     11460 gataactgac ggtcagtgga cgccgttgtt caaatatcca agagatgcga gaaactttgg    11520
gtcaagtgaa catgtcctct ctgttcaagt aaaccatcaa ctatgggtag tatatttagt    11580
aaggacaaga gttgagattc tttggagtcc tagaaacgta ttttcgcgtt ccaagatcaa    11640
attagtagag taatacgggc acgggaatcc attcatagtc tcaatcctgc aggtgagtta    11700
attaagatga cgacatttgc gagctggacg aggaatagat ggagcgtgtg ttctgagtcg    11760
atgttttcta tggagttgtg agtgttagta gacatgatgg gtttatatat gatgaatgaa    11820
tagatgtgat tttgatttgc acgatggaat tgagaacttt gtaaacgtac atgggaatgt    11880
atgaatgtgg gggttttgtg actggataac tgacggtcag tggacgccgt tgttcaaata    11940
tccaagagat gcgagaaact ttgggtcaag tgaacatgtc ctctctgttc aagtaaacca    12000
tcaactatgg gtagtatatt tagtaaggac aagagttgag attctttgga gtcctagaaa    12060
cgtattttcg cgttccaaga tcaaattagt agagtaatac gggcacggga atccattcat    12120
agtctcaatt ttcccatagg tgtgctacaa ggtgttgaga tgtggtacag taccaccatg    12180
attcgaggta aagagcccag aagtcattga tgaggtcaag aaatacacag atctacagct    12240
caatacaatg aatatcttct ttcatattct tcaggtgaca ccaagggtgt ctattttccc    12300
cagaaatgcg tgaaaggcg cgtgtgtagc gtggagtatg ggttcggttg gcgtatcctt     12360
catatatcga cgaaatagta gggcaagaga tgacaaaaag tatctatatg tagacagcgt    12420
agaatatgga tttgattggt ataaattcat ttattgcgtg tctcacaaat actctcgata    12480
agttggggtt aaactggaga tggaacaatg tcgatatctc gacgcatgcg acgtcgggcc    12540
caattcgccc tatagtgagt cgtattacaa ttcactggcc gtcgttttac aacgtcgtga    12600
ctgggaaaac cctggcgtta cccaacttaa tcgccttgca gcacatcccc ctttcgccag    12660
ctggcgtaat agcgaagagg cccgcaccga tcgcccttcc caacagttgc gcagcctgaa    12720
tggcgaatgg acgcgccctg tagcggcgca ttaagcgcgg cgggtgtggt ggttacgcgc    12780
agcgtgaccg ctacacttgc cagcgcccta gcgcccgctc ctttcgcttt cttcccttcc    12840
tttctcgcca cgttcgccgg ctttccccgt caagctctaa atcgggggct ccctttaggg    12900
ttccgattta gtgctttacg gcacctcgac cccaaaaaac ttgattaggg tgatggttca    12960
cgtagtgggc catcgccctg atagacggtt tttcgccctt tgacgttgga gtccacgttc    13020
tttaatagtg gactcttgtt ccaaactgga acaacactca acccta                   13066
```

<210> SEQ ID NO 42

```
<211> LENGTH: 15743
<212> TYPE: DNA
<213> ORGANISM: Artificial Sequence
<220> FEATURE:
<223> OTHER INFORMATION: Plasmid pZP2-2988

<400> SEQUENCE: 42
ggccgcatgt acatacaaga ttatttatag aaatgaatcg cgatcgaaca aagagtacga      60
gtgtacgagt aggggatgat gataaaagtg gaagaagttc cgcatctttg gatttatcaa     120
cgtgtaggac gatacttcct gtaaaaatgc aatgtcttta ccataggttc tgctgtagat     180
gttattaact accattaaca tgtctacttg tacagttgca gaccagttgg agtatagaat     240
ggtacactta ccaaaaagtg ttgatggttg taactacgat atataaaact gttgacggga     300
tctgtatatt cggtaagata tattttgtgg ggttttagtg gtgtttaaac agtgtacgca     360
gtactataga ggaacaattg ccccggagaa gacggccagg ccgcctagat gacaaattca     420
acaactcaca gctgactttc tgccattgcc actagggggg ggcctttta tatggccaag     480
ccaagctctc cacgtcggtt gggctgcacc caacaataaa tgggtagggt tgcaccaaca     540
aagggatggg atgggggta gaagatacga ggataacggg gctcaatggc acaaataaga     600
acgaatactg ccattaagac tcgtgatcca gcgactgaca ccattgcatc atctaagggc     660
ctcaaaacta cctcggaact gctgcgctga tctggacacc acagaggttc cgagcacttt     720
aggttgcacc aaatgtccca ccaggtgcag gcagaaaacg ctggaacagc gtgtacagtt     780
tgtcttaaca aaaagtgagg gcgctgaggt cgagcagggt ggtgtgactt gttatagcct     840
ttagagctgc gaaagcgcgt atggatttgg ctcatcaggc cagattgagg gtctgtggac     900
acatgtcatg ttagtgtact tcaatcgccc cctggatata gccccgacaa taggccgtgg     960
cctcattttt ttgccttccg cacatttcca ttgctcggta cccacacctt gcttctcctg    1020
cacttgccaa ccttaatact ggtttacatt gaccaacatc ttacaagcgg ggggcttgtc    1080
tagggtatat ataaacagtg gctctcccaa tcggttgcca gtctcttttt tccttctttt    1140
ccccacagat tcgaaatcta aactacacat cacaccatgg aggtcgtgaa cgaaatcgtc    1200
tccattggcc aggaggttct tcccaaggtc gactatgctc agctctggtc tgatgcctcg    1260
cactgcgagg tgctgtacct ctccatcgcc ttcgtcatcc tgaagttcac ccttggtcct    1320
ctcggaccca agggtcagtc tcgaatgaag tttgtgttca ccaactacaa cctgctcatg    1380
tccatctact cgctgggctc cttcctctct atggcctacg ccatgtacac cattggtgtc    1440
atgtccgaca actgcgagaa ggcttttcgac aacaatgtct tccgaatcac cactcagctg    1500
ttctacctca gcaagttcct cgagtacatt gactccttct atctgcccct catgggcaag    1560
cctctgacct ggttgcagtt cttttcaccat ctcggagctc ctatggacat gtggctgttc    1620
tacaactacc gaaacgaagc cgtttggatc tttgtgctgc tcaacggctt cattcactgg    1680
atcatgtacg gctactattg gacccgactg atcaagctca agttccctat gcccaagtcc    1740
ctgattactt ctatgcagat cattcagttc aacgttggct tctacatcgt ctggaagtac    1800
cggaacattc cctgctaccg acaagatgga atgagaatgt ttggctggtt tttcaactac    1860
ttctacgttg gtactgtcct gtgtctgttc ctcaacttct acgtgcagac ctacatcgtc    1920
cgaaagcaca agggagccaa aaagattcag tgagcggccg caagtgtgga tgggaagtg    1980
agtgcccggt tctgtgtgca caattggcaa tccaagatgg atggattcaa cacagggata    2040
tagcgagcta cgtggtggtg cgaggatata gcaacggata tttatgtttg acacttgaga    2100
atgtacgata caagcactgt ccaagtacaa tactaaacat actgtacata ctcatactcg    2160
```

```
tacccgggca acggtttcac ttgagtgcag tggctagtgc tcttactcgt acagtgtgca    2220
atactgcgta tcatagtctt tgatgtatat cgtattcatt catgttagtt gcgtacgggc    2280
gtcgttgctt gtgtgatttt tgaggaccca tccctttggt atataagtat actctggggt    2340
taaggttgcc cgtgtagtct aggttatagt tttcatgtga ataccgaga gccgagggag     2400 aataaacggg ggtatttgga cttgtttttt tcgcggaaaa gcgtcgaatc aaccctgcgg    2460
gccttgcacc atgtccacga cgtgtttctc gccccaattc gccccttgca cgtcaaaatt    2520
aggcctccat ctagacccct ccataacatg tgactgtggg gaaaagtata agggaaacca   2580
tgcaaccata gacgacgtga aagacgggga ggaaccaatg gaggccaaag aaatggggta    2640
gcaacagtcc aggagacaga caaggagaca aggagagggc gcccgaaaga tcggaaaaac    2700
aaacatgtcc aattgggca gtgacggaaa cgacacggac acttcagtac aatggaccga    2760
ccatctccaa gccagggtta ttccggtatc accttggccg taacctcccg ctggtacctg    2820
atattgtaca cgttcacatt caatatactt tcagctacaa taagagaggc tgtttgtcgg    2880
gcatgtgtgt ccgtcgtatg gggtgatgtc cgagggcgaa attcgctaca agcttaactc    2940
tggcgcttgt ccagtatgaa tagacaagtc aagaccagtg gtgccatgat tgacagggag    3000
gtacaagact tcgatactcg agcattactc ggacttgtgg cgattgaaca gacgggcgat    3060
cgcttctccc ccgtattgcc ggcgcgccag ctgcattaat gaatcggcca acgcgcgggg    3120
agaggcggtt tgcgtattgg gcgctcttcc gcttcctcgc tcactgactc gctgcgctcg    3180
gtcgttcggc tgcggcgagc ggtatcagct cactcaaagg cggtaatacg gttatccaca    3240
gaatcagggg ataacgcagg aaagaacatg tgagcaaaag gccagcaaaa ggccaggaac    3300
cgtaaaaagg ccgcgttgct ggcgtttttc cataggctcc gcccccctga cgagcatcac    3360
aaaaatcgac gctcaagtca gaggtggcga acccgacag gactataaag ataccaggcg    3420
tttccccctg gaagctccct cgtgcgctct cctgttccga ccctgccgct taccggatac    3480
ctgtccgcct ttctcccttc gggaagcgtg gcgctttctc atagctcacg ctgtaggtat    3540
ctcagttcgg tgtaggtcgt tcgctccaag ctgggctgtg tgcacgaacc ccccgttcag    3600
cccgaccgct gcgccttatc cggtaactat cgtcttgagt ccaacccggt aagacacgac    3660
ttatcgccac tggcagcagc cactggtaac aggattagca gagcgaggta tgtaggcggt    3720
gctacagagt tcttgaagtg gtggcctaac tacggctaca ctagaagaac agtatttggt    3780
atctgcgctc tgctgaagcc agttaccttc ggaaaaagag ttggtagctc ttgatccggc    3840
aaacaaacca ccgctggtag cggtggtttt tttgtttgca agcagcagat tacgcgcaga    3900
aaaaaaggat ctcaagaaga tcctttgatc ttttctacgg ggtctgacgc tcagtggaac    3960
gaaaactcac gttaagggat tttggtcatg agattatcaa aaaggatctt cacctagatc    4020
cttttaaatt aaaaatgaag ttttaaatca atctaaagta tatatgagta aacttggtct    4080
gacagttacc aatgcttaat cagtgaggca cctatctcag cgatctgtct atttcgttca    4140
tccatagttg cctgactccc cgtcgtgtag ataactacga tacgggaggg cttaccatct    4200
ggccccagtg ctgcaatgat accgcgagac ccacgctcac cggctccaga tttatcagca    4260
ataaaccagc cagccggaag ggccgagcgc agaagtggtc ctgcaacttt atccgcctcc    4320
atccagtcta ttaattgttg ccgggaagct agagtaagta gttcgccagt taatagtttg    4380
cgcaacgttg ttgccattgc tacaggcatc gtggtgtcac gctcgtcgtt tggtatggct    4440
tcattcagct ccggttccca acgatcaagg cgagttacat gatcccccat gttgtgcaaa    4500
aaagcggtta gctccttcgg tcctccgatc gttgtcagaa gtaagttggc cgcagtgtta    4560
```

```
tcactcatgg ttatggcagc actgcataat tctcttactg tcatgccatc cgtaagatgc   4620 tttctgtga ctggtgagta ctcaaccaag tcattctgag aatagtgtat gcggcgaccg   4680
agttgctctt gcccggcgtc aatacgggat aataccgcgc cacatagcag aactttaaaa   4740
gtgctcatca ttgaaaaacg ttcttcgggg cgaaaactct caaggatctt accgctgttg   4800
agatccagtt cgatgtaacc cactcgtgca cccaactgat cttcagcatc ttttactttc   4860
accagcgttt ctgggtgagc aaaaacagga aggcaaaatg ccgcaaaaaa gggaataagg   4920
gcgacacgga aatgttgaat actcatactc ttcctttttc aatattattg aagcatttat   4980
cagggttatt gtctcatgag cggatacata tttgaatgta tttagaaaaa taaacaaata   5040
ggggttccgc gcacatttcc ccgaaaagtg ccacctgatg cggtgtgaaa taccgcacag   5100
atgcgtaagg agaaaatacc gcatcaggaa attgtaagcg ttaatatttt gttaaaattc   5160
gcgttaaatt tttgttaaat cagctcattt tttaaccaat aggccgaaat cggcaaaatc   5220
ccttataaat caaagaaata gaccgagata ggggttgagtg ttgttccagt ttggaacaag   5280
agtccactat taaagaacgt ggactccaac gtcaaagggc gaaaaaccgt ctatcagggc   5340
gatgccccac tacgtgaacc atcacccctaa tcaagttttt tggggtcgag gtgccgtaaa   5400
gcactaaatc ggaaccctaa agggagcccc cgatttagag cttgacgggg aaagccggcg   5460
aacgtggcga gaaaggaagg gaagaaagcg aaaggagcgg gcgctagggc gctggcaagt   5520
gtagcggtca cgctgcgcgt aaccaccaca cccgccgcgc ttaatgcgcc gctacagggc   5580
gcgtccattc gccattcagg ctgcgcaact gttgggaagg gcgatcggtg cgggcctctt   5640
cgctattacg ccagctggcg aaagggggat gtgctgcaag gcgattaagt tgggtaacgc   5700
cagggttttc ccagtcacga cgttgtaaaa cgacggccag tgaattgtaa tacgactcac   5760
tatagggcga attgggcccg acgtcgcatg cgctgatgac actttggtct gaaagagatg   5820
cattttgaat cccaaacttg cagtgcccaa gtgacataca tctccgcgtt ttggaaaatg   5880
ttcagaaaca gttgattgtg ttggaatggg gaatggggaa tggaaaaatg actcaagtat   5940
caattccaaa aacttctctg gctggcagta cctactgtcc atactactgc attttctcca   6000
gtcaggccac tctatactcg acgacacagt agtaaaaccc agataatttc gacataaaca   6060
agaaaacaga cccaataata tttatatata gtcagccgtt tgtccagttc agactgtaat   6120
agccgaaaaa aaatcaaag tttctattct aggaaaatat attccaatat ttttaattct   6180
taatctcatt tatttattc tagcgaaata catttcagct acttgagaca tgtgataccc   6240
acaaatcgga ttcggactcg gttgttcaga agagcatatg gcattcgtgc tcgcttgttc   6300
acgtattctt cctgttccat ctcttggccg acaatcacac aaaaatgggg tttttttttt   6360
aattctaatg attcattaca gcaaaattga gatatagcag accacgtatt ccataatcac   6420
caaggaagtt cttgggcgtc ttaattaact cacctgcagg attgagacta tgaatggatt   6480
cccgtgcccg tattactcta ctaatttgat cttggaacgc gaaaatacgt ttctaggact   6540
ccaaagaatc tcaactcttg tccttactaa atatactacc catagttgat ggtttacttg   6600
aacagagagg acatgttcac ttgacccaaa gtttctcgca tctcttggat atttgaacaa   6660
cggcgtccac tgaccgtcag ttatccagtc acaaaacccc cacattcata cattcccatg   6720
tacgtttaca aagttctcaa ttccatcgtg caaatcaaaa tcacatctat tcattcatca   6780
tatataaacc catcatgtct actaacactc acaactccat agaaaacatc gactcagaac   6840
acacgctcca tgcggccgct tactgagcct tggcaccggg ctgcttctcg gccattcgag   6900
cgaactggga caggtatcgg agcaggatga cgagaccttc atggggcaga gggtttcggt   6960
```

```
aggggaggtt gtgcttctgg cacagctgtt ccacctggta ggaaacggca gtgaggttgt   7020
gtcgaggcag ggtgggccag agatggtgct cgatctggta gttcaggcct ccaaagaacc   7080
agtcagtaat gatgcctcgt cgaatgttca tggtctcatg gatctgaccc acagagaagc   7140
catgtccgtc ccagacggaa tcaccgatct tctccagagg gtagtggttc atgaagacca   7200
cgatggcaat tccgaagcca ccgacgagct cggaaacaaa gaacaccagc atcgaggtca   7260
ggatggaggg cataaagaag aggtggaaca gggtcttgag agtccagtgc agagcgagtc   7320
caatggcctc tttcttgtac tgagatcggt agaactggtt gtctcggtcc ttgagggatc   7380
gaacggtcag cacagactgg aaacaccaga tgaatcgcag gagaatacag atgaccagga   7440
aatagtactg ttggaactga atgagctttc gggagatggg agaagctcga gtgacatcgt   7500
cctcggacca ggcgagcaga ggcaggttat caatgtcggg atcgtgaccc tgaacgttgg   7560
tagcagaatg atgggcgttg tgtctgtcct tccaccaggt cacggagaag ccctggagtc   7620
cgttgccaaa gaccagaccc aggacgttat tccagtttcg gttcttgaag gtctggtggt   7680
ggcagatgtc atgagacagc catcccattt gctggtagtg cataccgagc acgagagcac   7740
caatgaagta caggtggtac tggaccagca tgaagaaggc aagcacgcca agacccaggg   7800
tggtcaagat cttgtacgag taccagaggg gagaggcgtc aaacatgcca gtggcgatca   7860
gctcttctcg gagcttttcgg aaatcctcct gagcttcgtt gacggcagcc tggggaggca   7920
gctcggaagc ctggttgatc ttgggcattc gcttgagctt gtcgaaggct tcctgagagt   7980
gcataaccat gaaggcgtca gtagcatctc gtccctggta gttctcaatg atttcagctc   8040
caccagggtg gaagttcacc caagcggaga cgtcgtacac ctttccgtcg atgacgaggg   8100
gcagagcctg tcgagaagcc ttcaccatgg ttgtgaatta gggtggtgag aatggttggt   8160
tgtagggaag aatcaaaggc cggtctcggg atccgtgggt atatatatat atatatatat   8220
atacgatcct tcgttacctc cctgttctca aaactgtggt ttttcgtttt tcgtttttg    8280
cttttttttga ttttttttagg gccaactaag cttccagatt tcgctaatca cctttgtact   8340
aattacaaga aaggaagaag ctgattagag ttgggctttt tatgcaactg tgctactcct   8400
tatctctgat atgaaagtgt agacccaatc acatcatgtc atttagagtt ggtaatactg   8460
ggaggataga taaggcacga aaacgagcca tagcagacat gctgggtgta gccaagcaga   8520
agaaagtaga tgggagccaa ttgacgagcg agggagctac gccaatccga catacgacac   8580
gctgagatcg tcttggccgg ggggtaccta cagatgtcca agggtaagtg cttgactgta   8640
attgtatgtc tgaggacaaa tatgtagtca gccgtataaa gtcataccag gcaccagtgc   8700
catcatcgaa ccactaactc tctatgatac atgcctccgg tattattgta ccatgcgtcg   8760
ctttgttaca tacgtatctt gccttttttct ctcagaaact ccagactttg gctattggtc   8820
gagataagcc cggaccatag tgagtctttc acactctaca tttctcccct gctccaacta   8880
tttaaattcc ttcacttcaa gttcattctt catctgcttc tgttttactt tgacaggcaa   8940
atgaagacat ggtacgactt gatggaggcc aagaacgcca tttcacccg agacaccgaa    9000
gtgcctgaaa tcctggctgc ccccattgat aacatcggaa actacggtat tccggaaagt   9060
gtatatagaa cctttcccca gcttgtgtct gtggatatgg atggtgtaat ccccttgag    9120
tactcgtctt ggcttctctc cgagcagtat gaggctctct aatctagcgc atttaatatc   9180
tcaatgtatt tatatatttta tcttctcatg cggccgctta ctgagccttg gcaccgggct   9240
gcttctcggc cattcgagcg aactgggaca ggtatcggag caggatgacg agaccttcat   9300
ggggcagagg gtttcggtag gggaggttgt gcttctggca cagctgttcc acctggtagg   9360
```

```
aaacggcagt gaggttgtgt cgaggcaggg tgggccagag atggtgctcg atctggtagt   9420
tcaggcctcc aaagaaccag tcagtaatga tgcctcgtcg aatgttcatg gtctcatgga   9480
tctgacccac agagaagcca tgtccgtccc agacggaatc accgatcttc tccagagggt   9540
agtggttcat gaagaccacg atggcaattc cgaagccacc gacgagctcg gaaacaaaga   9600
acaccagcat cgaggtcagg atggagggca taaagaagag gtggaacagg gtcttgagag   9660
tccagtgcag agcgagtcca atggcctctt tcttgtactg agatcggtag aactggttgt   9720
ctcggtcctt gagggatcga acggtcagca cagactggaa acaccagatg aatcgcagga   9780
gaatacagat gaccaggaaa tagtactgtt ggaactgaat gagctttcgg agatgggag    9840 aagctcgagt gacatcgtcc tcggaccagg cgagcagagg caggttatca atgtcgggat   9900
cgtgaccctg aacgttggta gcagaatgat gggcgttgtg tctgtccttc caccaggtca   9960
cggagaagcc ctggagtccg ttgccaaaga ccagacccag gacgttattc cagtttcggt  10020
tcttgaaggt ctggtggtgg cagatgtcat gagacagcca tcccatttgc tggtagtgca  10080
taccgagcac gagagcacca atgaagtaca ggtggtactg gaccagcatg aagaaggcaa  10140
gcacgccaag acccagggtg gtcaagatct tgtacgagta ccagagggga gaggcgtcaa  10200
acatgccagt ggcgatcagc tcttctcgga gctttcggaa atcctcctga gcttcgttga  10260
cggcagcctg gggaggcagc tcggaagcct ggttgatctt gggcattcgc ttgagcttgt  10320
cgaaggcttc ctgagagtgc ataaccatga aggcgtcagt agcatctcgt ccctggtagt  10380
tctcaatgat ttcagctcca ccagggtgga agttcaccca agcggagacg tcgtacacct  10440
ttccgtcgat gacgaggggc agagcctgtc gagaagcctt caccatgggc aggacctgtg  10500
ttagtacatt gtcggggagt catcaattgg ttcgacaggt tgtcgactgt tagtatgagc  10560
tcaattgggc tctggtgggt cgatgacact tgtcatctgt ttctgttggg tcatgtttcc  10620
atcaccttct atggtactca caattcgtcc gattcgcccg aatccgttaa taccgacttt  10680
gatggccatg ttgatgtgtg tttaattcaa gaatgaatat agaagagaga agaagaaaaa  10740
agattcaatt gagccggcga tgcagaccct tatataaatg ttgccttgga cagacggagc  10800
aagcccgccc aaacctacgt tcggtataat atgttaagct tttaacaca aaggtttggc   10860 ttggggtaac ctgatgtggt gcaaaagacc gggcgttggc gagccattgc gcgggcgaat  10920
ggggccgtga ctcgtctcaa attcgagggc gtgcctcaat tcgtgccccc gtggcttttt  10980
cccgccgttt ccgccccgtt tgcaccactg cagccgcttc tttggttcgg acaccttgct  11040
gcgagctagg tgccttgtgc tacttaaaaa gtggcctccc aacaccaaca tgacatgagt  11100
gcgtgggcca agacacgttg gcggggtcgc agtcggctca atggcccgga aaaaacgctg  11160
ctggagctgg ttcggacgca gtccgccgcg gcgtatggat atccgcaagg ttccatagcg  11220
ccattgccct ccgtcggcgt ctatcccgca acctctaaat agagcgggaa tataacccaa  11280
gcttcttttt tttcctttaa cacgcacacc cccaactatc atgttgctgc tgctgtttga  11340
ctctactctg tggaggggtg ctcccaccca acccaaccta caggtggatc cggcgctgtg  11400
attggctgat aagtctccta tccggactaa ttctgaccaa tggacatgc gcgcaggacc    11460 caaatgccgc aattacgtaa ccccaacgaa atgcctaccc ctctttggag cccagcggcc  11520
ccaaatcccc ccaagcagcc cggttctacc ggcttccatc tccaagcaca agcagcccgg  11580 aattcccttta cctgcaggat aacttcgtat aatgtatgct atacgaagtt atgatctctc  11640
tcttgagctt ttccataaca agttcttctg cctccaggaa gtccatgggt ggtttgatca  11700
tggttttggt gtagtggtag tgcagtggtg gtattgtgac tggggatgta gttgagaata  11760
```

```
agtcatacac aagtcagctt tcttcgagcc tcatataagt ataagtagtt caacgtatta    11820
gcactgtacc cagcatctcc gtatcgagaa acacaacaac atgccccatt ggacagatca    11880
tgcggataca caggttgtgc agtatcatac atactcgatc agacaggtcg tctgaccatc    11940
atacaagctg aacaagcgct ccatacttgc acgctctcta tatacacagt taaattacat    12000
atccatagtc taacctctaa cagttaatct tctggtaagc ctcccagcca gccttctggt    12060
atcgcttggc ctcctcaata ggatctcggt tctggccgta cagacctcgg ccgacaatta    12120
tgatatccgt tccggtagac atgacatcct caacagttcg gtactgctgt ccgagagcgt    12180
ctcccttgtc gtcaagaccc accccggggg tcagaataag ccagtcctca gagtcgccct    12240
taggtcggtt ctgggcaatg aagccaacca caaactcggg gtcggatcgg gcaagctcaa    12300
tggtctgctt ggagtactcg ccagtggcca gagagccctt gcaagacagc tcggccagca    12360
tgagcagacc tctggccagc ttctcgttgg gagagggggac taggaactcc ttgtactggg    12420
agttctcgta gtcagagacg tcctccttct tctgttcaga gacagtttcc tcggcaccag    12480
ctcgcaggcc agcaatgatt ccggttccgg gtacaccgtg ggcgttggtg atatcggacc    12540
actcggcgat tcggtgacac cggtactggt gcttgacagt gttgccaata tctgcgaact    12600
ttctgtcctc gaacaggaag aaaccgtgct taagagcaag ttccttgagg gggagcacag    12660
tgccggcgta ggtgaagtcg tcaatgatgt cgatatgggt tttgatcatg cacacataag    12720
gtccgacctt atcggcaagc tcaatgagct ccttggtggt ggtaacatcc agagaagcac    12780
acaggttggt tttcttggct gccacgagct tgagcactcg agcggcaaag gcggacttgt    12840
ggacgttagc tcgagcttcg taggagggca ttttggtggt gaagaggaga ctgaaataaa    12900
tttagtctgc agaactttttt atcggaacct tatctggggc agtgaagtat atgttatggt    12960
aatagttacg agttagttga acttatagat agactggact atacggctat cggtccaaat    13020 tagaagaac gtcaatggct ctctgggcgt cgcctttgcc gacaaaaatg tgatcatgat    13080
gaaagccagc aatgacgttg cagctgatat tgttgtcggc caaccgcgcc gaaaacgcag    13140
ctgtcagacc cacagcctcc aacgaagaat gtatcgtcaa agtgatccaa gcacactcat    13200
agttggagtc gtactccaaa ggcggcaatg acgagtcaga cagatactcg tcgacgcgat    13260
aacttcgtat aatgtatgct atacgaagtt atcgtacgat agttagtaga caacaatcga    13320
taacgtctcg taccaaccac agattacgac ccattcgcag tcacagttca ctagggtttg    13380
ggttgcatcc gttgagagcg gtttgttttt aaccttctcc atgtgctcac tcaggttttg    13440
ggttcagatc aaatcaaggc gtgaaccact ttgtttgagg acaaatgtga cacaaccaac    13500
cagtgtcagg ggcaagtccg tgacaaaggg gaagatacaa tgcaattact gacagttaca    13560
gactgcctcg atgccctaac cttgccccaa aataagacaa ctgtcctcgt ttaagcgcaa    13620
ccctattcag cgtcacgtca taatagcgtt tggatagcac tagtctatga ggagcgtttt    13680
atgttgcggt gagggcgatt ggtgctcata tgggttcaat tgaggtggcg gaacgagctt    13740
agtcttcaat tgaggtgcga gcgacacaat ggggtgtcac gtggcctaat tgacctcggg    13800
tcgtggagtc cccagttata cagcaaccac gaggtgcatg ggtaggagac gtcaccagac    13860
aatagggttt tttttggact ggagagggtt gggcaaaagc gctcaacggg ctgtttgggg    13920
agctgtgggg gaggaattgg cgatatttgt gaggttaacg gctccgattt gcgtgttttg    13980
tcgctcctgc atctccccat acccatatct tccctcccca cctctttcca cgataatttt    14040
acggatcagc aataaggttc cttctcctag tttccacgtc catatatatc tatgctgcgt    14100 cgtcctttc gtgacatcac caaaacacat acaacaatgg ctgttactga cgtccttaag    14160
```

-continued

```
cgaaagtccg gtgtcatcgt cggcgacgat gtccgagccg tgagtatcca cgacaagatc     14220
agtgtcgaga cgacgcgttt tgtgtaatga cacaatccga aagtcgctag caacacacac     14280
tctctacaca aactaaccca gctctccatg gcctccacct cggctctgcc caagcagaac     14340
cctgccctcc gacgaaccgt cacttccacc actgtgaccg actcggagtc tgctgccgtc     14400
tctccctccg attctcccag acactcggcc tcctctacat cgctgtcttc catgtccgag     14460
gtggacattg ccaagcccaa gtccgagtac ggtgtcatgc tggataccta cggcaaccag     14520
ttcgaagttc ccgacttcac catcaaggac atctacaacg ctattcccaa gcactgcttc     14580
aagcgatctg ctctcaaggg atacggctac attcttcgag acattgtcct cctgactacc     14640
actttcagca tctggtacaa ctttgtgaca cccgagtaca ttccctccac tcctgctcga     14700
gccggtctgt gggctgtgta caccgttctt cagggactct tcggtactgg actgtgggtc     14760
attgcccacg agtgtggaca tggtgctttc tccgattccc gaatcatcaa cgacattact     14820
ggctgggtgc ttcactcttc cctgcttgtt ccctacttca gctggcaaat ctcccaccgg     14880
aagcatcaca aggccactgg aaacatggag cgagacatgg tcttcgttcc tcgaacccga     14940
gagcagcaag ctactcgact cggcaagatg acccacgaac tcgcccatct taccgaggaa     15000
actcctgctt tcaccctgct catgcttgtg cttcagcaac tggtcggttg gcccaactat     15060
ctcattacca acgttactgg acacaactac catgagcggc agcgagaggg tcgaggcaag     15120
ggaaagcaca acggtcttgg cggtggagtt aaccatttcg atccccgatc tcctctgtac     15180
gagaacagcg acgccaagct catcgtgctc tccgacattg cattggtct tatggccacc     15240 gctctgtact ttctcgttca gaagttcgga ttctacaaca tggccatctg gtacttcgtt     15300
ccctacttgt gggttaacca ctggctcgtc gccattacct ttctgcagca cacagatcct     15360
actcttcccc actacaccaa cgacgagtgg aactttgtgc gaggtgccgc tgcaaccatc     15420
gaccgagaga tgggcttcat tggacgtcat ctgctccacg gcattatcga gactcacgtc     15480
ctgcatcact acgtctcttc cattcccttc tacaatgcgg acgaagctac cgaggccatc     15540
aaacctatca tgggcaagca ctatcgagct gatgtccagg acggtcctcg aggattcatt     15600
cgagccatgt accgatctgc acgaatgtgc cagtgggttg aaccctccgc tggtgccgag     15660
ggagctggca agggtgtcct gttctttcga aaccgaaaca atgtgggcac tcctcccgct     15720
gtcatcaagc ccgttgccta agc                                             15743
```

<210> SEQ ID NO 43
<211> LENGTH: 15812
<212> TYPE: DNA
<213> ORGANISM: Artificial Sequence
<220> FEATURE:
<223> OTHER INFORMATION: Plasmid pZKL2-5U89GC

<400> SEQUENCE: 43

```
gtacgttatc atttgaacag tgaaaggcta cagtaacaga agcagttgta aacttcattc       60
cgttgattct gtactacagt accccactac gccgcttccg ctgacactgt tcaacccaaa      120
aactacatct gcgtgcgctg tgtaaggcta tcatcagata catactgtag attctgtaga      180
tgcgaacctg cttgtatcat atacatcccc ctcccctga cctgcacaag caagcaatgt      240
gacattgata ttgctgctta tctagtgccg aggatgtgaa agccgagact caaacatttc      300
ttttactctc ttgttcctga ccagacctgg cggagattac gccagtatga ttcttgcagg      360
tctgagacaa gcctggaaca gccaacattt atttttcgaa gcgagaaaca tgccacaccc      420
cggcacgttc agagatgcat atgatttgtt tttcgagtaa cagtacccccc ccccccccc      480
```

```
ccaatgaaac cagtattact cacaccatcc tcattcaaag cgttacactg attacgcgcc    540
catcaacgac agcatgaggg gactgctgat ctgatctaat caaatgacta caaaaatcgc    600
aataatgaag agcaaacgac aaaaaagaaa caggttaacc aatcccgctt caatgtctca    660
ccacaatcca gcactgtttc tcattacctc ctccctctaa tttcagagtt gcatcagggt    720
ccttgatggc gcgccagctg cattaatgaa tcggcaacg cgcggggaga ggcggtttgc     780
gtattgggcg ctcttccgct tcctcgctca ctgactcgct gcgctcggtc gttcggctgc    840
ggcgagcggt atcagctcac tcaaaggcgg taatacggtt atccacagaa tcagggata    900 acgcaggaaa gaacatgtga gcaaaaggcc agcaaaaggc caggaaccgt aaaaaggccg    960
cgttgctggc gttttccat aggctccgcc ccctgacga gcatcacaaa aatcgacgct     1020
caagtcagag gtggcgaaac ccgacaggac tataaagata ccaggcgttt ccccctggaa    1080
gctccctcgt gcgctctcct gttccgaccc tgccgcttac cggatacctg tccgcctttc    1140
tcccttcggg aagcgtggcg ctttctcata gctcacgctg taggtatctc agttcggtgt    1200
aggtcgttcg ctccaagctg gctgtgtgc acgaacccc cgttcagccc gaccgctgcg      1260
ccttatccgg taactatcgt cttgagtcca acccggtaag acacgactta tcgccactgg    1320
cagcagccac tggtaacagg attagcagag cgaggtatgt aggcggtgct acagagttct    1380
tgaagtggtg gcctaactac ggctacacta gaagaacagt atttggtatc tgcgctctgc    1440
tgaagccagt taccttcgga aaagagttg gtagctcttg atccggcaaa caaccaccg      1500 ctggtagcgg tggttttttt gtttgcaagc agcagattac gcgcagaaaa aaggatctc     1560 aagaagatcc tttgatcttt tctacggggt ctgacgctca gtggaacgaa aactcacgtt    1620
aagggatttt ggtcatgaga ttatcaaaaa ggatcttcac ctagatcctt ttaaattaaa    1680
aatgaagttt taaatcaatc taaagtatat atgagtaaac ttggtctgac agttaccaat    1740
gcttaatcag tgaggcacct atctcagcga tctgtctatt tcgttcatcc atagttgcct    1800
gactccccgt cgtgtagata actacgatac gggagggctt accatctggc cccagtgctg    1860
caatgatacc gcgagaccca cgctcaccgg ctccagattt atcagcaata aaccagccag    1920
ccggaagggc cgagcgcaga agtggtcctg caactttatc cgcctccatc cagtctatta    1980
attgttgccg ggaagctaga gtaagtagtt cgccagttaa tagtttgcgc aacgttgttg    2040
ccattgctac aggcatcgtg gtgtcacgct cgtcgtttgg tatggcttca ttcagctccg    2100
gttcccaacg atcaaggcga gttacatgat cccccatgtt gtgcaaaaaa gcggttagct    2160
ccttcggtcc tccgatcgtt gtcagaagta agttggccgc agtgttatca ctcatggtta    2220
tggcagcact gcataattct cttactgtca tgccatccgt aagatgcttt tctgtgactg    2280
gtgagtactc aaccaagtca ttctgagaat agtgtatgcg gcgaccgagt tgctcttgcc    2340
cggcgtcaat acgggataat accgcgccac atagcagaac tttaaaagtg ctcatcattg    2400
gaaaacgttc ttcggggcga aaactctcaa ggatcttacc gctgttgaga tccagttcga    2460
tgtaacccac tcgtgcaccc aactgatctt cagcatcttt tactttcacc agcgtttctg    2520
ggtgagcaaa aacaggaagg caaaatgccg caaaaaaggg aataagggcg acacggaaat    2580
gttgaatact catactcttc cttttcaat attattgaag catttatcag ggttattgtc      2640
tcatgagcgg atacatattt gaatgtattt agaaaaataa acaaataggg gttccgcgca    2700
catttccccg aaaagtgcca cctgatgcgg tgtgaaatac cgcacagatg cgtaaggaga    2760
aaataccgca tcaggaaatt gtaagcgtta atattttgtt aaaattcgcg ttaaattttt     2820
gttaaatcag ctcatttttt aaccaatagg ccgaaatcgg caaaatccct tataaatcaa    2880
```

```
aagaatagac cgagataggg ttgagtgttg ttccagtttg gaacaagagt ccactattaa   2940
agaacgtgga ctccaacgtc aaagggcgaa aaaccgtcta tcagggcgat ggcccactac   3000
gtgaaccatc accctaatca agttttttgg ggtcgaggtg ccgtaaagca ctaaatcgga   3060
accctaaagg gagcccccga tttagagctt gacggggaaa gccggcgaac gtggcgagaa   3120
aggaagggaa gaaagcgaaa ggagcgggcg ctagggcgct ggcaagtgta gcggtcacgc   3180
tgcgcgtaac caccacaccc gccgcgctta atgcgccgct acagggcgcg tccattcgcc   3240
attcaggctg cgcaactgtt gggaagggcg atcggtgcgg gcctcttcgc tattacgcca   3300
gctggcgaaa gggggatgtg ctgcaaggcg attaagttgg gtaacgccag gttttccca   3360 gtcacgacgt tgtaaaacga cggccagtga attgtaatac gactcactat agggcgaatt   3420
gggcccgacg tcgcatgctg gtttcgattt gtcttagagg aacgcatata cagtaatcat   3480
agagaataaa cgatattcat ttattaaagt agatagttga ggtagaagtt gtaaagagtg   3540
ataaatagct tagataccac agacaccctc ggtgacgaag tactgcagat ggtttccaat   3600
cacattgacc tgctggagca gagtgttacc ggcagagcac tgtttattgc tctggccctg   3660
gcacatgaca acgttggaga gaggagggtg gatcaggggc cagtcaataa agacctcacc   3720
agagcagtgc tggtaaccgt cccagaaggg cacttgaggg acgatatctc ctcggtgggt   3780
gattcggtag agctttcggt cttggacac cttggagaca tcgggttct cctgccaaa    3840 gaagagttta tcgacccagt tagcaaagcc agcgttaccg acaatgggct gaccaagagt   3900
aacaacgagg ggatcgtggc cgttaacctt gaggttgatt ccgaacagaa gggctgcagc   3960
tcctccgaga gagtgaccgg tgacagcaat ctggtagtcg ggatactgct caatcacaga   4020
gtcgagcttg gggccgatct gattgtaggt gttgttgtag gactggatga agccattgtg   4080
gacaagacag tcatcacaag tagcagtaga agagatgtta gcagcaagat caaagttaat   4140
taactcacct gcaggattga gactatgaat ggattcccgt gcccgtatta ctctactaat   4200
ttgatcttgg aacgcgaaaa tacgtttcta ggactccaaa gaatctcaac tcttgtcctt   4260
actaaatata ctacccatag ttgatggttt acttgaacag agaggacatg ttcacttgac   4320
ccaaagtttc tcgcatctct tggatatttg aacaacggcg tccactgacc gtcagttatc   4380
cagtcacaaa accccacat tcatacattc ccatgtacgt ttacaaagtt ctcaattcca    4440
tcgtgcaaat caaaatcaca tctattcatt catcatatat aaacccatca tgtctactaa   4500
cactcacaac tccatagaaa acatcgactc agaacacacg ctccatgcgg ccgcttagga   4560
atcctgagcg tccttgacac agtgaaccac accgactttg tgcatgtact tgagggtgga   4620
aatgatgttg cccacaatgg tagggtagaa gacgtaccga actccgtgtc gttcgcaaca   4680
ctctcggaca gcttgctgca cgaagggata gtgccaagac gacattcgag gaagaggtg    4740 atgctcgatc tggaagttga gaccgccagt aaagaacatg gcaatgggtc caccgtaggt   4800
ggaagaggtc tccacctgag ctctgtacca gtcgatctga tcggcttcaa cgtccttctc   4860
ggagctcttg accttgcagt tcttgtcggg gattcgctcc gagccatcga agttgtgaga   4920
caagatgaaa aagaaggtga ggaaggcacc ggtagcagtg gcaccagag gaatggtgat    4980 gagcagggag gttccagtga gataccaggg caagaaggcg gttcgaaaga tgaagaaagc   5040
tcgcataacg aatgcaaggg ttcggtaccg tcgcagaaag ccgttctctc gcatggctgt   5100
gacagactcg ggaatggtgt cgttgtgctg cattcggaag atgtagagag ggttgtacac   5160
cagcgaaacg ccgtaggctc caagcacgag gtacatgtac caggcctgga atcggtgaaa   5220
ccactttcga gcagtgttgg cagcagggta gttgtggaac acaaggaatg gttctgcgga   5280
```

```
ctcggcatcc aggtcgagac catgctgatt ggtgtaggtg tgatgtcgca tgatgtgaga      5340
ctgcagccag atccatctgg acgatccaat gacgtcgatg ccgtaggcaa agagagcgtt      5400
gacccagggc ttttgctga tggcaccatg agaggcatcg tgctgaatgg acaggccgat      5460
ctgcatgtgc atgaatccag tcaagagacc ccacagcacc attccggtag tagcccagtg      5520
ccactcgcaa aaggcggtga cagcaatgat gccaacggtt cgcagccaga atccaggtgt      5580
ggcataccag ttccgacctt tcatgacctc tcgcatagtt cgcttgacgt cctgtgcaaa      5640
gggagagtcg taggtgtaga caatgtcctt ggaggttcgg tcgtgcttgc ctcgcacgaa      5700
ctgttgaagc agcttcgagt tctcgggctt gacgtaaggg tgcatggagt agaacagagg      5760
agaagcatcg gaggcaccag aagcgaggat caagtcgcct ccgggatgga ccttggcaag      5820
accttccaga tcgtagagaa tgccgtcgat ggcaaccagg tcgggtcgct cgagcagctg      5880
ctcggtagta agggagagag ccatggttgt gaattagggt ggtgagaatg gttggttgta      5940
gggaagaatc aaaggccggt ctcgggatcc gtgggtatat atatatatat atatatatac      6000
gatccttcgt tacctccctg ttctcaaaac tgtggttttt cgttttcgt tttttgcttt       6060 ttttgatttt tttagggcca actaagcttc cagatttcgc taatcacctt tgtactaatt      6120
acaagaaagg aagaagctga ttagagttgg gcttttatg caactgtgct actccttatc       6180
tctgatatga aagtgtagac ccaatcacat catgtcattt agagttggta atactgggag      6240
gatagataag gcacgaaaac gagccatagc agacatgctg ggtgtagcca agcagaagaa      6300
agtagatggg agccaattga cgagcgaggg agctacgcca atccgacata cgacacgctg      6360
agatcgtctt ggccgggggg tacctacaga tgtccaaggg taagtgcttg actgtaattg      6420
tatgtctgag gacaaatatg tagtcagccg tataaagtca taccaggcac cagtgccatc      6480
atcgaaccac taactctcta tgatacatgc ctccggtatt attgtaccat gcgtcgcttt      6540
gttacatacg tatcttgcct ttttctctca gaaactccag aattctctct cttgagcttt      6600
tccataacaa gttcttctgc ctccaggaag tccatgggtg gtttgatcat ggttttggtg      6660
tagtggtagt gcagtggtgg tattgtgact ggggatgtag ttgagaataa gtcatacaca      6720
agtcagcttt cttcgagcct catataagta taagtagttc aacgtattag cactgtaccc      6780
agcatctccg tatcgagaaa cacaacaaca tgccccattg gacagatcat gcggatacac      6840
aggttgtgca gtatcataca tactcgatca gacaggtcgt ctgaccatca tacaagctga      6900
acaagcgctc catacttgca cgctctctat atacacagtt aaattacata tccatagtct      6960
aacctctaac agttaatctt ctggtaagcc tcccagccag ccttctggta tcgcttggcc      7020
tcctcaatag gatctcggtt ctggccgtac agacctcggc cgacaattat gatatccgtt      7080
ccggtagaca tgcatcctc aacagttcgg tactgctgtc cgagagcgtc tcccttgtcg       7140
tcaagaccca ccccgggggt cagaataagc cagtcctcag agtcgccctt aggtcggttc      7200
tgggcaatga agccaaccac aaactcgggg tcggatcggg caagctcaat ggtctgcttg      7260
gagtactcgc cagtggccag agagcccttg caagacagct cggccagcat gagcagacct      7320
ctggccagct tctcgttggg agaggggact aggaactcct tgtactggga gttctcgtag      7380
tcagagacgt cctccttctt ctgttcagag acagtttcct cggcaccagc tcgcaggcca      7440
gcaatgattc cggttccggg tacaccgtgg gcgttggtga tatcggacca ctcggcgatt      7500
cggtgacacc ggtactggtg cttgacagtg ttgccaatat ctgcgaactt tctgtcctcg      7560
aacaggaaga aaccgtgctt aagagcaagt tccttgaggg ggagcacagt gccggcgtag      7620
gtgaagtcgt caatgatgtc gatatgggtt ttgatcatgc acacataagg tccgaccttc      7680
```

-continued

```
tcggcaagct caatgagctc cttggtggtg gtaacatcca gagaagcaca caggttggtt    7740
ttcttggctg ccacgagctt gagcactcga gcggcaaagg cggacttgtg gacgttagct    7800
cgagcttcgt aggagggcat tttggtggtg aagaggagac tgaaataaat ttagtctgca    7860
gaacttttta tcggaacctt atctggggca gtgaagtata tgttatggta atagttacga    7920
gttagttgaa cttatagata gactggacta tacggctatc ggtccaaatt agaaagaacg    7980
tcaatggctc tctgggcgtc gcctttgccg acaaaaatgt gatcatgatg aaagccagca    8040
atgacgttgc agctgatatt gttgtcggcc aaccgcgccg aaaacgcagc tgtcagaccc    8100
acagcctcca acgaagaatg tatcgtcaaa gtgatccaag cacactcata gttggagtcg    8160
tactccaaag gcggcaatga cgagtcagac agatactcgt cgaccttttc cttgggaacc    8220
accaccgtca gcccttctga ctcacgtatt gtagccaccg acacaggcaa cagtccgtgg    8280
atagcagaat atgtcttgtc ggtccatttc tcaccaactt taggcgtcaa gtgaatgttg    8340
cagaagaagt atgtgccttc attgagaatc ggtgttgctg atttcaataa agtcttgaga    8400
tcagtttggc cagtcatgtt gtgggggggta attggattga gttatcgcct acagtctgta    8460
caggtatact cgctgcccac tttatacttt ttgattccgc tgcacttgaa gcaatgtcgt    8520
ttaccaaaag tgagaatgct ccacagaaca caccccaggg tatggttgag caaaaaataa    8580
acactccgat acggggaatc gaaccccggt ctccacggtt ctcaagaagt attcttgatg    8640
agagcgtatc gatcgaggaa gaggacaagc ggctgcttct taagtttgtg acatcagtat    8700
ccaaggcacc attgcaagga ttcaaggctt tgaacccgtc atttgccatt cgtaacgctg    8760
gtagacaggt tgatcggttc cctacggcct ccacctgtgt caatcttctc aagctgcctg    8820
actatcagga cattgatcaa cttcggaaga aactttttgta tgccattcga tcacatgctg    8880
gtttcgattt gtcttagagg aacgcatata cagtaatcat agagaataaa cgatattcat    8940
ttattaaagt agatagttga ggtagaagtt gtaaagagtg ataaatagcg gccgctcact    9000
gaatcttttt ggctcccttg tgctttcgga cgatgtaggt ctgcacgtag aagttgagga    9060
acagacacag gacagtacca acgtagaagt agttgaaaaa ccagccaaac attctcattc    9120
catcttgtcg gtagcaggga atgttccggt acttccagac gatgtagaag ccaacgttga    9180
actgaatgat ctgcatagaa gtaatcaggg acttgggcat agggaacttg agcttgatca    9240
gtcgggtcca atagtagccg tacatgatcc agtgaatgaa gccgttgagc agcacaaaga    9300
tccaaacggc ttcgtttcgg tagttgtaga acagccacat gtccatagga gctccgagat    9360
ggtgaaagaa ctgcaaccag gtcagaggct tgcccatgag gggcagatag aaggagtcaa    9420
tgtactcgag gaacttgctg aggtagaaca gctgagtggt gattcggaag acattgttgt    9480
cgaaagcctt ctcgcagttg tcggacatga caccaatggt gtacatggcg taggccatag    9540
agaggaagga gcccagcgag tagatggaca tgagcaggtt gtagttggtg aacacaaact    9600
tcattcgaga ctgacccctg ggtccgagag gaccaagggt gaacttcagg atgacgaagg    9660
cgatggagag gtacagcacc tcgcagtgcg aggcatcaga ccagagctga gcatagtcga    9720
ccttgggaag aacctcctgg ccaatggaga cgatttcgtt cacgacctcc atggttgatg    9780
tgtgtttaat tcaagaatga atatagagaa gagaagaaga aaaagattc aattgagccg    9840
gcgatgcaga cccttatata aatgttgcct tggacagacg gagcaagccc gcccaaacct    9900
acgttcggta taatatgtta agcttttttaa cacaaaggtt tggcttgggg taacctgatg    9960
tggtgcaaaa gaccgggcgt tggcgagcca ttgcgcgggc gaatgggcc gtgactcgtc    10020
tcaaattcga gggcgtgcct caattcgtgc ccccgtggct ttttcccgcc gtttccgccc    10080
```

```
cgtttgcacc actgcagccg cttctttggt tcggacacct tgctgcgagc taggtgcctt   10140
gtgctactta aaaagtggcc tcccaacacc aacatgacat gagtgcgtgg gccaagacac   10200
gttggcgggg tcgcagtcgg ctcaatggcc cggaaaaaac gctgctggag ctggttcgga   10260
cgcagtccgc cgcggcgtat ggatatccgc aaggttccat agcgccattg ccctccgtcg   10320
gcgtctatcc cgcaacctct aaatagagcg ggaatataac ccaagcttct ttttttcct    10380
ttaacacgca caccccaac tatcatgttg ctgctgctgt ttgactctac tctgtggagg    10440
ggtgctccca cccaacccaa cctacaggtg gatccggcgc tgtgattggc tgataagtct   10500
cctatccgga ctaattctga ccaatgggac atgcgcgcag gacccaaatg ccgcaattac   10560
gtaaccccaa cgaaatgcct acccctcttt ggagcccagc ggccccaaat cccccaagc    10620
agcccggttc taccggcttc catctccaag cacaagcagc ccggttctac cggcttccat   10680
ctccaagcac cccttctcc acaccccaca aaaagacccg tgcaggacat cctactgcgt    10740
gtttaaacac cactaaaacc ccacaaaata tatcttaccg aatatacaga tctactatag   10800
aggaacaatt gccccggaga agacggccag gccgcctaga tgacaaattc aacaactcac   10860
agctgacttt ctgccattgc cactaggggg gggcctttttt atatggccaa gccaagctct   10920
ccacgtcggt tgggctgcac ccaacaataa atgggtaggg ttgcaccaac aaagggatgg   10980
gatgggggt agaagatacg aggataacgg ggctcaatgg cacaaataag aacgaatact    11040
gccattaaga ctcgtgatcc agcgactgac accattgcat catctaaggg cctcaaaact   11100
acctcggaac tgctgcgctg atctggacac cacagaggtt ccgagcactt taggttgcac   11160
caaatgtccc accaggtgca ggcagaaaac gctggaacag cgtgtacagt ttgtcttaac   11220
aaaaagtgag ggcgctgagg tcgagcaggg tggtgtgact tgttatagcc tttagagctg   11280
cgaaagcgcg tatggatttg gctcatcagg ccagattgag ggtctgtgga cacatgtcat   11340
gttagtgtac ttcaatcgcc ccctggatat agccccgaca ataggccgtg gcctcatttt   11400
tttgccttcc gcacatttcc attgctcggt acccacacct tgcttctcct gcacttgcca   11460
accttaatac tggtttacat tgaccaacat cttacaagcg ggggcttgt ctagggtata    11520
tataaacagt ggctctccca atcggttgcc agtctctttt ttcctttctt tccccacaga   11580
ttcgaaatct aaactacaca tcacacaatg cctgttactg acgtccttaa gcgaaagtcc   11640
ggtgtcatcg tcgcgacga tgtccgagcc gtgagtatcc acgacaagat cagtgtcgag    11700
acgacgcgtt ttgtgtaatg acacaatccg aaagtcgcta gcaacacaca ctctctacac   11760
aaactaaccc agctctccat ggtgaaggct tctcgacagg ctctgcccct cgtcatcgac   11820
ggaaaggtgt acgacgtctc cgcttgggtg aacttccacc ctggtggagc tgaaatcatt   11880
gagaactacc agggacgaga tgctactgac gccttcatgg ttatgcactc tcaggaagcc   11940
ttcgacaagc tcaagcgaat gcccaagatc aaccaggctt ccgagctgcc tccccaggct   12000
gccgtcaacg aagctcagga ggatttccga aagctccgag aagagctgat cgccactggc   12060
atgtttgacg cctctcccct ctggtactcg tacaagatct tgaccaccct gggtcttggc   12120
gtgcttgcct tcttcatgct ggtccagtac cacctgtact tcattggtgc tctcgtgctc   12180
ggtatgcact accagcaaat gggatggctg tctcatgaca tctgccacca ccagaccttc   12240
aagaaccgaa actggaataa cgtcctgggt ctggtctttg gcaacggact ccagggcttc   12300
tccgtgacct ggtggaagga cagacacaac gcccatcatt ctgctaccaa cgttcagggt   12360
cacgatcccg acattgataa cctgcctctg ctcgcctggt ccgaggacga tgtcactcga   12420
gcttctccca tctcccgaaa gctcattcag ttccaacagt actatttcct ggtcatctgt   12480
```

```
attctcctgc gattcatctg gtgtttccag tctgtgctga ccgttcgatc cctcaaggac   12540
cgagacaacc agttctaccg atctcagtac aagaaagagg ccattggact cgctctgcac   12600
tggactctca agaccctgtt ccacctcttc tttatgccct ccatcctgac ctcgatgctg   12660
gtgttctttg tttccgagct cgtcggtggc ttcggaattg ccatcgtggt cttcatgaac   12720
cactaccctc tggagaagat cggtgattcc gtctgggacg acatggctt ctctgtgggt    12780 cagatccatg agaccatgaa cattcgacga ggcatcatta ctgactggtt ctttggaggc   12840
ctgaactacc agatcgagca ccatctctgg cccaccctgc ctcgacacaa cctcactgcc   12900
gtttcctacc aggtggaaca gctgtgccag aagcacaacc tcccctaccg aaaccctctg   12960
ccccatgaag gtctcgtcat cctgctccga tacctgtccc agttcgctcg aatggccgag   13020
aagcagcccg gtgccaaggc tcagtaagcg gccgcatgag aagataaata tataaataca   13080
ttgagatatt aaatgcgcta gattagagag cctcatactg ctcggagaga agccaagacg   13140
agtactcaaa ggggattaca ccatccatat ccacagacac aagctgggga aaggttctat   13200
atacactttc cggaataccg tagtttccga tgttatcaat gggggcagcc aggatttcag   13260
gcacttcggt gtctcggggt gaaatggcgt tcttggcctc catcaagtcg taccatgtct   13320
tcatttgcct gtcaaagtaa aacagaagca gatgaagaat gaacttgaag tgaaggaatt   13380
taaatagttg gagcaaggga gaaatgtaga gtgtgaaaga ctcactatgg tccgggctta   13440
tctcgaccaa tagccaaagt ctggagtttc tgagagaaaa aggcaagata cgtatgtaac   13500
aaagcgacgc atggtacaat aataccggag gcatgtatca tagagagtta gtggttcgat   13560
gatggcactg gtgcctggta tgactttata cggctgacta catatttgtc ctcagacata   13620
caattacagt caagcactta cccttggaca tctgtaggta ccccccggcc aagacgatct   13680
cagcgtgtcg tatgtcggat tggcgtagct ccctcgctcg tcaattggct cccatctact   13740
ttcttctgct tggctacacc cagcatgtct gctatggctc gttttcgtgc cttatctatc   13800
ctcccagtat taccaactct aaatgacatg atgtgattgg gtctacactt tcatatcaga   13860
gataaggagt agcacagttg cataaaaagc ccaactctaa tcagcttctt cctttcttgt   13920
aattagtaca aaggtgatta gcgaaatctg gaagcttagt tggccctaaa aaaatcaaaa   13980
aaagcaaaaa acgaaaaacg aaaaaccaca gttttgagaa cagggaggta acgaaggatc   14040
gtatatatat atatatatat atataccac ggatcccgag accggccttt gattcttccc    14100
tacaaccaac cattctcacc accctaattc acaaccatgg gcgtattcat taaacaggag   14160
cagcttccgg ctctcaagaa gtacaagtac tccgccgagg atcactcgtt catctccaac   14220
aacattctgc gccccttctg gcgacagttt gtcaaaatct tccctctgtg gatggccccc   14280
aacatggtga ctctgctggg cttcttcttt gtcattgtga acttcatcac catgctcatt   14340
gttgatccca cccacgaccg cgagcctccc agatgggtct acctcaccta cgctctgggt   14400
ctgttccttt accagacatt tgatgcctgt gacggatccc atgcccgacg aactggccag   14460
agtggacccc ttggagagct gttttgaccac tgtgtcgacg ccatgaatac ctctctgatt   14520
ctcacggtgg tggtgtccac cacccatatg ggatataaca tgaagctact gattgtgcag   14580
attgccgctc tcggaaactt ctacctgtcg acctgggaga cctaccatac cggaactctg   14640
tacctttctg gcttctctgg tcctgttgaa ggtatcttga ttctggtggc tcttttcgtc   14700
ctcaccttct tcactggtcc caacgtgtac gctctgaccg tctacgaggc tcttcccgag   14760
tccatcactt cgctgctgcc tgccagcttc ctggacgtca ccatcaccca gatctacatt   14820
ggattcggag tgctgggcat ggtgttcaac atctacggcg cctgcggaaa cgtgatcaag   14880
```

```
tactacaaca acaagggcaa gagcgctctc cccgccattc tcggaatcgc cccctttggc    14940
atcttctacg tcggcgtctt tgcctgggcc catgttgctc ctctgcttct ctccaagtac    15000
gccatcgtct atctgtttgc cattggggct gcctttgcca tgcaagtcgg ccagatgatt    15060
cttgcccatc tcgtgcttgc tcccttccc cactggaacg tgctgctctt cttcccctt     15120
gtgggactgg cagtgcacta cattgcaccc gtgtttggct gggacgccga tatcgtgtcg    15180
gttaacactc tcttcacctg tttggcgcc accctctcca tttacgcctt ctttgtgctt    15240
gagatcatcg acgagatcac caactacctc gatatctggt gtctgcgaat caagtaccct    15300
caggagaaga agaccgaata agcggccgca tggagcgtgt gttctgagtc gatgttttct    15360
atggagttgt gagtgttagt agacatgatg ggtttatata tgatgaatga atagatgtga    15420
ttttgatttg cacgatggaa ttgagaactt tgtaaacgta catgggaatg tatgaatgtg    15480
ggggttttgt gactggataa ctgacggtca gtggacgccg ttgttcaaat atccaagaga    15540
tgcgagaaac tttgggtcaa gtgaacatgt cctctctgtt caagtaaacc atcaactatg    15600
ggtagtatat ttagtaagga caagagttga gattctttgg agtcctagaa acgtattttc    15660
gcgttccaag atcaaattag tagagtaata cgggcacggg aatccattca tagtctcaat    15720
cctgcaggtg agttaattaa tcgagcttgg cgtaatcatg gtcatagctg tttcctgtgt    15780
gaaattgtta tccgctcaca attccacaca ac                                  15812
```

<210> SEQ ID NO 44
<211> LENGTH: 15877
<212> TYPE: DNA
<213> ORGANISM: Artificial Sequence
<220> FEATURE:
<223> OTHER INFORMATION: Plasmid pZKL1-2SP98C

<400> SEQUENCE: 44

```
aaatgatgtc gacgcagtag gatgtcctgc acgggtcttt ttgtgggggtg tggagaaagg      60
ggtgcttgga tcgatggaag ccggtagaac cgggctgctt gtgcttggag atggaagccg     120
gtagaaccgg gctgcttggg gggatttggg gccgctgggc tccaaagagg ggtaggcatt     180
tcgttggggt tacgtaattg cggcatttgg gtcctgcgcg catgtcccat tggtcagaat     240
tagtccggat aggagactta tcagccaatc acagcgccgg atccacctgt aggttgggtt     300
gggtggggagc accccctccac agagtagagt caaacagcag cagcaacatg atagttgggg     360
gtgtgcgtgt taaaggaaaa aaaagaagct tgggttatat tcccgctcta tttagaggtt     420
gcgggataga cgccgacgga gggcaatggc gctatgaac cttgcggata tccatacgcc     480
gcggcggact gcgtccgaac cagctccagc agcgtttttt ccgggccatt gagccgactg     540
cgaccccgcc aacgtgtctt ggcccacgca ctcatgtcat gttggtgttg ggaggccact     600
ttttaagtag cacaaggcac ctagctcgca gcaaggtgtc cgaaccaaag aagcggctgc     660
agtggtgcaa acggggcgga aacgcggga aaaagccacg ggggcacgaa ttgaggcacg      720
ccctcgaatt tgagacgagt cacggccca ttcgcccgcg caatggctcg ccaacgcccg     780
gtcttttgca ccacatcagg ttaccccaag ccaaaccttt gtgttaaaaa gcttaacata     840
ttataccgaa cgtaggtttg gcgggcttg ctccgtctgt ccaaggcaac atttatataa      900
gggtctgcat cgccggctca attgaatctt ttttcttctt ctcttctcta tattcattct     960
tgaattaaac acacatcaac catgggcgta ttcattaaac aggagcagct tccggctctc    1020
aagaagtaca agtactccgc cgaggatcac tcgttcatct ccaacaacat tctgcgcccc    1080
ttctggcgac agtttgtcaa aatcttccct ctgtggatgg cccccaacat ggtgactctg    1140
```

```
ctgggcttct tctttgtcat tgtgaacttc atcaccatgc tcattgttga tcccacccac    1200
gaccgcgagc ctcccagatg ggtctacctc acctacgctc tgggtctgtt cctttaccag    1260
acatttgatg cctgtgacgg atcccatgcc cgacgaactg gccagagtgg acccccttgga   1320 gagctgtttg accactgtgt cgacgccatg aatacctctc tgattctcac ggtggtggtg    1380
tccaccaccc atatgggata taacatgaag ctactgattg tgcagattgc cgctctcgga    1440
aacttctacc tgtcgacctg ggagacctac ataccggaa ctctgtacct ttctggcttc     1500
tctggtcctg ttgaaggtat cttgattctg gtggctcttt tcgtcctcac cttcttcact    1560
ggtcccaacg tgtacgctct gaccgtctac gaggctcttc ccgagtccat cacttcgctg    1620
ctgcctgcca gcttcctgga cgtcaccatc acccagatct acattggatt cggagtgctg    1680
ggcatggtgt tcaacatcta cggcgcctgc ggaaacgtga tcaagtacta caacaacaag    1740
ggcaagagcg ctctccccgc cattctcgga atcgcccct ttggcatctt ctacgtcggc     1800
gtctttgcct gggcccatgt tgctcctctg cttctctcca gtacgccat cgtctatctg     1860 tttgccattg gggctgcctt tgccatgcaa gtcggccaga tgattcttgc ccatctcgtg    1920
cttgctccct ttccccactg gaacgtgctg ctcttcttcc cctttgtggg actggcagtg    1980
cactacattg cacccgtgtt tggctgggac gccgatatcg tgtcggttaa cactctcttc    2040 acctgtttg gcgccaccct ctccatttac gccttctttg tgcttgagat catcgacgag     2100
atcaccaact acctcgatat ctggtgtctg cgaatcaagt accctcagga agaagacc      2160 gaataagcgg ccgcatggag cgtgtgttct gagtcgatgt tttctatgga gttgtgagtg    2220
ttagtagaca tgatgggttt atatatgatg aatgaataga tgtgattttg atttgcacga    2280
tggaattgag aactttgtaa acgtacatgg aatgtatga atgtgggggt tttgtgactg     2340
gataactgac ggtcagtgga cgccgttgtt caaatatcca agagatgcga gaaactttgg    2400
gtcaagtgaa catgtcctct ctgttcaagt aaaccatcaa ctatgggtag tatatttagt    2460
aaggacaaga gttgagattc tttggagtcc tagaaacgta ttttcgcgtt ccaagatcaa    2520
attagtagag taatacgggc acgggaatcc attcatagtc tcaatcctgc aggtgagtta    2580
attaatcgag cttggcgtaa tcatggtcat agctgtttcc tgtgtgaaat tgttatccgc    2640
tcacaattcc acacaacgta cgatagttag tagacaacaa tcagaacatc tccctcctta    2700
tataatcaca caggccagaa cgcgctaaac taaagcgctt tggacactat gttacattgg    2760
cattgattga actgaaacca cagtctccct cgcctgaatc gagcaatgga tgttgtcgga    2820
agtcaacttc actagaagag cggttctatg ccttgtcaag atcatatcat aaactcactc    2880
tgtattaccc catctataga acacttgtta tgaatgggcg gaaacattcc gctatatgca    2940
cctttccaca ctaatgcaaa gatgtgcatc ttcaacgggt agtaagactg gttccgactt    3000
ccgttgcatg gagagcaatg acctcgataa tgcgaacatc ccccacatat acactcttac    3060
acaggccaat ataatctgtg catttactaa atatttaagt ctatgcacct gcttgatgaa    3120
aagcggcacg gatggtatca tctagttttcc gccaatccaa gaaccaactg tgttggcagt   3180
ggtgtagccc atggcacaca gaccaaagat gaaaatacag acatcggcgg ttcgagccgt    3240
ggtgcctcga gcaacacccct tgtaatgcaa aagaggaggg taaatgtaca ccagaggcac    3300
acatgcaaac gatccggtga gagcgacgaa ccgatcgaga tcgtcggcac ctccccatgc    3360
aacaaaggcg gtgacaaaca caaggaagaa ccggaaaatg ttcttctgcc acttgatggt    3420
agagttgtac ttgcctgatc gggtgaagag accattctcg atgattcgga tggcgcgcca    3480
gctgcattaa tgaatcggcc aacgcgcggg gagaggcggt ttgcgtattg ggcgctcttc    3540
```

```
cgcttcctcg ctcactgact cgctgcgctc ggtcgttcgg ctgcggcgag cggtatcagc   3600
tcactcaaag gcggtaatac ggttatccac agaatcaggg gataacgcag gaaagaacat   3660
gtgagcaaaa ggccagcaaa aggccaggaa ccgtaaaaag gccgcgttgc tggcgttttt   3720
ccataggctc cgcccccctg acgagcatca caaaaatcga cgctcaagtc agaggtggcg   3780
aaacccgaca ggactataaa gataccaggc gtttccccct ggaagctccc tcgtgcgctc   3840
tcctgttccg accctgccgc ttaccggata cctgtccgcc tttctccctt cgggaagcgt   3900
ggcgctttct catagctcac gctgtaggta tctcagttcg gtgtaggtcg ttcgctccaa   3960
gctgggctgt gtgcacgaac cccccgttca gcccgaccgc tgcgccttat ccggtaacta   4020
tcgtcttgag tccaacccgg taagacacga cttatcgcca ctggcagcag ccactggtaa   4080
caggattagc agagcgaggt atgtaggcgg tgctacagag ttcttgaagt ggtggcctaa   4140
ctacggctac actagaagaa cagtatttgg tatctgcgct ctgctgaagc cagttacctt   4200
cggaaaaaga gttggtagct cttgatccgg caaacaaacc accgctggta gcggtggttt   4260
ttttgtttgc aagcagcaga ttacgcgcag aaaaaaagga tctcaagaag atcctttgat   4320
cttttctacg gggtctgacg ctcagtggaa cgaaaactca cgttaaggga ttttggtcat   4380
gagattatca aaaaggatct tcacctagat ccttttaaat taaaaatgaa gttttaaatc   4440
aatctaaagt atatatgagt aaacttggtc tgacagttac caatgcttaa tcagtgaggc   4500
acctatctca gcgatctgtc tatttcgttc atccatagtt gcctgactcc ccgtcgtgta   4560
gataactacg atacgggagg gcttaccatc tggccccagt gctgcaatga taccgcgaga   4620
cccacgctca ccggctccag atttatcagc aataaaccag ccagccggaa gggccgagcg   4680
cagaagtggt cctgcaactt tatccgcctc catccagtct attaattgtt gccgggaagc   4740
tagagtaagt agttcgccag ttaatagttt gcgcaacgtt gttgccattg ctacaggcat   4800
cgtggtgtca cgctcgtcgt ttggtatggc ttcattcagc tccggttccc aacgatcaag   4860
gcgagttaca tgatccccca tgttgtgcaa aaaagcggtt agctccttcg gtcctccgat   4920
cgttgtcaga agtaagttgg ccgcagtgtt atcactcatg gttatggcag cactgcataa   4980
ttctcttact gtcatgccat ccgtaagatg cttttctgtg actggtgagt actcaaccaa   5040
gtcattctga gaatagtgta tgcggcgacc gagttgctct tgcccggcgt caatacggga   5100
taataccgcg ccacatagca gaactttaaa agtgctcatc attggaaaac gttcttcggg   5160
gcgaaaactc tcaaggatct taccgctgtt gagatccagt tcgatgtaac ccactcgtgc   5220
acccaactga tcttcagcat cttttacttt caccagcgtt tctgggtgag caaaaacagg   5280
aaggcaaaat gccgcaaaaa agggaataag ggcgacacgg aaatgttgaa tactcatact   5340
cttccttttt caatattatt gaagcattta tcagggttat tgtctcatga gcggatacat   5400
atttgaatgt atttagaaaa ataaacaaat aggggttccg cgcacatttc cccgaaaagt   5460
gccacctgat gcggtgtgaa ataccgcaca gatgcgtaag gagaaaatac cgcatcagga   5520
aattgtaagc gttaatattt tgttaaaatt cgcgttaaat ttttgttaaa tcagctcatt   5580
ttttaaccaa taggccgaaa tcggcaaaat cccttataaa tcaaaagaat agaccgagat   5640
agggttgagt gttgttccag tttggaacaa gagtccacta ttaaagaacg tggactccaa   5700
cgtcaaaggg cgaaaaaccg tctatcaggg cgatggccca ctacgtgaac catcacccta   5760
atcaagtttt ttggggtcga ggtgccgtaa agcactaaat cggaacccta agggagccc    5820 ccgatttaga gcttgacggg gaaagccggc gaacgtggcg agaaaggaag ggaagaaagc   5880
gaaaggagcg ggcgctaggg cgctggcaag tgtagcggtc acgctgcgcg taaccaccac   5940
```

```
acccgccgcg cttaatgcgc cgctacaggg cgcgtccatt cgccattcag gctgcgcaac    6000
tgttgggaag ggcgatcggt gcgggcctct tcgctattac gccagctggc gaaaggggga    6060
tgtgctgcaa ggcgattaag ttgggtaacg ccagggtttt cccagtcacg acgttgtaaa    6120
acgacggcca gtgaattgta atacgactca ctatagggcg aattgggccc gacgtcgcat    6180
gcttagaagt gaggattaca agaagcctct ggatatcaat gatgaacgta ctcagcggct    6240
ggtcaagcat ttcgaccgtc gaatcgacga ggtgttcacc tttgacaagc gagggttccc    6300
aattgatcac gttctcgagt tgttcaaatc ttctctcaac atctctctgc atgaactatc    6360
tctgttgacg aacgtgtcac ccactgttcc tcgaacgccc ttctccgagt ttggtctgaa    6420
catcttcgat ctcaaactga cccccgcagt gatcaatagt gccatgccac tgccgatgcg    6480
gtgcgaacat ccctggaggg attctcggag ctctacacaa tgcagattct gtcgtcgagt    6540
actctctacc ttgctcgaat gacttattgt gctactactg cactcatgct tcgatcatgt    6600
gccctactgc accccaaatt tggtgatctg attgagacag agtaccctct tcagctgatt    6660
cagaagatca tcagcaacat gaatgatgtg gttgaccagg caggctgttg tagtcacgtc    6720
cttcacttca agttcattct tcatctgctt ctgttttact ttgacaggca aatgaagaca    6780
tggtacgact tgatggaggc caagaacgcc atttcacccc gagacaccga agtgcctgaa    6840
atcctggctg cccccattga taacatcgga aactacggta ttccggaaag tgtatataga    6900
acctttcccc agcttgtgtc tgtggatatg gatggtgtaa tccccttaat taactcacct    6960
gcaggattga gactatgaat ggattccgt gcccgtatta ctctactaat ttgatcttgg    7020
aacgcgaaaa tacgtttcta ggactccaaa gaatctcaac tcttgtcctt actaaatata    7080
ctacccatag ttgatggttt acttgaacag agaggacatg ttcacttgac ccaaagtttc    7140
tcgcatctct tggatatttg aacaacggcg tccactgacc gtcagttatc cagtcacaaa    7200
accccacat tcatacattc ccatgtacgt ttacaaagtt ctcaattcca tcgtgcaaat    7260
caaaatcaca tctattcatt catcatatat aaacccatca tgtctactaa cactcacaac    7320
tccatagaaa acatcgactc agaacacacg ctccatgcgg ccgcttaggc aacgggcttg    7380
atgacagcgg gaggagtgcc cacattgttt cggtttcgaa agaacaggac acccttgcca    7440
gctccctcgg caccagcgga gggttcaacc cactggcaca ttcgtgcaga tcggtacatg    7500
gctcgaatga atcctcgagg accgtcctgg acatcagctc gatagtgctt gcccatgata    7560
ggtttgatgg cctcggtagc ttcgtccgca ttgtagaagg gaatggaaga gacgtagtga    7620
tgcaggacgt gagtctcgat aatgccgtgg agcagatgac gtccaatgaa gcccatctct    7680
cggtcgatgg ttgcagcggc acctcgcaca aagttccact cgtcgttggt gtagtgggga    7740
agagtaggat ctgtgtgctg cagaaaggta atggcgacga gccagtggtt aacccacaag    7800
tagggaacga agtaccagat ggccatgttg tagaatccga acttctgaac gagaaagtac    7860
agagcggtgg ccataagacc aatgccaatg tcggagagca cgatgagctt ggcgtcgctg    7920
ttctcgtaca gaggagatcg gggatcgaaa tggttaactc caccgccaag accgttgtgc    7980
tttcccttgc ctcgaccctc tcgctgccgc tcatggtagt tgtgtccagt aacgttggta    8040
atgagatagt tgggccaacc gaccagttgc tgaagcacaa gcatgagcag ggtgaaagca    8100
ggagtttcct cggtaagatg ggcgagttcg tgggtcatct tgccgagtcg agtagcttgc    8160
tgctctcggg ttcgaggaac gaagaccatg tctcgctcca tgtttccagt ggccttgtga    8220
tgcttccggt gggagatttg ccagctgaag tagggaacaa gcagggaaga gtgaagcacc    8280
cagccagtaa tgtcgttgat gattcgggaa tcggagaaag caccatgtcc acactcgtgg    8340
```

```
gcaatgaccc acagtccagt accgaagagt ccctgaagaa cggtgtacac agcccacaga   8400
ccggctcgag caggagtgga gggaatgtac tcgggtgtca caaagttgta ccagatgctg   8460
aaagtggtag tcaggaggac aatgtctcga agaatgtagc cgtatccctt gagagcagat   8520
cgcttgaagc agtgcttggg aatagcgttg tagatgtcct tgatggtgaa gtcgggaact   8580
tcgaactggt tgccgtaggt atccagcatg acaccgtact cggacttggg cttggcaatg   8640
tccacctcgg acatggaaga cagcgatgta gaggaggccg agtgtctggg agaatcggag   8700
ggagagacgg cagcagactc cgagtcggtc acagtggtgg aagtgacggt tcgtcggagg   8760
gcagggttct gcttgggcag agccgaggtg gaggccatgg ccattgctgt agatatgtct   8820
tgtgtgtaag ggggttgggg tggttgtttg tgttcttgac ttttgtgtta gcaagggaag   8880
acgggcaaaa aagtgagtgt ggttgggagg gagagacgag ccttatatat aatgcttgtt   8940
tgtgtttgtg caagtggacg ccgaaacggg caggagccaa actaaacaag gcagacaatg   9000
cgagcttaat tggattgcct gatgggcagg ggttagggct cgatcaatgg gggtgcgaag   9060
tgacaaaatt gggaattagg ttcgcaagca aggctgacaa gactttggcc caaacatttg   9120
tacgcggtgg acaacaggag ccacccatcg tctgtcacgg gctagccggt cgtgcgtcct   9180
gtcaggctcc acctaggctc catgccactc catacaatcc cactagtgta ccgctaggcc   9240
gcttttagct cccatctaag acccccccaa aacctccact gtacagtgca ctgtactgtg   9300
tggcgatcaa gggcaaggga aaaaaggcgc aaacatgcac gcatggaatg acgtaggtaa   9360
ggcgttacta gactgaaaag tggcacattt cggcgtgcca aagggtccta ggtgcgtttc   9420
gcgagctggg cgccaggcca agccgctcca aaacgcctct ccgactccct ccagcggcct   9480
ccatatcccc atccctctcc acagcaatgt tgttaagcct tgcaaacgaa aaaatagaaa   9540
ggctaataag cttccaatat tgtggtgtac gctgcataac gcaacaatga gcgccaaaca   9600
acacacacac acagcacaca gcagcattaa ccacgatgaa cagcatgaat cctttacct   9660 gcaggataac ttcgtataat gtatgctata cgaagttatg atctctctct tgagcttttc   9720
cataacaagt tcttctgcct ccaggaagtc catgggtggt ttgatcatgg ttttggtgta   9780
gtggtagtgc agtggtggta ttgtgactgg ggatgtagtt gagaataagt catacacaag   9840
tcagctttct tcgagcctca tataagtata agtagttcaa cgtattagca ctgtacccag   9900
catctccgta tcgagaaaca caacaacatg ccccattgga cagatcatgc ggatacacag   9960
gttgtgcagt atcatacata ctcgatcaga caggtcgtct gaccatcata caagctgaac  10020
aagcgctcca tacttgcacg ctctctatat acacagttaa attacatatc catagtctaa  10080
cctctaacag ttaatcttct ggtaagcctc ccagccagcc ttctggtatc gcttggcctc  10140
ctcaatagga tctcggttct ggccgtacag acctcggccg acaattatga tatccgttcc  10200
ggtagacatg acatcctcaa cagttcggta ctgctgtccg agagcgtctc ccttgtcgtc  10260
aagacccacc ccgggggtca gaataagcca gtcctcagag tcgcccttag gtcggttctg  10320
ggcaatgaag ccaaccacaa actcggggtc ggatcgggca agctcaatgg tctgcttgga  10380
gtactcgcca gtggccagag agcccttgca agacagctcg gccagcatga gcagacctct  10440
ggccagcttc tcgttgggag agggggactag gaactccttg tactgggagt tctcgtagtc  10500
agagacgtcc tccttcttct gttcagagac agtttcctcg gcaccagctc gcaggccagc  10560
aatgattccg gttccgggta caccgtgggc gttggtgata tcggaccact cggcgattcg  10620
gtgacaccgg tactggtgct tgacagtgtt gccaatatct gcgaactttc tgtcctcgaa  10680
caggaagaaa ccgtgcttaa gagcaagttc cttgagggggg agcacagtgc cggcgtaggt  10740
```

```
gaagtcgtca atgatgtcga tatgggtttt gatcatgcac acataaggtc cgaccttatc   10800
ggcaagctca atgagctcct tggtggtggt aacatccaga gaagcacaca ggttggtttt   10860
cttggctgcc acgagcttga gcactcgagc ggcaaaggcg gacttgtgga cgttagctcg   10920
agcttcgtag gagggcattt tggtggtgaa gaggagactg aaataaattt agtctgcaga   10980 acttttatc ggaaccttat ctggggcagt gaagtatatg ttatggtaat agttacgagt    11040
tagttgaact tatagataga ctggactata cggctatcgg tccaaattag aaagaacgtc   11100
aatggctctc tgggcgtcgc cttttccgac aaaaatgtga tcatgatgaa agccagcaat   11160
gacgttgcag ctgatattgt tgtcggccaa ccgcgccgaa aacgcagctg tcagacccac   11220
agcctccaac gaagaatgta tcgtcaaagt gatccaagca cactcatagt tggagtcgta   11280
ctccaaaggc ggcaatgacg agtcagacag atactcgtcg acgcgataac ttcgtataat   11340
gtatgctata cgaagttatc gtacgatagt tagtagacaa caatcgatcg aggaagagga   11400
caagcggctg cttcttaagt ttgtgacatc agtatccaag gcaccattgc aaggattcaa   11460
ggctttgaac ccgtcatttg ccattcgtaa cgctggtaga caggttgatc ggttccctac   11520
ggcctccacc tgtgtcaatc ttctcaagct gcctgactat caggacattg atcaacttcg   11580
gaagaaactt ttgtatgcca ttcgatcaca tgctggtttc gatttgtctt agaggaacgc   11640
atatacagta atcatagaga ataaacgata ttcatttatt aaagtagata gttgaggtag   11700
aagttgtaaa gagtgataaa tagcggccgc tcactgaatc ttttttggctc ccttgtgctt   11760 tcggacgatg taggtctgca cgtagaagtt gaggaacaga cacaggacag taccaacgta   11820
gaagtagttg aaaaaccagc caaacattct cattccatct tgtcggtagc agggaatgtt   11880
ccggtacttc cagacgatgt agaagccaac gttgaactga atgatctgca tagaagtaat   11940
cagggacttg gcatagggga acttgagctt gatcagtcgg gtccaatagt agccgtacat   12000
gatccagtga atgaagccgt tgagcagcac aaagatccaa acggcttcgt ttcggtagtt   12060
gtagaacagc cacatgtcca taggagctcc gagatggtga agaactgca accaggtcag   12120 aggcttgccc atgaggggca gatagaagga gtcaatgtac tcgaggaact tgctgaggta   12180
gaacagctga gtggtgattc ggaagacatt gttgtcgaaa gccttctcgc agttgtcgga   12240
catgacacca atggtgtaca tggcgtaggc catagagagg aaggagccca gcgagtagat   12300
ggacatgagc aggttgtagt tggtgaacac aaacttcatt cgagactgac ccttgggtcc   12360
gagaggacca agggtgaact tcaggatgac gaaggcgatg gagaggtaca gcacctcgca   12420
gtgcgaggca tcagaccaga gctgagcata gtcgaccttg ggaagaacct cctggccaat   12480
ggagacgatt tcgttcacga cctccatggt tgtgaattag ggtggtgaga atggttggtt   12540
gtagggaaga atcaaaggcc ggtctcggga tccgtgggta tatatatata tatatatata   12600
tacgatcctt cgttacctcc ctgttctcaa aactgtggtt tttcgttttt cgttttttgc   12660 ttttttgat tttttaggg ccaactaagc ttccagattt cgctaatcac ctttgtacta    12720
attacaagaa aggaagaagc tgattagagt tgggcttttt atgcaactgt gctactcctt   12780
atctctgata tgaaagtgta gacccaatca catcatgtca tttagagttg gtaatactgg   12840
gaggatagat aaggcacgaa aacgagccat agcagacatg ctgggtgtag ccaagcagaa   12900
gaaagtagat gggagccaat tgacgagcga gggagctacg ccaatccgac atacgacacg   12960
ctgagatcgt cttggccggg gggtacctac agatgtccaa gggtaagtgc ttgactgtaa   13020
ttgtatgtct gaggacaaat atgtagtcag ccgtataaag tcataccagg caccagtgcc   13080
atcatcgaac cactaactct ctatgataca tgcctccggt attattgtac catgcgtcgc   13140
```

```
tttgttacat acgtatcttg ccttttctc tcagaaactc cagactttgg ctattggtcg    13200
agataagccc ggaccatagt gagtctttca cactctgttt aaacaccact aaaaccccac    13260
aaaatatatc ttaccgaata tacagatcta ctatagagga acaattgccc cggagaagac    13320
ggccaggccg cctagatgac aaattcaaca actcacagct gactttctgc cattgccact    13380
agggggggggc cttttatat ggccaagcca agctctccac gtcggttggg ctgcacccaa    13440
caataaatgg gtagggttgc accaacaaag ggatgggatg gggggtagaa gatacgagga    13500
taacggggct caatggcaca aataagaacg aatactgcca ttaagactcg tgatccagcg    13560
actgacacca ttgcatcatc taagggcctc aaaactacct cggaactgct gcgctgatct    13620
ggacaccaca gaggttccga gcactttagg ttgcaccaaa tgtcccacca ggtgcaggca    13680
gaaaacgctg aacagcgtg tacagttgt cttaacaaaa agtgagggcg ctgaggtcga    13740
gcagggtggt gtgacttgtt atagccttta gagctgcgaa agcgcgtatg gatttggctc    13800
atcaggccag attgagggtc tgtggacaca tgtcatgtta gtgtacttca atcgccccct    13860
ggatatagcc ccgacaatag gccgtggcct catttttttg ccttccgcac atttccattg    13920
ctcggtaccc acaccttgct tctcctgcac ttgccaacct taatactggt ttacattgac    13980
caacatctta caagcggggg gcttgtctag ggtatatata aacagtggct ctcccaatcg    14040
gttgccagtc tctttttcc tttctttccc cacagattcg aaatctaaac tacacatcac    14100
acaatgcctg ttactgacgt ccttaagcga aagtccggtg tcatcgtcgg cgacgatgtc    14160
cgagccgtga gtatccacga caagatcagt gtcgagacga cgcgttttgt gtaatgacac    14220
aatccgaaag tcgctagcaa cacacactct ctacacaaac taacccagct ctccatggtg    14280
aaggcttctc gacaggctct gcccctcgtc atcgacggaa aggtgtacga cgtctccgct    14340
tgggtgaact tccaccctgg tggagctgaa atcattgaga actaccaggg acgagatgct    14400
actgacgcct tcatggttat gcactctcag gaagccttcg acaagctcaa gcgaatgccc    14460
aagatcaacc aggcttccga gctgcctccc caggctgccg tcaacgaagc tcaggaggat    14520
ttccgaaagc tccgagaaga gctgatcgcc actggcatgt ttgacgcctc tcccctctgg    14580
tactcgtaca agatcttgac caccctgggt cttggcgtgc ttgccttctt catgctggtc    14640
cagtaccacc tgtacttcat tggtgctctc gtgctcggta tgcactacca gcaaatggga    14700
tggctgtctc atgacatctg ccaccaccag accttcaaga accgaaactg gaataacgtc    14760
ctgggtctgg tctttggcaa cggactccag ggcttctccg tgacctggtg gaaggacaga    14820
cacaacgccc atcattctgc taccaacgtt cagggtcacg atcccgacat tgataacctg    14880
cctctgctcg cctggtccga ggacgatgtc actcgagctt ctcccatctc ccgaaagctc    14940
attcagttcc aacagtacta tttcctggtc atctgtattc tcctgcgatt catctggtgt    15000
ttccagtctg tgctgaccgt tcgatccctc aaggaccgag acaaccagtt ctaccgatct    15060
cagtacaaga aagaggccat tggactcgct ctgcactgga ctctcaagac cctgttccac    15120
ctcttcttta tgccctccat cctgacctcg atgctggtgt tctttgtttc cgagctcgtc    15180
ggtggcttcg gaattgccat cgtggtcttc atgaaccact accctctgga gaagatcggt    15240
gattccgtct gggacggaca tggcttctct gtgggtcaga tccatgagac catgaacatt    15300
cgacgaggca tcattactga ctggttcttt ggaggcctga actaccagat cgagcaccat    15360
ctctggccca ccctgcctcg acacaacctc actgccgttt cctaccaggt ggaacagctg    15420
tgccagaagc acaacctccc ctaccgaaac cctctgcccc atgaaggtct cgtcatcctg    15480
ctccgatacc tgtcccagtt cgctcgaatg gccgagaagc agcccggtgc caaggctcag    15540
```

```
<210> SEQ ID NO 45
<211> LENGTH: 6645
<212> TYPE: DNA
<213> ORGANISM: Artificial Sequence
<220> FEATURE:
<223> OTHER INFORMATION: Plasmid pYAT-GUS1

<400> SEQUENCE: 45
```

| | | | | | |
|---|---|---|---|---|---|
| taagcggccg | catgagaaga | taaatatata | aatacattga | gatattaaat | gcgctagatt 15600 |
| agagagcctc | atactgctcg | gagagaagcc | aagacgagta | ctcaaagggg | attacaccat 15660 |
| ccatatccac | agacacaagc | tggggaaagg | ttctatatac | actttccgga | ataccgtagt 15720 |
| ttccgatgtt | atcaatgggg | gcagccagga | tttcaggcac | ttcggtgtct | cggggtgaaa 15780 |
| tggcgttctt | ggcctccatc | aagtcgtacc | atgtcttcat | ttgcctgtca | agtaaaaca 15840 |
| gaagcagatg | aagaatgaac | ttgaagtgaa | ggaattt | | 15877 |

| | | | | | |
|---|---|---|---|---|---|
| catggatggt | acgtcctgta | gaaaccccaa | cccgtgaaat | caaaaaactc | gacggcctgt 60 |
| gggcattcag | tctggatcgc | gaaaactgtg | gaattgatca | gcgttggtgg | gaaagcgcgt 120 |
| tacaagaaag | ccgggcaatt | gctgtgccag | gcagttttaa | cgatcagttc | gccgatgcag 180 |
| atattcgtaa | ttatgcgggc | aacgtctggt | atcagcgcga | agtctttata | ccgaaaggtt 240 |
| gggcaggcca | gcgtatcgtg | ctgcgtttcg | atgcggtcac | tcattacggc | aaagtgtggg 300 |
| tcaataatca | ggaagtgatg | gagcatcagg | gcggctatac | gccatttgaa | gccgatgtca 360 |
| cgccgtatgt | tattgccggg | aaaagtgtac | gtatcaccgt | ttgtgtgaac | aacgaactga 420 |
| actggcagac | tatcccgccg | ggaatggtga | ttaccgacga | aaacggcaag | aaaaagcagt 480 |
| cttacttcca | tgatttcttt | aactatgccg | gatccatcg | cagcgtaatg | ctctacacca 540 |
| cgccgaacac | ctgggtggac | gatatcaccg | tggtgacgca | tgtcgcgcaa | gactgtaacc 600 |
| acgcgtctgt | tgactggcag | gtggtggcca | atggtgatgt | cagcgttgaa | ctgcgtgatg 660 |
| cggatcaaca | ggtggttgca | actggacaag | gcactagcgg | gactttgcaa | gtggtgaatc 720 |
| cgcacctctg | gcaaccgggt | gaaggttatc | tctatgaact | gtgcgtcaca | gccaaaagcc 780 |
| agacagagtg | tgatatctac | ccgcttcgcg | tcggcatccg | gtcagtggca | gtgaagggcg 840 |
| aacagttcct | gattaaccac | aaaccgttct | actttactgg | ctttggtcgt | catgaagatg 900 |
| cggacttacg | tggcaaagga | ttcgataacg | tgctgatggt | gcacgaccac | gcattaatgg 960 |
| actggattgg | ggccaactcc | taccgtacct | cgcattaccc | ttacgctgaa | gagatgctcg 1020 |
| actgggcaga | tgaacatggc | atcgtggtga | ttgatgaaac | tgctgctgtc | ggctttaacc 1080 |
| tctctttagg | cattggtttc | gaagcgggca | acaagccgaa | agaactgtac | agcgaagagg 1140 |
| cagtcaacgg | ggaaactcag | caagcgcact | tacaggcgat | taaagagctg | atagcgcgtg 1200 |
| acaaaaacca | cccaagcgtg | gtgatgtgga | gtattgccaa | cgaaccggat | acccgtccgc 1260 |
| aagtgcacgg | gaatatttcg | ccactggcgg | aagcaacgcg | taaactcgac | ccgacgcgtc 1320 |
| cgatcacctg | cgtcaatgta | atgttctgcg | acgctcacac | cgataccatc | agcgatctct 1380 |
| ttgatgtgct | gtgcctgaac | cgttattacg | gatggtatgt | ccaaagcggc | gatttggaaa 1440 |
| cggcagagaa | ggtactggaa | aaagaacttc | tggcctggca | ggagaaactg | catcagccga 1500 |
| ttatcatcac | cgaatacggc | gtggatacgt | tagccgggct | gcactcaatg | tacaccgaca 1560 |
| tgtggagtga | agagtatcag | tgtgcatggc | tggatatgta | tcaccgcgtc | tttgatcgcg 1620 |
| tcagcgccgt | cgtcggtgaa | caggtatgga | atttcgccga | ttttgcgacc | tcgcaaggca 1680 |
| tattgcgcgt | tggcggtaac | aagaaaggga | tcttcactcg | cgaccgcaaa | ccgaagtcgg 1740 |

```
cggcttttct gctgcaaaaa cgctggactg gcatgaactt cggtgaaaaa ccgcagcagg    1800
gaggcaaaca atgattaatt aactagagcg gccgccaccg cggcccgaga ttccggcctc    1860
ttcggccgcc aagcgacccg ggtggacgtc tagaggtacc tagcaattaa cagatagttt    1920
gccggtgata attctcttaa cctcccacac tcctttgaca taacgattta tgtaacgaaa    1980
ctgaaatttg accagatatt gtgtccgcgg tggagctcca gcttttgttc cctttagtga    2040
gggttaattt cgagcttggc gtaatcatgg tcatagctgt ttcctgtgtg aaattgttat    2100
ccgctcacaa ttccacacaa catacgagcc ggaagcataa agtgtaaagc ctggggtgcc    2160
taatgagtga gctaactcac attaattgcg ttgcgctcac tgcccgcttt ccagtcggga    2220
aacctgtcgt gccagctgca ttaatgaatc ggccaacgcg cggggagagg cggtttgcgt    2280
attgggcgct cttccgcttc ctcgctcact gactcgctgc gctcggtcgt tcggctgcgg    2340
cgagcggtat cagctcactc aaaggcggta atacggttat ccacagaatc aggggataac    2400
gcaggaaaga acatgtgagc aaaaggccag caaaaggcca ggaaccgtaa aaaggccgcg    2460
ttgctggcgt ttttccatag gctccgcccc cctgacgagc atcacaaaaa tcgacgctca    2520
agtcagaggt ggcgaaaccc gacaggacta taaagatacc aggcgtttcc ccctggaagc    2580
tccctcgtgc gctctcctgt tccgaccctg ccgcttaccg gatacctgtc cgcctttctc    2640
ccttcgggaa gcgtggcgct ttctcatagc tcacgctgta ggtatctcag ttcggtgtag    2700
gtcgttcgct ccaagctggg ctgtgtgcac gaaccccccg ttcagcccga ccgctgcgcc    2760
ttatccggta actatcgtct tgagtccaac ccggtaagac acgacttatc gccactggca    2820
gcagccactg gtaacaggat tagcagagcg aggtatgtag gcggtgctac agagttcttg    2880
aagtggtggc ctaactacgg ctacactaga aggacagtat ttggtatctg cgctctgctg    2940
aagccagtta ccttcggaaa aagagttggt agctcttgat ccggcaaaca aaccaccgct    3000
ggtagcggtg gtttttttgt ttgcaagcag cagattacgc gcagaaaaaa aggatctcaa    3060
gaagatcctt tgatctttc tacggggtct gacgctcagt ggaacgaaaa ctcacgttaa    3120
gggattttgg tcatgagatt atcaaaaagg atcttcacct agatcctttt aaattaaaaa    3180
tgaagtttta aatcaatcta agtatatat gagtaaactt ggtctgacag ttaccaatgc    3240
ttaatcagtg aggcacctat ctcagcgatc tgtctatttc gttcatccat agttgcctga    3300
ctccccgtcg tgtagataac tacgatacgg gagggcttac catctggccc cagtgctgca    3360
atgataccgc gagacccacg ctcaccggct ccagatttat cagcaataaa ccagccagcc    3420
ggaagggccg agcgcagaag tggtcctgca actttatccg cctccatcca gtctattaat    3480
tgttgccggg aagctagagt aagtagttcg ccagttaata gtttgcgcaa cgttgttgcc    3540
attgctacag gcatcgtggt gtcacgctcg tcgtttggta tggcttcatt cagctccggt    3600
tcccaacgat caaggcgagt tacatgatcc cccatgttgt gcaaaaaagc ggttagctcc    3660
ttcggtcctc cgatcgttgt cagaagtaag ttggccgcag tgttatcact catggttatg    3720
gcagcactgc ataattctct tactgtcatg ccatccgtaa gatgcttttc tgtgactggt    3780
gagtactcaa ccaagtcatt ctgagaatag tgtatgcggc gaccgagttg ctcttgcccg    3840
gcgtcaatac gggataatac cgcgccacat agcagaactt taaaagtgct catcattgga    3900
aaacgttctt cggggcgaaa actctcaagg atcttaccgc tgttgagatc cagttcgatg    3960
taacccactc gtgcacccaa ctgatcttca gcatctttta ctttcaccag cgtttctggg    4020
tgagcaaaaa caggaaggca aaatgccgca aaaagggaa taaggcgac acggaaatgt    4080 tgaatactca tactcttcct ttttcaatat tattgaagca tttatcaggg ttattgtctc    4140
```

```
atgagcggat acatatttga atgtatttag aaaaataaac aaatagggt tccgcgcaca    4200
tttccccgaa aagtgccacc tgacgcgccc tgtagcggcg cattaagcgc ggcgggtgtg    4260
gtggttacgc gcagcgtgac cgctacactt gccagcgccc tagcgcccgc tcctttcgct    4320
ttcttccctt cctttctcgc cacgttcgcc ggctttcccc gtcaagctct aaatcggggg    4380
ctcccttttag ggttccgatt tagtgcttta cggcacctcg accccaaaaa acttgattag    4440
ggtgatggtt cacgtagtgg gccatcgccc tgatagacgg ttttcgccc tttgacgttg    4500
gagtccacgt tctttaatag tggactcttg ttccaaactg gaacaacact caaccctatc    4560
tcggtctatt cttttgattt ataagggatt ttgccgattt cggcctattg gttaaaaaat    4620
gagctgattt aacaaaaatt taacgcgaat tttaacaaaa tattaacgct tacaatttcc    4680
attcgccatt caggctgcgc aactgttggg aagggcgatc ggtgcgggcc tcttcgctat    4740
tacgccagct ggcgaaaggg ggatgtgctg caaggcgatt aagttgggta acgccagggt    4800
tttcccagtc acgacgttgt aaaacgacgg ccagtgaatt gtaatacgac tcactatagg    4860
gcgaattggg taccgggccc cccctcgagg tcgatggtgt cgataagctt gatatcgaat    4920
tcgtccttga ggactcgagt gacagtcttt cgccaaagtc gagaggaggc cagcacgttg    4980
gccttgtcaa gagaccacac gggaagaggg gggttgtgct gaagggccag gaaggcggcc    5040
attcgggcaa ttcgctcaac ctcaggaacg gagtaggtct cggtgtcgga agcgacgcca    5100
gatccgtcat cctcctttcg ctctccaaag tagatacctc cgacgagctc tcggacaatg    5160
atgaagtcgg tgccctcaac gtttcggatg ggggagagat cggcgagctt gggcgacagc    5220
agctggcagg gtcgcaggtt ggcgtacagg ttcaggtcct ttcgcagctt gaggagaccc    5280
tgctcgggtc gcacgtcggt tcgtccgtcg ggagtggtcc atacggtgtt ggcagcgcct    5340
ccgacagcac cgagcataat agagtcagcc tttcggcaga tgtcgagagt agcgtcggtg    5400
atgggctcgc cctccttctc aatggcagct cctccaatga gtcggtcctc aaacacaaac    5460
tcggtgccgg aggcctcagc aacagacttg agcaccttga cggcctcggc aatcacctcg    5520
gggccacaga agtcgccgcc gagaagaaca atcttcttgg agtcagtctt ggtcttctta    5580
gtttcgggtt ccattgtgga tgtgtgtggt tgtatgtgtg atgtggtgtg tggagtgaaa    5640
atctgtggct ggcaaacgct cttgtatata tacgcacttt tgcccgtgct atgtggaaga    5700
ctaaacctcc gaagattgtg actcaggtag tgcggtatcg gctagggacc caaaccttgt    5760
cgatgccgat agcgctatcg aacgtacccc agccggccgg gagtatgtcg gaggggacat    5820
acgagatcgt caagggtttg tggccaactg gtaaataaat gatgtcgaca taagtttgca    5880
aaagatcgt attatagttg gagcaaggga gaaatgtaga gtgtgaaaga ctcactatgg    5940
tccgggctta tctcgaccaa tagccaaagt ctggagtttc tgagagaaaa aggcaagata    6000
cgtatgtaac aaagcgacgc atggtacaat aataccggag gcatgtatca tagagagtta    6060
gtggttcgat gatggcactg gtgcctggta tgactttata cggctgacta catatttgtc    6120
ctcagacata caattacagt caagcactta cccttggaca tctgtaggta ccccccggcc    6180
aagacgatct cagcgtgtcg tatgtcggat tggcgtagct ccctcgctcg tcaattggct    6240
cccatctact ttcttctgct tggctacacc cagcatgtct gccatggctc gttttcgtgc    6300
cttatctatc ctcccagtat taccaactct aaatgacatg atgtgattgg gtctacactt    6360
tcatatcaga gataaggagt agcacagttg cataaaaagc ccaactctaa tcagcttctt    6420
cctttcttgt aattagtaca aaggtgatta gcgaaatctg gaagcttagt tggccctaaa    6480
aaaatcaaaa aaagcaaaaa acgaaaaacg aaaaaccaca gttttgagaa cagggaggta    6540
```

```
acgaaggatc gtatatatat atatatatat atatacccac ggatcccgag accggcctttt    6600 gattcttccc tacaaccaac cattctcacc accctaattc acaac                    6645
```

US 8,323,960 B2

AMMONIUM TRANSPORTER PROMOTERS FOR GENE EXPRESSION IN OLEAGINOUS YEAST

This application is a Continuation-In-Part of U.S. patent application Ser. No. 11/185,301, filed Jul. 20, 2005, now abandoned, and claims the benefit of U.S. Provisional Application No. 60/624,812, filed Nov. 4, 2004, the disclosures of which are hereby incorporated by reference in their entirety.

FIELD OF THE INVENTION

This invention is in the field of biotechnology. More specifically, this invention pertains to promoter regions isolated from *Yarrowia lipolytica* that are useful for gene expression in oleaginous yeast.

BACKGROUND OF THE INVENTION

Oleaginous yeast are defined as those organisms that are naturally capable of oil synthesis and accumulation, wherein oil accumulation ranges from at least about 25% up to about 80% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

The technology for growing oleaginous yeast with high oil content is well developed (for example, see EP 0 005 277B1; Ratledge, C., *Prog. Ind. Microbiol.*, 16:119-206 (1982)). And, these organisms have been commercially used for a variety of purposes in the past. For example, various strains of *Yarrowa lipolytica* have historically been used for the manufacture and production of: isocitrate lyase, lipases, polyhydroxy-alkanoates, citric acid, erythritol, 2-oxoglutaric acid, γ-decalactone, γ-dodecalactone and pyruvic acid. More recently, however, the natural abilities of oleaginous yeast have been enhanced by advances in genetic engineering, resulting in organisms capable of producing polyunsaturated fatty acids ["PUFAs"]. Specifically, Zhu et al. have demonstrated that *Y. lipolytica* can be engineered for production of ω-3 and ω-6 fatty acids, by introducing and expressing genes encoding the ω-3/ω-6 biosynthetic pathway (see U.S. Pat. No. 7,238,482, U.S. Pat. Appl. Pub. No. 2006-0115881-A1 and U.S. Pat. Appl. Pub. No. 2009-0093543-A1).

Recombinant production of any heterologous protein is generally accomplished by constructing an expression cassette in which the DNA coding for the protein of interest is placed under the control of appropriate regulatory sequences (i.e., promoters) suitable for the host cell. The expression cassette is then introduced into the host cell, usually by plasmid-mediated transformation or targeted integration into the host genome, and production of the heterologous protein is achieved by culturing the transformed host cell under conditions necessary for the proper function of the promoter contained within the expression cassette. Thus, the development of new host cells such as oleaginous yeast for recombinant production of proteins generally requires the availability of promoters that are suitable for controlling the expression of a protein of interest in the host cell.

A variety of strong promoters have been isolated from *Yarrowia lipolytica* that are useful for heterologous gene expression in yeast. For example, U.S. Pat. No. 4,937,189 and EP220864 (Davidow et al.) disclose the sequence of the XPR2 gene (which encodes an inducible alkaline extracellular protease) and upstream promoter region for use in expression of heterologous proteins. U.S. Pat. No. 6,265,185 (Muller et al.) describes promoters for the translation elongation factor EF1-α ["TEF"] protein and ribosomal protein S7 that are suitable for expression cloning in yeast and heterologous expression of proteins. These promoters were improved relative to the XPR2 promoter, when tested for yeast promoter activity on growth plates (Example 9, U.S. Pat. No. 6,265,185) and based on their activity in the pH range of 4-11. U.S. Pat. No. 7,259,255 and U.S. Pat. No. 7,459,546 describe regulatory sequences (e.g., promoters, introns) of the glyceraldehyde-3-phosphate dehydrogenase (gpd) and phosphoglycerate mutase (gpm) genes; U.S. Pat. No. 7,202,356 describes regulatory sequences (e.g., promoters, introns) of the fructose-bisphosphate aldolase (fba) gene; and, U.S. Pat. No. 7,264,949 describes promoters of the glycerol-3-phosphate O-acyltransferase (gpat) gene. Similarly, Juretzek et al. (*Biotech. Bioprocess Eng.*, 5:320-326 (2000)) compares the glycerol-3-phosphate dehydrogenase (G3P), isocitrate lyase (ICL1), 3-oxo-acyl-CoA thiolase (POT1) and acyl-CoA oxidase (POX1, POX2 and POX5) promoters with respect to their regulation and activities during growth on different carbon sources.

Despite the utility of these known promoters, however, there is a need for new improved yeast promoters for metabolic engineering of yeast (oleaginous and non-oleaginous) and for controlling the expression of heterologous genes in yeast. Furthermore, possession of a suite of promoters that are regulatable under a variety of natural growth and induction conditions in yeast will play an important role in industrial settings, wherein it is desirable to express heterologous polypeptides in commercial quantities in said hosts for economical production of those polypeptides. Thus, it is an object herein to provide such promoters that will be useful for gene expression in a variety of yeast cultures, and preferably in *Yarrowia* sp. cultures and other oleaginous yeast. Specifically, YAT1 promoters from *Yarrowia lipolytica*, have been identified that are responsible for driving expression of the gene (yat1) encoding an ammonium transporter (YAT1). Advantageously, the promoters are useful for regulated expression of heterologous genes in *Yarrowia*, have improved activity with respect to the TEF promoter and are inducible under oleaginous conditions (i.e., nitrogen limitation).

SUMMARY OF THE INVENTION

In a first embodiment, the invention concerns a recombinant expression cassette comprising at least one coding region of interest expressible in an oleaginous yeast cell operably linked to an isolated nucleic acid fragment comprising a promoter region of a *Yarrowia* yat 1 gene, said promoter region consisting essentially of a nucleotide sequence as set forth in SEQ ID NO:25 wherein said sequence can be unmodified or modified, wherein the modification is selected from the group consisting of:
  a) a truncation of one or more consecutive nucleotides occurring at the 5' end ranging from nucleotide 1 up to and including nucleotide 102;
  b) a mutation at nucleotide 414 in which deoxycytidine is replaced by deoxythymidine, deoxyadenosine, or deoxyguanosine;
  c) an insertion of two deoxycytidines at nucleotide 776;
  d) a truncation of one or more consecutive nucleotides occurring at the 5' end ranging from nucleotide 1 up to and including nucleotide 102 and a mutation at nucleotide 414 in which deoxycytidine is replaced by deoxythymidine, deoxyadenosine, or deoxyguanosine;

e) a truncation of one or more consecutive nucleotides occurring at the 5' end ranging from nucleotide 1 up to and including nucleotide 102 and an insertion of two deoxycytidines at nucleotide 776;

f) a mutation at nucleotide 414 in which deoxycytidine is replaced by deoxythymidine, deoxyadenosine, or deoxyguanosine and an insertion of two deoxycytidines at nucleotide 776;

g) a truncation of one or more consecutive nucleotides occurring at the 5' end ranging from nucleotide 1 up to and including nucleotide 102, a mutation at nucleotide 414 in which deoxycytidine is replaced by deoxythymidine, deoxyadenosine, or deoxyguanosine, and an insertion of two deoxycytidines at nucleotide 776.

In a second embodiment, the recombinant expression cassette of the invention further comprises a restriction enzyme site inserted upstream and adjacent to the promoter region.

In a third embodiment, the recombinant expression cassette of the invention which comprises a promoter region of a *Yarrowia* yat 1 gene wherein the *Yarrowia* yat 1 gene is isolated from *Yarrowia lipolytica*.

In a fourth embodiment, the recombinant expression cassette of the invention comprises a promoter region that consists essentially of a nucleotide sequence selected from the group consisting of: SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35 and SEQ ID NO:36.

In a fifth embodiment, the invention concerns a method for expressing at least one coding region of interest in an oleaginous yeast cell which comprises:

a) transforming an oleaginous yeast cell with the recombinant expression cassette of any of claims 1-4; and, b) growing the transformed oleaginous yeast cell of step (a) under conditions whereby the coding region of interest is expressed in the transformed oleaginous yeast cell.

Specifically, the oleaginous yeast can be a member of a genus selected from the group consisting of *Yarrowia, Candida, Rhodotorula, Rhodosporidium, Cryptococcus, Trichosporon Lipomyces* and *Saccharomyces* having the property of oleaginy. More specifically, the oleaginous yeast can be *Yarrowia lipolytica*.

In a sixth embodiment, the method of the invention relates to expression of at least one coding region of interest wherein the coding region of interest encodes a polypeptide selected from the group consisting of: desaturases, elongases, acyltransferases, aminopeptidases, amylases, carbohydrases, carboxypeptidases, catalyases, cellulases, chitinases, cutinases, cyclodextrin glycosyltransferases, deoxyribonucleases, esterases, α-galactosidases, galactosidases, glucoamylases, α-glucosidases, β-glucanases, β-glucosidases, invertases, laccases, lipases, mannosidases, mutanases, oxidases, pectinolytic enzymes, peroxidases, phospholipases, phytases, polyphenoloxidases, proteolytic enzymes, ribonucleases, transglutaminases and xylanases. Specifically, the desaturase is selected from the group consisting of: Δ9 desaturase, Δ12 desaturase, Δ6 desaturase, Δ5 desaturase, Δ17 desaturase, Δ15 desaturase, Δ8 desaturase and Δ4 desaturase; and, the elongase is selected from the group consisting of: Δ9 elongase, $C_{14/16}$ elongase, $C_{16/18}$ elongase, $C_{18/20}$ elongase and/or $C_{20/22}$ elongase.

In a seventh embodiment, the method of the invention can be practiced wherein the transformed oleaginous yeast cell is grown under conditions of nitrogen limitation.

In an eighth embodiment, the method of the invention relates to expression of at least one coding region of interest wherein the coding region of interest encodes at least one enzyme selected from the group consisting of an enzyme of the ω-3/ω-6 fatty acid biosynthetic pathway, an enzyme of the neutral lipid biosynthetic pathway and an enzyme of the phospholipid biosynthetic pathway. Specifically, the at least one enzyme of the ω-3 or ω-6 fatty acid produces a polyunsaturated fatty acid product selected from the group consisting of: linoleic acid, α-linolenic acid, γ-linolenic acid, stearidonic acid, dihomo-γ-linolenic acid, eicosatetraenoic acid, arachidonic acid, eicosapentaenoic acid, ω-6 docosapentaenoic acid, ω-3 docosapentaenoic acid, docosahexaenoic acid, eicosadienoic acid and eicosatrienoic acid.

Biological Deposits

The following biological materials have been deposited with the American Type Culture Collection (ATCC), 10801 University Boulevard, Manassas, Va. 20110-2209, and bear the following designations, accession numbers and dates of deposit.

| Biological Material | Accession No. | Date of Deposit |
|---|---|---|
| *Yarrowia lipolytica* Y4128 | ATCC PTA-8614 | Aug. 23, 2007 |

The biological materials listed above were deposited under the terms of the Budapest Treaty on the International Recognition of the Deposit of Microorganisms for the Purposes of Patent Procedure. The listed deposit will be maintained in the indicated international depository for at least 30 years and will be made available to the public upon the grant of a patent disclosing it. The availability of a deposit does not constitute a license to practice the subject invention in derogation of patent rights granted by government action.

BRIEF DESCRIPTION OF THE DRAWINGS AND SEQUENCE DESCRIPTIONS

FIG. 1 graphically represents the relationship between SEQ ID NOs:1, 2, 3, 24, 25, 30, 33 and 35, each of which relates to the yat1 ammonium transporter in *Y. lipolytica*.

Figure 2:
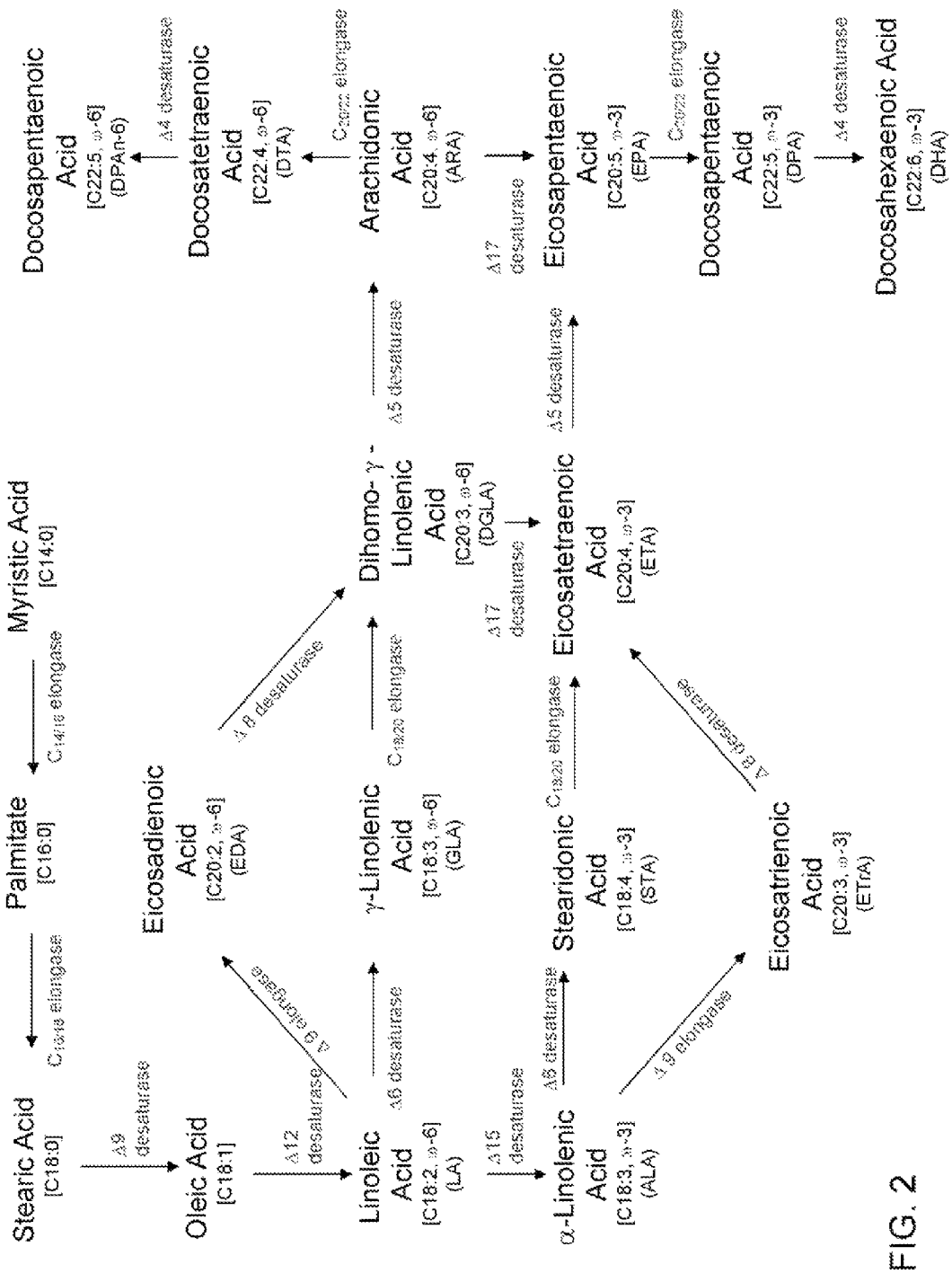

FIG. 2 illustrates the ω-3/ω-6 fatty acid biosynthetic pathway.

Figure 3:
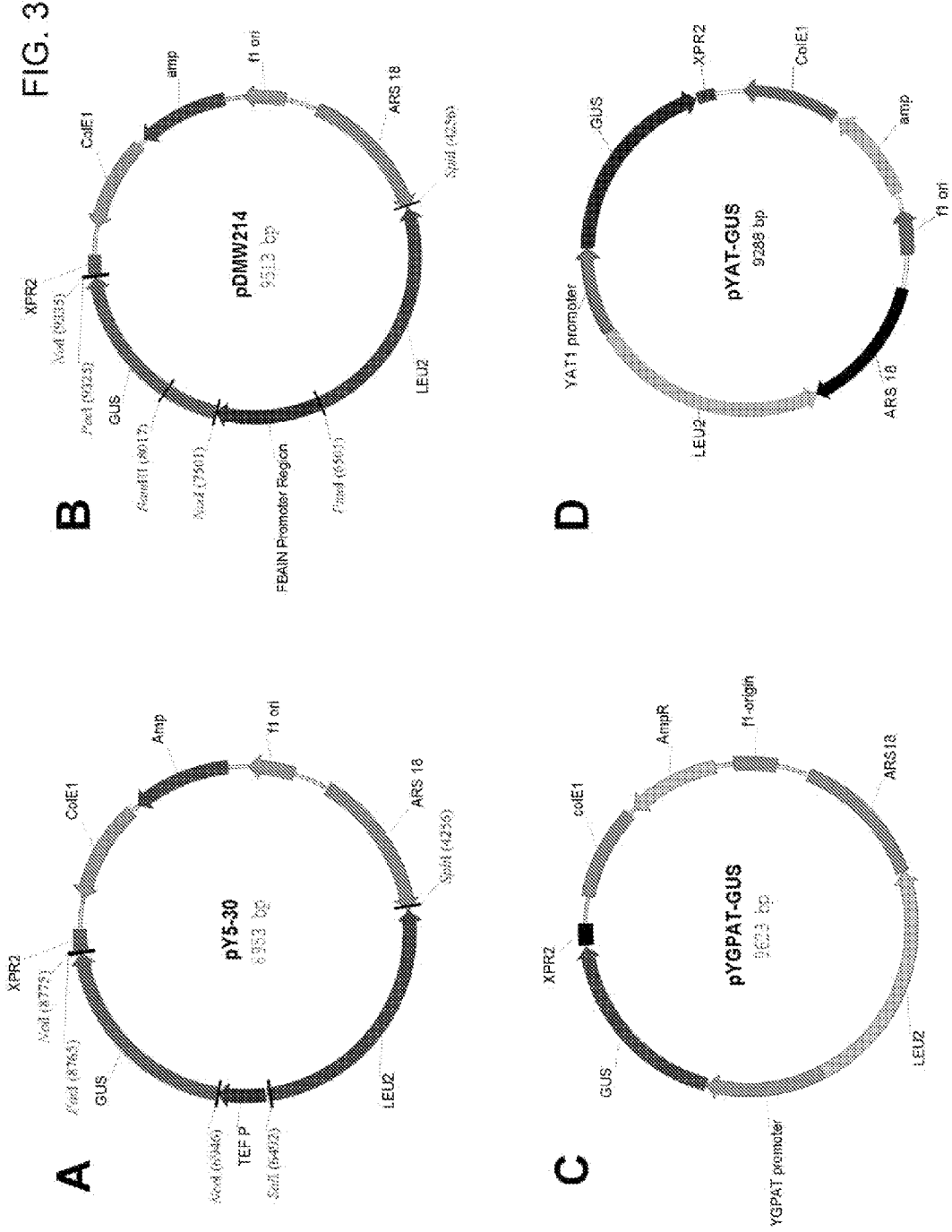

FIG. 3 provides plasmid maps for the following: (A) pY5-30; (B) pDMW214; (C) pYGPAT-GUS; and (D) pYAT-GUS, respectively.

Figure 4:
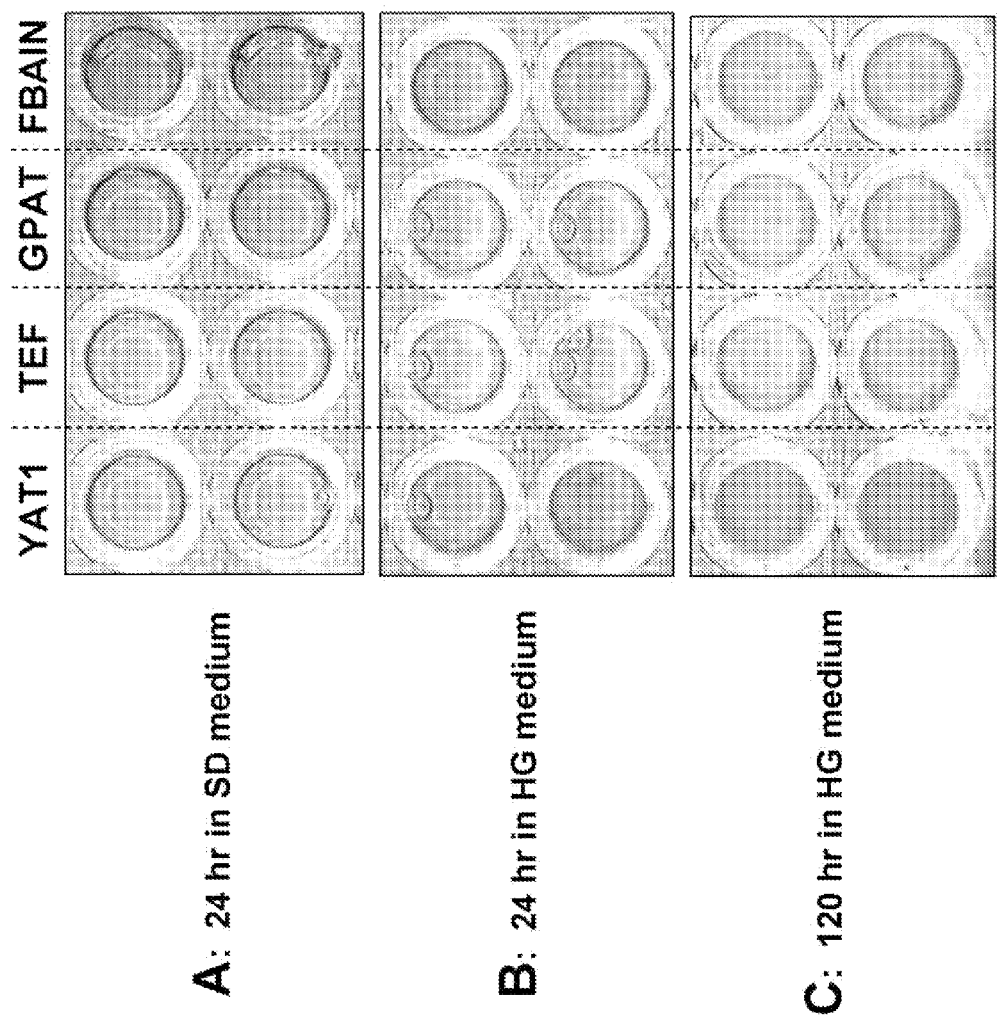

FIG. 4A, FIG. 4B and FIG. 4C illustrate the relative promoter activities of YAT1, TEF, GPAT and FBAIN in *Y. lipolytica* grown in various media as determined by histochemical staining.

Figure 5:
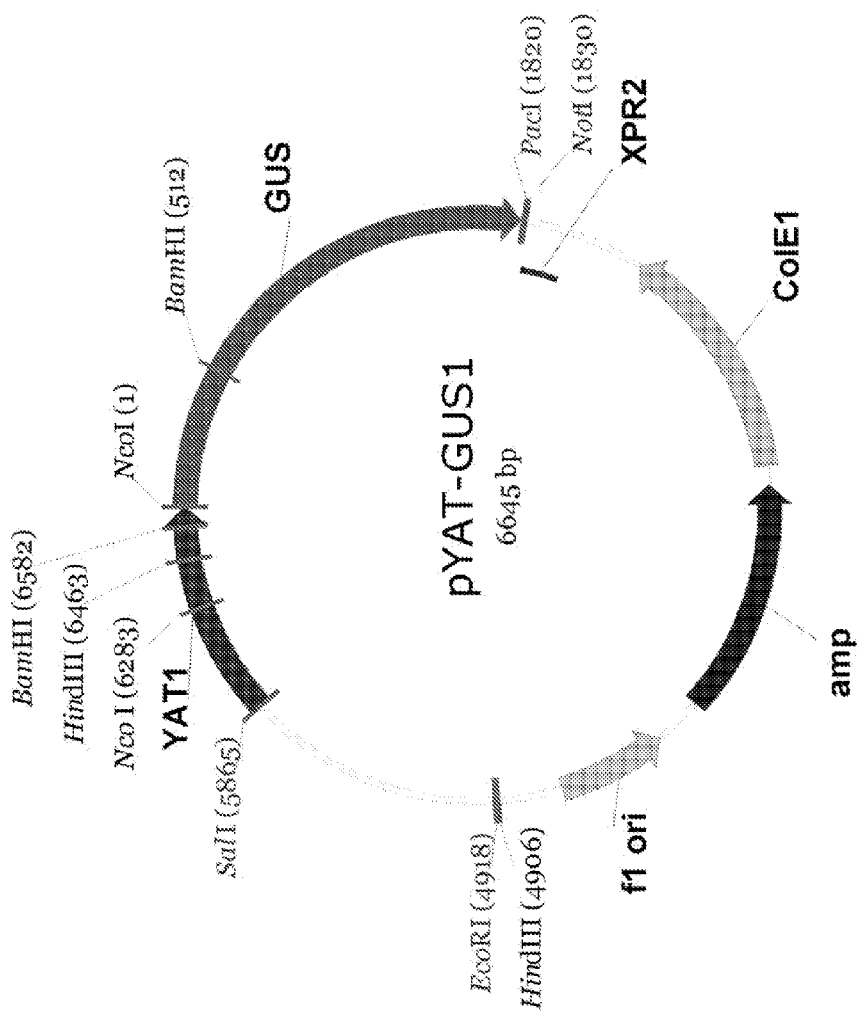

FIG. 5 provides a plasmid map for pYAT-GUS1.

FIG. 6A, FIG. 6B, FIG. 6C, FIG. 6D, FIG. 6E, FIG. 6F, FIG. 6G and FIG. 6H, when viewed together, show an alignment of twelve YAT1 promoters. Eleven of these promoters are derived from the wildtype YAT1 promoter (SEQ ID NO:25; "775 by wtYAT1"), which corresponds to the −775 to −1 region upstream of the yat1 gene. Specifically, aligned are the 777 by YAT1-CC promoter (SEQ ID NO:26), the 783 by YAT1-CC-SalI promoter (SEQ ID NO:27), the 777 by YAT1-CC-NcoI* promoter (SEQ ID NO:28), the 783 by YAT1-CC-NcoI*-SalI promoter (SEQ ID NO:29), the 751 by YAT1-CC-NcoI*-26 promoter (SEQ ID NO:30), the 757 by YAT1-CC-NcoI*-26-ClaI promoter (SEQ ID NO:31), the 759 by YAT1-

CC-NcoI*-26-SwaI promoter (SEQ ID NO:32), the 729 by YAT1-CC-NcoI*-48 promoter (SEQ ID NO:33), the 737 by YAT1-CC-NcoI*-48-PmeI promoter (SEQ ID NO:34), the 675 by YAT1-CC-NcoI*-102 promoter (SEQ ID NO:35) and the 681 bp YAT1-CC-NcoI*-102-EcoRI promoter (SEQ ID NO:36).

Figure 7:
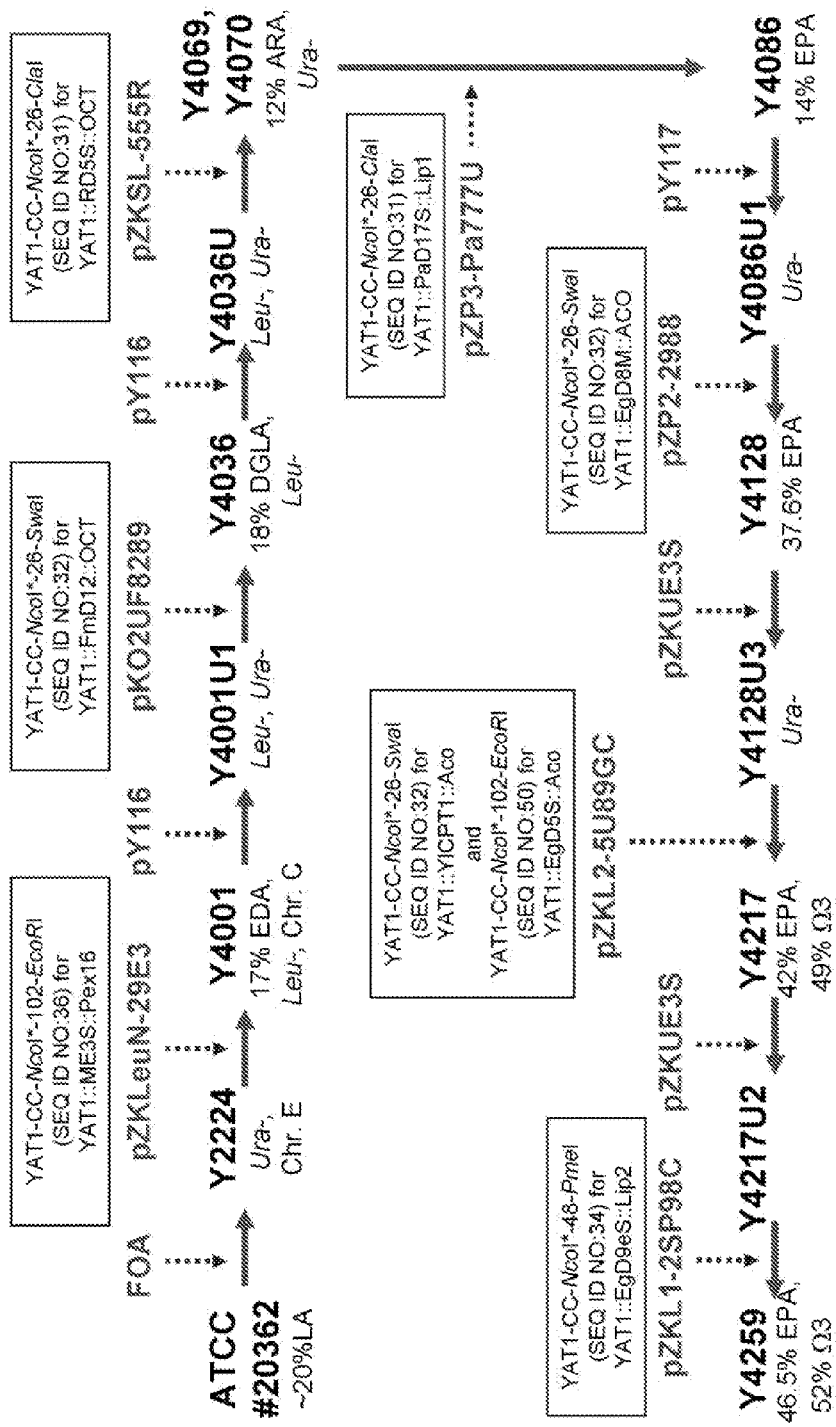

FIG. 7 diagrams the development of *Yarrowia lipolytica* strain Y4259, producing greater than 46.5% EPA in the total lipid fraction and identifies various YAT1 promoters used within chimeric genes in specific expression cassettes and constructs.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-45 correspond to ORFs (i.e., encoding genes or proteins), primers, promoters and plasmids, as identified in Table 1.

TABLE 1

Summary Of Nucleotide And Protein SEQ ID Numbers

| Description | Nucleotide SEQ ID NO | Protein SEQ ID NO |
|---|---|---|
| *Yarrowia lipolytica* ammonium transporter (yat1) (GenBank Accession No. XM_504457) | 1 (1461 bp) | 2 (486 AA) |
| YAT1 promoter fragment | 3 (778 bp) | — |
| BD-Clontech's Creator Smart ® cDNA library kit primer SMART IV oligonucleotide | 4 | — |
| BD-Clontech's Creator Smart ® cDNA library kit primer CDSIII/3' PCR | 5 | — |
| BD-Clontech's Creator Smart ® cDNA library kit primer 5'-PCR | 6 | — |
| M13 forward primer | 7 | — |
| Primer 27203-F | 8 | — |
| Primer 27203-R | 9 | — |
| Plasmid pY5-30 | 10 (8953 bp) | — |
| FBAIN promoter | 11 (973 bp) | — |
| GPAT promoter | 12 (1130 bp) | — |
| Plasmid pKUNF12T6E | 13 (12,649 bp) | — |
| Synthetic elongase gene derived from *Mortierella alpina*, codon-optimized for expression in *Yarrowia lipolytica* | 14 (957 bp) | 15 (318 AA) |
| Synthetic Δ6 desaturase, derived from *Mortierella alpina*, codon-optimized for expression in *Yarrowia lipolytica* | 16 (1374 bp) | 17 (457 AA) |
| *Fusarium moniliforme* Δ12 desaturase | 19 (1434 bp) | 20 (477 AA) |
| Synthetic elongase gene derived from *Thraustochytrium aureum*, codon-optimized for expression in *Yarrowia lipolytica* | 21 (819 bp) | 22 (272 AA) |
| Plasmid pDMW232 | 23 (10,945 bp) | — |
| *Yarrowia lipolytica* yat1 gene: -775 to +1461 region | 24 (2236 bp) | — |
| Wildtype YAT1 promoter, corresponding to the -775 to -1 region upstream of the yat1 gene | 25 (775 bp) | — |
| Modified YAT1-CC promoter | 26 (777 bp) | — |
| Modified YAT1-CC-Sa/I promoter | 27 (783 bp) | — |
| Modified YAT1-CC-NcoI* promoter | 28 (777 bp) | — |
| Modified YAT1-CC-NcoI*-Sa/I promoter | 29 (783 bp) | — |

TABLE 1-continued

Summary Of Nucleotide And Protein SEQ ID Numbers

| Description | Nucleotide SEQ ID NO | Protein SEQ ID NO |
|---|---|---|
| Modified YAT1-CC-NcoI*-26 promoter | 30 (751 bp) | — |
| Modified YAT1-CC-NcoI*-26-C/aI promoter | 31 (757 bp) | — |
| Modified YAT1-CC-NcoI*-26-SwaI promoter | 32 (759 bp) | — |
| Modified YAT1-CC-NcoI*-48 promoter | 33 (729 bp) | — |
| Modified YAT1-CC-NcoI*-48-PmeI promoter | 34 (737 bp) | — |
| Modified YAT1-CC-NcoI*-102 promoter | 35 (675 bp) | — |
| Modified YAT1-CC-NcoI*-102-EcoRI promoter | 36 (681 bp) | — |
| *Y. lipolytica* consensus sequence of translation initiation site | 37 | — |
| Plasmid pZKLeuN-29E3 | 38 (14,688 bp) | — |
| Plasmid pKO2UF8289 | 39 (15,337 bp) | — |
| Plasmid pZKSL-555R | 40 (13,707 bp) | — |
| Plasmid pZP3-Pa777U | 41 (13,066 bp) | — |
| Plasmid pZP2-2988 | 42 (15,743 bp) | — |
| Plasmid pZKL2-5U89GC | 43 (15,812 bp) | — |
| Plasmid pZKL1-2SP98C | 44 (15,877 bp) | — |
| Plasmid pYAT-GUS1 | 45 (6645 bp) | — |

DETAILED DESCRIPTION OF THE INVENTION

All patents, patent applications, and publications cited herein are incorporated by reference in their entirety.

In this disclosure, a number of terms and abbreviations are used. The following definitions are provided.

"Ammonium transporter" is abbreviated "YAT".

"Open reading frame" is abbreviated "ORF".

"Polymerase chain reaction" is abbreviated "PCR".

"Polyunsaturated fatty acid(s)" is abbreviated "PUFA(s)".

The term "oleaginous" refers to those organisms that tend to store their energy source in the form of oil (Weete, In: Fungal Lipid Biochemistry, 2nd Ed., Plenum, 1980). The term "oleaginous yeast" refers to those microorganisms classified as yeasts that can make oil. Generally, the cellular oil content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*. In alternate embodiments, a non-oleaginous organism can be genetically modified to become oleaginous, wherein the organism obtains the ability to accumulate in excess of about 25% of their dry cell weight as oil by means of genetic engineering, e.g., yeast such as *Saccharomyces cerevisiae*.

The term "ammonium transporter" refers to a family of transporters whose physiological role within a cell is to scavenge external ammonium for use as a nitrogen source (and, under some circumstances, to incorporate ammonium that leaks out of cells), based on studies of the MEP family of ammonium transporters in *Saccharomyces cerevisiae* (A.M. Marini et al., *EMBO J.*, 13(15):3456-3463 (1994); *Mol Cell Biol.*, 17(8):4282-93 (1997)). In general, the proteins are subject to nitrogen control and each has different kinetic properties, specificities and regulation; for example, the three *S. cerevisiae* isozymes are characterized as follows: MEP1, a low affinity/high capacity ammonia transporter ($K_m$, 5-10 µM); MEP2, a high affinity/low capacity ammonia transporter ($K_m$, 1-2 µM); and MEP3, a low affinity ammonia transporter ($K_m$, 1.4-2.1 mM). Other known members of this family include: the high affinity ammonium transporter (amt1), the ammonium and methylammonium transport system, the putative ammonium transporter amtB and nrgA.

As used herein, the term "YAT1" refers to an ammonium transporter enzyme (TC 2.A.49) encoded by the yat1 gene and isolated from *Yarrowia lipolytica* (GenBank Accession No. XM_504457). The sequence disclosed therein (/locus_tag="YALI0E27203g") was identified as a hypothetical protein having similarity "to sp|P41948 *Saccharomyces cerevisiae* YNL142w MEP2, hypothetical start". The *Y. lipolytica* yat1 gene is presented herein as SEQ ID NO:1, while the corresponding YAT1 protein is provided herein as SEQ ID NO:2. A 2236 by DNA contig comprising the 5' upstream region and the *Y. lipolytica* yat1 gene are set forth in SEQ ID NO:24.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "YAT1 promoter" or "YAT1 promoter region" refers to the 5' upstream untranslated region in front of the 'ATG' translation initiation codon of yat1 and that is necessary for expression. An example of a suitable YAT1 promoter region is provided as SEQ ID NO:25, corresponding to the −775 to −1 region upstream of the yat1 gene, but this is not intended to be limiting in nature. One skilled in the art will recognize that since the exact boundaries of the YAT1 promoter sequence have not been completely defined, DNA fragments of increased or diminished length may have identical promoter activity. Thus, for example, it is expected that a promoter region comprising at least the −673 to −1 region upstream of the yat1 gene will also be functional as a suitable YAT1 promoter, as will a promoter region comprising at least the −727 to −1 region and a promoter region comprising at least the −749 to −1 region upstream of the yat1 gene.

The term "mutant promoter" or "modified promoter" is defined herein as a promoter having a nucleotide sequence comprising a substitution, deletion, and/or insertion of one or more nucleotides relative to the parent promoter, wherein the modified promoter has more promoter activity, less promoter activity or equivalent promoter activity when compared to the corresponding parent promoter. The term "modified promoter" will encompass natural variants and in vitro generated variants obtained using methods well known in the art (e.g., classical mutagenesis, site-directed mutagenesis and "DNA shuffling"). Non-limiting examples of mutant promoters derived from the wildtype YAT1 promoter sequence of SEQ ID NO:25 include: 1) promoters comprising an insertion of two deoxycytidines ["CC"] at by +776 with respect to SEQ ID NO:25; 2) promoters comprising a deoxycytidine ["C"] to deoxyadenosine ["A"], deoxyguanosine ["G"], or deoxythymidine ["T"] mutation at +414 with respect to SEQ ID NO:25; and 3) promoters comprising a deoxyguanosine ["G"] to deoxythymidine ["T"] mutation at +100 with respect to SEQ ID NO:25.

Although mutant YAT1 promoters are different than wildtype YAT1 promoters in sequence (and may be different in promoter activity), the term "YAT1 promoter" will be applied throughout the specification to refer to either mutant or wildtype YAT1 promoters that are derived or identified from the 5' upstream region of the yat1 gene, unless specifically stated to be otherwise.

The term "GPAT" refers to a glycerol-3-phosphate O-acyltransferase enzyme (E.C. 2.3.1.15) encoded by the gpat gene and which converts acyl-CoA and sn-glycerol 3-phosphate to CoA and 1-acyl-sn-glycerol 3-phosphate (the first step of phospholipid biosynthesis). The term "GPAT promoter" or "GPAT promoter region" refers to the 5' upstream untranslated region in front of the 'ATG' translation initiation codon of gpat and that is necessary for expression. One example of a suitable GPAT promoter region is provided as SEQ ID NO:12, but this is not intended to be limiting in nature (see U.S. Pat. No. 7,264,949).

The term "FBA1" refers to a fructose-bisphosphate aldolase enzyme (E.C. 4.1.2.13) encoded by the fba1 gene and which converts D-fructose 1,6-bisphosphate into glycerone phosphate and D-glyceraldehyde 3-phosphate. The term "FBAIN promoter" or "FBAIN promoter region" refers to the 5' upstream untranslated region in front of the 'ATG' translation initiation codon of fba1 and that is necessary for expression, plus a portion of 5' coding region comprising an intron of the fba1 gene. An example of a suitable FBAIN promoter region is provided as SEQ ID NO:11, but this is not intended to be limiting in nature (see U.S. Pat. No. 7,202,356).

The term "promoter activity" will refer to an assessment of the transcriptional efficiency of a promoter. This may, for instance, be determined directly by measurement of the amount of mRNA transcription from the promoter (e.g., by Northern blotting or primer extension methods) or indirectly by measuring the amount of gene product expressed from the promoter, as for example by histochemical means.

The term "conditions of nitrogen limitation" refers to a medium having a low concentration of nitrogen, wherein the nitrogen may be supplied from an inorganic (e.g., $(NH_4)_2SO_4$) or organic (e.g., urea or glutamate) source, or a medium having no nitrogen source. Although one skilled in the art will be able to determine an appropriate low concentration of nitrogen suitable to induce the YAT1 promoters of the present disclosure, in one embodiment a preferred medium would be one characterized as having a high carbon to nitrogen (i.e., C:N) ratio and about 0.1% or less ammonium sulfate or other suitable ammonium salts.

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The term "genetic construct" is a non-limiting term meaning any contiguous series of nucleic acids capable of being expressed in a host organism. A genetic construct may include but is not limited to an open reading frame ["ORF"], an ORF operably linked to regulatory sequences, or a wildtype or mutant gene. Genetic constructs may encode polypeptides or be nucleic acid fragments or molecules that are oriented for antisense expression.

A nucleic acid molecule is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, N.Y. (1989), which is hereby incorporated herein by reference, particularly Chapter 11 and Table 11.1. The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215: 403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation, such as in situ hybridization of bacterial colonies or bacteriophage plaques. In addition, short oligonucleotides of 12-15 bases may be used as amplification primers in PCR in order to obtain a particular nucleic acid molecule comprising the primers. Accordingly, a "substantial portion" of a nucleotide sequence comprises enough of the sequence to specifically identify and/or isolate a nucleic acid molecule comprising the sequence.

As used herein, the terms "homology" and "homologous" are used interchangeably. They refer to nucleic acid fragments wherein changes in one or more nucleotide bases do not affect the ability of the nucleic acid fragment to mediate gene expression or produce a certain phenotype. These terms also refer to modifications of the nucleic acid fragments such as deletion or insertion of one or more nucleotides that do not substantially alter the functional properties of the resulting nucleic acid fragment relative to the initial, unmodified fragment.

Moreover, the skilled artisan recognizes that homologous nucleic acid sequences are also defined by their ability to hybridize, under moderately stringent conditions, e.g., 0.5× SSC, 0.1% SDS, 60° C., with the sequences exemplified herein, or to any portion of the nucleotide sequences disclosed herein and which are functionally equivalent thereto. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel et al., Eds., Greene Publishing and Wiley-Interscience, New York (1995).

Described herein are nucleotide sequences encoding a particular microbial promoter region. The skilled artisan, having the benefit of the sequences as reported herein, may now use all or a substantial portion of the disclosed sequences for purposes known to those skilled in this art. Accordingly, the disclosure comprises the complete sequences as reported in the accompanying Sequence Listing, as well as substantial portions of those sequences as defined above.

The term "oligonucleotide" refers to a nucleic acid, generally of at least 14 nucleotides, that is hybridizable to a genomic DNA molecule, a cDNA molecule, or an mRNA molecule. In one embodiment, a labeled oligonucleotide can be used as a "probe" to detect the presence of a nucleic acid. Thus, the term "probe" refers to a single-stranded nucleic acid molecule that can base pair with a complementary single-stranded target nucleic acid to form a double-stranded molecule. The term "label" will refer to any conventional molecule which can be readily attached to mRNA or DNA and which can produce a detectable signal, the intensity of which indicates the relative amount of hybridization of the labeled probe to the DNA fragment.

The term "complementary" is used to describe the relationship between nucleotide bases that are capable of hybridizing to one another.

For example, with respect to DNA, adenosine is complementary to thymine and cytosine is complementary to guanine. Accordingly, the disclosure also includes isolated nucleic acid molecules that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. "Percent identity" also means the degree of sequence relatedness between polypeptide or polynucleotide sequences, as the case may be, as determined by the match between strings of such sequences. "Percent identity" and "percent similarity" can be readily calculated by known methods, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humania: NJ (1994); 4) *Sequence Analysis in Molecular Biology* (von Heinje, G., Ed.) Academic (1987); and 5) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the Clustal method of alignment" which encompasses several varieties of the algorithm including the "Clustal V method of alignment" and the "Clustal W method of alignment" (described by Higgins and Sharp, *CABIOS*, 5:151-153 (1989); Higgins, D. G. et al., *Comput. Appl. Biosci.*, 8:189-191(1992)) and found in the MegAlign™ (version 8.0.2) program of the LASERGENE bioinformatics computing suite (DNASTAR Inc.). After alignment of the sequences using either Clustal program, it is possible to obtain a "percent identity" by viewing the "sequence distances" table in the program.

For multiple alignments using the Clustal V method of alignment, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. Default parameters for multiple alignment using the Clustal W method of alignment correspond to GAP PENALTY=10, GAP LENGTH PENALTY=0.2, Delay Divergent Seqs(%)=30, DNA Transition Weight=0.5, Protein Weight Matrix=Gonnet Series, DNA Weight Matrix=IUB.

It is well understood by one skilled in the art that various measures of sequence percent identity are useful in identifying polynucleotides and polypeptides, from other species, wherein such polynucleotides and polypeptides have the same or similar function or activity. Suitable promoter regions (isolated polynucleotides of the present invention) encode promoter regions that are at least about 70% identical, preferably at least about 75% identical, and more preferably at least about 80% identical to the nucleotide sequences reported herein. Preferred nucleic acid molecules are about 85% identical to the nucleotide sequences reported herein, more preferred nucleic acid molecules are at least about 90% identical, and most preferred are nucleic acid molecules at least about 95% identical to the nucleotide sequences reported herein. Suitable promoter regions not only have the above homologies but typically are at least 50 nucleotides in length, more preferably at least 100 nucleotides in length, more preferably at least 250 nucleotides in length, and more preferably at least 500 nucleotides in length.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for *Yarrowia lipolytica* is provided in U.S. Pat. No. 7,125,672.

"Gene" refers to a nucleic acid molecule that expresses a specific protein, and which may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. Chimeric genes of the present disclosure will typically comprise a YAT1 promoter region operably linked to a coding region of interest. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

The term "3' non-coding sequences" or "transcription terminator" refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; Intl. App. Pub. No. WO 99/28508).

The term "operably linked" refers to the association of nucleic acid sequences on a single nucleic acid molecule so that the function of one is affected by the other. For example, a promoter is operably linked with a coding sequence when it is capable of affecting the expression of that coding sequence. That is, the coding sequence is under the transcriptional control of the promoter. Coding sequences can be operably linked to regulatory sequences in sense or antisense orientation.

The term "expression", as used herein, refers to the transcription and stable accumulation of sense (mRNA) or antisense RNA derived from a coding sequence. Expression may also refer to translation of mRNA into a polypeptide.

"Transformation" refers to the transfer of a nucleic acid molecule into a host organism, resulting in genetically stable inheritance. The nucleic acid molecule may be a plasmid that replicates autonomously, for example; or, it may integrate into the genome of the host organism. Host organisms containing the transformed nucleic acid molecules are referred to as "transgenic", "recombinant" or "transformed" organisms or "transformants".

The term "recombinant" refers to an artificial combination of two otherwise separated segments of sequence, e.g., by chemical synthesis or by the manipulation of isolated segments of nucleic acids by genetic engineering techniques.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

"Expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence (i.e., ORF); and, 3) a 3' untranslated region (i.e., a terminator) that, in eukaryotes, usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1) the GCG suite of programs (Wisconsin Package Version 9.0, Genetics Computer Group (GCG), Madison, Wis.); 2) BLASTP, BLASTN, BLASTX (Altschul et al., *J. Mol. Biol.*, 215:403-410 (1990)); 3) DNAS-TAR (DNASTAR, Inc. Madison, Wis.); 4) Sequencher (Gene Codes Corporation, Ann Arbor, Mich.); and, 5) the FASTA program incorporating the Smith-Waterman algorithm (W. R. Pearson, *Comput. Methods Genome Res.*, [Proc. Int. Symp.] (1994), Meeting Date 1992, 111-20. Suhai, Sandor, Ed. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

Ammonium transporters are a family of transporters whose physiological role within a cell is to scavenge external ammonium for use as a nitrogen source (and, under some circumstances, to incorporate ammonium that leaks out of cells). In general, the proteins are subject to nitrogen control and each have different kinetic properties, specificities and regulation; for example, the three *S. cerevisiae* MEP1, MEP2, and MEP3 isozymes have been extensively characterized by A. M. Marini et al. (*EMBO J.*, 13(15): 3456-3463 (1994); *Mol Cell Biol.*, 17(8):4282-93 (1997)) as a low affinity/high capacity ammonia transporter, a high affinity/low capacity ammonia transporter, and a low affinity ammonia transporter, respectively.

A cDNA library was constructed from *Yarrowia lipolytica* cells grown in an oleaginous medium containing no nitrogen source for 4 hrs (i.e., oleaginous conditions that promoter oil production). The relative abundance of each species of cDNA was then examined to identify those genes that were highly expressed under the oleaginous conditions. One of the genes that appeared multiple times (16/9984 or 0.16%) was GenBank Accession No. XM_504457, locus_tag="YALI0E27203g". This gene was annotated as a hypothetical protein having similarity "to sp|P41948 *Saccharomyces cerevisiae* YNL142w MEP2 [the high affinity, low capacity ammonia transporter; GenBank Accession No. X83608], hypothetical start".

Based on sequence comparison to the MEP1, MEP2 and MEP3 genes (supra), it was hypothesized that the *Y. lipolytica* ORF likely encoded an ammonium transporter and designated the gene as the "yat1" gene (SEQ ID NOs:1 and 2). The "YAT1 promoter" was identified as the 5' upstream untranslated region in front of the 'ATG' translation initiation codon of yat1 and that is necessary for expression. Accordingly, this putative YAT1 promoter region will be useful for driving expression of any suitable coding region of interest in a transformed yeast cell. In general, a promoter useful in an oleaginous yeast should meet the following criteria:

1) Strength. A strong yeast promoter is a necessary premise for a high expression level, and the low copy number of the ars18 (Fournier, P. et al., *Yeast*, 7:25-36 (1991)) based expression vectors or chimeric genes integrated into the genome makes this demand even more important when *Y. lipolytica* is used as the host organism.
2) Activity in a medium suitable for expression of the coding region of interest, and high enzymatic activity of that coding region of interest.
3) pH Tolerance. If the coding region of interest is known to be produced only in e.g., an acidic environment, then the promoter operably linked to said coding region of interest must function at the appropriate pH. pH tolerance is of course limited by the tolerance of the host organism.
4) Inducibility. A tightly regulated yeast promoter makes it possible to separate the growth stage from the expression stage, thereby enabling expression of products that are known to inhibit cell growth.
5) Activity in the stationary phase of growth in oleaginous yeast hosts for accumulation of PUFAs.

Additionally, it is preferable for novel yeast promoters to possess differences in activity with respect to the known *Yarrowia lipolytica* TEF (U.S. Pat. No. 6,265,185), XPR2 (U.S. Pat. No. 4,937,189; EP220864; EP832258), GPD and GPM (U.S. Pat. No. 7,259,255 and U.S. Pat. No. 7,459,546), FBA, FBAIN and FBAINm (U.S. Pat. No. 7,202,356) and GPAT (U.S. Pat. No. 7,264,949) promoters and/or the G3P, ICL1, POT1, POX1, POX2 and POX5 promoters (Juretzek et al., *Biotech. Bioprocess Eng.*, 5:320-326 (2000)).

A comparative study of the TEF, FBAIN and GPAT promoters and the 775 by YAT1 promoter described herein as SEQ ID NO:25, corresponding to the −775 to −1 region upstream of the yat1 gene, is provided in Examples 8 and 9. As shown in Table 5 of Example 9, the yeast promoter has improved activity compared to the TEF promoter (i.e., 1.3:1 nmoles of 4-methylumbelliferone per minute per mg of total protein) under conditions where nitrogen is not limiting (i.e., minimal medium containing ammonium sulfate as the nitrogen source). Furthermore, under conditions of nitrogen limitation, the YAT1 promoter is significantly induced such that the activity is ~20-28 times greater than that of TEF; thus, when grown in such medium, the activity of the YAT1 promoter is comparable to that of the strong FBAIN promoter.

Based on these results, the Applicants characterize the YAT1 promoter of SEQ ID NO:25 as the first promoter identified within *Yarrowia* that is inducible under oleaginous conditions (i.e., nitrogen limitation).

An example of a suitable YAT1 promoter region is provided SEQ ID NO:25 (comprising the −775 to −1 region of the *Y. lipolytica* yat1 gene [wherein the 'A' position of the 'ATG' translation initiation codon is designated as +1]), but this is not intended to be limiting in nature. One skilled in the art will recognize that since the exact boundaries of the YAT1 promoter sequence have not been completely defined, DNA fragments of increased or diminished length may have identical promoter activity. For example, Example 10 describes a variety of "truncated" YAT1 promoters when compared to the wildtype promoter of SEQ ID NO:25, wherein the truncation is of one or more consecutive nucleotides occurring at the 5' end ranging from nucleotide 1 up to and including nucleotide 102. Thus, for example, the YAT1-CC-NcoI*-26 promoter of SEQ ID NO:30 comprises the −749 to −1 region upstream of the yat1 gene (i.e., nucleotides +1 to +26 of SEQ ID NO:25 were deleted), the YAT1-CC-NcoI*-48 promoter of SEQ ID NO:33 comprises the −727 to −1 region upstream of the yat1 gene (i.e., nucleotides +1 to +48 of SEQ ID NO:25 were deleted) and the YAT1-CC-NcoI*-102 promoter of SEQ ID NO:35 comprises the −673 to −1 region upstream of the yat1 gene (i.e., nucleotides +1 to +97 of SEQ ID NO:25 were deleted). In all cases, these "truncated" YAT1 promoters were found to be functional, with activity comparable to that of the wildtype YAT1 promoter of SEQ ID NO:25.

Accordingly, the term "YAT1 promoter" as used herein applies to any and all YAT1 promoters that are identified or created via truncation from the 5' upstream region of the yat1 gene, unless a specific SEQ ID NO is referenced.

Thus, as one of skill in the art will appreciate, suitable YAT1 promoters will correspond to the −775 to −1 region, −774 to −1 region, −773 to −1 region, −772 to −1 region, −771 to −1 region, −770 to −1 region, −769 to −1 region, −768 to −1 region, −767 to −1 region, −766 to −1 region, −765 to −1 region, −764 to −1 region, −763 to −1 region, −762 to −1 region, −761 to −1 region, −760 to −1 region, −759 to −1 region, −758 to −1 region, −757 to −1 region, −756 to −1 region, −755 to −1 region, −754 to −1 region, −753 to −1 region, −752 to −1 region, −751 to −1 region, −750 to −1 region, −749 to −1 region, −748 to −1 region, −747 to −1 region, −746 to −1 region, −745 to −1 region, −744 to −1 region, −743 to −1 region, −742 to −1 region, −741 to −1 region, −740 to −1 region, −739 to −1 region, −738 to −1 region, −737 to −1 region, −736 to −1 region, −735 to −1 region, −734 to −1 region, −733 to −1 region, −732 to −1 region, −731 to −1 region, −730 to −1 region, −729 to −1 region, −728 to −1 region, −727 to −1 region, −726 to −1 region, −725 to −1 region, −724 to −1 region, −723 to −1 region, −722 to −1 region, −721 to −1 region, −720 to −1 region, −719 to −1 region, −718 to −1 region, −717 to −1 region, −716 to −1 region, −715 to −1 region, −714 to −1 region, −713 to −1 region, −712 to −1 region, −711 to −1 region, −710 to −1 region, −709 to −1 region, −708 to −1 region, −707 to −1 region, −706 to −1 region, −705 to −1 region, −704 to −1 region, −703 to −1 region, −702 to −1 region, −701 to −1 region, −700 to −1 region, −699 to −1 region, −698 to −1 region, −697 to −1 region, −696 to −1 region, −695 to −1 region, −694 to −1 region, −693 to −1 region, −692 to −1 region, −691 to −1 region, −690 to −1 region, −689 to −1 region, −688 to −1 region, −687 to −1 region, −686 to −1 region, −685 to −1 region, −684 to −1 region, −683 to −1 region, −682 to −1 region, −681 to −1 region, −680 to −1 region, −679 to −1 region, −678 to −1 region, −677 to −1 region, −676 to −1 region, −675 to −1 region, −674 to −1 region and −673 to −1 region upstream of the yat1 gene (see, SEQ ID NO:24 and SEQ ID NO:25).

In an alternate embodiment, the YAT1 promoter may comprise nucleotides −500 to −1 upstream of the yat1 gene (i.e., nucleotides 276-775 of SEQ ID NO:25), thereby permitting relatively strong promoter activity; in another embodiment, the −100 to −1 region upstream of the yat1 gene (i.e., nucleotides 676-775 of SEQ ID NO:25) should be sufficient for basal activity of the promoter. Likewise, the promoter region of the invention may comprise additional nucleotides to those specified above. For example, the promoter sequences of the invention may be constructed on the basis of the −1000 to −1 region of the yat1 gene (e.g., nucleotide bases 3,222,879 to 3,223,879 of GenBank Accession No. CR382131, comprising the complete nucleotide sequence of chromosome E of strain CLIB99 of *Y. lipolytica*).

In addition to truncations which reduce the total length of the YAT1 promoter, from that described in SEQ ID NO:25, one of skill in the art will understand that mutant promoters may also be constructed, wherein the DNA sequence of the promoter has one or more nucleotide substitutions (i.e., deletions, insertions, or addition of one or more nucleotides in the sequence) which do not effect (in particular impair) the yeast promoter activity. Regions that can be modified without significantly affecting the yeast promoter activity can be identified by deletion studies. A mutant promoter has at least about 20%, preferably at least about 40%, more preferably at least about 60%, more preferably at least about 80%, more preferably at least about 90%, more preferably at least about 100%, more preferably at least about 200%, more preferably at least about 300% and most preferably at least about 400% of the promoter activity of the YAT1 promoter region described herein as SEQ ID NO:25.

Methods for mutagenesis are well known in the art and suitable for the generation of mutant promoters. For example, in vitro mutagenesis and selection, PCR based random mutagenesis, site-directed mutagenesis, chemical synthesis of a mutated DNA fragment or other means can be employed to obtain mutations of the naturally occurring promoter of e.g., SEQ ID NO:25 (wherein such mutations may include deletions, insertions and point mutations, or combinations thereof). This would permit production of a putative promoter having a more desirable level of promoter activity in the host cell. Or, if desired, the regions of a nucleotide of interest important for promoter activity can be determined through routine mutagenesis, expression of the resulting mutant promoters and determination of their activities. An overview of these techniques is described in U.S. Pat. No. 7,259,255. All such mutant promoters that are derived from the instant YAT1 promoter described herein are within the scope of the present disclosure.

Non-limiting examples of modified or "mutated" YAT1 promoters, when compared to the wildtype promoter of SEQ ID NO:25, are described in Example 10 and their use is demonstrated in Example 11. Specifically, the YAT1-CC promoter of SEQ ID NO:26 is identical to the YAT1 promoter of SEQ ID NO:25, with the exception of two deoxycytidines ["CC"] inserted at nucleotide 776 (thereby creating a preferred consensus sequence around the translation initiation site of operably linked genes, for optimal gene expression). SEQ ID NO:27, comprising the YAT1-CC-SalI promoter, is identical to SEQ ID NO:26, although a 6 by SalI restriction enzyme ["RE"] site is inserted upstream and adjacent to the promoter region, for cloning convenience. One of skill in the art will recognize that the particular RE site to be inserted upstream and adjacent to the promoter region will not affect the activity of the promoter. Similarly, the YAT1-CC-NcoI* promoter of SEQ ID NO:28 tolerates a mutation at nucleotide 414 in which a C nucleotide is replaced by a deoxythymidine ["T"] (thereby removing an internal NcoI RE site from the promoter fragment) and a CC insertion at nucleotide 776, with respect to SEQ ID NO:25. It is assumed that the C nucleotide at position 414 could also be substituted with a deoxyadenosine ["A"] or a deoxyguanosine ["G"]. In all cases, these "mutated" YAT1 promoters were found to be functional, with activity comparable to that of the wildtype YAT1 promoter of SEQ ID NO:25. Furthermore, it is also demonstrated that these mutations could be combined with the truncations previously described. Furthermore, the term "YAT1 promoter" also encompasses any and all YAT1 promoters that are identified or created via mutation from the 5' upstream region of the yat1 gene, unless a specific SEQ ID NO is referenced.

Promoter activity is typically measured against the activity of the wild type promoter under similar conditions. Promoter activity is generally measured as a function of gene expression and may be determined in a variety of ways including gene expression profiling, measurement of the level of RNA and/or protein expression, or the measurement of reporter activity where reporter gene fusions have been created.

It will be appreciated by a person of skill in the art that the promoter regions of the present disclosure have homologs in a variety of yeast species; and, the use of the promoters for regulated, heterologous gene expression are not limited to those promoters derived from *Yarrowia lipolytica*, but extend to homologs in other yeast species. For example, encompassed herein are homologs derived from oleaginous genera including, but not limited to: *Yarrowia, Candida, Rhodotorula, Rhodosporidium, Cryptococcus, Trichosporon* and *Lipomyces*; examples of preferred species within these genera include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus* and *R. graminis*.

Homology typically is measured using sequence analysis software, wherein the term "sequence analysis software" refers to any computer algorithm or software program (commercially available or independently developed) that is useful for the analysis of nucleotide or amino acid sequences. In general, such computer software matches similar sequences by assigning degrees of homology to various substitutions, deletions and other modifications.

As is well known in the art, isolation of homologous promoter regions using sequence-dependent protocols is readily possible using various techniques; and, these techniques can rely on either the direct identification of a promoter having homology to the YAT1 promoter described herein or the indirect identification of a promoter by initial identification of a gene having significant homology to the yat1 gene and then analysis of the 5' upstream sequence of the homologous gene. Examples of sequence-dependent protocols include, but are not limited to: 1) methods of nucleic acid hybridization; 2) methods of DNA and RNA amplification, as exemplified by various uses of nucleic acid amplification technologies such as polymerase chain reaction ["PCR"] (U.S. Pat. No. 4,683, 202); ligase chain reaction ["LCR"] (Tabor, S. et al., *Proc. Acad. Sci. U.S.A.*, 82:1074 (1985)); or strand displacement amplification ["SDA"] (Walker, et al., *Proc. Natl. Acad. Sci. U.S.A.*, 89:392 (1992)); and 3) methods of library construction and screening by complementation.

For example, putative promoter regions to those of the instant disclosure could be isolated by using all or a portion of the YAT1 nucleic acid molecules (e.g., corresponding to the promoter, gene or a combination thereof) as DNA hybridization probes to screen libraries from any desired microbe using methodology well known to those skilled in the art. Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation, or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis (Ed.), (1986) pp 33-50 IRL: Herndon, Va.; and Rychlik, W., In *Methods in Molecular Biology*, White, B. A. (Ed.), (1993) Vol. 15, pp 31-39, PCR Protocols: Current Methods and Applications. Humania: Totowa, N.J.).

Generally two short segments of the instant sequences may be used in PCR protocols to amplify longer nucleic acid molecules encoding homologous polynucleotides from DNA or RNA. The PCR may also be performed on a library of cloned nucleic acid molecules wherein the sequence of one primer is derived from the instant nucleic acid molecules, and the sequence of the other primer takes advantage of the presence of the polyadenylic acid tracts to the 3' end of the mRNA precursor encoding microbial genes.

Alternatively, the instant sequences may be employed as hybridization reagents for the identification of homologs. The basic components of a nucleic acid hybridization test include a probe, a sample suspected of containing the nucleotide sequence of interest, and a specific hybridization method. Probes are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.*, 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v) ["by volume"].

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol ["weight by volume"] glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers, such as dextran sulfate.

Transcription initiation control regions or promoter regions that are useful to drive expression of a coding gene of interest in the desired host cell are selected from those derived from the upstream portion of the yat1 gene (SEQ ID NO:1). The promoter regions may be identified from the upstream sequences of yat1 and its homologs and isolated according to common methods (Maniatis, supra). Once a promoter region is identified and isolated (e.g., SEQ ID NO:25), it may be operably linked to a coding region of interest to be expressed in a suitable expression cassette. These chimeric genes may then be expressed in natural host cells and heterologous host cells, particularly in the cells of oleaginous yeast hosts. Thus, one aspect of the present disclosure provides a recombinant expression cassette comprising a YAT1 yeast promoter.

In a further aspect, provided herein is a method of expressing at least one coding region of interest in a transformed yeast, wherein a transformed yeast is provided having a chimeric gene comprising: (i) a promoter region of a *Yarrowia* yat1 gene; and, (ii) a coding region of interest expressible in the yeast, wherein the promoter region is operably linked to the coding region of interest to create a recombinant expression cassette; and the transformed yeast is grown under conditions wherein the chimeric gene is expressed. The polypeptide so produced can optionally be recovered from the culture.

Microbial expression systems and expression vectors are well known to those skilled in the art. Any of these could be used to construct chimeric genes comprising a promoter region derived from the yat1 gene for production of any specific coding region of interest suitable for regulated expression in a desirable yeast host cell. These chimeric genes could then be introduced into appropriate microorganisms by integration via transformation to provide expression of the enzymes upon induction. Alternatively, the promoters can be cloned into a plasmid that is capable of transforming and replicating itself in the preferred yeast. The coding region of interest to be expressed can then be cloned downstream from the promoter. Once the recombinant host is established, regulated gene expression can be accomplished by growing the cells under suitable conditions (infra).

Useful chimeric genes will include the promoter region of the yat1 gene as defined herein or a mutant promoter thereof, operably linked to a suitable coding region of interest to be expressed in a preferred host cell.

Coding regions of interest to be expressed in the recombinant yeast host may be either endogenous to the host or heterologous and must be compatible with the host organism. Genes encoding proteins of commercial value are particularly suitable for expression. For example, suitable coding regions of interest may include (but are not limited to) those encoding viral, bacterial, fungal, plant, insect, or vertebrate coding regions of interest, including mammalian polypeptides. Further, these coding regions of interest may be, for example, structural proteins, enzymes such as oxidoreductases, transferases, hydrolyases, lyases, isomerases or ligases, or peptides. A non-limiting list includes genes encoding enzymes such as acyltransferases, aminopeptidases, amylases, carbohydrases, carboxypeptidases, catalyases, cellulases, chitinases, cutinases, cyclodextrin glycosyltransferases, deoxyribonucleases, esterases, α-galactosidases, β-glucanases, β-galactosidases, glucoamylases, α-glucosidases, β-glucosidases, invertases, laccases, lipases, mannosidases, mutanases, oxidases, pectinolytic enzymes, peroxidases, phospholipases, phytases, polyphenoloxidases, proteolytic enzymes, ribonucleases, transglutaminases, or xylanases.

In some embodiments, coding regions of the enzymes involved in the production of microbial oils, including ω-6 and ω-3 fatty acids, are preferred. These coding regions include desaturases and elongases (e.g., see U.S. Pat. No. 7,238,482 and U.S. Pat. Appl. Pub. No. 2009-0093543-A1 for a partial review of available genes in GenBank and/or the patent literature and considerations for choosing a specific polypeptide having desaturase or elongase activity).

Alternately, coding regions of the enzymes involved in the production of neutral lipids such as TAGs and phospholipids are preferred, These coding regions include various acyltransferases such as diacylglycerol cholinephosphotransferases, acyl-CoA:lysophospholipid acyltransferases (e.g., lysophosphatidic acid acyltransferases, lysophosphatidylcholine acyltransferases lysophosphatidylethanolamine acyltransferases, lysophosphatidylserine acyltransferases, lysophosphatidylglycerol acyltransferases and lysophosphatidylinositol acyltransferases), diacylglycerol acyltransferases and phospholipid:diacylglycerol acyltransferases, for example.

Vectors or DNA cassettes useful for the transformation of suitable host cells are well known in the art. In general, the choice of sequences included in the construct depends upon the desired expression products (supra), the nature of the host cell, and the proposed means of separating transformed cells versus non-transformed cells. The skilled artisan is aware of the genetic elements that must be present on the plasmid vector to successfully transform, select and propagate host cells containing the chimeric gene. Typically, however, the vector or cassette contains sequences directing transcription and translation of the relevant gene(s), a selectable marker, and sequences allowing autonomous replication or chromosomal integration. Suitable vectors comprise a region 5' of the gene that controls transcriptional initiation, i.e., a promoter, the gene coding sequence, and a region 3' of the DNA fragment that controls transcriptional termination, i.e., a terminator. It is most preferred when both control regions are derived from genes from the transformed host cell, although they need not be derived from genes native to the production host.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence motif to obtain optimal gene expression. For expression in yeast, this can be done by site-directed mutagenesis of an inefficiently expressed gene to include the favored translation initiation motif.

3' non-coding sequences encoding transcription termination regions may be provided in a recombinant construct and may be from the 3' region of the gene from which the initiation region was obtained or from a different gene. A large number of termination regions are known and function satisfactorily in a variety of hosts when utilized both in the same and different genera and species from which they were derived. Termination regions may also be derived from various genes native to the preferred hosts. The termination region is usually selected more for convenience rather than for any particular property.

Particularly useful termination regions for use in yeast are derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. The 3'-region can also be synthetic, as one of skill in the art can utilize available information to design and synthesize a 3'-region sequence that functions as a transcription terminator. A termination region may be unnecessary, but is highly preferred.

The vector may also comprise a selectable and/or scorable marker, in addition to the regulatory elements described above. Preferably, the marker gene is an antibiotic resistance gene such that treating cells with the antibiotic results in growth inhibition, or death, of untransformed cells and uninhibited growth of transformed cells. For selection of yeast transformants, any marker that functions in yeast is useful with resistance to kanamycin, hygromycin and the amino glycoside G418 and the ability to grow on media lacking uracil, lysine, histine or leucine being particularly useful.

Merely inserting a chimeric gene into a cloning vector does not ensure its expression at the desired rate, concentration, amount, etc. In response to the need for a high expression rate, many specialized expression vectors have been created by manipulating a number of different genetic elements that control aspects of transcription, RNA stability, translation, protein stability and location, oxygen limitation and secretion from the host cell. Some of the manipulated features include: the nature of the relevant transcriptional promoter and terminator sequences, whether the gene is plasmid-borne or integrated into the genome of the host cell and the number of copies of the cloned gene [e.g., additional copies a particular coding region of interest (operably linked to the promoter of the instant invention) may be introduced into the host to increase expression], the final cellular location of the synthesized protein, the efficiency of translation and correct folding of the protein in the host organism, the intrinsic stability of the mRNA and protein of the cloned gene within the host cell [e.g., expression of the coding region of interest can be increased by removing/deleting destabilizing sequences from either the mRNA or the encoded protein or by adding stabilizing sequences to the mRNA (U.S. Pat. No. 4,910,141)], and the codon usage within the cloned gene, such that its frequency approaches the frequency of preferred codon usage of the host cell [e.g. translational efficiency of the encoded mRNAs can be increased by replacement of codons in the native gene with those for optimal gene expression in the selected host microorganism, to thereby substantially enhance the expression of the foreign gene encoding the polypeptide]. Each of these may be used in the methods and host cells described herein to further optimize expression of a recombinant expression cassette comprising a promoter region of the yat1 gene.

After a recombinant construct is created comprising at least one chimeric gene comprising a YAT1 promoter, a suitable ORF and a terminator, it is placed in a plasmid vector capable of autonomous replication in the host cell or is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Where two or more genes are expressed from separate replicating vectors, each vector may have a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising a coding region of interest may be introduced into a host cell by any standard technique. These techniques include transformation, e.g., lithium acetate transformation (*Methods in Enzymology*, 194:186-187 (1991)), biolistic impact, electroporation, microinjection, vacuum filtration or any other method that introduces the gene of interest into the host cell. More specific teachings applicable for oleaginous yeast (i.e., *Yarrowia lipolytica*) include U.S. Pat. No. 4,880,741 and U.S. Pat. No. 5,071,764 and Chen, D. C. et al. (*Appl Microbiol Biotechnol.*, 48(2):232-235 (1997)).

For convenience, a host cell that has been manipulated by any method to take up a DNA sequence, for example, in an expression cassette, is referred to herein as "transformed" or "recombinant" or "transformant". The transformed host will have at least one copy of the expression cassette and may have two or more, depending upon whether the gene is integrated into the genome, amplified, or is present on an extrachromosomal element having multiple copy numbers.

The transformed host cell can be identified by selection for a marker contained on the introduced construct. Alternatively, a separate marker construct may be co-transformed with the desired construct, as many transformation techniques introduce many DNA molecules into host cells.

Typically, transformed hosts are selected for their ability to grow on selective media, which may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. Additional selection techniques are described in U.S. Pat. No. 7,238,482 and U.S. Pat. No. 7,259,255.

Preferred host cells for expression of coding regions of interest operably linked to the YAT1 promoter fragments herein are yeast cells, where oleaginous yeast are most preferred where the desired use is for the production of microbial oils, infra. Oleaginous yeast are naturally capable of oil synthesis and accumulation, wherein the total oil content can comprise greater than about 25% of the dry cell weight ["DCW"], more preferably greater than about 30% of the DCW, and most preferably greater than about 40% of the DCW. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*). In alternate embodiments, a non-oleaginous organism can be genetically modified to become oleaginous, e.g., yeast such as *Saccharomyces cerevisiae*.

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.*, 82(1):43-9 (2002)). The *Y. lipolytica* strain designated as ATCC #20362 was the particular strain from which the YAT1 promoter was isolated therefrom.

The transformed recombinant host cell is grown under conditions that optimize expression of the chimeric gene(s). In general, media conditions may be optimized for regulated expression of a particular coding region of interest by modifying the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method and the time of cell harvest.

Microorganisms of interest, such as oleaginous yeast, are generally grown in a complex media, such as yeast extract-peptone-dextrose broth ["YPD"] or a defined minimal media that lacks a component necessary for growth and thereby forces selection of the desired expression cassettes (e.g., Yeast Nitrogen Base (DIFCO Laboratories, Detroit, Mich.)).

Fermentation media for the methods and host cells described herein must contain a suitable carbon source, such as are taught in U.S. Pat. No. 7,238,482. Although it is contemplated that the source of carbon utilized may encompass a wide variety of carbon-containing sources, preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea, glutamate, or yeast extract) source. Although the YAT1 promoter is active in media containing nitrogen (e.g., up to about 0.5% ammonium sulfate), the activity of the promoter increases when the host cell is grown in nitrogen-limiting conditions (e.g., in medium containing very low levels of ammonium, or lacking ammonium). Thus, a preferred medium would be one that contains less than about 0.1% ammonium sulfate, or other suitable ammonium salts.

In a more preferred embodiment, the YAT1 promoter is induced when the host cell is grown in media with a high carbon to nitrogen (i.e., C:N) ratio, such as a high glucose medium containing about 1-15% glucose, and about 0.1% or less ammonium sulfate. These conditions are also sufficient to induce oleaginy in those yeast that are oleaginous (e.g., *Yarrowia lipolytica*).

In addition to appropriate carbon and nitrogen sources, the fermentation media must also contain suitable minerals, salts, cofactors, buffers, vitamins, and other components known to those skilled in the art suitable for the growth of the microorganism.

Preferred growth media for the methods and host cells described herein are common commercially prepared media, such as minimal media made with Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Host cells comprising a suitable coding region of interest operably linked to the promoters of the present disclosure may be cultured using methods known in the art. For example, the cell may be cultivated by shake flask cultivation, small-scale or large-scale fermentation in laboratory or industrial fermentors performed in a suitable medium and under conditions allowing regulated expression of the coding region of interest. Furthermore, where commercial production of a product that relies on the instant genetic chimera is desired, a variety of culture methodologies may be applied. For example, large-scale production of a specific gene product over-expressed from a recombinant host may be produced by a batch, fed-batch or continuous fermentation process, as is well known in the art (see, e.g., Thomas D. Brock in *Biotechnology: A Textbook of Industrial Microbiology*, $2^{nd}$ ed., (1989) Sinauer Associates: Sunderland, Mass.; or Deshpande, Mukund V., *Appl. Biochem. Biotechnol.*, 36:227 (1992), each herein incorporated by reference).

As was discussed above, the instant invention can be practiced in regulatingexpression of any suitable coding region of interest in an oleaginous yeast. In particularcoding regions of the enzymes involved in the production of microbial oils, including ω-6 and ω-3 fatty acids, are of interest. Examples of such enzymes include, but are not limited to, expression of desaturases and elongases.

The term "fatty acids" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon ["C"] atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" ["PUFAs"], and "ω-6 fatty acids" ["ω-6" or "n-6"] versus "ω-3 fatty acids" ["ω-3" or "n-3"] are provided in U.S. Pat. No. 7,238,482, which is hereby incorporated herein by reference. Nomenclature used to describe PUFAs herein is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids and their precursors, the abbreviations that will be used throughout the remainder of the specification, and the chemical name of each compound.

TABLE 2

Nomenclature Of Polyunsaturated Fatty Acids

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| γ-Linolenic | GLA | cis-6,9,12-octadecatrienoic | 18:3 ω-6 |
| Eicosadienoic | EDA | cis-11,14-eicosadienoic | 20:2 ω-6 |
| Dihomo-γ-linolenic | DGLA | cis-8,11,14-eicosatrienoic | 20:3 ω-6 |
| Sciadonic | SCI | cis-5,11,14-eicosatrienoic | 20:3b ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosa-tetraenoic | ETA | cis-8,11,14,17-eicosatetraenoic | 20:4 ω-3 |
| Juniperonic | JUP | cis-5,11,14,17-eicosatetraenoic | 20:4b ω-3 |
| Eicosapentaenoic | EPA | cis-5,8,11,14,17-eicosapentaenoic | 20:5 ω-3 |
| Docosatetraenoic | DTA | cis-7,10,13,16-docosatetraenoic | 22:4 ω-6 |
| Docosapentaenoic | DPAn-6 | cis-4,7,10,13,16-docosapentaenoic | 22:5 ω-6 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

The process of de novo synthesis of palmitate (16:0) in oleaginous microorganisms is described in commonly owned U.S. Pat. No. 7,238,482. This fatty acid is the precursor of longer-chain saturated and unsaturated fatty acid derivates, which are formed through the action of elongases and desaturases. For example, palmitate is converted to its unsaturated derivative [palmitoleic acid (16:1)] by the action of a Δ9 desaturase; similarly, palmitate is elongated to form stearic acid (18:0), which can be converted to its unsaturated derivative by a Δ9 desaturase to thereby yield oleic (18:1) acid.

The metabolic process that converts oleic acid to ω-6 fatty acids such as LA, EDA, GLA, DGLA, ARA, DTA and DPAn-6 and ω-3 fatty acids such as ALA, STA, ETrA, ETA, EPA, DPA and DHA is well described in the literature and is schematically depicted in FIG. 2 (e.g., see U.S. Pat. Appl. Pub. No. 2006-0115881-A1 and U.S. Pat. Appl. Pub. No. 2009-0093543-A1). Simplistically, this process involves elongation of the carbon chain through the addition of carbon atoms and desaturation of the molecule through the addition of double bonds, via a series of special elongation and desaturation enzymes present in the endoplasmic reticulum membrane (and hereinafter referred to as "PUFA biosynthetic pathway enzymes").

More specifically, "PUFA biosynthetic pathway enzymes" or "ω-3/ω-6 biosynthetic pathway enzymes" will refer to any of the following enzymes (and genes which encode said enzymes) associated with the biosynthesis of a PUFA, including: Δ4 desaturase, Δ5 desaturase, Δ6 desaturase, Δ12 desaturase, ≠15 desaturase, Δ17 desaturase, Δ9 desaturase, Δ8 desaturase, Δ9 elongase, $C_{14/16}$ elongase, $C_{16/18}$ elongase, $C_{18/20}$ elongase and/or $C_{20/22}$ elongase. For further clarity within the present disclosure, the term "desaturase" refers to a polypeptide that can desaturate one or more fatty acids to produce a mono- or polyunsaturated fatty acid or precursor of interest.

Thus, despite use of the omega-reference system to refer to specific fatty acids, it is more convenient to indicate the activity of a desaturase by counting from the carboxyl end of the source using the delta-system. For example, a Δ17 desaturase will desaturate a fatty acid between the $17^{th}$ and $18^{th}$ carbon atom numbered from the carboxyl-terminal end of the molecule and can, for example, catalyze the conversion of ARA to EPA and/or DGLA to ETA. In contrast, the term "elongase" refers to a polypeptide that can elongate a fatty acid carbon chain to produce a mono- or polyunsaturated fatty acid that is 2 carbons longer than the fatty acid source that the elongase acts upon. This process of elongation occurs in a multi-step mechanism in association with fatty acid synthase, whereby CoA is the acyl carrier (Lassner et al., *The Plant Cell*, 8:281-292 (1996)).

As will be understood by one skilled in the art, the particular functionalities required to be introduced into a host organism for production of a particular PUFA final product will depend on the host cell (and its native PUFA profile and/or desaturase/elongase profile), the availability of substrate and the desired end product(s). As shown in FIG. 2, LA, GLA, EDA, DGLA, ARA, DTA, DPAn-6, ALA, STA, ETrA, ETA, EPA, DPA and DHA may all be produced in oleaginous yeast, by introducing various combinations of the following PUFA enzyme functionalities: Δ4 desaturase, Δ5 desaturase, Δ6 desaturase, Δ12 desaturase, Δ15 desaturase, Δ17 desaturase, Δ9 desaturase, Δ8 desaturase, Δ9 elongase, $C_{14/16}$ elongase, $C_{16/18}$ elongase, $C_{18/20}$ elongase and/or $C_{20/22}$ elongase. One skilled in the art will be able to identify various candidate genes encoding each of the above enzymes, according to publicly available literature (e.g., GenBank), the patent literature, and experimental analysis of microorganisms having the ability to produce PUFAs. Thus, a variety of desaturases and elongases are suitable as coding regions of interest in the present disclosure. These coding regions of interest could be operably linked to the YAT1 promoters herein, and used as chimeric genes for expression of various ω-6 and ω-3 fatty acids, using techniques well known to those skilled in the art (e.g., see U.S. Pat. No. 7,238,482, U.S. Pat. Appl. Pub. No. 2006-0115881-A1 and U.S. Pat. Appl. Pub. No. 2009-0093543-A1).

Following PUFA biosynthesis, the fatty acids are generally incorporated into the "oil" fraction of oleaginous organisms, which constitutes a major part of the total lipid. More specifically, the term "oil" refers to a lipid substance that is liquid at 25° C. and usually polyunsaturated. "Oil" is composed primarily of triacylglycerols ["TAGs"] but may also contain other neutral lipids, phospholipids and free fatty acids. The fatty acid composition in the oil and the fatty acid composition of the total lipid are generally similar; thus, an increase or decrease in the concentration of PUFAs in the total lipid will correspond with an increase or decrease in the concentration of PUFAs in the oil, and vice versa.

"Neutral lipids" refer to those lipids commonly found in cells in lipid bodies as storage fats and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol ["MAG"], diacylglycerol ["DAG"] or triacylglycerol ["TAG"], respectively, or collectively, acylglycerols. A hydrolysis reaction must occur to release free fatty acids from acylglycerols.

Finally, for clarity, the term "triacylglycerols" ["TAGs"] refers to neutral lipids composed of three fatty acyl residues esterified to a glycerol molecule. TAGs can contain long chain PUFAs and saturated fatty acids, as well as shorter chain saturated and unsaturated fatty acids.

Thus, following PUFA biosynthesis, the fatty acids are generally stored as an energy resource within the cell in the form of neutral lipid (i.e., MAGs, DAGs, TAGs) and/or in the form of phospholipids. Various acyltransferases, responsible for transferring an acyl group from a donor lipid to an acceptor lipid molecule, enable this process, including: diacylglycerol cholinephosphotransferases, acyl-CoA:lysophospholipid acyltransferases (e.g., lysophosphatidic acid acyltransferases, lysophosphatidylcholine acyltransferases lysophosphatidylethanolamine acyltransferases, lysophosphatidylserine acyltransferases, lysophosphatidylglycerol acyltransferases and lysophosphatidylinositol acyltransferases), diacylglycerol acyltransferases and phospholipid:diacylglycerol acyltransferases, for example.

In preferred embodiments, the nucleic acid sequence of the promoter region is selected from the group consisting of: SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35 and SEQ ID NO:36. The coding region of interest is preferably any desaturase or elongase suitable for regulated expression in the oleaginous yeast for the production of ω-3 or ω-6 fatty acids, wherein the enzyme product is a PUFA selected from the group consisting of LA, EDA, ALA, GLA, STA, ETrA, DGLA, ETA, ARA, DTA, DPAn-6, EPA, DPAn-3 and DHA. Alternately, the coding region of interest is preferably any acyltransferase suitable for production of neutral lipids or phospholipids. And, the transformed oleaginous yeast is preferably cultured under conditions that induce oleaginy (i.e., conditions of nitrogen limitation).

More specifically, for production of the greatest and the most economical yield of PUFAs, the transformed oleaginous yeast host cell is grown under conditions that optimize expression of chimeric genes comprising a promoter region of a yat1 gene and a coding region of interest encoding a PUFA, neutral lipid or phospholipid biosynthetic pathway enzyme. Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast. In this approach, the first stage of the fermentation is dedicated to the generation and accumulation of cell mass and is characterized by rapid cell growth and cell division. In the second stage of the fermentation, it is preferable to establish conditions of nitrogen deprivation in the culture to promote high levels of lipid accumulation.

The effect of this nitrogen deprivation is two-fold. First, the nitrogen deprivation reduces the effective concentration of AMP in the cells, thereby reducing the activity of the NAD-dependent isocitrate dehydrogenase of mitochondria. When this occurs, citric acid will accumulate, thus forming abundant pools of acetyl-CoA in the cytoplasm and priming fatty acid synthesis. Secondly, the nitrogen deprivation induces the YAT1 promoter, thereby promoting expression of any chimeric genes comprising the YAT1 promoter and a coding region of interest encoding an enzyme of the ω-3/ω-6 fatty acid biosynthetic pathway, neutral lipid biosynthetic pathway or phospholipid biosynthetic pathway. Thus, this second phase of the two-stage fermentation is characterized by the cessation of cell division followed by the synthesis of fatty acids and accumulation of oil.

Although cells are typically grown at about 30° C., some studies have shown increased synthesis of unsaturated fatty acids at lower temperatures (Yongmanitchai and Ward, *Appl.*

Environ. Microbiol., 57:419-25 (1991)). Based on process economics, this temperature shift should likely occur after the first phase of the two-stage fermentation, when the bulk of the organisms' growth has occurred.

Additionally, particular attention is given to several metal ions (e.g., $Fe^{+2}$, $Cu^{+2}$, $Mn^{+2}$, $Co^{+2}$, $Zn^{+2}$, $Mg^{+2}$) that promote synthesis of lipids and PUFAs in the fermentation media (Nakahara, T. et al. *Ind. Appl. Single Cell Oils*, D. J. Kyle and R. Colin, eds. pp 61-97 (1992)).

The PUFAs produced in a host microorganism as described herein may also be found as free fatty acids or sulfolipids or glycolipids.

PUFAs may be extracted from the host cell through a variety of means well-known in the art. One review of extraction techniques, quality analysis and acceptability standards for yeast lipids is that of Z. Jacobs (*Critical Reviews in Biotechnology*, 12(5/6):463-491 (1992)). A brief review of downstream processing is also available by A. Singh and O. Ward (*Adv. Appl. Microbiol.*, 45:271-312 (1997)).

In general, means for the purification of fatty acids (including PUFAs) may include extraction (e.g., U.S. Pat. No. 6,797,303 and U.S. Pat. No. 5,648,564) with organic solvents, sonication, supercritical fluid extraction (e.g., using carbon dioxide), saponification and physical means such as presses, or combinations thereof. One is referred to the teachings of U.S. Pat. No. 7,238,482 for additional details.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1) Sambrook, J., Fritsch, E. F. and Maniatis, T. *Molecular Cloning: A Laboratory Manual*; Cold Spring Harbor Laboratory: Cold Spring Harbor, N.Y. (1989) (hereinafter "Maniatis"); 2) T. J. Silhavy, M. L. Bennan, and L. W. Enquist, Experiments with Gene Fusions; Cold Spring Harbor Laboratory: Cold Spring Harbor, N.Y. (1984); and 3) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology*, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.) or Sigma Chemical Company (St. Louis, Mo.), unless otherwise specified.

General molecular cloning was performed according to standard methods (Sambrook et al., supra). Oligonucleotides were synthesized by Sigma-Genosys (Spring, Tex.). When polymerase chain reaction ["PCR"] was involved in subcloning, the constructs were sequenced to confirm that no errors had been introduced to the sequence. PCR products were cloned into Promega's pGEM-T-easy vector (Madison, Wis.).

Manipulations of genetic sequences were accomplished using the suite of programs available from the Genetics Computer Group Inc. (Wisconsin Package Version 9.0, Genetics Computer Group ["GCG"], Madison, Wis.). The GCG program "Pileup" was used with the gap creation default value of 12, and the gap extension default value of 4. The GCG "Gap" or "Bestfit" programs were used with the default gap creation penalty of 50 and the default gap extension penalty of 3. Unless otherwise stated, in all other cases GCG program default parameters were used.

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s).

Nomenclature For Expression Cassettes

The structure of an expression cassette will be represented by a simple notation system of "X::Y::Z", wherein X describes the promoter fragment, Y describes the gene fragment, and Z describes the terminator fragment, which are all operably linked to one another.

Transformation And Cultivation Of *Yarrowia lipolytica*

*Y. lipolytica* strain ATCC #20362 was purchased from the American Type Culture Collection (Rockville, Md.). Strains were routinely grown at 28-30° C. on YPD agar (1% yeast extract, 2% bactopeptone, 2% glucose, 2% agar) or in YPD liquid medium (2% bacto-yeast extract, 3% bactopeptone, 2% glucose).

Transformation of *Y. lipolytica* was performed as described in U.S. Pat. Appl. Pub. No. 2009-0093543-A1, hereby incorporated herein by reference.

For selection of transformants, minimal medium ("MM") was generally used; the composition of MM is as follows: 0.17% yeast nitrogen base (DIFCO Laboratories, Detroit, Mich.) without ammonium sulfate or amino acids, 2% glucose, 0.1% proline, pH 6.1 and 20 g/L agar).

"SD" media comprises: 0.67% yeast nitrogen base with ammonium sulfate, without amino acids and 2% glucose. And finally, to promote conditions of oleaginy, High Glucose Media ("HGM") was prepared as follows: 14 g/L $KH_2PO_4$, 4 g/L $K_2HPO_4$, 2 g/L $MgSO_4.7H_2O$, 80 g/L glucose (pH 6.5).

Fatty Acid Analysis Of *Yarrowia lipolytica*

For fatty acid analysis, cells were collected by centrifugation and lipids were extracted as described in Bligh, E. G. & Dyer, W. J. (*Can. J. Biochem. Physiol.*, 37:911-917 (1959)). Fatty acid methyl esters ["FAMEs"] were prepared by transesterification of the lipid extract with sodium methoxide (Roughan, G., and Nishida I., *Arch Biochem Biophys.*, 276 (1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 µl of 1%) was added to the sample, and then the sample was vortexed and rocked for 20 min. After adding 3 drops of 1 M NaCl and 400 µl hexane, the sample was vortexed and spun. The upper layer was removed and analyzed by GC as described above.

Example 1

Construction And Sequencing Of A *Yarrowia lipolytica* cDNA Library

The present Example describes the construction of a cDNA library of *Y. lipolytica*, grown under oleaginous conditions. More specifically, *Y. lipolytica* cells accumulate considerable amounts of oil when switched to a medium with a high carbon to nitrogen ratio (>80). A cDNA library was constructed from cells grown in an oleaginous medium containing no nitrogen source for 4 hrs, using the BD-Clontech Creator Smart® cDNA library kit (Mississauga, ON, Canada) according to the manufacturer's protocol.

Synthesis of the cDNA library first required growth of *Y. lipolytica* strain ATCC #20362 in 30 mL YPD medium overnight at 30° C. with shaking. Cells were diluted in two cultures of 100 mL fresh YPD to $OD_{600}$=0.4, then grown until $OD_{600}$=1.5 (Perkin-Elmer Lambda 20 UV/VIS Spectrophotometer). Cells from each culture were pelleted twice by centrifugation at 3750 rpm in a Beckman GH3.8 rotor for 5 min and washed with sterile water, then resuspended in 100 mL HGM. Cells were then shaken at 30° C. for 4 hrs. Each 100 mL culture was divided into three equal portions and pelleted by centrifugation at 3750 rpm in a Beckman GH3.8 rotor for 5 min.

Total RNA was extracted from the pellets using the Qiagen Rneasy Midi Kit. Cells were resuspended in 600 µl buffer RLT from the kit, with β-mercaptoethanol added at a concentration of 10 µl/mL. Resuspended cells were transferred to six 2 mL screw cap tubes each containing 0.6 mL of 0.5 mm glass beads. The cells were homogenized at the HOMOGENIZE setting on a Biospec (Bartlesville, Okla.) mini bead beater for 2 min. The tubes were briefly spun to settle the beads. Liquid was transferred to 4 fresh 2 mL microfuge tubes and 600 µl of the RLT/BME mix was added to the beads. The bead tubes were vortexed and all liquid above the beads was transferred to the fresh 2 mL tubes. The fresh tubes were spun for 2 min in a microfuge to pellet cells debris, and the supernatant from each set of three tubes that came from a single culture were pooled in a 10 mL screwcap centrifuge tube. The procedure was then completed following the manufacturer's protocol. The two total RNA samples were then combined and mRNA was isolated from the combined sample using the Qiagen Oligotex Midi kit, following the manufacturer's protocol. Purified poly(A)+FRNA was obtained with a concentration of 35.7 ng/µl.

cDNA was generated, using the LD-PCR method specified by BD-Clontech and 0.1 µl of polyA(+) RNA sample. Specifically, for $1^{st}$ strand cDNA synthesis, 3 µl of the poly(A)+ RNA sample was mixed with 1 µl of SMART IV oligo nucleotide (SEQ ID NO:4) and 1 µl of CDSIII/3' PCR primer (SEQ ID NO:5). The mixture was heated at 72° C. for 2 min and cooled on ice for 2 min. To the tube was added the following: 2 µl $1^{st}$ strand buffer, 1 µl 20 mM DTT, 1 µl 10 mM dNTP mix and 1 µl Powerscript reverse transcriptase. The mixture was incubated at 42° C. for 1 hr and cooled on ice.

The $1^{st}$ strand cDNA synthesis mixture was used as template for the PCR reaction. Specifically, the reaction mixture contained the following: 2 µl of the $1^{st}$ strand cDNA mixture, 2 µl 5'-PCR primer (SEQ ID NO:6), 2 µl CDSIII/3'-PCR primer (SEQ ID NO:5), 80 µl water, 10 µl 10× Advantage 2 PCR buffer, 2 µl 50× dNTP mix and 2 µl 50× Advantage 2 polymerase mix. The thermocycler conditions were set for 95° C. for 20 sec, followed by 14 cycles of 95° C. for 5 sec and 68° C. for 6 min on a GenAmp 9600 instrument. PCR product was quantitated by agarose gel electrophoresis and ethidium bromide staining.

Seventy-five µl of the above PCR products (cDNA) were mixed with 3 µl of 20 µg/µl proteinase K supplied with the kit. The mixture was incubated at 45° C. for 20 min, then 75 µl of water was added and the mixture was extracted with 150 µl phenol:chloroform:isoamyl alcohol mixture (25:24:1). The aqueous phase was further extracted with 150 µl chloroform: isoamyl alcohol (25:1). The aqueous phase was then mixed with 15 µl of 3 M sodium acetate, 2 µl of 20 µg/µl glycogen and 400 µl of 100% ethanol. The mixture was immediately centrifuged at room temperature for 20 min at 14000 rpm in a microfuge. The pellet was washed once with 150 µl of 80% ethanol, air dried and dissolved in 79 µl of water.

Dissolved cDNA was subsequently digested with Sfil (79 µl of the cDNA was mixed with 10 µl of 10× Sfil buffer, 10 µl of Sfil enzyme and 1 µl of 100× BSA and the mixture was incubated at 50° C. for 2 hrs). Xylene cyanol dye (2 µl of 1%) was added. The mixture was then fractionated on the Chroma Spin-400 column provided with the kit, following the manufacturer's procedure exactly. Fractions collected from the column were analyzed by agarose gel electrophoresis. The first three fractions containing cDNA were pooled and cDNA precipitated with ethanol. The precipitated cDNA was redissolved in 7 µl of water, and ligated into kit-supplied pDNR-LIB.

Library Sequencing

The ligation products were used to transform *E. coli* XL-1 Blue electroporation competent cells (Stratagene). An estimated total of $5.4 \times 10^6$ colonies was obtained. Sequencing of the cDNA library was carried out by Agencourt Bioscience Corporation (Beverly, Mass.), using a M13 forward primer (SEQ ID NO:7)

Example 2

Identification Of The *Yarrowia lipolytica* Gene Encoding YAT1 As A Highly Expressed Gene Under Oleaginous Conditions This example describes the identification of YAT1 as a highly expressed gene under oleaginous conditions. Specifically, the relative abundance of each species of cDNA was examined (based on the sequencing results from Example 1) to identify those genes that were highly expressed under oleaginous conditions. One of the genes that appeared multiple times (16/9984 or 0.16%) was Yali0E27203 (GenBank Accession No. XM_504457; SEQ ID NO:1 herein), annotated as a homolog of the high affinity, low capacity ammonia transporter MEP2 of *Saccharomyces cerevisiae* (GenBank Accession No. X83608; see also A. M. Marini et al., *EMBO J.*, 13(15):3456-3463 (1994); A. M. Marini et al., *Mol Cell Biol.*, 17(8):4282-93 (1997)).

BLAST (Basic Local Alignment Search Tool; Altschul, S. F., et al., *J. Mol. Biol.*, 215:403-410 (1993)) searches were conducted using the corresponding amino acid sequence of Yali0E27203 (SEQ ID NO:2) as a query against the *S. cerevisiae* MEP1, MEP2 and MEP3 isozymes. The results of these BLAST comparisons are shown below in Table 3 and are reported according to the % identity, % similarity and Expectation value.

TABLE 3

Comparison Of *Yarrowia lipolytica* Homolog To *Saccharomyces cerevisiae* MEP1, MEP2 And MEP3

| Similarity Identified | % Identity[a] | % Similarity[b] | E-value[c] |
|---|---|---|---|
| MEP1 [GenBank Accession No. X77608] | 35 | 56 | 1.8e−79 |
| MEP2 [GenBank Accession No. X83608] | 52 | 66 | 1.9e−132 |
| MEP3 [GenBank Accession No. P53390] | 37 | 57 | 3.6e−83 |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

It was hypothesized that YALI0E27203 encoded a *Y. lipolytica* ammonia transporter of high affinity; thus, YALI0E27203 was tentatively named yat1.

Example 3

Isolation Of The 5' Upstream Region Of YAT1 From *Yarrowia lipolytica*

To isolate the YAT1 promoter region upstream of the yat1 gene identified in Example 2, primers 27203-F and 27203-R (SEQ ID NOs:8 and 9) were designed, based on the sequence of *Y. lipolytica* chromosome E between positions 3,222,879 and 3,223,875. These primers were expected to amplify a 778 by fragment (SEQ ID NO:3), including 775 by of the 5' upstream untranslated region in front of the 'ATG' translation initiation codon of the yat1 gene (from −775 to −1 [wherein the 'A' position of the 'ATG' translation initiation codon was designated as +1]) and the 'ATG' translation initiation codon of the yat1 gene (i.e., the +1 to +3 region).

PCR amplification was performed in a 50 µl total volume using a 1:1 dilution of a premixed 2× PCR solution (TaKaRa ExTaq, TaKaRa Bio Inc., Otsu Shiga, 520-2193, Japan). The final composition contained 25 mM TAPS, pH 9.3, 50 mM KCl, 2 mM $MgCl_2$, 1 mM 2-mercaptoethanol, 200 µM each deoxyribonucleotide triphosphate, 10 pmole each primer (supra), 50 ng *Y. lipolytica* ATCC #20362 genomic DNA, and 1.25 units of TaKaRa ExTaq™ DNA polymerase. The reaction mixture was first heated to 94° C. for 150 sec. Amplification was carried out for 30 cycles at 94° C. for 30 sec, 55° C. for 30 sec and 72° C. for 1 min. This was followed by a final extension for 7 min at 72° C.

The PCR product was analyzed by agarose gel electrophoresis and was shown to contain a single DNA fragment of ~780 bp. This fragment was purified using a Qiagen PCR purification kit following the manufacturer's protocol.

Sequence analyses permitted construction of a single contig of DNA (FIG. 1; 2236 by total length, corresponding to SEQ ID NO:24). This contig therefore contained the −775 to +1461 region of the YAT1 gene, wherein the 'A' position of the 'ATG' translation initiation codon was designated as +1.

Example 4

Synthesis Of Plasmids pY5-30, pYGPAT-GUS and pDMW214

A series of plasmids were created comprising a chimeric gene composed of various native *Y. lipolytica* promoters and the "GUS" reporter gene, wherein "GUS" corresponds to the *E. coli* gene encoding β-glucuronidase (Jefferson, R. A., *Nature*, 342(6251):837-838 (1989)). This was required for comparative studies investigating the promoter activity of TEF, YAT1, FBAIN and GPAT, as described in Example 8.

Synthesis Of Plasmid pY5-30 (TEF::GUS::XPR)

The synthesis of plasmid pY5-30, comprising a TEF:: GUS::XPR chimeric gene, is described in U.S. Pat. No. 7,259,255. More specifically, plasmid pY5-30 (FIG. 3A; SEQ ID NO:10) contained: a *Yarrowia* autonomous replication sequence (ARS18); a CoIE1 plasmid origin of replication; an ampicillin-resistance gene ($Amp^R$) for selection in *E. coli*; a *Yarrowia* LEU2 gene for selection in *Yarrowia*; and the chimeric TEF::GUS::XPR gene.

Synthesis Of Plasmid pDMW214 (FBAIN::GUS::XPR)

The synthesis of plasmid pDMW214, comprising a FBAIN::GUS::XPR chimeric gene, is described in U.S. Pat. No. 7,202,356. Briefly, the FBAIN promoter region (SEQ ID NO:11; which includes both an upstream DNA sequence and a downstream sequence from the putative 'ATG' translation initiation codon of the fructose-bisphosphate aldolase (fba1) gene [wherein the downstream region comprises an intron]) was amplified by PCR, digested with NcoI and SalI, and then purified following gel electrophoresis. The NcoI/SalII-digested PCR products were ligated to NcoI/SalI digested pY5-30 vector to produce plasmid "pDMW214" (FIG. 3B).

Synthesis Of pYGPAT-GUS (GPAT::GUS::XPR)

The synthesis of plasmid pYGPAT-GUS (FIG. 3C), comprising a GPAT::GUS::XPR chimeric gene, is described in U.S. Pat. No. 7,264,949. Briefly, synthesis of the plasmid required identification and isolation of the *Y. lipolytica* glycerol-3-phosphate O-acyltransferase (gpat) gene, isolation of the promoter region upstream of the putative 'ATG' translation initiation codon via genome-walking, and then cloning of the GPAT-Pro promoter region (SEQ ID NO:12) into a derivative of pY5-30 (supra).

Example 5

Synthesis of pYAT-GUS

The present Example describes the synthesis of pYAT-GUS (comprising a YAT1::GUS::XPR chimeric gene). Synthesis of this plasmid first required amplification of the putative YAT1 promoter region. Then, the putative promoter region was cloned into pYGPAT-GUS (supra, Example 4).

The purified YAT1 PCR product from Example 3 was digested with HindlII and SalI and a ~600 by fragment was isolated by agarose gel electrophoresis followed by purification with Qiagen MinElute Gel purification kit according to the manufacturer's protocol. Furthermore, the YAT1 PCR product was also digested with NcoI and HindlII, and a ~200 by fragment was isolated and purified as above. Finally, plasmid pYGPAT-GUS was digested with SalI and NcoI, and a ~9.5 kB fragment was isolated and purified. The three DNA fragments were ligated together to create pYAT-GUS (FIG. 3D). In the resulting plasmid, the YAT1 promoter region (SEQ ID NO:25; corresponding to 775 by of the 5' upstream region of YALI0E27203 (i.e., the −775 to −1 upstream region of the yat1 gene) was fused to the GUS gene, followed by the XPR terminator region.

Example 6

Generation Of ARA-Producinq *Yarrowia lipolvtica* ATCC #20362 Strain Y2034

The present Example describes the construction of strain Y2034, derived from *Yarrowia lipolytica* ATCC #20362, capable of producing significant concentrations of ARA relative to the total lipids. Comparison of the TEF, YAT1, GPAT and FBAIN promoters was examined in this ARA-producing strain based on analysis of GUS expression, as described in Example 8 (infra).

The development of strain Y2034, producing 10% ARA, required the construction of strain M4 (producing 8% DGLA). Further details regarding the construction of strains M4 and Y2034 are described in Example 10 of U.S. Pat. No. 7,273,746, hereby incorporated herein by reference. Briefly, however, integration of expression plasmids pKUNF12T6E (SEQ ID NO:13) and pDMW232 (SEQ ID NO:23) into wildtype *Yarrowia lipolytica* ATCC #20362 resulted in expression of the following chimeric genes in strain Y2034: FBAIN::EL1S:Pex20, TEF::Δ6S::Lip1, FBA::F.Δ12::Lip2, TEF::EL2S::XPR, FBAIN::MAΔ5::Pex20 and TEF::MAΔ5::Lip1 [wherein EL1S is a codon-optimized elongase 1 gene (SEQ ID NO:14), derived from *Mortierella alpina* (GenBank Accession No. AX464731); Δ6S is a codon-optimized Δ6 desaturase gene (SEQ ID NO:16), derived from *Mortierella alpina* (GenBank Accession No. AF465281); F.Δ12 is a *Fusarium moniliforme* Δ12 desaturase gene (SEQ ID NO:19; U.S. Pat. No. 7,504,259); EL2S is a codon-optimized elongase gene (SEQ ID NO:21), derived from *Thraustochytrium aureum* (U.S. Pat. No. 6,677,145); and, MAΔ5 is a *Mortierella alpina* Δ5 desaturase gene (Gen Bank Accession No. AF067654)].

Example 7

Transformation Of *Y. lipolytica* With pY5-30, pYAT-GUS, pYGPAT-GUS And pDMW214

The plasmids pY5-30 (Example 4; comprising a TEF::GUS::XPR chimeric gene), pYAT-GUS (Example 5; comprising a YAT1::GUS::XPR chimeric gene), pYGPAT-GUS (Example 4; comprising a GPAT::GUS::XPR chimeric gene) and pDMW214 (Example 4; comprising a FBAIN::GUS::XPR chimeric gene) were transformed separately into *Y. lipolytica* ATCC #20362 strain Y2034, according to the General Methods. Selection was performed on SD medium comprising 2.5% agar.

Using this technique, transformants were obtained that contained pY5-30, pYAT-GUS, pYGPAT-GUS and pDMW214, respectively.

Example 8

Comparative Analysis Of The TEF, YAT1, GPAT and FBAIN Promoter Activities In *Yarrowia lipolytica*, As Determined By Histochemical Assay The activity of the TEF, YAT1, GPAT and FBAIN promoters was determined in *Y. lipolytica* containing the pY5-30, pYAT-GUS, pYGPAT-GUS and pDMW214 constructs, each of which possessed a GUS reporter gene and an XPR terminator (from Example 7). GUS activity in each expressed construct was measured by histochemical assays (Jefferson, R. A., *Plant Mol. Biol. Reporter*, 5:387-405 (1987)).

Specifically, *Y. lipolytica* strains containing plasmids pY5-30, pYAT-GUS, pYGPAT-GUS and pDMW214, respectively, were grown from single colonies in 5 mL SD media at 30° C. for 24 hrs to an $OD_{600}$~8.0. Then, 1 mL of cells were collected by centrifugation. The remaining cultures were centrifuged and washed 2× with HGM, resuspended in 5 mL each of HGM and allowed to grow at 30° C. further. After 24 and 120 hrs, ~0.25 mL of each culture were centrifuged to collect the cells. Cell samples were resuspended individually in 100 μl of histochemical staining buffer [Staining buffer prepared by dissolving 5 mg of 5-bromo-4-chloro-3-indolyl glucuronide (X-Gluc) in 50 μl dimethyl formamide, followed by addition of 5 mL 50 mM $NaPO_4$, pH 7.0.]. Zymolase 20T (5 μl of 1 mg/mL; ICN Biomedicals, Costa Mesa, Calif.) was added to each, and the mixture incubated at 30° C.

The results of histochemical staining showed that the YAT1 promoter in construct pYAT-GUS was active. Comparatively, the YAT1 promoter appeared to be stronger than the TEF promoter (FIG. 4A) but significantly weaker than the FBAIN promoter and GPAT promoter, when cells were grown in SD medium for 24 hrs. More interestingly, however, it appeared that the YAT1 promoter was stronger than the GPAT promoter and comparable with the FBAIN promoter in cells grown in HGM for 24 hrs (FIG. 4B). This remained true after 120 hrs in HGM (FIG. 4C). Thus, the YAT1 promoter appeared to be induced in HGM, a medium that promotes oleaginous growth conditions due to nitrogen limitation.

Example 9

Comparative Analysis Of The TEF, YAT1, FBAIN And GPAT Promoter Activities In *Yarrowia lipolytica*, As Determined by Fluorometric Assay A variety of methods are available to compare the activity of various promoters, to thereby facilitate determination of each promoter's strength for use in future applications wherein a suite of promoters would be necessary to construct chimeric genes. Thus, although it may be useful to indirectly quantitate promoter activity based on reporter gene expression using histochemical staining (Example 8), quantification of GUS expression using more quantitative means may be desirable. One suitable method to assay GUS activity is by fluorometric determination of the production of 4-methylumbelliferone (4-MU) from the corresponding β-glucuronide (4-MUG; see Jefferson, R. A., *Plant Mol. Biol. Reporter*, 5:387-405 (1987)).

*Yarrowia lipolytica* strain Y2034 containing plasmids pY5-30, pYAT-GUS, pYGPAT-GUS and pDMW214 constructs, respectively (from Example 7), were grown from single colonies in 10 mL SD medium at 30° C. for 48 hrs to an $OD_{600}$~5.0. Two mL of each culture was collected for GUS activity assays, as described below, while 5 mL of each culture was switched into HGM.

Specifically, cells from the 5 mL aliquot were collected by centrifugation, washed once with 5 mL of HGM and resuspended in HGM medium. The cultures in HGM were then grown in a shaking incubator at 30° C. for 24 hrs. Two mL of each HGM culture were collected for GUS activity assay, while the remaining culture was allowed to grow for an additional 96 hrs before collecting an additional 2 mL of each culture for the assay.

Each 2 mL culture sample in SD medium was resuspended in 1 mL of 0.5× cell culture lysis reagent (Promega). Resuspended cells were mixed with 0.6 mL of glass beads (0.5 mm diameter) in a 2.0 mL screw cap tube with a rubber O-ring. The cells were then homogenized in a Biospec mini beadbeater (Bartlesville, Okla.) at the highest setting for 90 sec. The homogenization mixtures were centrifuged for 2 min at 14,000 rpm in an Eppendof centrifuge to remove cell debris and beads. The supernatant was used for GUS assay and protein determination.

For each fluorometric assay, 200 μl of extract was added to 800 μl of GUS assay buffer (2 mM 4-methylumbelliferyl-β-D-glucuronide ["MUG"] in extraction buffer) and placed at 37° C. Aliquots of 100 μl were taken at 0, 30 and 60 min time points and added to 900 μl of stop buffer (1 M Na$_2$CO$_3$). Each time point was read using a Fluorimeter (CytoFluorR Series 4000, Framingham, Mass.) set to an excitation wavelength of 360 nm and an emission wavelength of 455 nm. Total protein concentration of each sample was determined using 20 μl of extract and 980 μl of BioRad Bradford reagent (Bradford, M. M., *Anal. Biochem.*, 72:248-254 (1976)). GUS activity is expressed as nmoles of 4-MU per minute per mg of total protein.

As shown in the Table below, the activity of the YAT1 promoter was highly induced after 24 hrs in HGM.

TABLE 5

Comparison of TEF, FBAIN, YAT1 And GPAT Promoter Activity Under Various Growth Conditions

| Culture Conditions | Promoter | | | |
|---|---|---|---|---|
| | TEF | FBAIN | YAT1 | GPAT |
| 48 hr, SD | 0.401 | 43.333 | 0.536 | 5.252 |
| 24 hr, HGM | 0.942 | 30.694 | 19.154 | 2.969 |
| 120 hr HGM | 0.466 | 17.200 | 13.400 | 3.050 |

Based on the data above wherein the activity of the YAT1 promoter was quantitated based on GUS activity of cell extracts, the activity of the YAT1 promoter increased by ~37 fold when cells were switched from SD medium into HGM and grown for 24 hrs. After 120 hrs in HGM, the activity was reduced somewhat but was still 25× higher than the activity in SD medium. In contrast, the activity of the FBAIN promoter and the GPAT promoter was reduced by 30% and 40%, respectively, when switched from SD medium into HGM for 24 hrs. The activity of the TEF promoter increased by 2.3 fold after 24 hrs in HGM. Thus, the YAT1 promoter is inducible under oleaginous conditions and will thereby function as an effective promoter for the regulated expression of heterologous genes in *Yarrowia lipolytica*.

Example 10

Construction And Expression Of Modified YAT1 Promoters In *Yarrowa lipolytica*

The present Example describes the construction and expression of various modified YAT1 promoters derived from the exemplary wildtype 775 by YAT1 promoter set forth as SEQ ID NO:25, which corresponds to the −775 to −1 upstream region of the yat1 gene. These modified promoters range in length from 675 bases to 783 bases and comprise various insertions and substitutions. Each of the modified YAT1 promoters was found to enable successful expression of the coding region to which it was linked, upon expression in *Yarrowia lipolytica*. Thus, it is demonstrated herein that DNA fragments of diminished length may have identical promoter activity to the promoter region provided by the full length wildtype 775 by YAT1 promoter (SEQ ID NO:25) and constitute promoter regions that differ from SEQ ID NO:25.

Construction Of Modified YAT1 Promoters

Mutations to the wildtype 775 by YAT1 promoter set forth as SEQ ID NO:25 were made using a site-directed mutagenesis kit (Stratagene, La Jolla, Calif.) and recommended protocols, using plasmid pYAT-GUS1 (FIG. 5) as template.

Plasmid pYAT-GUS1 (SEQ ID NO:45) was generated by EcoRI digestion of pYAT-GUS (Example 5), and then the large fragment of the digestion (i.e., 6645 bp) was self-ligated. This self-ligation excised a portion of the vector backbone and left an intact YAT1::GUS::XPR chimeric gene, wherein the sequence of the YAT1 promoter is set forth as SEQ ID NO:25 (i.e., the wildtype YAT1 promoter, corresponding to the −775 to −1 region upstream of the yat1 gene).

Using plasmid pYAT-GUS1 as template, 11 different modified YAT1 promoters were thus created, as described below in Table 6.

TABLE 6

WildType And Modified YAT1 Promoters

| Promoter | SEQ ID NO | Mutations with Respect to SEQ ID NO: 25 | Promoter Length | Promoter Region With Respect to yat1 Gene* |
|---|---|---|---|---|
| Wildtype YAT1 promoter | SEQ ID NO: 25 | NONE | 775 bp | Comprises the −775 to −1 region |
| Modified YAT1-CC promoter | SEQ ID NO: 26 | CC added at +776 | 777 bp | Comprises the −775 to −1 region |
| Modified YAT1-CC-SalI promoter | SEQ ID NO: 27 | SalI site (G/TCGAC) added at +1; CC added at +776 | 783 bp | Comprises the −775 to −1 region |
| Modified YAT1-CC-NcoI* promoter | SEQ ID NO: 28 | Internal NcoI site (C/CATGG) mutated to CTATGG (C to T mutation at +414); CC added at +776 | 777 bp | Comprises the −775 to −1 region |
| Modified YAT1-CC-Ncol*-SalI promoter | SEQ ID NO: 29 | SalI site (G/TCGAC) added at +1; Internal NcoI site (C/CATGG) mutated to CTATGG (C to T) mutation at +414); CC added at +776 | 783 bp | Comprises the −775 to −1 region |

TABLE 6-continued

WildType And Modified YAT1 Promoters

| Promoter | SEQ ID NO | Mutations with Respect to SEQ ID NO: 25 | Promoter Length | Promoter Region With Respect to yat1 Gene* |
|---|---|---|---|---|
| Modified YAT1-CC-NcoI*-26 promoter | SEQ ID NO: 30 | Deletion of +1 to +26; Internal NcoI site (C/CATGG) mutated to CTATGG (C to T) mutation at +414); CC added at +776 | 751 bp | Comprises the −749 to −1 region |
| Modified YAT1-CC-NcoI*-26-ClaI promoter | SEQ ID NO: 31 | Deletion of +1 to +26; ClaI site (AT/CGAT) added at +27; Internal NcoI site (C/CATGG) mutated to CTATGG (C to T) mutation at +414); CC added at +776 | 757 bp | Comprises the −749 to −1 region |
| Modified YAT1-CC-NcoI*-26-SwaI promoter | SEQ ID NO: 32 | Deletion of +1 to +26; SwaI site (ATTT/AAAT) added at +27; Internal NcoI site (C/CATGG) mutated to CTATGG (C to T mutation at +414); CC added at +776 | 759 bp | Comprises the −749 to −1 region |
| Modified YAT1-CC-NcoI*-48 promoter | SEQ ID NO: 33 | Deletion of +1 to +48; Internal NcoI site (C/CATGG) mutated to CTATGG (C to T mutation at +414); CC added at +776 | 729 bp | Comprises the −727 to −1 region |
| Modified YAT1-CC-NcoI*-48-PmeI promoter | SEQ ID NO: 34 | Deletion of +1 to +48; PmeI site (GTTT/AAAC) added at +49; Internal NcoI site (C/CATGG) mutated to CTATGG (C to T mutation at +414); CC added at +776 | 737 bp | Comprises the −727 to −1 region |
| Modified YAT1-CC-NcoI*-102 promoter | SEQ ID NO: 35 | Deletion of +1 to +102; Internal NcoI site (C/CATGG) mutated to CTATGG (C to T mutation at +414); CC added at +776 | 675 bp | Comprises the −673 to −1 region |
| Modified YAT1-CC-NcoI*-102-EcoRI promoter | SEQ ID NO: 36 | Deletion of +1 to +102; EcoRI site (G/AATTC) added at +103 (creating effectively a deletion of only +1 to +97 of SEQ ID NO: 25 and a G to T mutation at +100); Internal NcoI site (C/CATGG) mutated to CTATGG (C to T mutation at +414); CC added at +776 | 681 bp | Comprises the −673 to −1 region |

*Promoter region with respect to Yarrowia lipolytica yat1 gene is described based on nucleotide numbering such that the 'A' position of the 'ATG' translation initiation codon is designated as +1.

A multiple sequence alignment of these promoters (i.e., the YAT1-CC promoter [SEQ ID NO:26], the YAT1-CC-SalI promoter [SEQ ID NO:27], the YAT1-CC-NcoI* promoter [SEQ ID NO:28], the YAT1-CC-NcoI*-SalI promoter [SEQ ID NO:29], the YAT1-CC-NcoI*-26 promoter [SEQ ID NO:30], the YAT1-CC-NcoI*-26-ClaI promoter [SEQ ID NO:31], the YAT1-CC-NcoI*-26-SwaI promoter [SEQ ID NO:32], the YAT1-CC-NcoI*-48 promoter [SEQ ID NO:33], the YAT1-CC-NcoI*-48-PmeI promoter [SEQ ID NO:34], the YAT1-CC-NcoI*-102 promoter [SEQ ID NO:35] and the YAT1-CC-NcoI*-102-EcoRI promoter [SEQ ID NO:36]), as well as the wildtype YAT1 promoter (SEQ ID NO:25) which corresponds to the −775 to −1 region upstream of the yat1 gene, is shown in FIG. 6. The alignment was performed using default parameters [gap opening penalty=15, gap extension penalty=6.66, and gap separation penalty range=8] of Vector NTI®'s Advance 9.1.0 AlignX program (Invitrogen Corporation, Carlsbad, Calif.).

Expression Of Modified YAT1 Promoters: YAT1-CC-SalI, YAT1-CC-NcoI*-SalI, YAT1-CC-NcoI*-26-ClaI, YAT1-CC-NcoI*-48-PmeI And YAT1-CC-NcoI*-102-EcoRI Using standard cloning methodology, the resultant modified YAT1 promoters (i.e., YAT1-CC-SalI, YAT1-CC-NcoI*-SalI, YAT1-CC-NcoI*-26-ClaI, YAT1-CC-NcoI*-48-PmeI and YAT1-CC-NcoI*-102-EcoRI) were operably linked to the coding regions of several different PUFA biosynthetic pathway genes and suitable terminators derived from Yarrowia in various plasmid vectors.

The various plasmid vectors were transformed separately into several different strains of Y. lipolytica derived from Y. lipolytica ATCC #20362 that had been previously engineered to produce the substrate appropriate for the introduced gene (see General Methods). Thus, e.g., a host producing suitable quantities of either LA or ALA was required to enable expression of an introduced Δ9 elongase, since the Δ9 elongase converts LA to EDA and/or ALA to ETrA. Similarly, a host producing suitable quantities of either EDA or ETrA was required to enable expression of an introduced Δ8 desaturase, since the Δ8 desaturase converts EDA to DGLA and/or ETrA to ETA. See, FIG. 2.

Single colonies from each transformation were streaked onto MM selection plates and grown at 30° C. for 24 to 48 hrs. A loop of cells from each MM selection plate was then inoculated into liquid MM at 30° C.; the cells were shaken at 250 rpm/min for 2 days, collected by centrifugation and lipids were extracted. FAMEs were prepared by trans-esterification, and subsequently analyzed with a Hewlett-Packard 6890 GC.

The promoter activity of each of the mutant YAT1 promoters (i.e., YAT1-CC-SalI, YAT1-CC-NcoI*-SalI, YAT1-CC-NcoI*-26-ClaI, YAT1-CC-NcoI*-48-PmeI and YAT1-CC-NcoI*-102-EcoRI) was determined based on the substrate conversion efficiency of the particular gene to which the promoter was operably linked. More specifically, the conversion efficiency refers to the efficiency by which a particular enzyme can convert substrate to product and was calculated according to the following formula: ([product]/[substrate+product])*100, where 'product' includes the immediate product and all products in the pathway derived from it.

The mutant promoter was deemed active if suitable substrate conversion was observed. Suitable conversion was determined by comparing with the substrate conversion observed in the untransformed, parent strain of *Y. lipolytica*.

Based on the above analyses, each of the modified YAT1 promoters (i.e., YAT1-CC-SalI [SEQ ID NO:27], YAT1-CC-NcoI*-SalI [SEQ ID NO:29], YAT1-CC-NcoI*-26-ClaI [SEQ ID NO:31], YAT1-CC-NcoI*-48-PmeI [SEQ ID NO:34] and YAT1-CC-NcoI*-102-EcoRI [SEQ ID NO:36]) was deemed active. Thus, SEQ ID NO:25 could be truncated from its 5' end in multiple ways, i.e., by having deleted from its sequence any set of consecutive nucleotides starting from nucleotide 1 (at its 5' end) and including up to nucleotide 97. For example: 1) deleting the region defined as +1 to +97 by of SEQ ID NO:25 results in the active mutant promoter described herein as YAT1-CC-NcoI*-102-EcoRI, which corresponds to bases 98 to 775 of SEQ ID NO:25 (i.e., also corresponding to the −673 to −1 region of the *Yarrowia lipolytica* yat1 gene); 2) deleting the region defined as +1 to +26 by of SEQ ID NO:25 results in the active mutant promoter described herein YAT1-CC-NcoI*-26-ClaI, which corresponds to bases 27 to 775 of SEQ ID NO:25 (i.e., also corresponding to the −749 to −1 region of the *Yarrowia lipolytica* yat1 gene); and 3) deleting the region defined as +1 to +48 by of SEQ ID NO:25 results in the active mutant promoter described herein YAT1-CC-NcoI*-48-PmeI, which corresponds to bases 49 to 775 of SEQ ID NO:25 (i.e., also corresponding to the −727 to −1 region of the *Yarrowia lipolytica* yat1 gene).

In addition to tolerating various truncations from the 5' end of SEQ ID NO:25, the modified YAT1-CC-SalI (SEQ ID NO:27), YAT1-CC-NcoI*-SalI (SEQ ID NO:29), YAT1-CC-NcoI*-26-ClaI (SEQ ID NO:31), YAT1-CC-NcoI*-48-PmeI (SEQ ID NO:34) and YAT1-CC-NcoI*-102-EcoRI (SEQ ID NO:36) promoters are demonstrated to sustain mutations in the active region (i.e., in the region corresponding to bases 98 to 775 of SEQ ID NO:25) that do not change the active status of the promoter.

Specifically, for all modified YAT1 promoters, a CC insertion at by +776 does not impair their active status. As described in U.S. Pat. No. 7,125,672, the preferred consensus sequence of the codon-optimized translation initiation site for optimal expression of genes in *Y. lipolytica* is 'MAMMATGNHS' (SEQ ID NO:37), wherein the nucleic acid degeneracy code used is as follows: M=A/C; S=C/G; H=A/C/T; and N=A/C/G/T. While the four nucleotides immediately preceding the 'ATG' translation initiation site are 'ACAA' in the wildtype YAT1 promoter set forth as SEQ ID NO:25 (therefore not corresponding to the preferred consensus sequence), the CC insertion at by +776 in the modified YAT1 promoters results in a more preferred sequence of 'AACC' immediately upstream of the 'ATG' translation initiation site.

For YAT1-CC-NcoI*-SalI (SEQ ID NO:29), YAT1-CC-NcoI*-26-ClaI (SEQ ID NO:31), YAT1-CC-NcoI*-48-PmeI (SEQ ID NO:34) and YAT1-CC-NcoI*-102-EcoRI (SEQ ID NO:36) promoters, a substitution at by +414 from C to T (effectively removing the internal NcoI site from the promoter region) does not impair the active status of the mutant promoter. It is hypothesized that a substitution at by +414 from C to G or from C to A would also result in a functional promoter. Furthermore, for the YAT1-CC-NcoI*-102-EcoRI (SEQ ID NO:36) promoter, a substitution at by +100 from G to T (effectively inserting a EcoRI site at the 5' region of the promoter) does not impair its active status.

Based on the results obtained for YAT1-CC-SalI (SEQ ID NO:27), YAT1-CC-NcoI*-SalI (SEQ ID NO:29), YAT1-CC-NcoI*-26-ClaI (SEQ ID NO:31), YAT1-CC-NcoI*-48-PmeI (SEQ ID NO:34) and YAT1-CC-NcoI*-102-EcoRI (SEQ ID NO:36), it is also hypothesized herein that related promoters (i.e., those that comprise at least the −673 to −1 region upstream of the *Y. lipolytica* yat1 gene, optionally with or without either a C to A, G or T mutation at +414 [to remove the internal NcoI site] or a CC insertion at +776 [to optimize the consensus sequence around the translation initiation codon]) will also be active.

Thus, for example, it is expected that the YAT1-CC (SEQ ID NO:26) promoter, the YAT1-CC-NcoI* (SEQ ID NO:28) promoter, the YAT1-CC-NcoI*-26 (SEQ ID NO:30) promoter, the YAT1-CC-NcoI*-26-SwaI (SEQ ID NO:32) promoter, the YAT1-CC-NcoI*-48 (SEQ ID NO:33) promoter, and the YAT1-CC-NcoI*-102 (SEQ ID NO:35) promoter will all be active promoters for the purposes of enabling expression of a coding region of interest that is expressible in a yeast cell, when the promoter region is operably linked to the coding region. More specifically, the YAT1-CC promoter set forth as SEQ ID NO:26 is identical to the YAT1-CC-SalI promoter of SEQ ID NO:27, with the exception that a SalI restriction enzyme site was added upstream of the promoter sequence (corresponding to the −775 to −1 region upstream of the *Y. lipolytica* yat1 gene) in the latter, for cloning convenience. Since SEQ ID NO:27 was proven to be active, one can assume that SEQ ID NO:26 will also be active. Thus, description of a functional modified promoter will not be limited by the particular restriction enzyme that is introduced immediately preceding the promoter sequence. Similarly, since the YAT1-CC-NcoI*-SalI (SEQ ID NO:29) promoter was proven active (also corresponding to the −775 to −1 region upstream of the *Y. lipolytica* yat1 gene), the related YAT1-CC-NcoI* (SEQ ID NO:28) promoter which lacks only the upstream SalI restriction enzyme site is also expected to be active. Likewise, since the YAT1-CC-NcoI*-26-ClaI (SEQ ID NO:31) promoter was proven active (corresponding to the −749 to −1 region upstream of the *Y. lipolytica* yat1 gene), the related YAT1-CC-NcoI*-26 (SEQ ID NO:30) promoter which lacks only the upstream ClaI restriction enzyme site is also expected to be active, as is the YAT1-CC-NcoI*-26-SwaI (SEQ ID NO:32) promoter which has an upstream SwaI restriction enzyme site in place of the upstream ClaI restriction enzyme site. Similar conclusions can be drawn concerning the YAT1-CC-NcoI*-48 (SEQ ID NO:33) promoter based on the activity of the YAT1-CC-NcoI*-48-PmeI (SEQ ID NO:34) promoter and concerning the YAT1-CC-NcoI*-102

(SEQ ID NO:35) promoter, based on the activity of the YAT1-CC-NcoI*-102-EcoRI (SEQ ID NO:36) promoter.

Example 11

Use Of Select Modified YAT1 Promoters In *Yarrowa lipolytica* Strain Y4259, Producing 46.5% Eicosapentaenoic Acid The present Example describes the construction of strain Y4259, derived from *Yarrowia lipolytica* ATCC #20362, capable of producing about 46.5% EPA relative to the total lipids via expression of a Δ9 elongase/Δ8 desaturase pathway. The development of strain Y4259 (FIG. 7) required the construction of strains Y2224, Y4001, Y4001U, Y4036, Y4036U, Y4070, Y4086, Y4086U1, Y4128 [deposited with the American Type Culture Collection on Aug. 23, 2007, bearing the designation ATCC PTA-8614], Y4128U3 (Ura-), Y4217 and Y4217U2 (Ura-).

The final genotype of strain Y4259 with respect to wild type *Yarrowia lipolytica* ATCC #20362 included eight chimeric genes described as: YAT1::FmD12::OCT, YAT1::ME3S::Pex16, YAT1::EgD9eS::Lip2, YAT1::EgD8M::Aco, YAT1::EgD5S::Aco, YAT1::RD5S::OCT, YAT1::PaD17S::Lip1 and YAT1::YICPT1::ACO. The YAT1 promoter in each of these cassettes corresponds to one of the modified YAT1 promoters of Example 10, as summarized in Table 7 and described in additional detail in the Example below (FIG. 7).

genes (i.e., a Δ12 desaturase, a $C_{16/18}$ elongase and two Δ9 elongases), the chimeric YAT1::ME3S::Pex16 gene is of relevance to the present disclosure. Specifically, the ME3S gene, corresponding to a codon-optimized $C_{16/18}$ elongase gene derived from *Mortierella alpina* (U.S. Pat. No. 7,470,532), was operably linked to a YAT1 promoter sequence that corresponds to YAT1-CC-NcoI*-102-EcoRI (SEQ ID NO:36) (Example 10).

Generation Of Strain Y4036 To Produce About 18% DGLA Of Total Lipids

The generation of strain Y4036 is described in Example 7 of Intl. App. Pub. No. WO 2008/073367, hereby incorporated herein by reference. Briefly, following the isolation of strain Y4001 U, having a Leu- and Ura-phenotype, construct pKO2UF8289 was integrated into the Δ12 loci of strain Y4001U1. This resulted in isolation of strain Y4036, producing about 18.2% DGLA of total lipids. Although construct pKO2UF8289 (SEQ ID NO:39) comprised four chimeric genes (i.e., a Δ12 desaturase, one Δ9 elongase and two mutant Δ8 desaturases), the chimeric YAT1::FmD12::OCT gene is of relevance to the present disclosure. Specifically, the FmD12 gene, corresponding to a *Fusarium moniliforme* Δ12 desaturase gene (U.S. Pat. No. 7,504,259), was operably linked to a YAT1 promoter sequence that corresponds to YAT1-CC-NcoI*-26-SwaI (SEQ ID NO:32) (Example 10).

TABLE 7

Use Of Modified YAT1 Promoters In Genetically Engineered Strains of *Yarrowia lipolytica* Producing PUFAs

| Plasmid | Plasmid SEQ ID NO | Promoter | Promoter SEQ ID NO | Chimeric Gene |
|---|---|---|---|---|
| pZKLeuN-29E3 | SEQ ID NO: 38 | YAT1-CC-NcoI*-102-EcoRI | SEQ ID NO: 36 | YAT1::ME3S::Pex16 |
| pKO2UF8289 | SEQ ID NO: 39 | YAT1-CC-NcoI*-26-SwaI | SEQ ID NO: 32 | YAT1::FmD12::OCT |
| pZKSL-555R | SEQ ID NO: 40 | YAT1-CC-NcoI*-26-ClaI | SEQ ID NO: 31 | YAT1::RD5S::OCT |
| pZP3-Pa777U | SEQ ID NO: 41 | YAT1-CC-NcoI*-26-ClaI | SEQ ID NO: 31 | YAT1::PaD17S::Lip1 |
| pZP2-2988 | SEQ ID NO: 42 | YAT1-CC-NcoI*-26-SwaI | SEQ ID NO: 32 | YAT1::EgD8M::ACO |
| pZKL2-5U89GC | SEQ ID NO:43 | YAT1-CC-NcoI*-26-SwaI | SEQ ID NO: 32 | YAT1::YICPT1::Aco |
| pZKL2-5U89GC | SEQ ID NO: 43 | YAT1-CC-NcoI*-102-EcoRI | SEQ ID NO: 36 | YAT1::EgD5S::ACO |
| pZKL1-25P98C | SEQ ID NO: 44 | YAT1-CC-NcoI*-48-PmeI | SEQ ID NO: 34 | YAT1::EgD9eS::Lip2 |

Generation Of Strain Y4001 To Produce About 17% EDA Of Total Lipids

The generation of strain Y4001 is described in Example 7 of Intl. App. Pub. No. WO 2008/073367, hereby incorporated herein by reference. Briefly, construct pZKLeuN-29E3 was integrated into the Leu2 loci of strain Y2224 (a FOA resistant mutant from an autonomous mutation of the Ura3 gene of wildtype *Yarrowia* strain ATCC #20362). Although construct pZKLeuN-29E3 (SEQ ID NO:38) comprised four chimeric Generation Of Strain Y4070 To Produce About 12% ARA Of Total Lipids The generation of strain Y4070 is described in Example 7 of Intl. App. Pub. No. WO 2008/073367, hereby incorporated herein by reference. Briefly, following the isolation of strain Y4036U, having a Leu- and Ura-phenotype, construct pZKSL-555R was integrated into the Lys loci of strain Y4036U. This resulted in isolation of strain Y4070, producing about 12% ARA of total lipids. Although construct pZKSL-555R (SEQ ID NO:40) comprised three chimeric AS desaturase genes, the chimeric YAT1::RD5S::OCT gene is of relevance to the present disclosure. Specifically, the RD5S gene, corresponding to a codon-optimized Δ5 desaturase derived from Peridinium sp. CCMP626 (U.S. Pat. Appl. Pub. No. 2007-0271632-A1), was operably linked to a YAT1 promoter sequence that corresponds to YAT1-CC-NcoI*-26-ClaI (SEQ ID NO:31) (Example 10).

Generation Of Y4086 Strain To Produce About 14% EPA Of Total Lipids

The generation of strain Y4086 is described in Example 1 of U.S. Pat. Appl. Pub. No. 2009-0093543-A1, hereby incorporated herein by reference. Briefly, construct pZP3-Pa777U was integrated into the Pox3 loci (GenBank Accession No. AJ001301) of strain Y4070. This resulted in isolation of strain Y4086, producing about 14% EPA of total lipids. Although construct pZP3-Pa777U (SEQ ID NO:41) comprised three chimeric Δ17 desaturase genes, the chimeric YAT1::PaD17S::Lip1 gene is of relevance to the present disclosure. Specifically, the PaD17S gene, corresponding to a codon-optimized Δ17 desaturase derived from Pythium aphanidermatum (Intl. App. Pub. No. WO 2008/054565), was operably linked to a YAT1 promoter sequence that corresponds to YAT1-CC-NcoI*-26-ClaI (SEQ ID NO:31) (Example 10).

Generation Of Y4128 Strain To Produce About 37% EPA Of Total Lipids

The generation of strain Y4128 is described in Example 2 of U.S. Pat. Appl. Pub. No. 2009-0093543-A1, hereby incorporated herein by reference. Briefly, following the isolation of strain Y4086U1, having a Ura-phenotype, construct pZP2-2988 was integrated into the Pox2 loci (GenBank Accession No. AJ001300) of strain Y4086U1. This resulted in isolation of strain Y4128, producing about 37% EPA of total lipids. Although construct pZP2-2988 (SEQ ID NO:42) comprised four chimeric genes (i.e., a Δ12 desaturase gene, two Δ8 desaturase genes and a Δ9 elongase), the chimeric YAT1::EgD8M::ACO gene is of relevance to the present disclosure. Specifically, the EgD8M gene, corresponding to a synthetic mutant Δ8 desaturase (U.S. Pat. Appl. Pub. No. 2008-0138868 A1) derived from Euglena gracilis (U.S. Pat. No. 7,256,033), was operably linked to a YAT1 promoter sequence that corresponds to YAT1-CC-NcoI*-26-SwaI (SEQ ID NO:32) (Example 10).

Generation Of Y4217 Strain To Produce About 42% EPA Of Total Lipids

The generation of strain Y4217 is described in Example 3 of U.S. Pat. Appl. Pub. No. 2009-0093543-A1, hereby incorporated herein by reference. Briefly, following the isolation of strain Y4128U3, having a Ura-phenotype, construct pZKL2-5U89GC was integrated into the Lip2 loci (GenBank Accession No. AJ012632) of strain Y4128U3. This resulted in isolation of strain Y4217, producing about 42% EPA of total lipids. Although construct pZKL2-5U89GC (SEQ ID NO:43) comprised four chimeric genes (i.e., a Δ9 elongase gene, a Δ8 desaturase gene, a Δ5 desaturase gene and a Yarrowia lipolytica diacylglycerol cholinephosphotransferase gene), the chimeric YAT1::YICPT1::Aco gene and chimeric YAT1::EgD5S::ACO gene are of relevance to the present disclosure. Specifically, the YICPT1 gene, corresponding to a Yarrowia lipolytica diacylglycerol cholinephosphotransferase (Intl. App. Pub. No. WO 2006/052870), was operably linked to a YAT1 promoter sequence that corresponds to YAT1-CC-NcoI*-26-SwaI (SEQ ID NO:32) (Example 10). The EgD5S gene, corresponding to a codon-optimized Δ5 desaturase derived from Euglena gracilis (Intl. App. Pub. No. WO 2007/136671), was operably linked to a YAT1 promoter sequence that corresponds to YAT1-CC-NcoI*-102-EcoRI (SEQ ID NO:36) (Example 10).

Generation Of Y4259 Strain To Produce About 46.5% EPA Of Total Lipids

The generation of strain Y4259 is described in Example 3 of U.S. Pat. Appl. Pub. No. 2009-0093543-A1, hereby incorporated herein by reference. Briefly, following the isolation of strain Y4217U2, having a Ura-phenotype, construct pZKL1-2SP98C was integrated into the Lip1 loci (GenBank Accession No. Z50020) of strain Y4217U2. This resulted in isolation of strain Y4259, producing about 46.5% EPA of total lipids. Although construct pZKL1-2SP98C (SEQ ID NO:44) comprised four chimeric genes (i.e., a Δ9 elongase gene, a Δ8 desaturase gene, a Δ12 desaturase gene and a Yarrowia lipolytica diacylglycerol cholinephosphotransferase gene), the chimeric YAT1::EgD9eS::Lip2 gene is of relevance to the present disclosure. Specifically, the EgD9eS gene, corresponding to a codon-optimized Δ9 elongase gene derived from Euglena gracilis (Intl. App. Pub. No. WO 2007/061742), was operably linked to a YAT1 promoter sequence that corresponds to YAT1-CC-NcoI*-48-PmeI (SEQ ID NO:34) (Example 10).

Thus, four different modified mutant YAT promoters derived from the exemplary 775 by YAT1 promoter set forth as SEQ ID NO:25 (corresponding to the −775 to −1 upstream region of the yat1 gene) were utilized in various chimeric genes within strain Y4259, to enable expression of various PUFA biosynthetic pathway genes. These truncated promoters comprise various regions of the upstream yat1 gene, including the −673 to −1 region, the −727 to −1 region and the −749 to −1 region, and comprise various insertions and substitutions. More specifically, each of the modified YAT1 promoters utilized within pZKLeuN-29E3 (SEQ ID NO:38), pKO2UF8289 (SEQ ID NO:39), pZKSL-555R (SEQ ID NO:40), pZP3-Pa777U (SEQ ID NO:41), pZP2-2988 (SEQ ID NO:42), pZKL2-5U89GC (SEQ ID NO:43) and pZKL1-2SP98C (SEQ ID NO:44) was found to enable successful expression of the coding region to which it was linked, upon expression in Yarrowia lipolytica. Thus, it is demonstrated herein that DNA fragments of diminished length may have identical promoter activity as the promoter region provided by the full length of SEQ ID NO:25 and constitute promoter regions that differ from SEQ ID NO:25.

What is claimed is:

1. A recombinant gene expression cassette comprising an isolated DNA sequence comprising a polynucleotide encoding a polypeptide expressible in an oleaginous yeast cell wherein said polynucleotide is operably linked to a promoter region comprising the nucleotide sequence a position 103 to 775 of SEQ ID NO:25 or a mutant of the nucleotide sequence at position 103 to 775 of SEQ ID NO:25 wherein deoxycytidine at position 414 of SEQ ID NO:25 is replaced by deoxythymidine, deoxyadenosine, or deoxyguanosine.

2. The recombinant gene expression cassette of claim 1 wherein a restriction enzyme site is inserted upstream and adjacent to the promoter region.

3. The recombinant gene expression cassette of claim 1 or claim 2 wherein said promoter region comprises a nucleotide sequence selected from the group consisting of: SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35 and SEQ ID NO:36.

4. The recombinant gene expression cassette of claim 1, wherein two deoxycytidines are adjacent to the 3' end of said nucleotides 103 to 775 of SEQ ID NO:25 or said mutant of the nucleotide sequence at position 103 to 775 of SEQ ID NO:25.

5. The recombinant gene expression cassette of claim 1, wherein said polynucleotide encodes at least one enzyme selected from the group consisting of an enzyme of the ω-3/ω-6 fatty acid biosynthetic pathway, an enzyme of the neutral lipid biosynthetic pathway, and an enzyme of the phospholipid biosynthetic pathway.

* * * * *